US011352650B2

(12) United States Patent
Rugbjerg et al.

(10) Patent No.: US 11,352,650 B2
(45) Date of Patent: Jun. 7, 2022

(54) SYSTEM FOR IMPROVED PRODUCTION TITERS IN FERMENTATIONS

(71) Applicant: DANMARKS TEKNISKE UNIVERSITET, Lyngby (DK)

(72) Inventors: Peter Rugbjerg, Copenhagen (DK); Kira Sarup-Lytzen, Frederiksberg (DK); Morten Sommer, Virum (DK)

(73) Assignee: DANMARKS TEKNISKE UNIVERSITET, Lyngby (DK)

( * ) Notice: Subject to any disclaimer, the term of this patent is extended or adjusted under 35 U.S.C. 154(b) by 0 days.

(21) Appl. No.: 15/763,257

(22) PCT Filed: Sep. 23, 2016

(86) PCT No.: PCT/EP2016/073132
§ 371 (c)(1),
(2) Date: Mar. 26, 2018

(87) PCT Pub. No.: WO2017/055360
PCT Pub. Date: Apr. 6, 2017

(65) Prior Publication Data
US 2018/0327790 A1 Nov. 15, 2018

(30) Foreign Application Priority Data

Sep. 28, 2015 (EP) .................................. 15187150

(51) Int. Cl.

| C12P 7/42 | (2006.01) |
|---|---|
| C12P 1/04 | (2006.01) |
| C12N 15/10 | (2006.01) |
| C12N 15/67 | (2006.01) |
| C12P 7/40 | (2006.01) |
| C12P 5/02 | (2006.01) |
| C12P 1/02 | (2006.01) |
| C12P 7/64 | (2022.01) |
| C12P 21/02 | (2006.01) |
| C12N 9/16 | (2006.01) |
| C12N 15/72 | (2006.01) |
| C12N 1/21 | (2006.01) |

(52) U.S. Cl.
CPC .................. *C12P 7/42* (2013.01); *C12N 9/16* (2013.01); *C12N 15/1086* (2013.01); *C12N 15/67* (2013.01); *C12N 15/72* (2013.01); *C12P 1/02* (2013.01); *C12P 1/04* (2013.01); *C12P 5/026* (2013.01); *C12P 7/40* (2013.01); *C12P 7/64* (2013.01); *C12P 21/02* (2013.01)

(58) Field of Classification Search
None
See application file for complete search history.

(56) References Cited

U.S. PATENT DOCUMENTS

| 2016/0017317 A1* | 1/2016 | Church .................... C12P 1/04 506/1 |
| 2017/0314053 A1* | 11/2017 | Van Melderen ....... C12N 15/10 |
| 2018/0273989 A1* | 9/2018 | Zhang .................... C12N 15/63 |

FOREIGN PATENT DOCUMENTS

| WO | 2012/087483 A1 | 6/2012 |
| WO | 2012/153142 A2 | 11/2012 |
| WO | 2015/044456 A1 | 5/2015 |
| WO | 2015/118541 A1 | 8/2015 |

OTHER PUBLICATIONS

Dietrich et al., Transcription Factor-Based Screens and Synthetic Selections for Microbial Small-Molecule Biosynthesis, ACS Synth. Biol., 2013, 2, 47-58.*
U.S. Appl. No. 62/214,248, filed Sep. 4, 2018.*
Korz et al., Simple fed-batch technique for high cell density cultivation of *Escherichia coli*, J. Biotechnol., 1995, 39, 59-65.*
Liu et al., Applications and advancesofmetabolite biosensors for metabolic engineering, Metabolic Eng., 2015, 31, 35-43.*
Doublet et al., The murI Gene of *Escherichia coli* is an Essential Gene That Encodes a Glutamate Racemase Activity, J. Bacteriol. 175, 1993, 2970-79.*
Janben et al., Fatty acid synthesis in Escherichia coli and its applications towards the production of fatty acid based biofuels, Biotechnol. Biofuels 7, 2014, 7.*
Hoskisson et al., Continuous culture, Microbiology 151, 2005, 3153-59.*
Uniprot, Accession No. P22634, 2015, www.uniprot.org.*
Peubez et al., Antibiotic-free selection in *E. coli*, Microbial Cell Factories 9, 2010, 65. (Year: 2010).*

(Continued)

*Primary Examiner* — Robert B Mondesi
*Assistant Examiner* — Todd M Epstein
(74) *Attorney, Agent, or Firm* — Casimir Jones S.C.; Lisa Mueller

(57) ABSTRACT

The invention provides a genetically modified micro-organism for intracellular biosynthesis of a cellular metabolite, comprising a synthetic error correction system having a penalty gene, whose expression leads to arrested growth or cell death (e.g. a toxin gene) in combination with a survival gene, whose expression provides an antidote that restores cell viability and normal growth (e.g. a cognate antitoxin gene). Alternatively, the system has a survival gene, alone, whose expression is essential for growth (i.e. essential gene). The synthetic error correction system further comprises a biosensor, whose function is to induce expression of the survival gene which leads to cell growth, only, when the cell produces a pre-defined level of a given metabolite. The invention further encompasses: a method for producing the genetically modified micro-organism; a method for producing a cellular metabolite with the genetically modified micro-organism; and use of the genetically modified micro-organism for producing a cellular metabolite.

6 Claims, 11 Drawing Sheets

Figure 1:
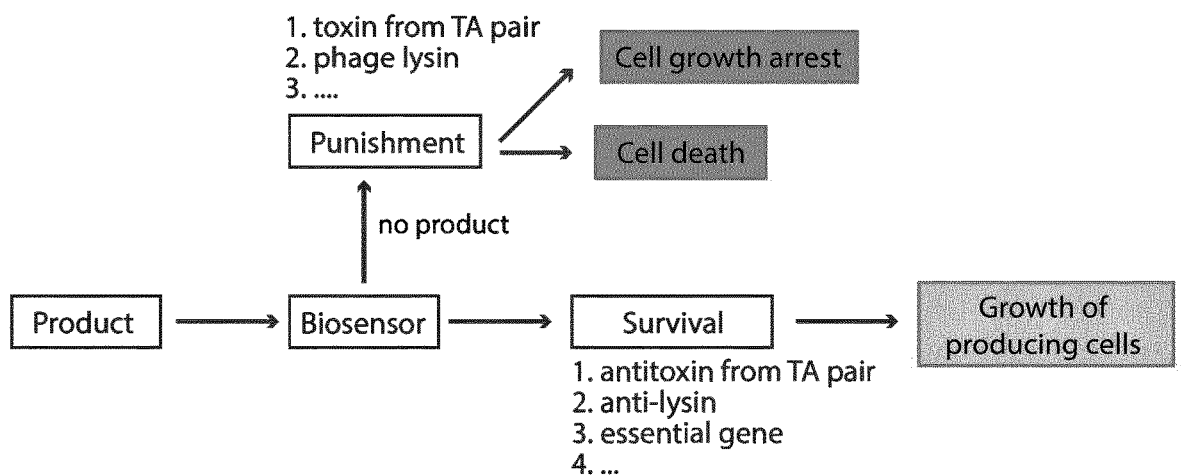

Specification includes a Sequence Listing.

(56) References Cited

OTHER PUBLICATIONS

Szpirer et al., Separate-component-stabilization system for protein and DNA production without the use of antibiotics, BioTechniques 38, 2005, 775-81. (Year: 2005).*

Uniprot, Accession No. POA749, 2014, www.uniprot.org. (Year: 2014).*

Lee, High cell-density culture of *Escherichia coli*, IBTECH 14, 1996, 98-105. (Year: 1996).*

Steele, Cornell researchers move beyond 'nano' to 'atto' to build a scale sensitive enough to weigh a virus, Cornell Chronicle, Apr. 2, 2004, news.cornell.edu/stories/2004/04/building-scale-sensitive-enough-weigh-virus. (Year: 2004).*

Mairhofer et al., A novel antibiotic free plasmid selection system: Advances in safe and efficient DNA therapy, Biotechnol J., 2008, 83-89. (Year: 2008).*

Cebolla et al., "Effector specificity mutants of the transcriptional activator NahR of naphthalene degrading Pseudomonas define protein sites involved in binding of aromatic inducers." J Biol Chem. Feb. 14, 1997; 272(7):3986-92.

Datsenko et al., "One-step inactivation of chromosomal genes in *Escherichia coli* K-12 using PCR products." Proc Natl Acad Sci USA. Jun. 6, 2000; 97(12):6640-5.

Tang et al., "Screening for enhanced triacetic acid lactone production by recombinant *Escherichia coli* expressing a designed triacetic acid lactone reporter." J Am Chem Soc. Jul. 10, 2013; 135(27):10099-103.

Guzman et al., "Tight regulation, modulation, and high-level expression by vectors containing the arabinose PBAD promoter", J Bacteriol 177(14) 4121-4130 (1995).

Salis et al., "Engineering bacterial signals and sensors", Contrib Microbiol 16: 194-225 (2009).

Wendisch et al., "Microbial production of amino acids and derived chemicals: synthetic biology approaches to strain development", CurrOpin Biotehcnol 30: 51-58 (2014).

Zhou et al., "Exploring lysine riboswitch for metabolic flux control and improvement of L-lysine synthesis in Corynebacterium glutamicum", ACS Synth Biol 4(6) 729-734 (2015).

Zelder et al., "Environmentally directed mutations and their impact on industrial biotransformation and fermentation processes." Current Opinion in Microbiology 2000, 3:248-251.

Werh et al., "Engineering Robust Production Microbes for Large-Scale Cultivation." Trends in Microbiology, Jun. 2019, 27(6): 524-537.

The Scale-Up Valley of Death: The real challenges of scaling your biomanufacturing process to 10,000 liters, SynBioBeta Event 2020, Sep. 29, 2020 [online] [Retrieved Oct. 5, 2020] Retrieved from the Internet <URL: https://synbiobeta.app.swapcard.com/event/synbiobeta-2020-the-global-synthetic-biology-conference/planning/UGxhbm5pbmdfMTU0NzUz>.

Lv et al., "Coupling metabolic addiction with negative autoregulation to improve strain stability and pathway yield." Metabolic Engineering 2020, 61:79-88.

* cited by examiner

A)

B)

C)

SEQUENCE LISTING

```
<160> NUMBER OF SEQ ID NOS: 118

<210> SEQ ID NO 1
<211> LENGTH: 5384
<212> TYPE: DNA
<213> ORGANISM: Escherichia coli
<220> FEATURE:
<221> NAME/KEY: promoter
<222> LOCATION: (1246)..(1318)
<223> OTHER INFORMATION: pBAD promoter
<220> FEATURE:
<221> NAME/KEY: CDS
<222> LOCATION: (1330)..(1581)
<223> OTHER INFORMATION: yefM antitoxin protein
<220> FEATURE:
<221> NAME/KEY: CDS
<222> LOCATION: (1845)..(2099)
<223> OTHER INFORMATION: yeoB toxin protein
<220> FEATURE:
<221> NAME/KEY: CDS
<222> LOCATION: (2652)..(3512)
<223> OTHER INFORMATION: AmpR encoded beta-lactamase

<400> SEQUENCE: 1
atcgatgcat aatgtgcctg tcaaatggac gaagcaggga ttctgcaaac cctatgctac      60
tccgtcaagc cgtcaattgt ctgattcgtt accaattatg caacttgac ggctacatca     120 ttcactttt cttcacaacc ggcacggaac tcgctcgggc tggccccggt gcatttttta    180
aatacccgcg agaaatagag ttgatcgtca aaaccaacat tgcgaccgac ggtggcgata    240
ggcatccggg tggtgctcaa aagcagcttc gcctggctga tacgttggtc ctcgcgccag    300
cttaagacgc taatccctaa ctgctggcgg aaaagatgtg acagacgcga cggcgacaag    360
caaacatgct gtgcgacgct ggcgatatca aaattgctgt ctgccaggtg atcgctgatg    420
tactgacaag cctcgcgtac ccgattatcc atcggtggat ggagcgactc gttaatcgct    480
tccatgcgcc gcagtaacaa ttgctcaagc agatttatcg ccagcagctc cgaatagcgc    540
ccttcccctt gcccggcgtt aatgatttgc ccaaacaggt cgctgaaatg cggctggtgc    600
gcttcatccg ggcgaaagaa ccccgtattg gcaaatattg acggccagtt aagccattca    660
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840 taaccttca ttcccagcgg tcggtcgata aaaaaatcga gataaccgtt ggcctcaatc     900
ggcgttaaac ccgccaccag atgggcatta acgagtatc ccgcagcag gggatcattt      960 tgcgcttcag ccatactttt catactcccg ccattcagag aagaaaccaa ttgtccatat   1020 tgcatcgac attgccgtca ctgcgtcttt tactggctct ctcgctaac caaaccggta    1080 accccgctta ttaaaagcat tctgtaacaa agcgggacca aagccatgac aaaaacgcgt   1140
aacaaaagtg tctataatca cggcagaaaa gtccacattg ttatttgca cggcgtcaca    1200 ctttgctatg ccatagcatt tttatccata agattagcgg atcctacctg acgctttta    1260 tcgcaactct ctactgtttc tccatacccg ttttttggg ctagcgaatt cgagctcgag   1320 gaggaaggt atg cgt aca att agc tac agc gaa gcg cgt cag aat ttg tcg   1371
```

```
          Met Arg Thr Ile Ser Tyr Ser Glu Ala Arg Gln Asn Leu Ser
          1               5                   10 gca aca atg atg aaa gcc gtt gaa gat cat gcc ccg atc ctt att act    1419
Ala Thr Met Met Lys Ala Val Glu Asp His Ala Pro Ile Leu Ile Thr
 15              20                  25                  30 cgt cag aat gga gag gct tgt gtt ctg atg tca ctc gaa gaa tac aac    1467
Arg Gln Asn Gly Glu Ala Cys Val Leu Met Ser Leu Glu Glu Tyr Asn
                 35                  40                  45 tcg ctg gaa gag acg gct tat cta ctg cgc tcc ccc gct aac gcc cgg    1515
Ser Leu Glu Glu Thr Ala Tyr Leu Leu Arg Ser Pro Ala Asn Ala Arg
             50                  55                  60 aga ttg atg gac tca atc gat agc ctg aaa tca ggc aaa gga acg gaa    1563
Arg Leu Met Asp Ser Ile Asp Ser Leu Lys Ser Gly Lys Gly Thr Glu
         65                  70                  75 aag gac atc att gag tga ggcaatcagc tgttgcccgt ctcactggtg           1611
Lys Asp Ile Ile Glu
         80 aaaagaaaaa ccaccctggc gcccaatacg caaaccgcct ctccccgcgc gttggccgat  1671 tcattaatgc agctggcacg acaggtttcc cgactggaaa gcgggcagtg agcgcaacgc  1731 aattaatgtg agttagctca ctcattaggc accccaggct ttacacttta tgcttccggc  1791 tcgtatgttg tgtggaattg tgagcggata acaatttcac acaggaagaa acc atg     1847
                                                          Met aaa cta atc tgg tct gag gaa tca tgg gac gat tat ctg tac tgg cag    1895
Lys Leu Ile Trp Ser Glu Glu Ser Trp Asp Asp Tyr Leu Tyr Trp Gln
 85                  90                  95                 100 gaa aca gat aag cga att gtt aaa aag atc aat gaa ctt atc aaa gat    1943
Glu Thr Asp Lys Arg Ile Val Lys Lys Ile Asn Glu Leu Ile Lys Asp
                105                 110                 115 acc cgc aga acg cca ttt gaa ggt aag ggg aag cca gaa ccc ctg aaa    1991
Thr Arg Arg Thr Pro Phe Glu Gly Lys Gly Lys Pro Glu Pro Leu Lys
            120                 125                 130 cat aat ttg tca ggt ttc tgg tcc cga cgc att aca gag gag cac cgt    2039
His Asn Leu Ser Gly Phe Trp Ser Arg Arg Ile Thr Glu Glu His Arg
        135                 140                 145 ctg gta tac gcg gtt acc gac gat tca ctg ctc att gca gca tgt cgt    2087
Leu Val Tyr Ala Val Thr Asp Asp Ser Leu Leu Ile Ala Ala Cys Arg
    150                 155                 160 tat cat tat tga atcctctaga gtcgacctgc aggcatgcaa gcttggctgt        2139
Tyr His Tyr
165 tttggcggat gagagaagat tttcagcctg atacagatta aatcagaacg cagaagcggt  2199 ctgataaaac agaatttgcc tggcggcagt agcgcggtgg tcccacctga ccccatgccg  2259 aactcagaag tgaaacgccg tagcgccgat ggtagtgtgg ggtctcccca tgcgagagta  2319 gggaactgcc aggcatcaaa taaaacgaaa ggctcagtcg aaagactggg cctttcgttt  2379 tatctgttgt ttgtcggtga acgctctcct gagtaggaca atccgccgg gagcggattt  2439 gaacgttgcg aagcaacggc ccggagggtg cgggcagga cgcccgccat aaactgccag   2499 gcatcaaatt aagcagaagg ccatcctgac ggatggcctt tttgcgtttc tacaaactct  2559 tttgtttatt tttctaaata cattcaaata tgtatccgct catgagacaa taaccctgat  2619 aaatgcttca ataatattga aaaggaaga gt atg agt att caa cat ttc cgt    2672
                                   Met Ser Ile Gln His Phe Arg
                                                170 gtc gcc ctt att ccc ttt ttt gcg gca ttt tgc ctt cct gtt ttt gct    2720
Val Ala Leu Ile Pro Phe Phe Ala Ala Phe Cys Leu Pro Val Phe Ala
175                 180                 185                 190
```

```
cac cca gaa acg ctg gtg aaa gta aaa gat gct gaa gat cag ttg ggt         2768
His Pro Glu Thr Leu Val Lys Val Lys Asp Ala Glu Asp Gln Leu Gly
                195                 200                 205 gca cga gtg ggt tac atc gaa ctg gat ctc aac agc ggt aag atc ctt         2816
Ala Arg Val Gly Tyr Ile Glu Leu Asp Leu Asn Ser Gly Lys Ile Leu
            210                 215                 220 gag agt ttt cgc ccc gaa gaa cgt ttt cca atg atg agc act ttt aaa         2864
Glu Ser Phe Arg Pro Glu Glu Arg Phe Pro Met Met Ser Thr Phe Lys
        225                 230                 235 gtt ctg cta tgt ggc gcg gta tta tcc cgt gtt gac gcc ggg caa gag         2912
Val Leu Leu Cys Gly Ala Val Leu Ser Arg Val Asp Ala Gly Gln Glu
    240                 245                 250 caa ctc ggt cgc cgc ata cac tat tct cag aat gac ttg gtt gag tac         2960
Gln Leu Gly Arg Arg Ile His Tyr Ser Gln Asn Asp Leu Val Glu Tyr
255                 260                 265                 270 tca cca gtc aca gaa aag cat ctt acg gat ggc atg aca gta aga gaa         3008
Ser Pro Val Thr Glu Lys His Leu Thr Asp Gly Met Thr Val Arg Glu
                275                 280                 285 tta tgc agt gct gcc ata acc atg agt gat aac act gcg gcc aac tta         3056
Leu Cys Ser Ala Ala Ile Thr Met Ser Asp Asn Thr Ala Ala Asn Leu
            290                 295                 300 ctt ctg aca acg atc gga gga ccg aag gag cta acc gct ttt ttg cac         3104
Leu Leu Thr Thr Ile Gly Gly Pro Lys Glu Leu Thr Ala Phe Leu His
        305                 310                 315 aac atg ggg gat cat gta act cgc ctt gat cgt tgg gaa ccg gag ctg         3152
Asn Met Gly Asp His Val Thr Arg Leu Asp Arg Trp Glu Pro Glu Leu
    320                 325                 330 aat gaa gcc ata cca aac gac gag cgt gac acc acg atg cct gca gca         3200
Asn Glu Ala Ile Pro Asn Asp Glu Arg Asp Thr Thr Met Pro Ala Ala
335                 340                 345                 350 atg gca aca acg ttg cgc aaa cta tta act ggc gaa cta ctt act cta         3248
Met Ala Thr Thr Leu Arg Lys Leu Leu Thr Gly Glu Leu Leu Thr Leu
                355                 360                 365 gct tcc cgg caa caa tta ata gac tgg atg gag gcg gat aaa gtt gca         3296
Ala Ser Arg Gln Gln Leu Ile Asp Trp Met Glu Ala Asp Lys Val Ala
            370                 375                 380 gga cca ctt ctg cgc tcg gcc ctt ccg gct ggc tgg ttt att gct gat         3344
Gly Pro Leu Leu Arg Ser Ala Leu Pro Ala Gly Trp Phe Ile Ala Asp
        385                 390                 395 aaa tct gga gcc ggt gag cgt ggg tct cgc ggt atc att gca gca ctg         3392
Lys Ser Gly Ala Gly Glu Arg Gly Ser Arg Gly Ile Ile Ala Ala Leu
    400                 405                 410 ggg cca gat ggt aag ccc tcc cgt atc gta gtt atc tac acg acg ggg         3440
Gly Pro Asp Gly Lys Pro Ser Arg Ile Val Val Ile Tyr Thr Thr Gly
415                 420                 425                 430 agt cag gca act atg gat gaa cga aat aga cag atc gct gag ata ggt         3488
Ser Gln Ala Thr Met Asp Glu Arg Asn Arg Gln Ile Ala Glu Ile Gly
                435                 440                 445 gcc tca ctg att aag cat tgg taa ctgtcagacc aagtttactc atatatactt        3542
Ala Ser Leu Ile Lys His Trp
                450 tagattgatt tacgcgccct gtagcggcgc attaagcgcg gcgggtgtgg tggttacgcg       3602 cagcgtgacc gctacacttg ccagcgccct agcgcccgct cctttcgctt tcttcccttc       3662 ctttctcgcc acgttcgccg gctttccccg tcaagctcta atcgggggc tccctttagg        3722 gttccgattt agtgctttac ggcacctcga ccccaaaaaa cttgatttgg gtgatggttc       3782 acgtagtggg ccatcgccct gatagacggt ttttcgccct ttgacgttgg agtccacgtt       3842
```

```
ctttaatagt ggactcttgt tccaaacttg aacaacactc aaccctatct cgggctattc    3902
ttttgattta agggatttt tgccgatttc ggcctattgg ttaaaaaatg agctgattta    3962
acaaaaattt aacgcgaatt ttaacaaaat attaacgttt acaatttaaa aggatctagg    4022
tgaagatcct ttttgataat ctcatgacca aaatccctta acgtgagttt tcgttccact    4082
gagcgtcaga cccgtagaa aagatcaaag gatcttcttg agatcctttt tttctgcgcg    4142
taatctgctg cttgcaaaca aaaaaaccac cgctaccagc ggtggtttgt ttgccggatc    4202
aagagctacc aactcttttt ccgaaggtaa ctggcttcag cagagcgcag ataccaaata    4262
ctgtccttct agtgtagccg tagttaggcc accacttcaa gaactctgta gcaccgccta    4322
catacctcgc tctgctaatc ctgttaccag tggctgctgc cagtggcgat aagtcgtgtc    4382
ttaccgggtt ggactcaaga cgatagttac cggataaggc gcagcggtcg ggctgaacgg    4442
ggggttcgtg cacacagccc agcttggagc gaacgaccta caccgaactg agatacctac    4502
agcgtgagct atgagaaagc gccacgcttc ccgaagggag aaaggcggac aggtatccgg    4562
taagcggcag ggtcggaaca ggagagcgca cgagggagct tccaggggga aacgcctggt    4622
atctttatag tcctgtcggg tttcgccacc tctgacttga gcgtcgattt ttgtgatgct    4682
cgtcagggg gcggagccta tggaaaaacg ccagcaacgc ggccttttta cggttcctgg    4742
ccttttgctg ccttttgct cacatgttct ttcctgcgtt atccctgat tctgtggata    4802
accgtattac cgcctttgag tgagctgata ccgctcgccg cagccgaacg accgagcgca    4862
gcgagtcagt gagcgaggaa gcggaagagc gcctgatgcg gtattttctc cttacgcatc    4922
tgtgcggtat ttcacaccgc atatggtgca ctctcagtac aatctgctct gatgccgcat    4982
agttaagcca gtatacactc cgctatcgct acgtgactgg gtcatggctg cgccccgaca    5042
cccgccaaca cccgctgacg cgccctgacg ggcttgtctg ctcccggcat ccgcttacag    5102
acaagctgtg accgtctccg ggagctgcat gtgtcagagg ttttcaccgt catcaccgaa    5162
acgcgcgagg cagcaaggag atggcgccca acagtccccc ggccacgggg cctgccacca    5222
tacccacgcc gaaacaagcg ctcatgagcc cgaagtggcg agcccgatct ccccatcgg    5282
tgatgtcggc gatataggcg ccagcaaccg cacctgtggc gccggtgatg ccggccacga    5342
tgcgtccggc gtagaggatc tgctcatgtt tgacagctta tc                      5384
```

<210> SEQ ID NO 2
<211> LENGTH: 83
<212> TYPE: PRT
<213> ORGANISM: Escherichia coli

<400> SEQUENCE: 2

Met Arg Thr Ile Ser Tyr Ser Glu Ala Arg Gln Asn Leu Ser Ala Thr
1               5                   10                  15

Met Met Lys Ala Val Glu Asp His Ala Pro Ile Leu Ile Thr Arg Gln
            20                  25                  30

Asn Gly Glu Ala Cys Val Leu Met Ser Leu Glu Glu Tyr Asn Ser Leu
        35                  40                  45

Glu Glu Thr Ala Tyr Leu Leu Arg Ser Pro Ala Asn Ala Arg Arg Leu
    50                  55                  60

Met Asp Ser Ile Asp Ser Leu Lys Ser Gly Lys Gly Thr Glu Lys Asp
65                  70                  75                  80

Ile Ile Glu

<210> SEQ ID NO 3

```
<211> LENGTH: 84
<212> TYPE: PRT
<213> ORGANISM: Escherichia coli

<400> SEQUENCE: 3

Met Lys Leu Ile Trp Ser Glu Glu Ser Trp Asp Asp Tyr Leu Tyr Trp
1               5                   10                  15

Gln Glu Thr Asp Lys Arg Ile Val Lys Lys Ile Asn Glu Leu Ile Lys
            20                  25                  30

Asp Thr Arg Arg Thr Pro Phe Glu Gly Lys Gly Lys Pro Glu Pro Leu
        35                  40                  45

Lys His Asn Leu Ser Gly Phe Trp Ser Arg Arg Ile Thr Glu Glu His
    50                  55                  60

Arg Leu Val Tyr Ala Val Thr Asp Asp Ser Leu Leu Ile Ala Ala Cys
65                  70                  75                  80

Arg Tyr His Tyr

<210> SEQ ID NO 4
<211> LENGTH: 286
<212> TYPE: PRT
<213> ORGANISM: Escherichia coli

<400> SEQUENCE: 4

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
            85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255
```

```
                    Val Val Ile Tyr Thr Thr Gly Ser Gln Ala Thr Met Asp Glu Arg Asn
                                260                 265                 270

Arg Gln Ile Ala Glu Ile Gly Ala Ser Leu Ile Lys His Trp
                            275                 280                 285

<210> SEQ ID NO 5
<211> LENGTH: 879
<212> TYPE: DNA
<213> ORGANISM: Escherichia coli
<220> FEATURE:
<221> NAME/KEY: CDS
<222> LOCATION: (1)..(879)
<223> OTHER INFORMATION: araC arabinose sensor protein

<400> SEQUENCE: 5 atg gct gaa gcg caa aat gat ccc ctg ctg ccg gga tac tcg ttt aat         48
Met Ala Glu Ala Gln Asn Asp Pro Leu Leu Pro Gly Tyr Ser Phe Asn
1               5                   10                  15 gcc cat ctg gtg gcg ggt tta acg ccg att gag gcc aac ggt tat ctc         96
Ala His Leu Val Ala Gly Leu Thr Pro Ile Glu Ala Asn Gly Tyr Leu
                20                  25                  30 gat ttt ttt atc gac cga ccg ctg gga atg aaa ggt tat att ctc aat        144
Asp Phe Phe Ile Asp Arg Pro Leu Gly Met Lys Gly Tyr Ile Leu Asn
            35                  40                  45 ctc acc att cgc ggt cag ggg gtg gtg aaa aat cag gga cga gaa ttt        192
Leu Thr Ile Arg Gly Gln Gly Val Val Lys Asn Gln Gly Arg Glu Phe
        50                  55                  60 gtt tgc cga ccg ggt gat att ttg ctg ttc ccg cca gga gag att cat        240
Val Cys Arg Pro Gly Asp Ile Leu Leu Phe Pro Pro Gly Glu Ile His
65                  70                  75                  80 cac tac ggt cgt cat ccg gag gct cgc gaa tgg tat cac cag tgg gtt        288
His Tyr Gly Arg His Pro Glu Ala Arg Glu Trp Tyr His Gln Trp Val
                85                  90                  95 tac ttt cgt ccg cgc gcc tac tgg cat gaa tgg ctt aac tgg ccg tca        336
Tyr Phe Arg Pro Arg Ala Tyr Trp His Glu Trp Leu Asn Trp Pro Ser
                100                 105                 110 ata ttt gcc aat acg ggg ttc ttt cgc ccg gat gaa gcg cac cag ccg        384
Ile Phe Ala Asn Thr Gly Phe Phe Arg Pro Asp Glu Ala His Gln Pro
            115                 120                 125 cat ttc agc gac ctg ttt ggg caa atc att aac gcc ggg caa ggg gaa        432
His Phe Ser Asp Leu Phe Gly Gln Ile Ile Asn Ala Gly Gln Gly Glu
        130                 135                 140 ggg cgc tat tcg gag ctg ctg gcg ata aat ctg ctt gag caa ttg tta        480
Gly Arg Tyr Ser Glu Leu Leu Ala Ile Asn Leu Leu Glu Gln Leu Leu
145                 150                 155                 160 ctg cgg cgc atg gaa gcg att aac gag tcg ctc cat cca ccg atg gat        528
Leu Arg Arg Met Glu Ala Ile Asn Glu Ser Leu His Pro Pro Met Asp
                165                 170                 175 aat cgg gta cgc gag gct tgt cag tac atc agc gat cac ctg gca gac        576
Asn Arg Val Arg Glu Ala Cys Gln Tyr Ile Ser Asp His Leu Ala Asp
                180                 185                 190 agc aat ttt gat atc gcc agc gtc gca cag cat gtt tgc ttg tcg ccg        624
Ser Asn Phe Asp Ile Ala Ser Val Ala Gln His Val Cys Leu Ser Pro
            195                 200                 205 tcg cgt ctg tca cat ctt ttc cgc cag cag tta ggg att agc gtc tta        672
Ser Arg Leu Ser His Leu Phe Arg Gln Gln Leu Gly Ile Ser Val Leu
        210                 215                 220 agc tgg cgc gag gac caa cgt atc agc cag gcg aag ctg ctt ttg agc        720
Ser Trp Arg Glu Asp Gln Arg Ile Ser Gln Ala Lys Leu Leu Leu Ser
225                 230                 235                 240 acc acc cgg atg cct atc gcc acc gtc ggt cgc aat gtt ggt ttt gac        768
Thr Thr Arg Met Pro Ile Ala Thr Val Gly Arg Asn Val Gly Phe Asp
```

```
Thr Thr Arg Met Pro Ile Ala Thr Val Gly Arg Asn Val Gly Phe Asp
            245                 250                 255 gat caa ctc tat ttc tcg cgg gta ttt aaa aaa tgc acc ggg gcc agc    816
Asp Gln Leu Tyr Phe Ser Arg Val Phe Lys Lys Cys Thr Gly Ala Ser
        260                 265                 270 ccg agc gag ttc cgt gcc ggt tgt gaa gaa aaa gtg aat gat gta gcc    864
Pro Ser Glu Phe Arg Ala Gly Cys Glu Glu Lys Val Asn Asp Val Ala
    275                 280                 285 gtc aag ttg tca taa                                                 879
Val Lys Leu Ser
    290

<210> SEQ ID NO 6
<211> LENGTH: 292
<212> TYPE: PRT
<213> ORGANISM: Escherichia coli

<400> SEQUENCE: 6
```

Met Ala Glu Ala Gln Asn Asp Pro Leu Leu Pro Gly Tyr Ser Phe Asn
1               5                   10                  15

Ala His Leu Val Ala Gly Leu Thr Pro Ile Glu Ala Asn Gly Tyr Leu
            20                  25                  30

Asp Phe Phe Ile Asp Arg Pro Leu Gly Met Lys Gly Tyr Ile Leu Asn
        35                  40                  45

Leu Thr Ile Arg Gly Gln Gly Val Val Lys Asn Gln Gly Arg Glu Phe
    50                  55                  60

Val Cys Arg Pro Gly Asp Ile Leu Leu Phe Pro Pro Gly Glu Ile His
65                  70                  75                  80

His Tyr Gly Arg His Pro Glu Ala Arg Glu Trp Tyr His Gln Trp Val
                85                  90                  95

Tyr Phe Arg Pro Arg Ala Tyr Trp His Glu Trp Leu Asn Trp Pro Ser
            100                 105                 110

Ile Phe Ala Asn Thr Gly Phe Phe Arg Pro Asp Glu Ala His Gln Pro
        115                 120                 125

His Phe Ser Asp Leu Phe Gly Gln Ile Ile Asn Ala Gly Gln Gly Glu
    130                 135                 140

Gly Arg Tyr Ser Glu Leu Leu Ala Ile Asn Leu Leu Glu Gln Leu Leu
145                 150                 155                 160

Leu Arg Arg Met Glu Ala Ile Asn Glu Ser Leu His Pro Pro Met Asp
                165                 170                 175

Asn Arg Val Arg Glu Ala Cys Gln Tyr Ile Ser Asp His Leu Ala Asp
            180                 185                 190

Ser Asn Phe Asp Ile Ala Ser Val Ala Gln His Val Cys Leu Ser Pro
        195                 200                 205

Ser Arg Leu Ser His Leu Phe Arg Gln Gln Leu Gly Ile Ser Val Leu
    210                 215                 220

Ser Trp Arg Glu Asp Gln Arg Ile Ser Gln Ala Lys Leu Leu Leu Ser
225                 230                 235                 240

Thr Thr Arg Met Pro Ile Ala Thr Val Gly Arg Asn Val Gly Phe Asp
                245                 250                 255

Asp Gln Leu Tyr Phe Ser Arg Val Phe Lys Lys Cys Thr Gly Ala Ser
            260                 265                 270

Pro Ser Glu Phe Arg Ala Gly Cys Glu Glu Lys Val Asn Asp Val Ala
        275                 280                 285

Val Lys Leu Ser
    290

```
<210> SEQ ID NO 7
<211> LENGTH: 5384
<212> TYPE: DNA
<213> ORGANISM: Escherichia coli
<220> FEATURE:
<221> NAME/KEY: promoter
<222> LOCATION: (1241)..(1318)
<223> OTHER INFORMATION: pBAD promoter
<220> FEATURE:
<221> NAME/KEY: CDS
<222> LOCATION: (1330)..(1581)
<223> OTHER INFORMATION: yefM anti-toxin gene
<220> FEATURE:
<221> NAME/KEY: CDS
<222> LOCATION: (1845)..(2099)
<223> OTHER INFORMATION: yoeB toxin protein
<220> FEATURE:
<221> NAME/KEY: CDS
<222> LOCATION: (2652)..(3512)
<223> OTHER INFORMATION: AmpR encoded beta-lactamase

<400> SEQUENCE: 7
```

| | |
|---|---:|
| atcgatgcat aatgtgcctg tcaaatggac gaagcaggga ttctgcaaac cctatgctac | 60 |
| tccgtcaagc cgtcaattgt ctgattcgtt accaattatg acaacttgac ggctacatca | 120 |
| ttcactttt cttcacaacc ggcacggaac tcgctcgggc tggccccggt gcattttta | 180 |
| aatacccgcg agaaatagag ttgatcgtca aaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc cgaatagcgc | 540 |
| ccttcccctt gcccggcgtt aatgatttgc ccaaacaggt cgctgaaatg cggctggtgc | 600 |
| gcttcatccg ggcgaaagaa ccccgtattg gcaaatattg acggccagtt aagccattca | 660 |
| tgccagtagg cgcgcggacg aaagtaaacc cactgtcgat accattcgcg agcctccgga | 720 |
| tgacgaccca agtgcagaat ctctcctggc gggaacagca aaatatcacc cggtcggcaa | 780 |
| acaaattctc gtccctgatt tttcaccacc ccctgaccgc gaatggtgag attgagaata | 840 |
| taacctttca ttcccagcgg tcggtcgata aaaaaatcga gataaccgtt ggcctcaatc | 900 |
| gggagtaaac ccgccaccag atgggcatta acgagtatc ccggcagcag gggatcattt | 960 |
| tgcgcttcag ccatactttt catactcccg ccattcagaa agaaaccaa ttgtccatat | 1020 |
| tgcatcagac attgccgtca ctgcgtcttt tactggctct tctcgctaac caaaccggta | 1080 |
| accccgctta ttaaaagcat tctgtaacaa agcgggacca aagccatgac aaaaacgcgt | 1140 |
| aacaaaagtg tctataatca cggcagaaaa gtccacattg attatttgca cggcgtcaca | 1200 |
| ctttgctatg ccatagcatt tttatccata agattagcgg atcctacctg acgctttta | 1260 |
| tcgcaactct ctactgtttc tccatacccg ttttttggg ctagcgaatt cgagctcgag | 1320 |
| gaggaaggt atg cgt aca att agc tac agc gaa gcg cgt cag aat ttg tcg | 1371 |
|          Met Arg Thr Ile Ser Tyr Ser Glu Ala Arg Gln Asn Leu Ser | |
|            1               5                   10 | |
| gca aca atg atg aaa gcc gtt gaa gat cat gcc ccg atc ctt att act | 1419 |
| Ala Thr Met Met Lys Ala Val Glu Asp His Ala Pro Ile Leu Ile Thr | |
|  15                  20                  25                  30 | |
| cgt cag aat gga gag gct tgt gtt ctg atg tca ctc gaa gaa tac aac | 1467 |
| Arg Gln Asn Gly Glu Ala Cys Val Leu Met Ser Leu Glu Glu Tyr Asn | |

-continued

```
                    35                    40                    45
tcg ctg gaa gag acg gct tat cta ctg cgc tcc ccc gct aac gcc cgg    1515
Ser Leu Glu Glu Thr Ala Tyr Leu Leu Arg Ser Pro Ala Asn Ala Arg
         50                   55                    60 aga ttg atg gac tca atc gat agc ctg aaa tca ggc aaa gga acg gaa    1563
Arg Leu Met Asp Ser Ile Asp Ser Leu Lys Ser Gly Lys Gly Thr Glu
         65                   70                    75 aag gac atc att gag tga ggcaatcagc tgttcccgt ctcactggtg            1611
Lys Asp Ile Ile Glu
         80 aaaagaaaaa ccaccctggc gcccaatacg caaaccgcct ctccccgcgc gttggccgat   1671 tcattaatgc agctggcacg acaggtttcc cgactggaaa gcgggcagtg agcgcaacgc   1731 aattaatgtg agttagctca ctcattaggc accccaggct ttacacttta tgcttccggc   1791 tcgtatgttg tgtggaattg tgagcggata caatttcac acaggaagaa acc atg      1847
                                                          Met aaa cta atc tgg tct gag gaa tca tgg gac gat tat ctg tac tgg cag    1895
Lys Leu Ile Trp Ser Glu Glu Ser Trp Asp Asp Tyr Leu Tyr Trp Gln
85                   90                    95                  100 gaa aca gat aag cga att gtt aaa aag atc aat gaa ctt atc aaa gat    1943
Glu Thr Asp Lys Arg Ile Val Lys Lys Ile Asn Glu Leu Ile Lys Asp
                105                  110                   115 acc cgc aga acg cca ttt gaa ggt aag ggg aag cca gaa ccc ctg aaa    1991
Thr Arg Arg Thr Pro Phe Glu Gly Lys Gly Lys Pro Glu Pro Leu Lys
        120                   125                   130 cat aat ttg tca ggt ttc tgg tcc cga cgc att aca gag gag cac cgt    2039
His Asn Leu Ser Gly Phe Trp Ser Arg Arg Ile Thr Glu Glu His Arg
        135                   140                   145 ctg gta tac gcg gtt acc gac gat tca ctg ctc att gca gca tgt cgt    2087
Leu Val Tyr Ala Val Thr Asp Asp Ser Leu Leu Ile Ala Ala Cys Arg
        150                   155                   160 tat cat tat tga atcctctaga gtcgacctgc aggcatgcaa gcttggctgt        2139
Tyr His Tyr
165 tttggcggat gagagaagat tttcagcctg atacagatta aatcagaacg cagaagcggt   2199 ctgataaaac agaatttgcc tggcggcagt agcgcggtgg tcccacctga ccccatgccg   2259 aactcagaag tgaaacgccg tagcgccgat ggtagtgtgg ggtctcccca tgcgagagta   2319 gggaactgcc aggcatcaaa taaaacgaaa ggctcagtcg aaagactggg cctttcgttt   2379 tatctgttgt ttgtcggtga acgctctcct gagtaggaca atccgccgg gagcggattt    2439 gaacgttgcg aagcaacggc ccggagggtg cgggcagga cgcccgccat aaactgccag    2499 gcatcaaatt aagcagaagg ccatcctgac ggatggcctt tttgcgtttc tacaaactct   2559 tttgtttatt tttctaaata cattcaaata tgtatccgct catgagacaa taaccctgat   2619 aaatgcttca ataatattga aaaggaaga gt atg agt att caa cat ttc cgt     2672
                                   Met Ser Ile Gln His Phe Arg
                                                       170 gtc gcc ctt att ccc ttt ttt gcg gca ttt tgc ctt cct gtt ttt gct    2720
Val Ala Leu Ile Pro Phe Phe Ala Ala Phe Cys Leu Pro Val Phe Ala
175                  180                   185                  190 cac cca gaa acg ctg gtg aaa gta aaa gat gct gaa gat cag ttg ggt    2768
His Pro Glu Thr Leu Val Lys Val Lys Asp Ala Glu Asp Gln Leu Gly
        195                   200                   205 gca cga gtg ggt tac atc gaa ctg gat ctc aac agc ggt aag atc ctt    2816
Ala Arg Val Gly Tyr Ile Glu Leu Asp Leu Asn Ser Gly Lys Ile Leu
        210                   215                   220
```

-continued

| | | |
|---|---|---|
| gag agt ttt cgc ccc gaa gaa cgt ttt cca atg atg agc act ttt aaa<br>Glu Ser Phe Arg Pro Glu Glu Arg Phe Pro Met Met Ser Thr Phe Lys<br>     225                    230                   235 | 2864 | |
| gtt ctg cta tgt ggc gcg gta tta tcc cgt gtt gac gcc ggg caa gag<br>Val Leu Leu Cys Gly Ala Val Leu Ser Arg Val Asp Ala Gly Gln Glu<br>240                       245                   250 | 2912 | |
| caa ctc ggt cgc cgc ata cac tat tct cag aat gac ttg gtt gag tac<br>Gln Leu Gly Arg Arg Ile His Tyr Ser Gln Asn Asp Leu Val Glu Tyr<br>255                       260                   265                 270 | 2960 | |
| tca cca gtc aca gaa aag cat ctt acg gat ggc atg aca gta aga gaa<br>Ser Pro Val Thr Glu Lys His Leu Thr Asp Gly Met Thr Val Arg Glu<br>                 275                   280                   285 | 3008 | |
| tta tgc agt gct gcc ata acc atg agt gat aac act gcg gcc aac tta<br>Leu Cys Ser Ala Ala Ile Thr Met Ser Asp Asn Thr Ala Ala Asn Leu<br>290                       295                   300 | 3056 | |
| ctt ctg aca acg atc gga gga ccg aag gag cta acc gct ttt ttg cac<br>Leu Leu Thr Thr Ile Gly Gly Pro Lys Glu Leu Thr Ala Phe Leu His<br>                 305                   310                   315 | 3104 | |
| aac atg ggg gat cat gta act cgc ctt gat cgt tgg gaa ccg gag ctg<br>Asn Met Gly Asp His Val Thr Arg Leu Asp Arg Trp Glu Pro Glu Leu<br>320                       325                   330 | 3152 | |
| aat gaa gcc ata cca aac gac gag cgt gac acc acg atg cct gca gca<br>Asn Glu Ala Ile Pro Asn Asp Glu Arg Asp Thr Thr Met Pro Ala Ala<br>335                       340                   345                 350 | 3200 | |
| atg gca aca acg ttg cgc aaa cta tta act ggc gaa cta ctt act cta<br>Met Ala Thr Thr Leu Arg Lys Leu Leu Thr Gly Glu Leu Leu Thr Leu<br>                 355                   360                   365 | 3248 | |
| gct tcc cgg caa caa tta ata gac tgg atg gag gcg gat aaa gtt gca<br>Ala Ser Arg Gln Gln Leu Ile Asp Trp Met Glu Ala Asp Lys Val Ala<br>370                       375                   380 | 3296 | |
| gga cca ctt ctg cgc tcg gcc ctt ccg gct ggc tgg ttt att gct gat<br>Gly Pro Leu Leu Arg Ser Ala Leu Pro Ala Gly Trp Phe Ile Ala Asp<br>                 385                   390                   395 | 3344 | |
| aaa tct gga gcc ggt gag cgt ggg tct cgc ggt atc att gca gca ctg<br>Lys Ser Gly Ala Gly Glu Arg Gly Ser Arg Gly Ile Ile Ala Ala Leu<br>400                       405                   410 | 3392 | |
| ggg cca gat ggt aag ccc tcc cgt atc gta gtt atc tac acg acg ggg<br>Gly Pro Asp Gly Lys Pro Ser Arg Ile Val Val Ile Tyr Thr Thr Gly<br>415                       420                   425                 430 | 3440 | |
| agt cag gca act atg gat gaa cga aat aga cag atc gct gag ata ggt<br>Ser Gln Ala Thr Met Asp Glu Arg Asn Arg Gln Ile Ala Glu Ile Gly<br>                 435                   440                   445 | 3488 | |
| gcc tca ctg att aag cat tgg taa ctgtcagacc aagtttactc atatatactt<br>Ala Ser Leu Ile Lys His Trp<br>                 450 | 3542 | |
| tagattgatt tacgcgccct gtagcggcgc attaagcgcg gcgggtgtgg tggttacgcg | 3602 | |
| cagcgtgacc gctacacttg ccagcgccct agcgcccgct cctttcgctt tcttcccttc | 3662 | |
| ctttctcgcc acgttcgccg gctttccccg tcaagctcta atcgggggc tccctttagg | 3722 | |
| gttccgattt agtgctttac ggcacctcga ccccaaaaaa cttgatttgg gtgatggttc | 3782 | |
| acgtagtggg ccatcgccct gatagacggt ttttcgccct tgacgttgg agtccacgtt | 3842 | |
| ctttaatagt ggactcttgt tccaaacttg aacaacactc aaccctatct cgggctattc | 3902 | |
| ttttgattta aagggatttt gccgatttc ggcctattgg ttaaaaatg agctgattta | 3962 | |
| acaaaaattt aacgcgaatt ttaacaaaat attaacgttt acaatttaaa aggatctagg | 4022 | |
| tgaagatcct ttttgataat ctcatgacca aaatccctta acgtgagttt tcgttccact | 4082 | |
| gagcgtcaga ccccgtagaa aagatcaaag gatcttcttg agatcctttt tttctgcgcg | 4142 | |

```
taatctgctg cttgcaaaca aaaaaaccac cgctaccagc ggtggtttgt ttgccggatc   4202
aagagctacc aactcttttt ccgaaggtaa ctggcttcag cagagcgcag ataccaaata   4262
ctgtccttct agtgtagccg tagttaggcc accacttcaa gaactctgta gcaccgccta   4322
catacctcgc tctgctaatc ctgttaccag tggctgctgc cagtggcgat aagtcgtgtc   4382
ttaccgggtt ggactcaaga cgatagttac cggataaggc gcagcggtcg ggctgaacgg   4442
ggggttcgtg cacacagccc agcttggagc gaacgaccta caccgaactg agatacctac   4502
agcgtgagct atgagaaagc gccacgcttc ccgaagggag aaaggcggac aggtatccgg   4562
taagcggcag ggtcggaaca ggagagcgca cgagggagct tccaggggga aacgcctggt   4622
atctttatag tcctgtcggg tttcgccacc tctgacttga gcgtcgattt tgtgatgct    4682 cgtcagggggg gcggagccta tggaaaaacg ccagcaacgc ggccttttta cggttcctgg   4742
ccttttgctg gccttttgct cacatgttct ttcctgcgtt atccctgat tctgtggata    4802 accgtattac cgcctttgag tgagctgata ccgctcgccg cagccgaacg accgagcgca   4862
gcgagtcagt gagcgaggaa gcggaagagc gcctgatgcg gtattttctc cttacgcatc   4922
tgtgcggtat ttcacaccgc atatggtgca ctctcagtac aatctgctct gatgccgcat   4982
agttaagcca gtatacactc cgctatcgct acgtgactgg gtcatggctg cgccccgaca   5042
cccgccaaca cccgctgacg cgccctgacg ggcttgtctg ctcccggcat ccgcttacag   5102
acaagctgtg accgtctccg ggagctgcat gtgtcagagg ttttcaccgt catcaccgaa   5162
acgcgcgagg cagcaaggag atggcgccca acagtccccc ggccacgggg cctgccacca   5222
tacccacgcc gaaacaagcg ctcatgagcc cgaagtggcg agcccgatct tccccatcgg   5282
tgatgtcggc gatataggcg ccagcaaccg cacctgtggc gccggtgatg ccggccacga   5342
tgcgtccggc gtagaggatc tgctcatgtt tgacagctta tc                     5384

<210> SEQ ID NO 8
<211> LENGTH: 83
<212> TYPE: PRT
<213> ORGANISM: Escherichia coli

<400> SEQUENCE: 8

Met Arg Thr Ile Ser Tyr Ser Glu Ala Arg Gln Asn Leu Ser Ala Thr
1               5                   10                  15

Met Met Lys Ala Val Glu Asp His Ala Pro Ile Leu Ile Thr Arg Gln
                20                  25                  30

Asn Gly Glu Ala Cys Val Leu Met Ser Leu Glu Glu Tyr Asn Ser Leu
            35                  40                  45

Glu Glu Thr Ala Tyr Leu Leu Arg Ser Pro Ala Asn Ala Arg Arg Leu
        50                  55                  60

Met Asp Ser Ile Asp Ser Leu Lys Ser Gly Lys Gly Thr Glu Lys Asp
65                  70                  75                  80

Ile Ile Glu

<210> SEQ ID NO 9
<211> LENGTH: 84
<212> TYPE: PRT
<213> ORGANISM: Escherichia coli

<400> SEQUENCE: 9

Met Lys Leu Ile Trp Ser Glu Glu Ser Trp Asp Asp Tyr Leu Tyr Trp
1               5                   10                  15
```

```
Gln Glu Thr Asp Lys Arg Ile Val Lys Lys Ile Asn Glu Leu Ile Lys
            20                  25                  30

Asp Thr Arg Arg Thr Pro Phe Glu Gly Lys Gly Lys Pro Glu Pro Leu
        35                  40                  45

Lys His Asn Leu Ser Gly Phe Trp Ser Arg Ile Thr Glu Glu His
    50                  55                  60

Arg Leu Val Tyr Ala Val Thr Asp Asp Ser Leu Leu Ile Ala Ala Cys
65                  70                  75                  80

Arg Tyr His Tyr

<210> SEQ ID NO 10
<211> LENGTH: 286
<212> TYPE: PRT
<213> ORGANISM: Escherichia coli

<400> SEQUENCE: 10

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
            85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 11
<211> LENGTH: 879
```

<212> TYPE: DNA
<213> ORGANISM: Escherichia coli
<220> FEATURE:
<221> NAME/KEY: CDS
<222> LOCATION: (1)..(879)
<223> OTHER INFORMATION: araCmev mevalonate sensor protein

<400> SEQUENCE: 11

```
atg gct gaa gcg caa aat gat ccc ctg ctg ccg gga tac tcg ttt aat        48
Met Ala Glu Ala Gln Asn Asp Pro Leu Leu Pro Gly Tyr Ser Phe Asn
1               5                   10                  15 gcc cat ctg gtg gcg ggt tta ctc ccg att gag gcc aac ggt tat ctc        96
Ala His Leu Val Ala Gly Leu Leu Pro Ile Glu Ala Asn Gly Tyr Leu
                20                  25                  30 gat ttt ttt atc gac cga ccg ctg gga atg aaa ggt tat att ctc aat       144
Asp Phe Phe Ile Asp Arg Pro Leu Gly Met Lys Gly Tyr Ile Leu Asn
            35                  40                  45 ctc acc att cgc ggt cag ggg gtg gtg aaa aat cag gga cga gaa ttt       192
Leu Thr Ile Arg Gly Gln Gly Val Val Lys Asn Gln Gly Arg Glu Phe
        50                  55                  60 gtt tgc cga ccg ggt gat att ttg ctg ttc ccg cca gga gag att ctg       240
Val Cys Arg Pro Gly Asp Ile Leu Leu Phe Pro Pro Gly Glu Ile Leu
65                  70                  75                  80 cac ttg ggt cgt cat ccg gag gct cgc gaa tgg tat cga cag tgg gtt       288
His Leu Gly Arg His Pro Glu Ala Arg Glu Trp Tyr Arg Gln Trp Val
                85                  90                  95 tac ttt cgt ccg cgc gcc tac tgg cat gaa tgg ctt aac tgg ccg tca       336
Tyr Phe Arg Pro Arg Ala Tyr Trp His Glu Trp Leu Asn Trp Pro Ser
                100                 105                 110 ata ttt gcc aat acg ggg ttc ttt cgc ccg gat gaa gcg cac cag ccg       384
Ile Phe Ala Asn Thr Gly Phe Phe Arg Pro Asp Glu Ala His Gln Pro
            115                 120                 125 cat ttc agc gac ctg ttt ggg caa atc att aac gcc ggg caa ggg gaa       432
His Phe Ser Asp Leu Phe Gly Gln Ile Ile Asn Ala Gly Gln Gly Glu
        130                 135                 140 ggg cgc tat tcg gag ctg ctg gcg ata aat ctg ctt gag caa ttg tta       480
Gly Arg Tyr Ser Glu Leu Leu Ala Ile Asn Leu Leu Glu Gln Leu Leu
145                 150                 155                 160 ctg cgg cgc atg gaa gcg att aac gag tcg ctc cat cca ccg atg gat       528
Leu Arg Arg Met Glu Ala Ile Asn Glu Ser Leu His Pro Pro Met Asp
                165                 170                 175 aat cgg gta cgc gag gct tgt cag tac atc agc gat cac ctg gca gac       576
Asn Arg Val Arg Glu Ala Cys Gln Tyr Ile Ser Asp His Leu Ala Asp
            180                 185                 190 agc aat ttt gat atc gcc agc gtc gca cag cat gtt tgc ttg tcg ccg       624
Ser Asn Phe Asp Ile Ala Ser Val Ala Gln His Val Cys Leu Ser Pro
        195                 200                 205 tcg cgt ctg tca cat ctt ttc cgc cag cag tta ggg att agc gtc tta       672
Ser Arg Leu Ser His Leu Phe Arg Gln Gln Leu Gly Ile Ser Val Leu
    210                 215                 220 agc tgg cgc gag gac caa cgt atc agc cag gcg aag ctg ctt ttg agc       720
Ser Trp Arg Glu Asp Gln Arg Ile Ser Gln Ala Lys Leu Leu Leu Ser
225                 230                 235                 240 acc acc cgg atg cct atc gcc acc gtc ggt cgc aat gtt ggt ttt gac       768
Thr Thr Arg Met Pro Ile Ala Thr Val Gly Arg Asn Val Gly Phe Asp
                245                 250                 255 gat caa ctc tat ttc tcg cgg gta ttt aaa aaa tgc acc ggg gcc agc       816
Asp Gln Leu Tyr Phe Ser Arg Val Phe Lys Lys Cys Thr Gly Ala Ser
            260                 265                 270 ccg agc gag ttc cgt gcc ggt tgt gaa gaa aaa gtg aat gat gta gcc       864
Pro Ser Glu Phe Arg Ala Gly Cys Glu Glu Lys Val Asn Asp Val Ala
```

```
            275                 280                 285 gtc aag ttg tca taa                                                       879
Val Lys Leu Ser
    290

<210> SEQ ID NO 12
<211> LENGTH: 292
<212> TYPE: PRT
<213> ORGANISM: Escherichia coli

<400> SEQUENCE: 12

Met Ala Glu Ala Gln Asn Asp Pro Leu Leu Pro Gly Tyr Ser Phe Asn
1               5                   10                  15

Ala His Leu Val Ala Gly Leu Leu Pro Ile Glu Ala Asn Gly Tyr Leu
            20                  25                  30

Asp Phe Phe Ile Asp Arg Pro Leu Gly Met Lys Gly Tyr Ile Leu Asn
        35                  40                  45

Leu Thr Ile Arg Gly Gln Gly Val Val Lys Asn Gln Gly Arg Glu Phe
    50                  55                  60

Val Cys Arg Pro Gly Asp Ile Leu Leu Phe Pro Pro Gly Glu Ile Leu
65                  70                  75                  80

His Leu Gly Arg His Pro Glu Ala Arg Glu Trp Tyr Arg Gln Trp Val
                85                  90                  95

Tyr Phe Arg Pro Arg Ala Tyr Trp His Glu Trp Leu Asn Trp Pro Ser
            100                 105                 110

Ile Phe Ala Asn Thr Gly Phe Phe Arg Pro Asp Glu Ala His Gln Pro
        115                 120                 125

His Phe Ser Asp Leu Phe Gly Gln Ile Ile Asn Ala Gly Gln Gly Glu
    130                 135                 140

Gly Arg Tyr Ser Glu Leu Leu Ala Ile Asn Leu Leu Glu Gln Leu Leu
145                 150                 155                 160

Leu Arg Arg Met Glu Ala Ile Asn Glu Ser Leu His Pro Pro Met Asp
                165                 170                 175

Asn Arg Val Arg Glu Ala Cys Gln Tyr Ile Ser Asp His Leu Ala Asp
            180                 185                 190

Ser Asn Phe Asp Ile Ala Ser Val Ala Gln His Val Cys Leu Ser Pro
        195                 200                 205

Ser Arg Leu Ser His Leu Phe Arg Gln Gln Leu Gly Ile Ser Val Leu
    210                 215                 220

Ser Trp Arg Glu Asp Gln Arg Ile Ser Gln Ala Lys Leu Leu Leu Ser
225                 230                 235                 240

Thr Thr Arg Met Pro Ile Ala Thr Val Gly Arg Asn Val Gly Phe Asp
                245                 250                 255

Asp Gln Leu Tyr Phe Ser Arg Val Phe Lys Lys Cys Thr Gly Ala Ser
            260                 265                 270

Pro Ser Glu Phe Arg Ala Gly Cys Glu Glu Lys Val Asn Asp Val Ala
        275                 280                 285

Val Lys Leu Ser
    290

<210> SEQ ID NO 13
<211> LENGTH: 1772
<212> TYPE: DNA
<213> ORGANISM: Escherichia coli
<220> FEATURE:
<221> NAME/KEY: CDS
<222> LOCATION: (649)..(1443)
```

<223> OTHER INFORMATION: Neomycin phosphotransferase II protein

<400> SEQUENCE: 13

```
cgttatctcc tgatacacct tagatctata aggctacgct agcgtatcaa aactgacaat      60
tcattctatg aatgaatctg ttcaataatg ataacgacat gctgcaatga gcagtgaatc     120
gtcggtaacc gcgtatacca gacggtgctc ctctgtaatg cgtcgggacc agaaacctga     180
caaattatgt ttcaggggtt ctggcttcca catatgaata ttccggggat ccgtcgacct     240
gcagttcgaa gttcctattc tctagaaagt ataggaactt cagagcgctt ttgaagctca     300
cgctgccgca agcactcagg gcgcaagggc tgctaaagga gcggaacac gtagaaagcc      360 agtccgcaga aacggtgctg accccggatg aatgtcagct actgggctat ctggacaagg     420
gaaaacgcaa gcgcaaagag aaagcaggta gcttgcagtg gcttacatg gcgatagcta      480 gactgggcgg ttttatggac agcaagcgaa ccggaattgc cagctggggc gccctctggt     540
aaggttggga agccctgcaa agtaaactgg atggctttct tgccgccaag gatctgatgg     600
cgcaggggat caagatctga tcaagagaca ggatgaggat cgtttcgc atg att gaa      657
                                                        Met Ile Glu
                                                         1
```

| | | | | | | | | | | | | | | | | |
|---|---|---|---|---|---|---|---|---|---|---|---|---|---|---|---|---|
caa gat gga ttg cac gca ggt tct ccg gcc gct tgg gtg gag agg cta      705
Gln Asp Gly Leu His Ala Gly Ser Pro Ala Ala Trp Val Glu Arg Leu
 5                  10                  15 ttc ggc tat gac tgg gca caa cag aca atc ggc tgc tct gat gcc gcc      753
Phe Gly Tyr Asp Trp Ala Gln Gln Thr Ile Gly Cys Ser Asp Ala Ala
20                  25                  30                  35 gtg ttc cgg ctg tca gcg cag ggg cgc ccg gtt ctt ttt gtc aag acc      801
Val Phe Arg Leu Ser Ala Gln Gly Arg Pro Val Leu Phe Val Lys Thr
            40                  45                  50 gac ctg tcc ggt gcc ctg aat gaa ctg cag gac gag gca gcg cgg cta      849
Asp Leu Ser Gly Ala Leu Asn Glu Leu Gln Asp Glu Ala Ala Arg Leu
        55                  60                  65 tcg tgg ctg gcc acg acg ggc gtt cct tgc gca gct gtg ctc gac gtt      897
Ser Trp Leu Ala Thr Thr Gly Val Pro Cys Ala Ala Val Leu Asp Val
    70                  75                  80 gtc act gaa gcg gga agg gac tgg ctg cta ttg ggc gaa gtg ccg ggg      945
Val Thr Glu Ala Gly Arg Asp Trp Leu Leu Leu Gly Glu Val Pro Gly
85                  90                  95 cag gat ctc ctg tca tct cac ctt gct cct gcc gag aaa gta tcc atc      993
Gln Asp Leu Leu Ser Ser His Leu Ala Pro Ala Glu Lys Val Ser Ile
100                 105                 110                 115 atg gct gat gca atg cgg cgg ctg cat acg ctt gat ccg gct acc tgc     1041
Met Ala Asp Ala Met Arg Arg Leu His Thr Leu Asp Pro Ala Thr Cys
            120                 125                 130 cca ttc gac cac caa gcg aaa cat cgc atc gag cga gca cgt act cgg     1089
Pro Phe Asp His Gln Ala Lys His Arg Ile Glu Arg Ala Arg Thr Arg
        135                 140                 145 atg gaa gcc ggt ctt gtc gat cag gat gat ctg gac gaa gag cat cag     1137
Met Glu Ala Gly Leu Val Asp Gln Asp Asp Leu Asp Glu Glu His Gln
    150                 155                 160 ggg ctc gcg cca gcc gaa ctg ttc gcc agg ctc aag gcg cgc atg ccc     1185
Gly Leu Ala Pro Ala Glu Leu Phe Ala Arg Leu Lys Ala Arg Met Pro
165                 170                 175 gac ggc gag gat ctc gtc gtg acc cat ggc gat gcc tgc ttg ccg aat     1233
Asp Gly Glu Asp Leu Val Val Thr His Gly Asp Ala Cys Leu Pro Asn
180                 185                 190                 195 atc atg gtg gaa aat ggc cgc ttt tct gga ttc atc gac tgt ggc cgg     1281
Ile Met Val Glu Asn Gly Arg Phe Ser Gly Phe Ile Asp Cys Gly Arg
                200                 205                 210

```
ctg ggt gtg gcg gac cgc tat cag gac ata gcg ttg gct acc cgt gat    1329
Leu Gly Val Ala Asp Arg Tyr Gln Asp Ile Ala Leu Ala Thr Arg Asp
        215                 220                 225 att gct gaa gag ctt ggc ggc gaa tgg gct gac cgc ttc ctc gtg ctt    1377
Ile Ala Glu Glu Leu Gly Gly Glu Trp Ala Asp Arg Phe Leu Val Leu
            230                 235                 240 tac ggt atc gcc gct ccc gat tcg cag cgc atc gcc ttc tat cgc ctt    1425
Tyr Gly Ile Ala Ala Pro Asp Ser Gln Arg Ile Ala Phe Tyr Arg Leu
        245                 250                 255 ctt gac gag ttc ttc taa taagggatc ttgaagttcc tattccgaag            1473
Leu Asp Glu Phe Phe
260 ttcctattct ctagaaagta taggaacttc gaagcagctc cagcctacac aatcgctgtc    1533 aatctcctct tttgtacagt tcattgtaca atgatgagcg ttaattaact atttattaat    1593 tagtttgtag atcaaggtat tgtcagtgag acgaaaatcc aggcttcgct attttggtg     1653 ccatcagcta agaggacagt cctcttagcc ccctcctttc cccgctcatt cattaaacaa    1713 atccattgcc ataaaatata taaaaagcc cttgctttct aacgtgaaag tggtttagg     1772

<210> SEQ ID NO 14
<211> LENGTH: 264
<212> TYPE: PRT
<213> ORGANISM: Escherichia coli

<400> SEQUENCE: 14

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240
```

-continued

```
Leu Val Leu Tyr Gly Ile Ala Ala Pro Asp Ser Gln Arg Ile Ala Phe
            245                 250                 255

Tyr Arg Leu Leu Asp Glu Phe Phe
            260

<210> SEQ ID NO 15
<211> LENGTH: 6707
<212> TYPE: DNA
<213> ORGANISM: Escherichia coli
<220> FEATURE:
<221> NAME/KEY: promoter
<222> LOCATION: (149)..(181)
<223> OTHER INFORMATION: J23100 promoter
<220> FEATURE:
<221> NAME/KEY: CDS
<222> LOCATION: (255)..(1439)
<223> OTHER INFORMATION: E. coli atoB gene encoding acetyl-CoA
      acetyltransferase
<220> FEATURE:
<221> NAME/KEY: CDS
<222> LOCATION: (1461)..(2627)
<223> OTHER INFORMATION: L. casei mvaS gene encoding HMG-CoA synthase
<220> FEATURE:
<221> NAME/KEY: CDS
<222> LOCATION: (2648)..(3928)
<223> OTHER INFORMATION: L. casei mvaE gene encoding HMG-CoA reductase
<220> FEATURE:
<221> NAME/KEY: rep_origin
<222> LOCATION: (5766)..(6605)
<223> OTHER INFORMATION: p15A origin of replication

<400> SEQUENCE: 15
acgatgcgtc cggcgtagag gatctgctca tgtttgacag cttatcatcg atgcatgcgc      60
ccaatacgca aaccgcctct ccccgcgcgt tggccgattc attaatgcag ctggcacgac     120
aggtttcccg actggaaagc gactcattga cggctagctc agtcctaggt acagtgctag     180
cattacgcca agcgcgcaat taaccctcac taaagggaac aaaagctgaa ttcattaaag     240
aggagaaagg tacc atg aaa aat tgt gtc atc gtc agt gcg gta cgt act        290
                 Met Lys Asn Cys Val Ile Val Ser Ala Val Arg Thr
                 1               5                   10 gct atc ggt agt ttt aac ggt tca ctc gct tcc acc agc gcc atc gac        338
Ala Ile Gly Ser Phe Asn Gly Ser Leu Ala Ser Thr Ser Ala Ile Asp
        15                  20                  25 ctg ggg gcg aca gta att aaa gcc gcc att gaa cgt gca aaa atc gat        386
Leu Gly Ala Thr Val Ile Lys Ala Ala Ile Glu Arg Ala Lys Ile Asp
    30                  35                  40 tca caa cac gtt gat gaa gtg att atg ggt aac gtg tta caa gcc ggg        434
Ser Gln His Val Asp Glu Val Ile Met Gly Asn Val Leu Gln Ala Gly
45                  50                  55                  60 ctg ggg caa aat ccg gcg cgt cag gca ctg tta aaa agc ggg ctg gca        482
Leu Gly Gln Asn Pro Ala Arg Gln Ala Leu Leu Lys Ser Gly Leu Ala
                65                  70                  75 gaa acg gtg tgc gga ttc acg gtc aat aaa gta tgt ggt tcg ggt ctt        530
Glu Thr Val Cys Gly Phe Thr Val Asn Lys Val Cys Gly Ser Gly Leu
            80                  85                  90 aaa agt gtg gcg ctt gcc gcc cag gcc att cag gca ggt cag gcg cag        578
Lys Ser Val Ala Leu Ala Ala Gln Ala Ile Gln Ala Gly Gln Ala Gln
        95                  100                 105 agc att gtg gcg ggg ggt atg gaa aat atg agt tta gcc ccc tac tta        626
Ser Ile Val Ala Gly Gly Met Glu Asn Met Ser Leu Ala Pro Tyr Leu
    110                 115                 120 ctc gat gca aaa gca cgc tct ggt tat cgt ctt gga gac gga cag gtt        674
Leu Asp Ala Lys Ala Arg Ser Gly Tyr Arg Leu Gly Asp Gly Gln Val
125                 130                 135                 140
```

```
tat gac gta atc ctg cgc gat ggc ctg atg tgc gcc acc cat ggt tat    722
Tyr Asp Val Ile Leu Arg Asp Gly Leu Met Cys Ala Thr His Gly Tyr
            145                 150                 155 cat atg ggg att acc gcc gaa aac gtg gct aaa gag tac gga att acc    770
His Met Gly Ile Thr Ala Glu Asn Val Ala Lys Glu Tyr Gly Ile Thr
        160                 165                 170 cgt gaa atg cag gat gaa ctg gcg cta cat tca cag cgt aaa gcg gca    818
Arg Glu Met Gln Asp Glu Leu Ala Leu His Ser Gln Arg Lys Ala Ala
    175                 180                 185 gcc gca att gag tcc ggt gct ttt aca gcc gaa atc gtc ccg gta aat    866
Ala Ala Ile Glu Ser Gly Ala Phe Thr Ala Glu Ile Val Pro Val Asn
190                 195                 200 gtt gtc act cga aag aaa acc ttc gtc ttc agt caa gac gaa ttc ccg    914
Val Val Thr Arg Lys Lys Thr Phe Val Phe Ser Gln Asp Glu Phe Pro
205                 210                 215                 220 aaa gcg aat tca acg gct gaa gcg tta ggt gca ttg cgc ccg gcc ttc    962
Lys Ala Asn Ser Thr Ala Glu Ala Leu Gly Ala Leu Arg Pro Ala Phe
                225                 230                 235 gat aaa gca gga aca gtc acc gct ggg aac gcg tct ggt att aac gac   1010
Asp Lys Ala Gly Thr Val Thr Ala Gly Asn Ala Ser Gly Ile Asn Asp
        240                 245                 250 ggt gct gcc gct ctg gtg att atg gaa gaa tct gcg gcg ctg gca gca   1058
Gly Ala Ala Ala Leu Val Ile Met Glu Glu Ser Ala Ala Leu Ala Ala
    255                 260                 265 ggc ctt acc ccc ctg gct cgc att aaa agt tat gcc agc ggt ggc gtg   1106
Gly Leu Thr Pro Leu Ala Arg Ile Lys Ser Tyr Ala Ser Gly Gly Val
270                 275                 280 ccc ccc gca ttg atg ggt atg ggg cca gta cct gcc acg caa aaa gcg   1154
Pro Pro Ala Leu Met Gly Met Gly Pro Val Pro Ala Thr Gln Lys Ala
285                 290                 295                 300 tta caa ctg gcg ggg ctg caa ctg gcg gat att gat ctc att gag gct   1202
Leu Gln Leu Ala Gly Leu Gln Leu Ala Asp Ile Asp Leu Ile Glu Ala
                305                 310                 315 aat gaa gca ttt gct gca cag ttc ctt gcc gtt ggg aaa aac ctg ggc   1250
Asn Glu Ala Phe Ala Ala Gln Phe Leu Ala Val Gly Lys Asn Leu Gly
        320                 325                 330 ttt gat tct gag aaa gtg aat gtc aac ggc ggg gcc atc gcg ctc ggg   1298
Phe Asp Ser Glu Lys Val Asn Val Asn Gly Gly Ala Ile Ala Leu Gly
    335                 340                 345 cat cct atc ggt gcc agt ggt gct cgt att ctg gtc aca cta tta cat   1346
His Pro Ile Gly Ala Ser Gly Ala Arg Ile Leu Val Thr Leu Leu His
350                 355                 360 gcc atg cag gca cgc gat aaa acg ctg ggg ctg gca aca ctg tgc att   1394
Ala Met Gln Ala Arg Asp Lys Thr Leu Gly Leu Ala Thr Leu Cys Ile
365                 370                 375                 380 ggc ggt ggt cag gga att gcg atg gtg att gaa cgg ttg aat taa        1439
Gly Gly Gly Gln Gly Ile Ala Met Val Ile Glu Arg Leu Asn
                385                 390 gctgcagagg agaaattaac t atg aaa atc ggg att gat gca atc gct atg   1490
                         Met Lys Ile Gly Ile Asp Ala Ile Ala Met
                         395                 400 gac acc cca gat ttc tac gtt gat tta gta aaa ctc gcg cag gtt cga   1538
Asp Thr Pro Asp Phe Tyr Val Asp Leu Val Lys Leu Ala Gln Val Arg
405                 410                 415                 420 ggt gat gat ccg gac aaa tat acg att ggc att ggc caa gac gag caa   1586
Gly Asp Asp Pro Asp Lys Tyr Thr Ile Gly Ile Gly Gln Asp Glu Gln
                425                 430                 435 gcg gta cca cct tct agc caa gac att gtc acg atg ggt gcg aat gca   1634
Ala Val Pro Pro Ser Ser Gln Asp Ile Val Thr Met Gly Ala Asn Ala
```

-continued

```
                440                 445                 450
gcg aca aag ttg ttg acg cca gcg att cgc gct agc ttg ggc atg gtc    1682
Ala Thr Lys Leu Leu Thr Pro Ala Ile Arg Ala Ser Leu Gly Met Val
        455                 460                 465 ttg gtt ggt act gaa agt ggt gtt gat gcc agt aaa tcg gct gca ttg    1730
Leu Val Gly Thr Glu Ser Gly Val Asp Ala Ser Lys Ser Ala Ala Leu
470                 475                 480 ttt att cat gat tta ttg gca ctc cct gag tgg gtg cgg gcc gtt gag    1778
Phe Ile His Asp Leu Leu Ala Leu Pro Glu Trp Val Arg Ala Val Glu
485                 490                 495                 500 tta aag gaa gct tgt tat ggc ggt act gcc gca cta atg atg gcg cgt    1826
Leu Lys Glu Ala Cys Tyr Gly Gly Thr Ala Ala Leu Met Met Ala Arg
        505                 510                 515 gac tac atc gcc gct cac cca gat aaa acc gtt tta gtc att gct gcg    1874
Asp Tyr Ile Ala Ala His Pro Asp Lys Thr Val Leu Val Ile Ala Ala
        520                 525                 530 gat atc gcc cgg tac ggt ttg gca aca gca gga gaa gtc aca caa ggt    1922
Asp Ile Ala Arg Tyr Gly Leu Ala Thr Ala Gly Glu Val Thr Gln Gly
        535                 540                 545 gcg ggc gcg gtt gcc atg tta atc aaa gca gag ccg cac atc atg acc    1970
Ala Gly Ala Val Ala Met Leu Ile Lys Ala Glu Pro His Ile Met Thr
550                 555                 560 att gaa gac gat tcg gtt tat cgg tct gaa tct att gac gat ttt tgg    2018
Ile Glu Asp Asp Ser Val Tyr Arg Ser Glu Ser Ile Asp Asp Phe Trp
565                 570                 575                 580 cgg ccg gtt tat caa gac aca gca att gca caa gga aag tat tca acg    2066
Arg Pro Val Tyr Gln Asp Thr Ala Ile Ala Gln Gly Lys Tyr Ser Thr
            585                 590                 595 gaa caa tat tta gct ttt ttt caa gca att tgg tca cga tac cag acc    2114
Glu Gln Tyr Leu Ala Phe Phe Gln Ala Ile Trp Ser Arg Tyr Gln Thr
            600                 605                 610 caa cgc cat cac aca gca agt gat ttt gct gcg atg aca ttc cat tta    2162
Gln Arg His His Thr Ala Ser Asp Phe Ala Ala Met Thr Phe His Leu
        615                 620                 625 ccg tat acc aaa atg ggc aag aaa gct tta aag ctt gtt ctg ccg gac    2210
Pro Tyr Thr Lys Met Gly Lys Lys Ala Leu Lys Leu Val Leu Pro Asp
        630                 635                 640 aca gat gaa gcc act ggc gag cga ctg caa cgg cgc ttt gag gca agc    2258
Thr Asp Glu Ala Thr Gly Glu Arg Leu Gln Arg Arg Phe Glu Ala Ser
645                 650                 655                 660 act cgg tac tgc cgg cga gtt ggc aat att tat acc ggt tct ttg tat    2306
Thr Arg Tyr Cys Arg Arg Val Gly Asn Ile Tyr Thr Gly Ser Leu Tyr
            665                 670                 675 ttg ggt ctg ctg tcg ttg ttg gac aat gat act agc ttg aaa gcg cgt    2354
Leu Gly Leu Leu Ser Leu Leu Asp Asn Asp Thr Ser Leu Lys Ala Arg
        680                 685                 690 gac cgg atc ggt tta ttc tcg tat ggc tcc ggg gcc gtg gca gaa ttt    2402
Asp Arg Ile Gly Leu Phe Ser Tyr Gly Ser Gly Ala Val Ala Glu Phe
        695                 700                 705 ttt agc ggc atc ttg caa ccg gat ttt gcc gca caa ctg cat gca gcc    2450
Phe Ser Gly Ile Leu Gln Pro Asp Phe Ala Ala Gln Leu His Ala Ala
710                 715                 720 aat cac gct aaa atg ttg gct gat cgt cag gaa tta acc gtt cct gaa    2498
Asn His Ala Lys Met Leu Ala Asp Arg Gln Glu Leu Thr Val Pro Glu
725                 730                 735                 740 tac gaa gct gtt ttc agc gat aag gtg cct tat gat cca gaa gat tat    2546
Tyr Glu Ala Val Phe Ser Asp Lys Val Pro Tyr Asp Pro Glu Asp Tyr
                745                 750                 755 cgt agt gat ccg act tat tat cat ggt cag ttt gtt ttg acc ggt gtg    2594
Arg Ser Asp Pro Thr Tyr Tyr His Gly Gln Phe Val Leu Thr Gly Val
```

```
                        Arg Ser Asp Pro Thr Tyr Tyr His Gly Gln Phe Val Leu Thr Gly Val
                                        760                 765                 770 atc ggt caa gaa cgt caa tat cag cag cgg taa ggatccagga gaaattaact        2647
Ile Gly Gln Glu Arg Gln Tyr Gln Gln Arg
            775                 780 atg aaa ttt tac gag ttg tct ccg gaa aaa cgc cgt gac caa ttg gtt          2695
Met Lys Phe Tyr Glu Leu Ser Pro Glu Lys Arg Arg Asp Gln Leu Val
            785                 790                 795 caa gaa ggg tgg tta aca aca cag gat gct gcg ttg tta gct ggt acg          2743
Gln Glu Gly Trp Leu Thr Thr Gln Asp Ala Ala Leu Leu Ala Gly Thr
            800                 805                 810 cat agc ttg cct gaa gtc aca gga gcg cgt ctg atc gaa aat gcc atc          2791
His Ser Leu Pro Glu Val Thr Gly Ala Arg Leu Ile Glu Asn Ala Ile
815                 820                 825                 830 ggc gag ttc cct tta ccc cta ggc gtt gct cgc aat tta ttg gtc aat          2839
Gly Glu Phe Pro Leu Pro Leu Gly Val Ala Arg Asn Leu Leu Val Asn
                835                 840                 845 gga cag cta cat caa gtg cct ata gcg gat gag gaa cct tct gtg att          2887
Gly Gln Leu His Gln Val Pro Ile Ala Asp Glu Glu Pro Ser Val Ile
            850                 855                 860 gca gct gcc agt aat ggg gcc agg ctt gcg act gca aac ggg ggc gtt          2935
Ala Ala Ala Ser Asn Gly Ala Arg Leu Ala Thr Ala Asn Gly Gly Val
865                 870                 875 agg acc cat gta gcg gcg cat cga gtg gtc gct gaa gta gtc ctg act          2983
Arg Thr His Val Ala Ala His Arg Val Val Ala Glu Val Val Leu Thr
            880                 885                 890 aac ttg acg gac tta gtg caa gca agg caa acg att ttg gct cat cag          3031
Asn Leu Thr Asp Leu Val Gln Ala Arg Gln Thr Ile Leu Ala His Gln
895                 900                 905                 910 act gat att cag aaa gtc att gcg gtt gcg cat cct tcg atg att caa          3079
Thr Asp Ile Gln Lys Val Ile Ala Val Ala His Pro Ser Met Ile Gln
                915                 920                 925 cgt ggc ggt ggt ctt gat cag tta acg gtc gaa tca cta gga gca cag          3127
Arg Gly Gly Gly Leu Asp Gln Leu Thr Val Glu Ser Leu Gly Ala Gln
            930                 935                 940 ttc ttg aaa atc cgt tta acg ctc gat ccg caa cag gca atg ggg gcc          3175
Phe Leu Lys Ile Arg Leu Thr Leu Asp Pro Gln Gln Ala Met Gly Ala
            945                 950                 955 aat tat gcg aat aca gtt gcc gaa gcg gtc gca gcg gcg gtg aca agc          3223
Asn Tyr Ala Asn Thr Val Ala Glu Ala Val Ala Ala Ala Val Thr Ser
            960                 965                 970 tgg gta gac ggt gat gtg ctt gtc agt att tta act aac gcg cca aca          3271
Trp Val Asp Gly Asp Val Leu Val Ser Ile Leu Thr Asn Ala Pro Thr
975                 980                 985                 990 gaa ctc gtg acg gct gag gtt tca ctt gag ccg gtt tct tta gcg acg         3319
Glu Leu Val Thr Ala Glu Val Ser Leu Glu Pro Val Ser Leu Ala Thr
                995                 1000                1005 aaa gct ctt tct gga gat gtg att gct aag aaa att gtt cag ctt             3364
Lys Ala Leu Ser Gly Asp Val Ile Ala Lys Lys Ile Val Gln Leu
            1010                1015                1020 agc gat tta gcc ttt gtc gat gct gag cgg gca gtg acc cac aac             3409
Ser Asp Leu Ala Phe Val Asp Ala Glu Arg Ala Val Thr His Asn
            1025                1030                1035 aag ggc att ctt aac ggt att att ggt gct gta ttg gct act ggc             3454
Lys Gly Ile Leu Asn Gly Ile Ile Gly Ala Val Leu Ala Thr Gly
            1040                1045                1050 aat gat acc cgc gct gtc gca gca agt atc ggt gca ttt gca tgt             3499
Asn Asp Thr Arg Ala Val Ala Ala Ser Ile Gly Ala Phe Ala Cys
            1055                1060                1065
```

-continued

| | | |
|---|---|---|
| gcg tct ggc agg tat cag cct tta tcg cgc tgg tat atg gat cag<br>Ala Ser Gly Arg Tyr Gln Pro Leu Ser Arg Trp Tyr Met Asp Gln<br>      1070              1075                 1080 | | 3544 |
| ggc cat tta gtt ggt cac tta cag ctg ccc ttg ccg atg ggg gca<br>Gly His Leu Val Gly His Leu Gln Leu Pro Leu Pro Met Gly Ala<br>      1085              1090                 1095 | | 3589 |
| gtt ggc ggg gcg atc ggt gct tta cca atg gcg cag gtt gtc cgt<br>Val Gly Gly Ala Ile Gly Ala Leu Pro Met Ala Gln Val Val Arg<br>      1100              1105                 1110 | | 3634 |
| cgg ctc ggt ggg tat cag aat tta gct atc atg cag caa gtt att<br>Arg Leu Gly Gly Tyr Gln Asn Leu Ala Ile Met Gln Gln Val Ile<br>      1115              1120                 1125 | | 3679 |
| gcc gcc ctc ggg ttg gtg caa aat ctt gct gcg atg cga gca ttg<br>Ala Ala Leu Gly Leu Val Gln Asn Leu Ala Ala Met Arg Ala Leu<br>      1130              1135                 1140 | | 3724 |
| gct gga ccg ggg att caa gct ggt cac atg aag ttg cag gct aat<br>Ala Gly Pro Gly Ile Gln Ala Gly His Met Lys Leu Gln Ala Asn<br>      1145              1150                 1155 | | 3769 |
| gcc ctc gcc att gct gcc ggg gca aca gaa aca gaa ttg ccg atg<br>Ala Leu Ala Ile Ala Ala Gly Ala Thr Glu Thr Glu Leu Pro Met<br>      1160              1165                 1170 | | 3814 |
| ctt gtg aac gca ctt cgt caa ggt agt atg gat tta aaa cat gcg<br>Leu Val Asn Ala Leu Arg Gln Gly Ser Met Asp Leu Lys His Ala<br>      1175              1180                 1185 | | 3859 |
| caa caa tat tta aca acc att cgt tta aac aag aaa gta ggc caa<br>Gln Gln Tyr Leu Thr Thr Ile Arg Leu Asn Lys Lys Val Gly Gln<br>      1190              1195                 1200 | | 3904 |
| tca aaa gat gaa aat cgg gat tga gtcgacctgc aggcatgcaa gcttggctgt<br>Ser Lys Asp Glu Asn Arg Asp<br>      1205 | | 3958 |
| tttggcggat gagagaagat tttcagcctg atacagatta aatcagaacg cagaagcggt | | 4018 |
| ctgataaaac agaatttgcc tggcggcagt agcgcggtgg tcccacctga ccccatgccg | | 4078 |
| aactcagaag tgaaacgccg tagcgccgat ggtagtgtgg ggtctcccca tgcgagagta | | 4138 |
| gggaactgcc aggcatcaaa taaaacgaaa ggctcagtcg aaagactggg cctttcgttt | | 4198 |
| tatctgttgt ttgtcggtga acgctctcct gagtaggaca aatccgccgg agcggatttt | | 4258 |
| gaacgttgcg aagcaacggc ccggagggtg cgggcagga cgcccgccat aaactgccag | | 4318 |
| gcatcaaatt aagcagaagg ccatcctgac ggtaccgcta ccagcggtgg tttgtttgcc | | 4378 |
| ggatcaagag ctaccaactc ttttccgaa ggtaactggc ttcagcagag cgcagatacc | | 4438 |
| aaatactgtc cttctagtgt agccgtagtt aggccaccac ttcaagaact ctgtagcacc | | 4498 |
| gcctacatac ctcgctctgc taatcctgtt accagtgggg catttgagaa gcacacggtc | | 4558 |
| acactgcttc cggtagtcaa taaaccggta aaccagcaat agacataagc ggctatttaa | | 4618 |
| cgaccctgcc ctgaaccgac gaccgggtcg aatttgcttt cgaatttctg ccattcatcc | | 4678 |
| gcttattatc acttattcag gcgtagcacc aggcgtttaa gggcaccaat aactgcctta | | 4738 |
| aaaaaattac gccccgccct gccactcatc gcagtactgt tgtaattcat taagcattct | | 4798 |
| gccgacatgg aagccatcac agacggcatg atgaacctga atcgccagcg gcatcagcac | | 4858 |
| cttgtcgcct tgcgtataat atttgcccat ggtgaaaacg ggggcgaaga agttgtccat | | 4918 |
| attggccacg tttaaatcaa aactggtgaa actcacccag ggattggctg agacgaaaaa | | 4978 |
| catattctca ataaaccctt tagggaaata ggccaggttt tcaccgtaac acgccacatc | | 5038 |
| ttgcgaatat atgtgtagaa actgccgaaa atcgtcgtgg tattcactcc agagcgatga | | 5098 |
| aaacgtttca gtttgctcat ggaaaacggt gtaacaaggg tgaacactat cccatatcac | | 5158 |

| | |
|---|---|
| cagctcaccg tctttcattg ccatacggaa ttccggatga gcattcatca ggcgggcaag | 5218 |
| aatgtgaata aaggccggat aaaacttgtg cttattttc tttacggtct ttaaaaaggc | 5278 |
| cgtaatatcc agctgaacgg tctggttata ggtacattga gcaactgact gaaatgcctc | 5338 |
| aaaatgttct ttacgatgcc attgggatat atcaacggtg gtatatccag tgattttttt | 5398 |
| ctccatttta gcttccttag ctcctgaaaa tctcgataac tcaaaaaata cgcccggtag | 5458 |
| tgatcttatt tcattatggt gaaagttgga acctcttacg tgccgatcaa cgtctcattt | 5518 |
| tcgccaaaag ttggcccagg gcttcccggt atcaacaggg acaccaggat ttatttattc | 5578 |
| tgcgaagtga tcttccgtca caggtattta tcggcgcaa agtgcgtcgg gtgatgctgc | 5638 |
| caacttactg atttagtgta tgatggtgtt tttgaggtgc tccagtggct tctgtttcta | 5698 |
| tcagctgtcc ctcctgttca gctactgacg gggtggtgcg taacggcaaa agcaccgccg | 5758 |
| gacatcagcg ctagcggagt gtatactggc ttactatgtt ggcactgatg agggtgtcag | 5818 |
| tgaagtgctt catgtggcag gagaaaaaag gctgcaccgg tgcgtcagca gaatatgtga | 5878 |
| tacaggatat attccgcttc ctcgctcact gactcgctac gctcggtcgt tcgactgcgg | 5938 |
| cgagcggaaa tggcttacga acggggcgga gatttcctgg aagatgccag gaagatactt | 5998 |
| aacagggaag tgagagggcc gcggcaaagc cgttttcca taggctccgc cccctgaca | 6058 |
| agcatcacga aatctgacgc tcaaatcagt ggtggcgaaa cccgacagga ctataaagat | 6118 |
| accaggcgtt tccccctggc ggctccctcg tgcgctctcc tgttcctgcc tttcggttta | 6178 |
| ccggtgtcat tccgctgtta tggccgcgtt tgtctcattc cacgcctgac actcagttcc | 6238 |
| gggtaggcag ttcgctccaa gctggactgt atgcacgaac ccccgttca gtccgaccgc | 6298 |
| tgcgccttat ccggtaacta tcgtcttgag tccaacccgg aaagacatgc aaaagcacca | 6358 |
| ctggcagcag ccactggtaa ttgatttaga ggagttagtc ttgaagtcat cgccggtta | 6418 |
| aggctaaact gaaaggacaa gttttggtga ctgcgctcct ccaagccagt tacctcggtt | 6478 |
| caaagagttg gtagctcaga gaaccttcga aaaaccgccc tgcaaggcgg ttttttcgtt | 6538 |
| ttcagagcaa gagattacgc gcagaccaaa acgatctcaa gaagatcatc ttattaatca | 6598 |
| gataaaatat ttgctcatga gcccgaagtg gcgagcccga tcttccccat cggtgatgtc | 6658 |
| ggcgatatag gcgccagcaa ccgcacctgt ggcgccggtg atgccggcc | 6707 |

<210> SEQ ID NO 16
<211> LENGTH: 394
<212> TYPE: PRT
<213> ORGANISM: Escherichia coli

<400> SEQUENCE: 16

Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

```
Leu Ala Ala Gln Ala Ile Gln Ala Gly Gln Ala Gln Ser Ile Val Ala
                100                 105                 110

Gly Gly Met Glu Asn Met Ser Leu Ala Pro Tyr Leu Leu Asp Ala Lys
            115                 120                 125

Ala Arg Ser Gly Tyr Arg Leu Gly Asp Gly Gln Val Tyr Asp Val Ile
        130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ile Glu
            180                 185                 190

Ser Gly Ala Phe Thr Ala Glu Ile Val Pro Val Asn Val Thr Arg
        195                 200                 205

Lys Lys Thr Phe Val Phe Ser Gln Asp Glu Phe Pro Lys Ala Asn Ser
210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
                260                 265                 270

Leu Ala Arg Ile Lys Ser Tyr Ala Ser Gly Gly Val Pro Pro Ala Leu
            275                 280                 285

Met Gly Met Gly Pro Val Pro Ala Thr Gln Lys Ala Leu Gln Leu Ala
        290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350

Ala Ser Gly Ala Arg Ile Leu Val Thr Leu Leu His Ala Met Gln Ala
        355                 360                 365

Arg Asp Lys Thr Leu Gly Leu Ala Thr Leu Cys Ile Gly Gly Gly Gln
    370                 375                 380

Gly Ile Ala Met Val Ile Glu Arg Leu Asn
385                 390

<210> SEQ ID NO 17
<211> LENGTH: 388
<212> TYPE: PRT
<213> ORGANISM: Escherichia coli

<400> SEQUENCE: 17

Met Lys Ile Gly Ile Asp Ala Ile Ala Met Asp Thr Pro Asp Phe Tyr
1               5                   10                  15

Val Asp Leu Val Lys Leu Ala Gln Val Arg Gly Asp Asp Pro Asp Lys
                20                  25                  30

Tyr Thr Ile Gly Ile Gly Gln Asp Glu Gln Ala Val Pro Pro Ser Ser
            35                  40                  45

Gln Asp Ile Val Thr Met Gly Ala Asn Ala Ala Thr Lys Leu Leu Thr
        50                  55                  60

Pro Ala Ile Arg Ala Ser Leu Gly Met Val Leu Val Gly Thr Glu Ser
65                  70                  75                  80
```

Gly Val Asp Ala Ser Lys Ser Ala Ala Leu Phe Ile His Asp Leu Leu
                85                  90                  95

Ala Leu Pro Glu Trp Val Arg Ala Val Glu Leu Lys Glu Ala Cys Tyr
            100                 105                 110

Gly Gly Thr Ala Ala Leu Met Met Ala Arg Asp Tyr Ile Ala Ala His
            115                 120                 125

Pro Asp Lys Thr Val Leu Val Ile Ala Asp Ile Ala Arg Tyr Gly
        130                 135                 140

Leu Ala Thr Ala Gly Glu Val Thr Gln Gly Ala Gly Ala Val Ala Met
145                 150                 155                 160

Leu Ile Lys Ala Glu Pro His Ile Met Thr Ile Glu Asp Asp Ser Val
                165                 170                 175

Tyr Arg Ser Glu Ser Ile Asp Asp Phe Trp Arg Pro Val Tyr Gln Asp
            180                 185                 190

Thr Ala Ile Ala Gln Gly Lys Tyr Ser Thr Glu Gln Tyr Leu Ala Phe
            195                 200                 205

Phe Gln Ala Ile Trp Ser Arg Tyr Gln Thr Gln Arg His His Thr Ala
210                 215                 220

Ser Asp Phe Ala Ala Met Thr Phe His Leu Pro Tyr Thr Lys Met Gly
225                 230                 235                 240

Lys Lys Ala Leu Lys Leu Val Leu Pro Asp Thr Asp Glu Ala Thr Gly
                245                 250                 255

Glu Arg Leu Gln Arg Arg Phe Glu Ala Ser Thr Arg Tyr Cys Arg Arg
            260                 265                 270

Val Gly Asn Ile Tyr Thr Gly Ser Leu Tyr Leu Gly Leu Leu Ser Leu
            275                 280                 285

Leu Asp Asn Asp Thr Ser Leu Lys Ala Arg Asp Arg Ile Gly Leu Phe
290                 295                 300

Ser Tyr Gly Ser Gly Ala Val Ala Glu Phe Phe Ser Gly Ile Leu Gln
305                 310                 315                 320

Pro Asp Phe Ala Ala Gln Leu His Ala Ala Asn His Ala Lys Met Leu
                325                 330                 335

Ala Asp Arg Gln Glu Leu Thr Val Pro Glu Tyr Glu Ala Val Phe Ser
            340                 345                 350

Asp Lys Val Pro Tyr Asp Pro Glu Asp Tyr Arg Ser Asp Pro Thr Tyr
            355                 360                 365

Tyr His Gly Gln Phe Val Leu Thr Gly Val Ile Gly Gln Glu Arg Gln
            370                 375                 380

Tyr Gln Gln Arg
385

<210> SEQ ID NO 18
<211> LENGTH: 426
<212> TYPE: PRT
<213> ORGANISM: Escherichia coli

<400> SEQUENCE: 18

Met Lys Phe Tyr Glu Leu Ser Pro Glu Lys Arg Arg Asp Gln Leu Val
1               5                   10                  15

Gln Glu Gly Trp Leu Thr Thr Gln Asp Ala Ala Leu Leu Ala Gly Thr
            20                  25                  30

His Ser Leu Pro Glu Val Thr Gly Ala Arg Leu Ile Glu Asn Ala Ile
        35                  40                  45

Gly Glu Phe Pro Leu Pro Leu Gly Val Ala Arg Asn Leu Leu Val Asn

Gly Gln Leu His Gln Val Pro Ile Ala Asp Glu Pro Ser Val Ile
 65                  70                  75                  80

Ala Ala Ala Ser Asn Gly Ala Arg Leu Ala Thr Ala Asn Gly Gly Val
                 85                  90                  95

Arg Thr His Val Ala Ala His Arg Val Val Ala Glu Val Val Leu Thr
             100                 105                 110

Asn Leu Thr Asp Leu Val Gln Ala Arg Gln Thr Ile Leu Ala His Gln
         115                 120                 125

Thr Asp Ile Gln Lys Val Ile Ala Val Ala His Pro Ser Met Ile Gln
130                 135                 140

Arg Gly Gly Gly Leu Asp Gln Leu Thr Val Glu Ser Leu Gly Ala Gln
145                 150                 155                 160

Phe Leu Lys Ile Arg Leu Thr Leu Asp Pro Gln Gln Ala Met Gly Ala
                165                 170                 175

Asn Tyr Ala Asn Thr Val Ala Glu Ala Val Ala Ala Val Thr Ser
             180                 185                 190

Trp Val Asp Gly Asp Val Leu Val Ser Ile Leu Thr Asn Ala Pro Thr
         195                 200                 205

Glu Leu Val Thr Ala Glu Val Ser Leu Glu Pro Val Ser Leu Ala Thr
210                 215                 220

Lys Ala Leu Ser Gly Asp Val Ile Ala Lys Ile Val Gln Leu Ser
225                 230                 235                 240

Asp Leu Ala Phe Val Asp Ala Glu Arg Ala Val Thr His Asn Lys Gly
                245                 250                 255

Ile Leu Asn Gly Ile Ile Gly Ala Val Leu Ala Thr Gly Asn Asp Thr
             260                 265                 270

Arg Ala Val Ala Ala Ser Ile Gly Ala Phe Ala Cys Ala Ser Gly Arg
         275                 280                 285

Tyr Gln Pro Leu Ser Arg Trp Tyr Met Asp Gln Gly His Leu Val Gly
290                 295                 300

His Leu Gln Leu Pro Leu Pro Met Gly Ala Val Gly Gly Ala Ile Gly
305                 310                 315                 320

Ala Leu Pro Met Ala Gln Val Val Arg Arg Leu Gly Gly Tyr Gln Asn
                325                 330                 335

Leu Ala Ile Met Gln Gln Val Ile Ala Ala Leu Gly Leu Val Gln Asn
             340                 345                 350

Leu Ala Ala Met Arg Ala Leu Ala Gly Pro Gly Ile Gln Ala Gly His
         355                 360                 365

Met Lys Leu Gln Ala Asn Ala Leu Ala Ile Ala Ala Gly Ala Thr Glu
370                 375                 380

Thr Glu Leu Pro Met Leu Val Asn Ala Leu Arg Gln Gly Ser Met Asp
385                 390                 395                 400

Leu Lys His Ala Gln Gln Tyr Leu Thr Thr Ile Arg Leu Asn Lys Lys
                405                 410                 415

Val Gly Gln Ser Lys Asp Glu Asn Arg Asp
             420                 425

<210> SEQ ID NO 19
<211> LENGTH: 660
<212> TYPE: DNA
<213> ORGANISM: Escherichia coli
<220> FEATURE:
<221> NAME/KEY: CDS
<222> LOCATION: (1)..(660)

<223> OTHER INFORMATION: camR gene encoding chloramphenicol acetyltransferase

<400> SEQUENCE: 19

```
atg gag aaa aaa atc act gga tat acc acc gtt gat ata tcc caa tgg      48
Met Glu Lys Lys Ile Thr Gly Tyr Thr Thr Val Asp Ile Ser Gln Trp
1               5                   10                  15 cat cgt aaa gaa cat ttt gag gca ttt cag tca gtt gct caa tgt acc      96
His Arg Lys Glu His Phe Glu Ala Phe Gln Ser Val Ala Gln Cys Thr
                20                  25                  30 tat aac cag acc gtt cag ctg gat att acg gcc ttt tta aag acc gta     144
Tyr Asn Gln Thr Val Gln Leu Asp Ile Thr Ala Phe Leu Lys Thr Val
            35                  40                  45 aag aaa aat aag cac aag ttt tat ccg gcc ttt att cac att ctt gcc     192
Lys Lys Asn Lys His Lys Phe Tyr Pro Ala Phe Ile His Ile Leu Ala
        50                  55                  60 cgc ctg atg aat gct cat ccg gaa ttc cgt atg gca atg aaa gac ggt     240
Arg Leu Met Asn Ala His Pro Glu Phe Arg Met Ala Met Lys Asp Gly
65                  70                  75                  80 gag ctg gtg ata tgg gat agt gtt cac cct tgt tac acc gtt ttc cat     288
Glu Leu Val Ile Trp Asp Ser Val His Pro Cys Tyr Thr Val Phe His
                85                  90                  95 gag caa act gaa acg ttt tca tcg ctc tgg agt gaa tac cac gac gat     336
Glu Gln Thr Glu Thr Phe Ser Ser Leu Trp Ser Glu Tyr His Asp Asp
                100                 105                 110 ttc cgg cag ttt cta cac ata tat tcg caa gat gtg gcg tgt tac ggt     384
Phe Arg Gln Phe Leu His Ile Tyr Ser Gln Asp Val Ala Cys Tyr Gly
            115                 120                 125 gaa aac ctg gcc tat ttc cct aaa ggg ttt att gag aat atg ttt ttc     432
Glu Asn Leu Ala Tyr Phe Pro Lys Gly Phe Ile Glu Asn Met Phe Phe
        130                 135                 140 gtc tca gcc aat ccc tgg gtg agt ttc acc agt ttt gat tta aac gtg     480
Val Ser Ala Asn Pro Trp Val Ser Phe Thr Ser Phe Asp Leu Asn Val
145                 150                 155                 160 gcc aat atg gac aac ttc ttc gcc ccc gtt ttc acc atg ggc aaa tat     528
Ala Asn Met Asp Asn Phe Phe Ala Pro Val Phe Thr Met Gly Lys Tyr
                165                 170                 175 tat acg caa ggc gac aag gtg ctg atg ccg ctg gcg att cag gtt cat     576
Tyr Thr Gln Gly Asp Lys Val Leu Met Pro Leu Ala Ile Gln Val His
                180                 185                 190 cat gcc gtc tgt gat ggc ttc cat gtc ggc aga atg ctt aat gaa tta     624
His Ala Val Cys Asp Gly Phe His Val Gly Arg Met Leu Asn Glu Leu
            195                 200                 205 caa cag tac tgc gat gag tgg cag ggc ggg gcg taa                     660
Gln Gln Tyr Cys Asp Glu Trp Gln Gly Gly Ala
        210                 215
```

<210> SEQ ID NO 20
<211> LENGTH: 219
<212> TYPE: PRT
<213> ORGANISM: Escherichia coli

<400> SEQUENCE: 20

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
```

```
                      50                  55                  60
Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
                100                 105                 110

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
        130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 21
<211> LENGTH: 7301
<212> TYPE: DNA
<213> ORGANISM: Escherichia coli
<220> FEATURE:
<221> NAME/KEY: promoter
<222> LOCATION: (103)..(135)
<223> OTHER INFORMATION: J23100 promoter
<220> FEATURE:
<221> NAME/KEY: CDS
<222> LOCATION: (281)..(1465)
<223> OTHER INFORMATION: atoB gene encoding acetyl-CoA acetyltransferase
<220> FEATURE:
<221> NAME/KEY: CDS
<222> LOCATION: (1479)..(2954)
<223> OTHER INFORMATION: Mutant ERG13 gene encoding non-functional HMG-
      CoA synthase
<220> FEATURE:
<221> NAME/KEY: CDS
<222> LOCATION: (2968)..(4473)
<223> OTHER INFORMATION: tHMGR gene encoding truncated HMG-CoA reductase
<220> FEATURE:
<221> NAME/KEY: rep_origin
<222> LOCATION: (6314)..(7153)

<400> SEQUENCE: 21
atcgatgcat gcgcccaata cgcaaaccgc ctctccccgc gcgttggccg attcattaat       60
gcagctggca cgacaggttt cccgactgga aagcgactca ttgacggcta gctcagtcct      120
aggtacagtg ctagcattac gccaagcgcg caattaaccc tcactaaagg aacaaaagc      180 tgggtaccgg gccccccctc gaggtcgacg gtatcgataa gcttgatatc gaattcctgc     240
agcccgggga tcctctagag tcgactagga ggaatataaa atg aaa aat tgt gtc      295
                                              Met Lys Asn Cys Val
                                               1               5 atc gtc agt gcg gta cgt act gct atc ggt agt ttt aac ggt tca ctc      343
Ile Val Ser Ala Val Arg Thr Ala Ile Gly Ser Phe Asn Gly Ser Leu
             10                  15                  20 gct tcc acc agc gcc atc gac ctg ggg gcg aca gta att aaa gcc gcc      391
Ala Ser Thr Ser Ala Ile Asp Leu Gly Ala Thr Val Ile Lys Ala Ala
         25                  30                  35
```

| | | | | | | | | | | | | | | | | |
|---|---|---|---|---|---|---|---|---|---|---|---|---|---|---|---|---|
| att | gaa | cgt | gca | aaa | atc | gat | tca | caa | cac | gtt | gat | gaa | gtg | att | atg | 439 |
| Ile | Glu | Arg | Ala | Lys | Ile | Asp | Ser | Gln | His | Val | Asp | Glu | Val | Ile | Met | |
| | | 40 | | | | | 45 | | | | | 50 | | | | |
| ggt | aac | gtg | tta | caa | gcc | ggg | ctg | ggg | caa | aat | ccg | gcg | cgt | cag | gca | 487 |
| Gly | Asn | Val | Leu | Gln | Ala | Gly | Leu | Gly | Gln | Asn | Pro | Ala | Arg | Gln | Ala | |
| | 55 | | | | | 60 | | | | | 65 | | | | | |
| ctg | tta | aaa | agc | ggg | ctg | gca | gaa | acg | gtg | tgc | gga | ttc | acg | gtc | aat | 535 |
| Leu | Leu | Lys | Ser | Gly | Leu | Ala | Glu | Thr | Val | Cys | Gly | Phe | Thr | Val | Asn | |
| 70 | | | | | 75 | | | | | 80 | | | | | 85 | |
| aaa | gta | tgt | ggt | tcg | ggt | ctt | aaa | agt | gtg | gcg | ctt | gcc | gcc | cag | gcc | 583 |
| Lys | Val | Cys | Gly | Ser | Gly | Leu | Lys | Ser | Val | Ala | Leu | Ala | Ala | Gln | Ala | |
| | | | | 90 | | | | | 95 | | | | | 100 | | |
| att | cag | gca | ggt | cag | gcg | cag | agc | att | gtg | gcg | ggg | ggt | atg | gaa | aat | 631 |
| Ile | Gln | Ala | Gly | Gln | Ala | Gln | Ser | Ile | Val | Ala | Gly | Gly | Met | Glu | Asn | |
| | | | 105 | | | | | 110 | | | | | 115 | | | |
| atg | agt | tta | gcc | ccc | tac | tta | ctc | gat | gca | aaa | gca | cgc | tct | ggt | tat | 679 |
| Met | Ser | Leu | Ala | Pro | Tyr | Leu | Leu | Asp | Ala | Lys | Ala | Arg | Ser | Gly | Tyr | |
| | | 120 | | | | | 125 | | | | | 130 | | | | |
| cgt | ctt | gga | gac | gga | cag | gtt | tat | gac | gta | atc | ctg | cgc | gat | ggc | ctg | 727 |
| Arg | Leu | Gly | Asp | Gly | Gln | Val | Tyr | Asp | Val | Ile | Leu | Arg | Asp | Gly | Leu | |
| | 135 | | | | | 140 | | | | | 145 | | | | | |
| atg | tgc | gcc | acc | cat | ggt | tat | cat | atg | ggg | att | acc | gcc | gaa | aac | gtg | 775 |
| Met | Cys | Ala | Thr | His | Gly | Tyr | His | Met | Gly | Ile | Thr | Ala | Glu | Asn | Val | |
| 150 | | | | | 155 | | | | | 160 | | | | | 165 | |
| gct | aaa | gag | tac | gga | att | acc | cgt | gaa | atg | cag | gat | gaa | ctg | gcg | cta | 823 |
| Ala | Lys | Glu | Tyr | Gly | Ile | Thr | Arg | Glu | Met | Gln | Asp | Glu | Leu | Ala | Leu | |
| | | | | 170 | | | | | 175 | | | | | 180 | | |
| cat | tca | cag | cgt | aaa | gcg | gca | gcc | gca | att | gag | tcc | ggt | gct | ttt | aca | 871 |
| His | Ser | Gln | Arg | Lys | Ala | Ala | Ala | Ala | Ile | Glu | Ser | Gly | Ala | Phe | Thr | |
| | | | 185 | | | | | 190 | | | | | 195 | | | |
| gcc | gaa | atc | gtc | ccg | gta | aat | gtt | gtc | act | cga | aag | aaa | acc | ttc | gtc | 919 |
| Ala | Glu | Ile | Val | Pro | Val | Asn | Val | Val | Thr | Arg | Lys | Lys | Thr | Phe | Val | |
| | | 200 | | | | | 205 | | | | | 210 | | | | |
| ttc | agt | caa | gac | gaa | ttc | ccg | aaa | gcg | aat | tca | acg | gct | gaa | gcg | tta | 967 |
| Phe | Ser | Gln | Asp | Glu | Phe | Pro | Lys | Ala | Asn | Ser | Thr | Ala | Glu | Ala | Leu | |
| | 215 | | | | | 220 | | | | | 225 | | | | | |
| ggt | gca | ttg | cgc | ccg | gcc | ttc | gat | aaa | gca | gga | aca | gtc | acc | gct | ggg | 1015 |
| Gly | Ala | Leu | Arg | Pro | Ala | Phe | Asp | Lys | Ala | Gly | Thr | Val | Thr | Ala | Gly | |
| 230 | | | | | 235 | | | | | 240 | | | | | 245 | |
| aac | gcg | tct | ggt | att | aac | gac | ggt | gct | gcc | gct | ctg | gtg | att | atg | gaa | 1063 |
| Asn | Ala | Ser | Gly | Ile | Asn | Asp | Gly | Ala | Ala | Ala | Leu | Val | Ile | Met | Glu | |
| | | | | 250 | | | | | 255 | | | | | 260 | | |
| gaa | tct | gcg | gcg | ctg | gca | gca | ggc | ctt | acc | ccc | ctg | gct | cgc | att | aaa | 1111 |
| Glu | Ser | Ala | Ala | Leu | Ala | Ala | Gly | Leu | Thr | Pro | Leu | Ala | Arg | Ile | Lys | |
| | | | 265 | | | | | 270 | | | | | 275 | | | |
| agt | tat | gcc | agc | ggt | ggc | gtg | ccc | ccc | gca | ttg | atg | ggt | atg | ggg | cca | 1159 |
| Ser | Tyr | Ala | Ser | Gly | Gly | Val | Pro | Pro | Ala | Leu | Met | Gly | Met | Gly | Pro | |
| | | 280 | | | | | 285 | | | | | 290 | | | | |
| gta | cct | gcc | acg | caa | aaa | gcg | tta | caa | ctg | gcg | ggg | ctg | caa | ctg | gcg | 1207 |
| Val | Pro | Ala | Thr | Gln | Lys | Ala | Leu | Gln | Leu | Ala | Gly | Leu | Gln | Leu | Ala | |
| | 295 | | | | | 300 | | | | | 305 | | | | | |
| gat | att | gat | ctc | att | gag | gct | aat | gaa | gca | ttt | gct | gca | cag | ttc | ctt | 1255 |
| Asp | Ile | Asp | Leu | Ile | Glu | Ala | Asn | Glu | Ala | Phe | Ala | Ala | Gln | Phe | Leu | |
| 310 | | | | | 315 | | | | | 320 | | | | | 325 | |
| gcc | gtt | ggg | aaa | aac | ctg | ggc | ttt | gat | tct | gag | aaa | gtg | aat | gtc | aac | 1303 |
| Ala | Val | Gly | Lys | Asn | Leu | Gly | Phe | Asp | Ser | Glu | Lys | Val | Asn | Val | Asn | |
| | | | | 330 | | | | | 335 | | | | | 340 | | |
| ggc | ggg | gcc | atc | gcg | ctc | ggg | cat | cct | atc | ggt | gcc | agt | ggt | gct | cgt | 1351 |
| Gly | Gly | Ala | Ile | Ala | Leu | Gly | His | Pro | Ile | Gly | Ala | Ser | Gly | Ala | Arg | |

```
                345               350               355
att ctg gtc aca cta tta cat gcc atg cag gca cgc gat aaa acg ctg    1399
Ile Leu Val Thr Leu Leu His Ala Met Gln Ala Arg Asp Lys Thr Leu
        360               365               370 ggg ctg gca aca ctg tgc att ggc ggc ggt cag gga att gcg atg gtg    1447
Gly Leu Ala Thr Leu Cys Ile Gly Gly Gly Gln Gly Ile Ala Met Val
375               380               385 att gaa cgg ttg aat taa ggaggacagc taa atg aaa ctc tca act aaa     1496
Ile Glu Arg Leu Asn                 Met Lys Leu Ser Thr Lys
390                                     395               400 ctt tgt tgg tgt ggt att aaa gga aga ctt agg ccg caa aag caa caa    1544
Leu Cys Trp Cys Gly Ile Lys Gly Arg Leu Arg Pro Gln Lys Gln Gln
                    405               410               415 caa tta cac aat aca aac ttg caa atg act gaa cta aaa aaa caa aag    1592
Gln Leu His Asn Thr Asn Leu Gln Met Thr Glu Leu Lys Lys Gln Lys
                420               425               430 acc gct gaa caa aaa acc aga cct caa aat gtc ggt att aaa ggt atc    1640
Thr Ala Glu Gln Lys Thr Arg Pro Gln Asn Val Gly Ile Lys Gly Ile
            435               440               445 caa att tac atc cca act caa tgt gtc aac caa tct gag cta gag aaa    1688
Gln Ile Tyr Ile Pro Thr Gln Cys Val Asn Gln Ser Glu Leu Glu Lys
        450               455               460 ttt gat ggc gtt tct caa ggt aaa tac aca att ggt ctg ggc caa acc    1736
Phe Asp Gly Val Ser Gln Gly Lys Tyr Thr Ile Gly Leu Gly Gln Thr
465               470               475               480 aac atg tct ttt gtc aat gac aga gaa gat atc tac tcg atg tcc cta    1784
Asn Met Ser Phe Val Asn Asp Arg Glu Asp Ile Tyr Ser Met Ser Leu
                    485               490               495 act gtt ttg tct aag ttg atc aag agt tac aac atc gac acc aac aaa    1832
Thr Val Leu Ser Lys Leu Ile Lys Ser Tyr Asn Ile Asp Thr Asn Lys
                500               505               510 att ggt aga tta gaa gtc ggt act gaa act ctg att gac aag tcc aag    1880
Ile Gly Arg Leu Glu Val Gly Thr Glu Thr Leu Ile Asp Lys Ser Lys
            515               520               525 tct gtc aag tct gtc ttg atg caa ttg ttt ggt gaa aac act gac gtc    1928
Ser Val Lys Ser Val Leu Met Gln Leu Phe Gly Glu Asn Thr Asp Val
        530               535               540 gaa ggt att gac acg ctt aat gcc gct tac ggt ggt acc aac gcg ttg    1976
Glu Gly Ile Asp Thr Leu Asn Ala Ala Tyr Gly Gly Thr Asn Ala Leu
545               550               555               560 ttc aac tct ttg aac tgg att gaa tct aac gca tgg gat ggt aga gac    2024
Phe Asn Ser Leu Asn Trp Ile Glu Ser Asn Ala Trp Asp Gly Arg Asp
                    565               570               575 gcc att gta gtt tgc ggt gat att gcc atc tac gat aag ggt gcc gca    2072
Ala Ile Val Val Cys Gly Asp Ile Ala Ile Tyr Asp Lys Gly Ala Ala
                580               585               590 aga cca acc ggt ggt gcc ggt act gtt gct atg tgg atc ggt cct gat    2120
Arg Pro Thr Gly Gly Ala Gly Thr Val Ala Met Trp Ile Gly Pro Asp
            595               600               605 gct cca att gta ttt gac tct gta aga gct tct tac atg gaa cac gcc    2168
Ala Pro Ile Val Phe Asp Ser Val Arg Ala Ser Tyr Met Glu His Ala
        610               615               620 tac gat ttt tac aag cca gat ttc acc agc gaa tat cct tac gtc gat    2216
Tyr Asp Phe Tyr Lys Pro Asp Phe Thr Ser Glu Tyr Pro Tyr Val Asp
625               630               635               640 ggt cat ttt tca tta act tgt tac gtc aag gct ctt gat caa gtt tac    2264
Gly His Phe Ser Leu Thr Cys Tyr Val Lys Ala Leu Asp Gln Val Tyr
                    645               650               655 aag agt tat tcc aag aag gct att tct aaa ggg ttg gtt agc gat ccc    2312
```

```
Lys Ser Tyr Ser Lys Lys Ala Ile Ser Lys Gly Leu Val Ser Asp Pro
            660                 665                 670 gct ggt tcg gat gct ttg aac gtt ttg aaa tat ttc gac tac aac gtt      2360
Ala Gly Ser Asp Ala Leu Asn Val Leu Lys Tyr Phe Asp Tyr Asn Val
        675                 680                 685 ttc cat gtt cca acc tgt aaa ttg gtc aca aaa tca tac ggt aga tta      2408
Phe His Val Pro Thr Cys Lys Leu Val Thr Lys Ser Tyr Gly Arg Leu
690                 695                 700 cta tat aac gat ttc aga gcc aat cct caa ttg ttc cca gaa gtt gac      2456
Leu Tyr Asn Asp Phe Arg Ala Asn Pro Gln Leu Phe Pro Glu Val Asp
705                 710                 715                 720 gcc gaa tta gct act cgc gat tat gac gaa tct tta acc gat aag aac      2504
Ala Glu Leu Ala Thr Arg Asp Tyr Asp Glu Ser Leu Thr Asp Lys Asn
                725                 730                 735 att gaa aaa act ttt gtt aat gtt gct aag cca ttc cac aaa gag aga      2552
Ile Glu Lys Thr Phe Val Asn Val Ala Lys Pro Phe His Lys Glu Arg
            740                 745                 750 gtt gcc caa tct ttg att gtt cca aca aac aca ggt aac atg tac acc      2600
Val Ala Gln Ser Leu Ile Val Pro Thr Asn Thr Gly Asn Met Tyr Thr
        755                 760                 765 gca tct gtt tat gcc gcc ttt gca tct cta tta aac tat gtt gga tct      2648
Ala Ser Val Tyr Ala Ala Phe Ala Ser Leu Leu Asn Tyr Val Gly Ser
770                 775                 780 gac gac tta caa ggc aag cgt gtt ggt tta ttt tct tac ggt tcc ggt      2696
Asp Asp Leu Gln Gly Lys Arg Val Gly Leu Phe Ser Tyr Gly Ser Gly
785                 790                 795                 800 tta gct gca tct cta tat tct tgc aaa att gtt ggt gac gtc caa cat      2744
Leu Ala Ala Ser Leu Tyr Ser Cys Lys Ile Val Gly Asp Val Gln His
                805                 810                 815 att atc aag gaa tta gat att act aac aaa tta gcc aag aga atc acc      2792
Ile Ile Lys Glu Leu Asp Ile Thr Asn Lys Leu Ala Lys Arg Ile Thr
            820                 825                 830 gaa act cca aag gat tac gaa gct gcc atc gaa ttg aga gaa aat gcc      2840
Glu Thr Pro Lys Asp Tyr Glu Ala Ala Ile Glu Leu Arg Glu Asn Ala
        835                 840                 845 cat ttg aag aag aac ttc aaa cct caa ggt tcc att gag cat ttg caa      2888
His Leu Lys Lys Asn Phe Lys Pro Gln Gly Ser Ile Glu His Leu Gln
850                 855                 860 agt ggt gtt tac tac ttg acc aac atc gat gac aaa ttt aga aga tct      2936
Ser Gly Val Tyr Tyr Leu Thr Asn Ile Asp Asp Lys Phe Arg Arg Ser
865                 870                 875                 880 tac gat gtt aaa aaa taa ggaggattac act atg gtt tta acc aat aaa      2985
Tyr Asp Val Lys Lys             Met Val Leu Thr Asn Lys
                885                             890 aca gtc att tct gga tcg aaa gtc aaa agt tta tca tct gcg caa tcg      3033
Thr Val Ile Ser Gly Ser Lys Val Lys Ser Leu Ser Ser Ala Gln Ser
            895                 900                 905 agc tca tca gga cct tca tca tct agt gag gaa gat gat tcc cgc gat      3081
Ser Ser Ser Gly Pro Ser Ser Ser Ser Glu Glu Asp Asp Ser Arg Asp
        910                 915                 920 att gaa agc ttg gat aag aaa ata cgt cct tta gaa gaa tta gaa gca      3129
Ile Glu Ser Leu Asp Lys Lys Ile Arg Pro Leu Glu Glu Leu Glu Ala
925                 930                 935 tta tta agt agt gga aat aca aaa caa ttg aag aac aaa gag gtc gct      3177
Leu Leu Ser Ser Gly Asn Thr Lys Gln Leu Lys Asn Lys Glu Val Ala
940                 945                 950                 955 gcc ttg gtt att cac ggt aag tta cct ttg tac gct ttg gag aaa aaa      3225
Ala Leu Val Ile His Gly Lys Leu Pro Leu Tyr Ala Leu Glu Lys Lys
                960                 965                 970
```

```
tta  ggt  gat  act  acg  aga  gcg  gtt  gcg  gta  cgt  agg  aag  gct  ctt  tca     3273
Leu  Gly  Asp  Thr  Thr  Arg  Ala  Val  Ala  Val  Arg  Arg  Lys  Ala  Leu  Ser
               975                      980                      985 att  ttg  gca  gaa  gct  cct  gta  tta  gca  tct  gat  cgt  tta  cca  tat  aaa    3321
Ile  Leu  Ala  Glu  Ala  Pro  Val  Leu  Ala  Ser  Asp  Arg  Leu  Pro  Tyr  Lys
               990                      995                      1000 aat  tat  gac  tac  gac  cgc  gta  ttt  ggc  gct  tgt  tgt  gaa  aat  gtt          3366
Asn  Tyr  Asp  Tyr  Asp  Arg  Val  Phe  Gly  Ala  Cys  Cys  Glu  Asn  Val
               1005                     1010                     1015 ata  ggt  tac  atg  cct  ttg  ccc  gtt  ggt  gtt  ata  ggc  ccc  ttg  gtt          3411
Ile  Gly  Tyr  Met  Pro  Leu  Pro  Val  Gly  Val  Ile  Gly  Pro  Leu  Val
               1020                     1025                     1030 atc  gat  ggt  aca  tct  tat  cat  ata  cca  atg  gca  act  aca  gag  ggt          3456
Ile  Asp  Gly  Thr  Ser  Tyr  His  Ile  Pro  Met  Ala  Thr  Thr  Glu  Gly
               1035                     1040                     1045 tgt  ttg  gta  gct  tct  gcc  atg  cgt  ggc  tgt  aag  gca  atc  aat  gct          3501
Cys  Leu  Val  Ala  Ser  Ala  Met  Arg  Gly  Cys  Lys  Ala  Ile  Asn  Ala
               1050                     1055                     1060 ggc  ggt  ggt  gca  aca  act  gtt  tta  act  aag  gat  ggt  atg  aca  aga          3546
Gly  Gly  Gly  Ala  Thr  Thr  Val  Leu  Thr  Lys  Asp  Gly  Met  Thr  Arg
               1065                     1070                     1075 ggc  cca  gta  gtc  cgt  ttc  cca  act  ttg  aaa  aga  tct  ggt  gcc  tgt          3591
Gly  Pro  Val  Val  Arg  Phe  Pro  Thr  Leu  Lys  Arg  Ser  Gly  Ala  Cys
               1080                     1085                     1090 aag  ata  tgg  tta  gac  tca  gaa  gag  gga  caa  aac  gca  att  aaa  aaa          3636
Lys  Ile  Trp  Leu  Asp  Ser  Glu  Glu  Gly  Gln  Asn  Ala  Ile  Lys  Lys
               1095                     1100                     1105 gct  ttt  aac  tct  aca  tca  aga  ttt  gca  cgt  ctg  caa  cat  att  caa          3681
Ala  Phe  Asn  Ser  Thr  Ser  Arg  Phe  Ala  Arg  Leu  Gln  His  Ile  Gln
               1110                     1115                     1120 act  tgt  cta  gca  gga  gat  tta  ctc  ttc  atg  aga  ttt  aga  aca  act          3726
Thr  Cys  Leu  Ala  Gly  Asp  Leu  Leu  Phe  Met  Arg  Phe  Arg  Thr  Thr
               1125                     1130                     1135 act  ggt  gac  gca  atg  ggt  atg  aat  atg  att  tct  aaa  ggt  gtc  gaa          3771
Thr  Gly  Asp  Ala  Met  Gly  Met  Asn  Met  Ile  Ser  Lys  Gly  Val  Glu
               1140                     1145                     1150 tac  tca  tta  aag  caa  atg  gta  gaa  gag  tat  ggc  tgg  gaa  gat  atg          3816
Tyr  Ser  Leu  Lys  Gln  Met  Val  Glu  Glu  Tyr  Gly  Trp  Glu  Asp  Met
               1155                     1160                     1165 gag  gtt  gtc  tcc  gtt  tct  ggt  aac  tac  tgt  acc  gac  aaa  aaa  cca          3861
Glu  Val  Val  Ser  Val  Ser  Gly  Asn  Tyr  Cys  Thr  Asp  Lys  Lys  Pro
               1170                     1175                     1180 gct  gcc  atc  aac  tgg  atc  gaa  ggt  cgt  ggt  aag  agt  gtc  gtc  gca          3906
Ala  Ala  Ile  Asn  Trp  Ile  Glu  Gly  Arg  Gly  Lys  Ser  Val  Val  Ala
               1185                     1190                     1195 gaa  gct  act  att  cct  ggt  gat  gtt  gtc  aga  aaa  gtg  tta  aaa  agt          3951
Glu  Ala  Thr  Ile  Pro  Gly  Asp  Val  Val  Arg  Lys  Val  Leu  Lys  Ser
               1200                     1205                     1210 gat  gtt  tcc  gca  ttg  gtt  gag  ttg  aac  att  gct  aag  aat  ttg  gtt          3996
Asp  Val  Ser  Ala  Leu  Val  Glu  Leu  Asn  Ile  Ala  Lys  Asn  Leu  Val
               1215                     1220                     1225 gga  tct  gca  atg  gct  ggg  tct  gtt  ggt  gga  ttt  aac  gca  cat  gca          4041
Gly  Ser  Ala  Met  Ala  Gly  Ser  Val  Gly  Gly  Phe  Asn  Ala  His  Ala
               1230                     1235                     1240 gct  aat  tta  gtg  aca  gct  gtt  ttc  ttg  gca  tta  gga  caa  gat  cct          4086
Ala  Asn  Leu  Val  Thr  Ala  Val  Phe  Leu  Ala  Leu  Gly  Gln  Asp  Pro
               1245                     1250                     1255 gca  caa  aat  gtt  gaa  agt  tcc  aac  tgt  ata  aca  ttg  atg  aaa  gaa          4131
Ala  Gln  Asn  Val  Glu  Ser  Ser  Asn  Cys  Ile  Thr  Leu  Met  Lys  Glu
               1260                     1265                     1270
```

|||||||||||||||
|---|---|---|---|---|---|---|---|---|---|---|---|---|---|
| gtg | gac | ggt | gat | ttg | aga | att | tcc | gta | tcc | atg | cca | tcc atc gaa | 4176 |
| Val | Asp | Gly | Asp | Leu | Arg | Ile | Ser | Val | Ser | Met | Pro | Ser Ile Glu | |
|  |  | 1275 |  |  |  | 1280 |  |  |  | 1285 |  |  | |
| gta | ggt | acc | atc | ggt | ggt | ggt | act | gtt | cta | gaa | cca | caa ggt gcc | 4221 |
| Val | Gly | Thr | Ile | Gly | Gly | Gly | Thr | Val | Leu | Glu | Pro | Gln Gly Ala | |
|  | 1290 |  |  |  |  | 1295 |  |  |  |  | 1300 |  | |
| atg | ttg | gac | tta | tta | ggt | gta | aga | ggc | ccg | cat | gct | acc gct cct | 4266 |
| Met | Leu | Asp | Leu | Leu | Gly | Val | Arg | Gly | Pro | His | Ala | Thr Ala Pro | |
| 1305 |  |  |  |  |  | 1310 |  |  |  |  |  | 1315 | |
| ggt | acc | aac | gca | cgt | caa | tta | gca | aga | ata | gtt | gcc | tgt gcc gtc | 4311 |
| Gly | Thr | Asn | Ala | Arg | Gln | Leu | Ala | Arg | Ile | Val | Ala | Cys Ala Val | |
|  | 1320 |  |  |  |  | 1325 |  |  |  |  | 1330 |  | |
| ttg | gca | ggt | gaa | tta | tcc | tta | tgt | gct | gcc | cta | gca | gcc ggc cat | 4356 |
| Leu | Ala | Gly | Glu | Leu | Ser | Leu | Cys | Ala | Ala | Leu | Ala | Ala Gly His | |
| 1335 |  |  |  |  |  | 1340 |  |  |  |  |  | 1345 | |
| ttg | gtt | caa | agt | cat | atg | acc | cac | aac | agg | aaa | cct | gct gaa cca | 4401 |
| Leu | Val | Gln | Ser | His | Met | Thr | His | Asn | Arg | Lys | Pro | Ala Glu Pro | |
| 1350 |  |  |  |  |  | 1355 |  |  |  |  |  | 1360 | |
| aca | aaa | cct | aac | aat | ttg | gac | gcc | act | gat | ata | aat | cgt ttg aaa | 4446 |
| Thr | Lys | Pro | Asn | Asn | Leu | Asp | Ala | Thr | Asp | Ile | Asn | Arg Leu Lys | |
|  | 1365 |  |  |  |  | 1370 |  |  |  |  | 1375 |  | |
| gat | ggg | tcc | gtc | acc | tgc | att | aaa | tcc | taagtcgacc tgcaggcatg | | | | 4493 |
| Asp | Gly | Ser | Val | Thr | Cys | Ile | Lys | Ser | | | | | |
|  | 1380 |  |  |  |  | 1385 |  |  | | | | | |

| | |
|---|---|
| caagcttggc tgttttggcg gatgagagaa gattttcagc ctgatacaga ttaaatcaga | 4553 |
| acgcagaagc ggtctgataa aacagaattt gcctggcggc agtagcgcgg tggtcccacc | 4613 |
| tgacccatg ccgaactcag aagtgaaacg ccgtagcgcc gatggtagtg tggggtctcc | 4673 |
| ccatgcgaga gtagggaact gccaggcatc aaataaaacg aaaggctcag tcgaaagact | 4733 |
| gggcctttcg ttttatctgt tgtttgtcgg tgaacgctct cctgagtagg acaaatccgc | 4793 |
| cgggagcgga tttgaacgtt gcgaagcaac ggcccggagg gtggcgggca ggacgcccgc | 4853 |
| cataaactgc caggcatcaa attaagcaga aggccatcct gacggtaccg ctaccagcgg | 4913 |
| tggtttgttt gccggatcaa gagctaccaa ctcttttttcc gaaggtaact ggcttcagca | 4973 |
| gagcgcagat accaaatact gtccttctag tgtagccgta gttaggccac cacttcaaga | 5033 |
| actctgtagc accgcctaca tacctcgctc tgctaatcct gttaccagtg ggcatttga | 5093 |
| gaagcacacg gtcacactgc ttccggtagt caataaaccg gtaaaccagc aatagacata | 5153 |
| agcggctatt taacgaccct gccctgaacc gacgaccggg tcgaatttgc tttcgaattt | 5213 |
| ctgccattca tccgcttatt atcacttatt caggcgtagc accaggcgtt taagggcacc | 5273 |
| aataactgcc ttaaaaaaat tacgccccgc cctgccactc atcgcagtac tgttgtaatt | 5333 |
| cattaagcat tctgccgaca tggaagccat cacagacggc atgatgaacc tgaatcgcca | 5393 |
| gcggcatcag caccttgtcg ccttgcgtat aatatttgcc catggtgaaa acggggcga | 5453 |
| agaagttgtc catattggcc acgtttaaat caaaactggt gaaactcacc cagggattgg | 5513 |
| ctgagacgaa aaacatattc tcaataaacc ctttagggaa ataggccagg ttttcaccgt | 5573 |
| aacacgccac atcttgcgaa tatatgtgta gaaactgccg gaaatcgtcg tggtattcac | 5633 |
| tccagagcga tgaaaacgtt tcagtttgct catggaaaac ggtgtaacaa gggtgaacac | 5693 |
| tatcccatat caccagctca ccgtctttca ttgccatacg gaattccgga tgagcattca | 5753 |
| tcaggcgggc aagaatgtga ataaaggccg gataaaactt gtgcttattt ttctttacgg | 5813 |
| tctttaaaaa ggccgtaata tccagctgaa cggtctggtt ataggtacat tgagcaactg | 5873 |

```
actgaaatgc ctcaaaatgt tctttacgat gccattggga tatatcaacg gtggtatatc    5933
cagtgatttt tttctccatt ttagcttcct tagctcctga aaatctcgat aactcaaaaa    5993
atacgcccgg tagtgatctt atttcattat ggtgaaagtt ggaacctctt acgtgccgat    6053
caacgtctca ttttcgccaa aagttggccc agggcttccc ggtatcaaca gggacaccag    6113
gatttattta ttctgcgaag tgatcttccg tcacaggtat ttattcggcg caaagtgcgt    6173
cgggtgatgc tgccaactta ctgatttagt gtatgatggt gtttttgagg tgctccagtg    6233
gcttctgttt ctatcagctg tccctcctgt tcagctactg acggggtggt gcgtaacggc    6293
aaaagcaccg ccggacatca gcgctagcgg agtgtatact ggcttactat gttggcactg    6353
atgagggtgt cagtgaagtg cttcatgtgg caggagaaaa aaggctgcac cggtgcgtca    6413
gcagaatatg tgatacagga tatattccgc ttcctcgctc actgactcgc tacgctcggt    6473
cgttcgactg cggcgagcgg aaatggctta cgaacggggc ggagatttcc tggaagatgc    6533
caggaagata cttaacaggg aagtgagagg gccgcggcaa agccgttttt ccataggctc    6593 cgccccctg acaagcatca cgaaatctga cgctcaaatc agtggtggcg aaacccgaca    6653
ggactataaa gataccaggc gtttccccct ggcggctccc tcgtgcgctc tcctgttcct    6713
gcctttcggt ttaccggtgt cattccgctg ttatggccgc gtttgtctca ttccacgcct    6773
gacactcagt tccgggtagg cagttcgctc caagctggac tgtatgcacg aaccccccgt    6833
tcagtccgac cgctgcgcct tatccggtaa ctatcgtctt gagtccaacc cggaaagaca    6893
tgcaaaagca ccactggcag cagccactgg taattgattt agaggagtta gtcttgaagt    6953
catgcgccgg ttaaggctaa actgaaagga caagttttgg tgactgcgct cctccaagcc    7013
agttacctcg gttcaaagag ttggtagctc agagaacctt cgaaaaaccg ccctgcaagg    7073
cggttttttc gttttcagag caagagatta cgcgcagacc aaaacgatct caagaagatc    7133
atcttattaa tcagataaaa tatttgctca tgagcccgaa gtggcgagcc cgatcttccc    7193
catcggtgat gtcggcgata taggcgccag caacccgcacc tgtggcgccg gtgatgccgg    7253
ccacgatgcg tccggcgtag aggatctgct catgtttgac agcttatc                7301
```

<210> SEQ ID NO 22
<211> LENGTH: 394
<212> TYPE: PRT
<213> ORGANISM: Escherichia coli

<400> SEQUENCE: 22

```
Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
                20                  25                  30

Val Ile Lys Ala Ala Ile Glu Arg Ala Lys Ile Asp Ser Gln His Val
            35                  40                  45

Asp Glu Val Ile Met Gly Asn Val Leu Gln Ala Gly Leu Gly Gln Asn
        50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125
```

```
Ala Arg Ser Gly Tyr Arg Leu Gly Asp Gly Gln Val Tyr Asp Val Ile
        130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ile Glu
            180                 185                 190

Ser Gly Ala Phe Thr Ala Glu Ile Val Pro Val Asn Val Thr Arg
            195                 200                 205

Lys Lys Thr Phe Val Phe Ser Gln Asp Glu Phe Pro Lys Ala Asn Ser
210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
                260                 265                 270

Leu Ala Arg Ile Lys Ser Tyr Ala Ser Gly Gly Val Pro Pro Ala Leu
                275                 280                 285

Met Gly Met Gly Pro Val Pro Ala Thr Gln Lys Ala Leu Gln Leu Ala
290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
                340                 345                 350

Ala Ser Gly Ala Arg Ile Leu Val Thr Leu Leu His Ala Met Gln Ala
                355                 360                 365

Arg Asp Lys Thr Leu Gly Leu Ala Thr Leu Cys Ile Gly Gly Gly Gln
370                 375                 380

Gly Ile Ala Met Val Ile Glu Arg Leu Asn
385                 390

<210> SEQ ID NO 23
<211> LENGTH: 491
<212> TYPE: PRT
<213> ORGANISM: Escherichia coli

<400> SEQUENCE: 23

Met Lys Leu Ser Thr Lys Leu Cys Trp Cys Gly Ile Lys Gly Arg Leu
1               5                   10                  15

Arg Pro Gln Lys Gln Gln Leu His Asn Thr Asn Leu Gln Met Thr
                20                  25                  30

Glu Leu Lys Lys Gln Lys Thr Ala Glu Gln Lys Thr Arg Pro Gln Asn
                35                  40                  45

Val Gly Ile Lys Gly Ile Gln Ile Tyr Ile Pro Thr Gln Cys Val Asn
            50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
```

-continued

```
               100                 105                 110
Asn Ile Asp Thr Asn Lys Ile Gly Arg Leu Glu Val Gly Thr Glu Thr
            115                 120                 125
Leu Ile Asp Lys Ser Lys Ser Val Lys Ser Val Leu Met Gln Leu Phe
        130                 135                 140
Gly Glu Asn Thr Asp Val Glu Gly Ile Asp Thr Leu Asn Ala Ala Tyr
145                 150                 155                 160
Gly Gly Thr Asn Ala Leu Phe Asn Ser Leu Asn Trp Ile Glu Ser Asn
                165                 170                 175
Ala Trp Asp Gly Arg Asp Ala Ile Val Val Cys Gly Asp Ile Ala Ile
            180                 185                 190
Tyr Asp Lys Gly Ala Ala Arg Pro Thr Gly Ala Gly Thr Val Ala
        195                 200                 205
Met Trp Ile Gly Pro Asp Ala Pro Ile Val Phe Asp Ser Val Arg Ala
    210                 215                 220
Ser Tyr Met Glu His Ala Tyr Asp Phe Tyr Lys Pro Asp Phe Thr Ser
225                 230                 235                 240
Glu Tyr Pro Tyr Val Asp Gly His Phe Ser Leu Thr Cys Tyr Val Lys
                245                 250                 255
Ala Leu Asp Gln Val Tyr Lys Ser Tyr Ser Lys Ala Ile Ser Lys
            260                 265                 270
Gly Leu Val Ser Asp Pro Ala Gly Ser Asp Ala Leu Asn Val Leu Lys
        275                 280                 285
Tyr Phe Asp Tyr Asn Val Phe His Val Pro Thr Cys Lys Leu Val Thr
    290                 295                 300
Lys Ser Tyr Gly Arg Leu Leu Tyr Asn Asp Phe Arg Ala Asn Pro Gln
305                 310                 315                 320
Leu Phe Pro Glu Val Asp Ala Glu Leu Ala Thr Arg Asp Tyr Asp Glu
                325                 330                 335
Ser Leu Thr Asp Lys Asn Ile Glu Lys Thr Phe Val Asn Val Ala Lys
            340                 345                 350
Pro Phe His Lys Glu Arg Val Ala Gln Ser Leu Ile Val Pro Thr Asn
        355                 360                 365
Thr Gly Asn Met Tyr Thr Ala Ser Val Tyr Ala Ala Phe Ala Ser Leu
    370                 375                 380
Leu Asn Tyr Val Gly Ser Asp Leu Gln Gly Lys Arg Val Gly Leu
385                 390                 395                 400
Phe Ser Tyr Gly Ser Gly Leu Ala Ala Ser Leu Tyr Ser Cys Lys Ile
                405                 410                 415
Val Gly Asp Val Gln His Ile Ile Lys Glu Leu Asp Ile Thr Asn Lys
            420                 425                 430
Leu Ala Lys Arg Ile Thr Glu Thr Pro Lys Asp Tyr Glu Ala Ala Ile
        435                 440                 445
Glu Leu Arg Glu Asn Ala His Leu Lys Lys Asn Phe Lys Pro Gln Gly
    450                 455                 460
Ser Ile Glu His Leu Gln Ser Gly Val Tyr Tyr Leu Thr Asn Ile Asp
465                 470                 475                 480
Asp Lys Phe Arg Arg Ser Tyr Asp Val Lys Lys
                485                 490

<210> SEQ ID NO 24
<211> LENGTH: 502
<212> TYPE: PRT
<213> ORGANISM: Escherichia coli
```

<400> SEQUENCE: 24

```
Met Val Leu Thr Asn Lys Thr Val Ile Ser Gly Ser Lys Val Lys Ser
1               5                   10                  15

Leu Ser Ser Ala Gln Ser Ser Ser Gly Pro Ser Ser Ser Ser Ser Glu
                20                  25                  30

Glu Asp Asp Ser Arg Asp Ile Glu Ser Leu Asp Lys Lys Ile Arg Pro
            35                  40                  45

Leu Glu Glu Leu Glu Ala Leu Leu Ser Ser Gly Asn Thr Lys Gln Leu
50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
                100                 105                 110

Asp Arg Leu Pro Tyr Lys Asn Tyr Asp Tyr Asp Arg Val Phe Gly Ala
            115                 120                 125

Cys Cys Glu Asn Val Ile Gly Tyr Met Pro Leu Pro Val Gly Val Ile
        130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
                180                 185                 190

Arg Gly Pro Val Val Arg Phe Pro Thr Leu Lys Arg Ser Gly Ala Cys
            195                 200                 205

Lys Ile Trp Leu Asp Ser Glu Glu Gly Gln Asn Ala Ile Lys Lys Ala
210                 215                 220

Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
                260                 265                 270

Gln Met Val Glu Glu Tyr Gly Trp Glu Asp Met Glu Val Val Ser Val
            275                 280                 285

Ser Gly Asn Tyr Cys Thr Asp Lys Lys Pro Ala Ala Ile Asn Trp Ile
        290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
                340                 345                 350

Gly Phe Asn Ala His Ala Ala Asn Leu Val Thr Ala Val Phe Leu Ala
            355                 360                 365

Leu Gly Gln Asp Pro Ala Gln Asn Val Glu Ser Ser Asn Cys Ile Thr
        370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Gly Thr Val Leu Glu Pro Gln
```

405                 410                 415
Gly Ala Met Leu Asp Leu Leu Gly Val Arg Gly Pro His Ala Thr Ala
            420                 425                 430

Pro Gly Thr Asn Ala Arg Gln Leu Ala Arg Ile Val Ala Cys Ala Val
        435                 440                 445

Leu Ala Gly Glu Leu Ser Leu Cys Ala Ala Leu Ala Ala Gly His Leu
    450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
                485                 490                 495

Val Thr Cys Ile Lys Ser
            500

<210> SEQ ID NO 25
<211> LENGTH: 2283
<212> TYPE: DNA
<213> ORGANISM: Escherichia coli
<220> FEATURE:
<221> NAME/KEY: misc_feature
<222> LOCATION: (329)..(363)
<223> OTHER INFORMATION: FRT site
<220> FEATURE:
<221> NAME/KEY: misc_feature
<222> LOCATION: (1551)..(1585)
<223> OTHER INFORMATION: FRT site
<220> FEATURE:
<221> NAME/KEY: promoter
<222> LOCATION: (1907)..(1979)
<223> OTHER INFORMATION: pBAD promoter
<220> FEATURE:
<221> NAME/KEY: CDS
<222> LOCATION: (1991)..(2281)
<223> OTHER INFORMATION: folp gene excerpt

<400> SEQUENCE: 25
aagatgctct catgaaatat gagactatcg acgcaccgca gattgatgac ctgatggcac      60
gtcgcgatgt acgtccgcca gcgggctggg aagaaccagg cgcttctaac aattctggcg     120
acaatggtag tccaaaggct cctcgtccgg ttgatgaacc gcgtacgccg aacccgggta     180
acaccatgtc agagcagtta ggcgacaagt aagttcccgc atcagatgac tgtatttgta     240
ccgaaaaccc cggggcgtgc tccggggttt tttcttatca attcatacca gggataacat     300
cagcgattgt gtaggctgga gctgcttcga agttcctata ctttctagag aataggaact     360
tcggaatagg aacttcaaga tccccttatt agaagaactc gtcaagaagg cgatagaagg     420
cgatgcgctg cgaatcggga gcggcgatac cgtaaagcac gaggaagcgg tcagcccatt     480
cgccgccaag ctcttcagca atatcacggg tagccaacgc tatgtcctga tagcggtccg     540
ccacacccag ccggccacag tcgatgaatc cagaaaagcg gccattttcc accatgatat     600
tcggcaagca ggcatcgcca tgggtcacga cgagatcctc gccgtcgggc atgcgcgcct     660
tgagcctggc gaacagttcg gctggcgcga gcccctgatg ctcttcgtcc agatcatcct     720
gatcgacaag accggcttcc atccgagtac gtgctcgctc gatgcgatgt ttcgcttggt     780
ggtcgaatgg gcaggtagcc ggatcaagcg tatgcagccg ccgcattgca tcagccatga     840
tggatacttt ctcggcagga gcaaggtgag atgacaggag atcctgcccc ggcacttcgc     900
ccaatagcag ccagtccctt cccgcttcag tgacaacgtc gagcacagct gcgcaaggaa     960
cgcccgtcgt ggccagccac gatagccgcg ctgcctcgtc ctgcagttca ttcagggcac    1020
cggacaggtc ggtcttgaca aaaagaaccg ggcgcccctg cgctgacagc cggaacacgg    1080

```
cggcatcaga gcagccgatt gtctgttgtg cccagtcata gccgaatagc ctctccaccc      1140
aagcggccgg agaacctgcg tgcaatccat cttgttcaat catgcgaaac gatcctcatc      1200
ctgtctcttg atcagatctt gatccctgc gccatcagat ccttggcggc aagaaagcca      1260
tccagtttac tttgcagggc ttcccaacct taccagaggg cgccccagct ggcaattccg      1320
gttcgcttgc tgtccataaa accgccagt ctagctatcg ccatgtaagc ccactgcaag      1380
ctacctgctt tctctttgcg cttgcgtttt cccttgtcca gatagcccag tagctgacat      1440
tcatccgggg tcagcaccgt ttctgcggac tggctttcta cgtgttccgc ttcctttagc      1500
agcccttgcg ccctgagtgc ttgcggcagc gtgagcttca aaagcgctct gaagttccta      1560
tactttctag aaataggaa cttcgaactg caggtcgacg gatccccgga atattcatat      1620
gtgcgcttca gccatacttt tcatactccc gccattcaga aagaaaacca attgtccata      1680
ttgcatcaga cattgccgtc actgcgtctt ttactggctc ttctcgctaa ccaaaccggt      1740
aaccccgctt attaaaagca ttctgtaaca aagcgggacc aaagccatga caaaaacgcg      1800
taacaaaagt gtctataatc acggcagaaa agtccacatt gattatttgc acggcgtcac      1860
actttgctat gccatagcat ttttatccat aagattagcg gatcctacct gacgctttt      1920 atcgcaactc tctactgttt ctccataccc gttttttggg gctagcgaat tcgagctcga      1980
cttggaaggt atg aaa ctc ttt gcc cag ggt act tca ctg gac ctt agc        2029
             Met Lys Leu Phe Ala Gln Gly Thr Ser Leu Asp Leu Ser
               1               5                  10 cat cct cac gta atg ggg atc ctc aac gtc acg cct gat tcc ttt tcg       2077
His Pro His Val Met Gly Ile Leu Asn Val Thr Pro Asp Ser Phe Ser
 15                  20                  25 gat ggt ggc acg cat aac tcg ctg ata gat gcg gtg aaa cat gcg aat       2125
Asp Gly Gly Thr His Asn Ser Leu Ile Asp Ala Val Lys His Ala Asn
 30              35                  40                  45 ctg atg atc aac gct ggc gcg acg atc att gac gtt ggt ggc gag tcc       2173
Leu Met Ile Asn Ala Gly Ala Thr Ile Ile Asp Val Gly Gly Glu Ser
                 50                  55                  60 acg cgc cca ggg gcg gcg gaa gtt agc gtt gaa gaa gag ttg caa cgt       2221
Thr Arg Pro Gly Ala Ala Glu Val Ser Val Glu Glu Glu Leu Gln Arg
             65                  70                  75 gtt att cct gtg gtt gag gca att gct caa cgc ttc gaa gtc tgg atc       2269
Val Ile Pro Val Val Glu Ala Ile Ala Gln Arg Phe Glu Val Trp Ile
         80                  85                  90 tca gtc gat aca tc                                                     2283
Ser Val Asp Thr
     95

<210> SEQ ID NO 26
<211> LENGTH: 97
<212> TYPE: PRT
<213> ORGANISM: Escherichia coli

<400> SEQUENCE: 26

Met Lys Leu Phe Ala Gln Gly Thr Ser Leu Asp Leu Ser His Pro His
 1               5                  10                  15

Val Met Gly Ile Leu Asn Val Thr Pro Asp Ser Phe Ser Asp Gly Gly
             20                  25                  30

Thr His Asn Ser Leu Ile Asp Ala Val Lys His Ala Asn Leu Met Ile
         35                  40                  45

Asn Ala Gly Ala Thr Ile Ile Asp Val Gly Gly Glu Ser Thr Arg Pro
     50                  55                  60
```

```
Gly Ala Ala Glu Val Ser Val Glu Glu Leu Gln Arg Val Ile Pro
 65                  70                  75                  80

Val Val Glu Ala Ile Ala Gln Arg Phe Glu Val Trp Ile Ser Val Asp
                 85                  90                  95

Thr

<210> SEQ ID NO 27
<211> LENGTH: 795
<212> TYPE: DNA
<213> ORGANISM: Escherichia coli
<220> FEATURE:
<221> NAME/KEY: CDS
<222> LOCATION: (1)..(795)
<223> OTHER INFORMATION: kanR gene encoding Neomycin phosphotransferase
      II

<400> SEQUENCE: 27 atg att gaa caa gat gga ttg cac gca ggt tct ccg gcc gct tgg gtg      48
Met Ile Glu Gln Asp Gly Leu His Ala Gly Ser Pro Ala Ala Trp Val
1               5                   10                  15 gag agg cta ttc ggc tat gac tgg gca caa cag aca atc ggc tgc tct      96
Glu Arg Leu Phe Gly Tyr Asp Trp Ala Gln Gln Thr Ile Gly Cys Ser
                20                  25                  30 gat gcc gcc gtg ttc cgg ctg tca gcg cag ggg cgc ccg gtt ctt ttt     144
Asp Ala Ala Val Phe Arg Leu Ser Ala Gln Gly Arg Pro Val Leu Phe
            35                  40                  45 gtc aag acc gac ctg tcc ggt gcc ctg aat gaa ctg cag gac gag gca     192
Val Lys Thr Asp Leu Ser Gly Ala Leu Asn Glu Leu Gln Asp Glu Ala
        50                  55                  60 gcg cgg cta tcg tgg ctg gcc acg acg ggc gtt cct tgc gca gct gtg     240
Ala Arg Leu Ser Trp Leu Ala Thr Thr Gly Val Pro Cys Ala Ala Val
65                  70                  75                  80 ctc gac gtt gtc act gaa gcg gga agg gac tgg ctg cta ttg ggc gaa     288
Leu Asp Val Val Thr Glu Ala Gly Arg Asp Trp Leu Leu Leu Gly Glu
                85                  90                  95 gtg ccg ggg cag gat ctc ctg tca tct cac ctt gct cct gcc gag aaa     336
Val Pro Gly Gln Asp Leu Leu Ser Ser His Leu Ala Pro Ala Glu Lys
                100                 105                 110 gta tcc atc atg gct gat gca atg cgg cgg ctg cat acg ctt gat ccg     384
Val Ser Ile Met Ala Asp Ala Met Arg Arg Leu His Thr Leu Asp Pro
            115                 120                 125 gct acc tgc cca ttc gac cac caa gcg aaa cat cgc atc gag cga gca     432
Ala Thr Cys Pro Phe Asp His Gln Ala Lys His Arg Ile Glu Arg Ala
        130                 135                 140 cgt act cgg atg gaa gcc ggt ctt gtc gat cag gat gat ctg gac gaa     480
Arg Thr Arg Met Glu Ala Gly Leu Val Asp Gln Asp Asp Leu Asp Glu
145                 150                 155                 160 gag cat cag ggg ctc gcg cca gcc gaa ctg ttc gcc agg ctc aag gcg     528
Glu His Gln Gly Leu Ala Pro Ala Glu Leu Phe Ala Arg Leu Lys Ala
                165                 170                 175 cgc atg ccc gac ggc gag gat ctc gtc gtg acc cat ggc gat gcc tgc     576
Arg Met Pro Asp Gly Glu Asp Leu Val Val Thr His Gly Asp Ala Cys
                180                 185                 190 ttg ccg aat atc atg gtg gaa aat ggc cgc ttt tct gga ttc atc gac     624
Leu Pro Asn Ile Met Val Glu Asn Gly Arg Phe Ser Gly Phe Ile Asp
            195                 200                 205 tgt ggc cgg ctg ggt gtg gcg gac cgc tat cag gac ata gcg ttg gct     672
Cys Gly Arg Leu Gly Val Ala Asp Arg Tyr Gln Asp Ile Ala Leu Ala
        210                 215                 220 acc cgt gat att gct gaa gag ctt ggc ggc gaa tgg gct gac cgc ttc     720
Thr Arg Asp Ile Ala Glu Glu Leu Gly Gly Glu Trp Ala Asp Arg Phe
```

```
                225                 230                 235                 240
ctc gtg ctt tac ggt atc gcc gct ccc gat tcg cag cgc atc gcc ttc           768
Leu Val Leu Tyr Gly Ile Ala Ala Pro Asp Ser Gln Arg Ile Ala Phe
                245                 250                 255 tat cgc ctt ctt gac gag ttc ttc taa                                        795
Tyr Arg Leu Leu Asp Glu Phe Phe
            260
```

<210> SEQ ID NO 28
<211> LENGTH: 264
<212> TYPE: PRT
<213> ORGANISM: Escherichia coli

<400> SEQUENCE: 28

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 29
<211> LENGTH: 4739
<212> TYPE: DNA
<213> ORGANISM: Escherichia coli
<220> FEATURE:
<221> NAME/KEY: CDS
<222> LOCATION: (1894)..(2865)
<223> OTHER INFORMATION: specR gene encoding aminoglycoside
      nucleotidyltransferase <220> FEATURE:
<221> NAME/KEY: rep_origin
<222> LOCATION: (3459)..(4078)
<223> OTHER INFORMATION: Origin of replication

<400> SEQUENCE: 29

```
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120
ttcacttttt cttcacaacc ggcacggaac tcgctcgggc tggccccggt gcatttttta     180
aatacccgcg agaaatagag ttgatcgtca aaaccaacat tgcgaccgac ggtggcgata     240
ggcatccggt tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc cgaatagcgc     540
ccttcccctt gcccggcgtt aatgatttgc ccaaacaggt cgctgaaatg cggctggtgc     600
gcttcatccg ggcgaaagaa ccccgtattg gcaaatattg acggccagtt aagccattca     660
tgccagtagg cgcgcggacg aaagtaaacc cactgtcgat accattcgcg agcctccgga     720
tgacgaccca agtgcagaat ctctcctggc gggaacagca aaatatcacc cggtcggcaa     780
acaaattctc gtccctgatt tttcaccacc ccctgaccgc gaatggtgag attgagaata     840 taaccttca ttcccagcgg tcggtcgata aaaaaatcga gataaccgtt ggcctcaatc     900
gggagtaaac ccgccaccag atgggcatta acgagtatc ccggcagcag gggatcattt     960
tgcgcttcag ccatactttt catactcccg ccattcagag aagaaaccaa ttgtccatat    1020
tgcatcagac attgccgtca ctgcgtcttt tactggctct tctcgctaac caaaccggta    1080
accccgctta ttaaaagcat tctgtaacaa agcgggacca aagccatgac aaaaacgcgt    1140
aacaaaagtg tctataatca cggcagaaaa gtccacattg ttatttgca cggcgtcaca    1200 ctttgctatg ccatagcatt tttatccata agattagcgg atcctacctg acgctttta    1260 tcgcaactct ctactgtttc tccatacccg tttttttggg ctagcgaatt cgagctcgag    1320
gaggaaacca tggtacccgg ggatcctcta gagtcgacct gcaggcatgc aagcttggct    1380
gttttggcgg atgagagaag attttcagcc tgatacagat taaatcagaa cgcagaagcg    1440
gtctgataaa acagaatttg cctggcggca gtagcgcggt ggtcccacct gaccccatgc    1500
cgaactcaga agtgaaacgc cgtagcgccg atggtagtgt ggggtctccc catgcgagag    1560
tagggaactg ccaggcatca aataaaacga aaggctcagt cgaaagactg gcctttcgt    1620 tttatctgtt gtttgtcggt gaacgctctc ctgagtagga caaatccgcc gggagcggat    1680
ttgaacgttg cgaagcaacg gcccggaggg tggcgggcag gacgcccgcc ataaactgcc    1740
aggcatcaaa ttaagcagaa ggccatcctg acggtgatat ccggatgaag cacgaaccc    1800 agtggacata agcctcgttc ggttcgtaag ctgtaatgca agtagcgtaa ctgccgtcac    1860
gcaactggtc cacaaccttg accgaacgca gcg gtg gta acg gcg cag tgg cgg    1914
                                    Val Val Thr Ala Gln Trp Arg
                                     1               5 ttt tca tgg ctt ctt gtt atg aca tgt ttt ttt ggg gta cag tct atg    1962
Phe Ser Trp Leu Leu Val Met Thr Cys Phe Phe Gly Val Gln Ser Met
       10                  15                  20 cct cgg gca tcc aag cag caa gcg cgt tac gcc gtg ggt cga tgt ttg    2010
Pro Arg Ala Ser Lys Gln Gln Ala Arg Tyr Ala Val Gly Arg Cys Leu
```

```
                25                  30                  35
atg tta tgg agc agc aac gat gtt acg cag cag ggc agt cgc cct aaa    2058
Met Leu Trp Ser Ser Asn Asp Val Thr Gln Gln Gly Ser Arg Pro Lys
 40                  45                  50                  55 aca aag tta aac atc atg agg gaa gcg gtg atc gcc gaa gta tcg act    2106
Thr Lys Leu Asn Ile Met Arg Glu Ala Val Ile Ala Glu Val Ser Thr
                 60                  65                  70 caa cta tca gag gta gtt ggc gtc atc gag cgc cat ctc gaa ccg acg    2154
Gln Leu Ser Glu Val Val Gly Val Ile Glu Arg His Leu Glu Pro Thr
             75                  80                  85 ttg ctg gcc gta cat ttg tac ggc tcc gca gtg gat ggc ggc ctg aag    2202
Leu Leu Ala Val His Leu Tyr Gly Ser Ala Val Asp Gly Gly Leu Lys
         90                  95                 100 cca cac agt gat att gat ttg ctg gtt acg gtg acc gta agg ctt gat    2250
Pro His Ser Asp Ile Asp Leu Leu Val Thr Val Thr Val Arg Leu Asp
     105                 110                 115 gaa aca acg cgg cga gct ttg atc aac gac ctt ttg gaa act tcg gct    2298
Glu Thr Thr Arg Arg Ala Leu Ile Asn Asp Leu Leu Glu Thr Ser Ala
 120                 125                 130                 135 tcc cct gga gag agc gag att ctc cgc gct gta gaa gtc acc att gtt    2346
Ser Pro Gly Glu Ser Glu Ile Leu Arg Ala Val Glu Val Thr Ile Val
                 140                 145                 150 gtg cac gac gac atc att ccg tgg cgt tat cca gct aag cgc gaa ctg    2394
Val His Asp Asp Ile Ile Pro Trp Arg Tyr Pro Ala Lys Arg Glu Leu
             155                 160                 165 caa ttt gga gaa tgg cag cgc aat gac att ctt gca ggt atc ttc gag    2442
Gln Phe Gly Glu Trp Gln Arg Asn Asp Ile Leu Ala Gly Ile Phe Glu
         170                 175                 180 cca gcc acg tac gac att gat ctg gct atc ttg ctg aca aaa gca aga    2490
Pro Ala Thr Tyr Asp Ile Asp Leu Ala Ile Leu Leu Thr Lys Ala Arg
     185                 190                 195 gaa cat agc gtt gcc ttg gta ggt cca gcg gcg gag gaa ctc ttt gat    2538
Glu His Ser Val Ala Leu Val Gly Pro Ala Ala Glu Glu Leu Phe Asp
 200                 205                 210                 215 ccg gtt cct gaa cag gat cta ttt gag gcg cta aat gaa acc tta acg    2586
Pro Val Pro Glu Gln Asp Leu Phe Glu Ala Leu Asn Glu Thr Leu Thr
                 220                 225                 230 cta tgg aac tcg ccg ccc gac tgg gct ggc gat gag cga aat gta gtg    2634
Leu Trp Asn Ser Pro Pro Asp Trp Ala Gly Asp Glu Arg Asn Val Val
             235                 240                 245 ctt acg ttg tcc cgc att tgg tac agc gca gta acc ggc aaa atc gcg    2682
Leu Thr Leu Ser Arg Ile Trp Tyr Ser Ala Val Thr Gly Lys Ile Ala
         250                 255                 260 ccg aag gat gtc gct gcc gac tgg gca atg gag cgc ctg ccg gcc cag    2730
Pro Lys Asp Val Ala Ala Asp Trp Ala Met Glu Arg Leu Pro Ala Gln
     265                 270                 275 tat cag ccc gtc ata ctt gaa gct aga cag gct tat ctt gga caa gaa    2778
Tyr Gln Pro Val Ile Leu Glu Ala Arg Gln Ala Tyr Leu Gly Gln Glu
 280                 285                 290                 295 gaa gat cgc ttg gcc tcg cgc gca gat cag ttg gaa gaa ttt gtc cac    2826
Glu Asp Arg Leu Ala Ser Arg Ala Asp Gln Leu Glu Glu Phe Val His
                 300                 305                 310 tac gtg aaa ggc gag atc acc aag gta gtc ggc aaa taa tgtctaacaa    2875
Tyr Val Lys Gly Glu Ile Thr Lys Val Val Gly Lys
             315                 320 ttcgttcaag ccgacggata tctagattga tttacgcgcc ctgtagcggc gcattaagcg    2935
cggcgggtgt ggtggttacg cgcagcgtga ccgctacact tgccagcgcc ctagcgcccg    2995
ctcctttcgc tttcttccct tcctttctcg ccacgttcgc cggctttccc cgtcaagctc    3055
```

```
taaatcgggg gctcccttta gggttccgat ttagtgcttt acggcacctc gacccccaaaa    3115 aacttgattt gggtgatggt tcacgtagtg ggccatcgcc ctgatagacg gttttcgcc      3175 ctttgacgtt ggagtccacg ttctttaata gtggactctt gttccaaact tgaacaacac    3235
tcaaccctat ctcgggctat tcttttgatt tataagggat tttgccgatt tcggcctatt    3295
ggttaaaaaa tgagctgatt taacaaaaat ttaacgcgaa ttttaacaaa atattaacgt    3355
ttacaattta aaaggatcta ggtgaagatc cttttgata atctcatgac caaaatccct    3415
taacgtgagt tttcgttcca ctgagcgtca gaccccgtag aaaagatcaa aggatcttct    3475
tgagatcctt ttttcctgcg cgtaatctgc tgcttgcaaa caaaaaaacc accgctacca    3535
gcggtggttt gtttgccgga tcaagagcta ccaactcttt ttccgaaggt aactggcttc    3595
agcagagcgc agataccaaa tactgtcctt ctagtgtagc cgtagttagg ccaccacttc    3655
aagaactctg tagcaccgcc tacatacctc gctctgctaa tcctgttacc agtggctgct    3715
gccagtggcg ataagtcgtg tcttaccggg ttggactcaa gacgatagtt accggataag    3775
gcgcagcggt cgggctgaac ggggggttcg tgcacacagc ccagcttgga gcgaacgacc    3835
tacaccgaac tgagatacct acagcgtgag ctatgagaaa gcgccacgct tcccgaaggg    3895
agaaaggcgg acaggtatcc ggtaagcggc agggtcggaa caggagagcg cacgagggag    3955
cttccagggg gaaacgcctg gtatctttat agtcctgtcg ggtttcgcca cctctgactt    4015
gagcgtcgat ttttgtgatg ctcgtcaggg gggcggagcc tatggaaaaa cgccagcaac    4075
gcggcctttt tacggttcct ggccttttgc tggccttttg ctcacatgtt ctttcctgcg    4135
ttatcccctg attctgtgga taaccgtatt accgcctttg agtgagctga taccgctcgc    4195
cgcagccgaa cgaccgagcg cagcgagtca gtgagcgagg aagcggaaga gcgcctgatg    4255
cggtattttc tccttacgca tctgtgcggt atttcacacc gcatatggtg cactctcagt    4315
acaatctgct ctgatgccgc atagttaagc cagtatacac tccgctatcg ctacgtgact    4375
gggtcatggc tgcgccccga cacccgccaa cacccgctga cgcgccctga cgggcttgtc    4435
tgctcccggc atccgcttac agacaagctg tgaccgtctc cgggagctgc atgtgtcaga    4495
ggttttcacc gtcatcaccg aaacgcgcga ggcagcaagg agatggcgcc caacagtccc    4555
ccggccacgg ggcctgccac catacccacg ccgaaacaag cgctcatgag cccgaagtgg    4615
cgagcccgat cttccccatc ggtgatgtcg gcgatatagg cgccagcaac cgcacctgtg    4675
gcgccggtga tgccggccac gatgcgtccg gcgtagagga tctgctcatg tttgacagct    4735
tatc                                                                 4739
```

<210> SEQ ID NO 30
<211> LENGTH: 323
<212> TYPE: PRT
<213> ORGANISM: Escherichia coli

<400> SEQUENCE: 30

```
Val Val Thr Ala Gln Trp Arg Phe Ser Trp Leu Leu Val Met Thr Cys
 1               5                  10                  15

Phe Phe Gly Val Gln Ser Met Pro Arg Ala Ser Lys Gln Gln Ala Arg
            20                  25                  30

Tyr Ala Val Gly Arg Cys Leu Met Leu Trp Ser Ser Asn Asp Val Thr
        35                  40                  45

Gln Gln Gly Ser Arg Pro Lys Thr Lys Leu Asn Ile Met Arg Glu Ala
    50                  55                  60
```

```
Val Ile Ala Glu Val Ser Thr Gln Leu Ser Glu Val Gly Val Ile
 65                  70                  75                  80

Glu Arg His Leu Glu Pro Thr Leu Leu Ala Val His Leu Tyr Gly Ser
                 85                  90                  95

Ala Val Asp Gly Gly Leu Lys Pro His Ser Asp Ile Asp Leu Leu Val
            100                 105                 110

Thr Val Thr Val Arg Leu Asp Glu Thr Thr Arg Arg Ala Leu Ile Asn
        115                 120                 125

Asp Leu Leu Glu Thr Ser Ala Ser Pro Gly Glu Ser Glu Ile Leu Arg
130                 135                 140

Ala Val Glu Val Thr Ile Val Val His Asp Asp Ile Ile Pro Trp Arg
145                 150                 155                 160

Tyr Pro Ala Lys Arg Glu Leu Gln Phe Gly Glu Trp Gln Arg Asn Asp
                165                 170                 175

Ile Leu Ala Gly Ile Phe Glu Pro Ala Thr Tyr Asp Ile Asp Leu Ala
            180                 185                 190

Ile Leu Leu Thr Lys Ala Arg Glu His Ser Val Ala Leu Val Gly Pro
        195                 200                 205

Ala Ala Glu Glu Leu Phe Asp Pro Val Pro Gly Gln Asp Leu Phe Glu
210                 215                 220

Ala Leu Asn Glu Thr Leu Thr Leu Trp Asn Ser Pro Pro Asp Trp Ala
225                 230                 235                 240

Gly Asp Glu Arg Asn Val Val Leu Thr Leu Ser Arg Ile Trp Tyr Ser
                245                 250                 255

Ala Val Thr Gly Lys Ile Ala Pro Lys Asp Val Ala Ala Asp Trp Ala
            260                 265                 270

Met Glu Arg Leu Pro Ala Gln Tyr Gln Pro Val Ile Leu Glu Ala Arg
        275                 280                 285

Gln Ala Tyr Leu Gly Gln Gly Glu Asp Arg Leu Ala Ser Arg Ala Asp
290                 295                 300

Gln Leu Glu Glu Phe Val His Tyr Val Lys Gly Glu Ile Thr Lys Val
305                 310                 315                 320

Val Gly Lys

<210> SEQ ID NO 31
<211> LENGTH: 5507
<212> TYPE: DNA
<213> ORGANISM: Escherichia coli
<220> FEATURE:
<221> NAME/KEY: misc_feature
<222> LOCATION: (1291)..(1452)
<223> OTHER INFORMATION: ThiMN15#19 riboswitch
<220> FEATURE:
<221> NAME/KEY: CDS
<222> LOCATION: (1408)..(1704)
<223> OTHER INFORMATION: tetA-yefM gene encoding tetA leader [nt 1408-
      1452] fused to yefM antitoxin [nt 1453-1704]
<220> FEATURE:
<221> NAME/KEY: CDS
<222> LOCATION: (1968)..(2222)
<223> OTHER INFORMATION: yoeB gene encoding yoeB toxin
<220> FEATURE:
<221> NAME/KEY: CDS
<222> LOCATION: (2775)..(3635)
<223> OTHER INFORMATION: ampR gene encoding beta-lactamase
<220> FEATURE:
<221> NAME/KEY: rep_origin
<222> LOCATION: (3694)..(3993)
<223> OTHER INFORMATION: f1_origin of replication
<220> FEATURE:
<221> NAME/KEY: rep_origin
<222> LOCATION: (4227)..(4846)
```

<223> OTHER INFORMATION: pBR322_origin of replication

<400> SEQUENCE: 31

```
atcgatgcat aatgtgcctg tcaaatggac gaagcaggga ttctgcaaac cctatgctac    60
tccgtcaagc cgtcaattgt ctgattcgtt accaattatg acaacttgac ggctacatca   120
ttcactttt cttcacaacc ggcacggaac tcgctcgggc tggccccggt gcatttttta   180
aatacccgcg agaaatagag ttgatcgtca aaaccaacat tgcgaccgac ggtggcgata   240
ggcatccggg tggtgctcaa aagcagcttc gcctggctga tacgttggtc ctcgcgccag   300
cttaagacgc taatccctaa ctgctggcgg aaaagatgtg acagacgcga cggcgacaag   360
caaacatgct gtgcgacgct ggcgatatca aaattgctgt ctgccaggtg atcgctgatg   420
tactgacaag cctcgcgtac ccgattatcc atcggtggat ggagcgactc gttaatcgct   480
tccatgcgcc gcagtaacaa ttgctcaagc agatttatcg ccagcagctc cgaatagcgc   540
ccttcccctt gcccggcgtt aatgatttgc ccaaacaggt cgctgaaatg cggctggtgc   600
gcttcatccg ggcgaaagaa ccccgtattg gcaaatattg acggccagtt aagccattca   660
tgccagtagg cgcgcggacg aaagtaaacc cactggtgat accattgcgc agcctccgga   720
tgacgaccgt agtgatgaat ctctcctggc gggaacagca aaatatcacc cggtcggcaa   780
acaaattctc gtccctgatt tttcaccacc ccctgaccgc gaatggtgag attgagaata   840
taacctttca ttcccagcgg tcggtcgata aaaaaatcga gataaccgtt ggcctcaatc   900
ggcgttaaac ccgccaccag atgggcatta acgagtatc ccggcagcag gggatcattt   960
tgcgcttcag ccatactttt catactcccg ccattcagag aagaaaccaa ttgtccatat  1020
tgcatcagac attgccgtca ctgcgtcttt tactggctct tctcgctaac caaaccggta  1080
acccccgctta ttaaaagcat tctgtaacaa agcgggacca aagccatgac aaaaacgcgt  1140
aacaaaagtg tctataatca cggcagaaaa gtccacattg attatttgca cggcgtcaca  1200
ctttgctatg ccatagcatt tttatccata agattagcgg atcctacctg acgctttta   1260
tcgcaactct ctactgtttc tccatacccg aattcaacca aacgactcgg ggtgccttc   1320
tgcgtgaagg ctgagaaata cccgtatcac ctgatctgga taatgccagc gtagggaagc  1380
tcttaagaat cagatcagga gcaaaact atg caa gtc gac ctg ctg gat cca aaa  1434
                                Met Gln Val Asp Leu Leu Asp Pro Lys
                                 1               5
tct aac aat gcg ctc atc atg cgt aca att agc tac agc gaa gcg cgt   1482
Ser Asn Asn Ala Leu Ile Met Arg Thr Ile Ser Tyr Ser Glu Ala Arg
 10              15                  20                  25
cag aat ttg tcg gca aca atg atg aaa gcc gtt gaa gat cat gcc ccg   1530
Gln Asn Leu Ser Ala Thr Met Met Lys Ala Val Glu Asp His Ala Pro
             30                  35                  40
atc ctt att act cgt cag aat gga gag gct tgt gtt ctg atg tca ctc   1578
Ile Leu Ile Thr Arg Gln Asn Gly Glu Ala Cys Val Leu Met Ser Leu
         45                  50                  55
gaa gaa tac aac tcg ctg gaa gag acg gct tat cta ctg cgc tcc ccc   1626
Glu Glu Tyr Asn Ser Leu Glu Glu Thr Ala Tyr Leu Leu Arg Ser Pro
     60                  65                  70
gct aac gcc cgg aga ttg atg gac tca atc gat agc ctg aaa tca ggc   1674
Ala Asn Ala Arg Arg Leu Met Asp Ser Ile Asp Ser Leu Lys Ser Gly
 75                  80                  85
aaa gga acg gaa aag gac atc att gag tga ggcaatcagc tgttgcccgt    1724
Lys Gly Thr Glu Lys Asp Ile Ile Glu
 90                  95 ctcactggtg aaaagaaaaa ccaccctggc gcccaatacg caaaccgcct ctccccgcgc  1784
```

```
gttggccgat tcattaatgc agctggcacg acaggtttcc cgactggaaa gcgggcagtg      1844
agcgcaacgc aattaatgtg agttagctca ctcattaggc accccaggct ttacactttta    1904 tgcttccggc tcgtatgttg tgtggaattg tgagcggata acaatttcac acaggaagaa     1964 acc atg aaa cta atc tgg tct gag gaa tca tgg gac gat tat ctg tac       2012
    Met Lys Leu Ile Trp Ser Glu Glu Ser Trp Asp Asp Tyr Leu Tyr
        100             105             110 tgg cag gaa aca gat aag cga att gtt aaa aag atc aat gaa ctt atc       2060
Trp Gln Glu Thr Asp Lys Arg Ile Val Lys Lys Ile Asn Glu Leu Ile
    115             120             125 aaa gat acc cgc aga acg cca ttt gaa ggt aag ggg aag cca gaa ccc       2108
Lys Asp Thr Arg Arg Thr Pro Phe Glu Gly Lys Gly Lys Pro Glu Pro
130             135             140             145 ctg aaa cat aat ttg tca ggt ttc tgg tcc cga cgc att aca gag gag       2156
Leu Lys His Asn Leu Ser Gly Phe Trp Ser Arg Arg Ile Thr Glu Glu
                150             155             160 cac cgt ctg gta tac gcg gtt acc gac gat tca ctg ctc att gca gca       2204
His Arg Leu Val Tyr Ala Val Thr Asp Asp Ser Leu Leu Ile Ala Ala
            165             170             175 tgt cgt tat cat tat tga atcctctaga gtcgacctgc aggcatgcaa              2252
Cys Arg Tyr His Tyr
            180 gcttggctgt tttggcggat gagagaagat tttcagcctg atacagatta aatcagaacg     2312 cagaagcggt ctgataaaac agaatttgcc tggcggcagt agcgcggtgg tcccacctga     2372 ccccatgccg aactcagaag tgaaacgccg tagcgccgat ggtagtgtgg ggtctcccca     2432 tgcgagagta gggaactgcc aggcatcaaa taaaacgaaa ggctcagtcg aaagactggg     2492 cctttcgttt tatctgttgt ttgtcggtga acgctctcct gagtaggaca atccgccgg      2552 gagcggattt gaacgttgcg aagcaacggc ccggagggtg cgggcagga cgcccgccat      2612 aaactgccag gcatcaaatt aagcagaagg ccatcctgac ggatggcctt tttgcgtttc    2672 tacaaactct tttgtttatt tttctaaata cattcaaata tgtatccgct catgagacaa    2732 taaccctgat aaatgcttca ataatattga aaaggaaga gt atg agt att caa        2786
                                            Met Ser Ile Gln
                                                185 cat ttc cgt gtc gcc ctt att ccc ttt ttt gcg gca ttt tgc ctt cct       2834
His Phe Arg Val Ala Leu Ile Pro Phe Phe Ala Ala Phe Cys Leu Pro
        190             195             200 gtt ttt gct cac cca gaa acg ctg gtg aaa gta aaa gat gct gaa gat       2882
Val Phe Ala His Pro Glu Thr Leu Val Lys Val Lys Asp Ala Glu Asp
    205             210             215 cag ttg ggt gca cga gtg ggt tac atc gaa ctg gat ctc aac agc ggt       2930
Gln Leu Gly Ala Arg Val Gly Tyr Ile Glu Leu Asp Leu Asn Ser Gly
220             225             230 aag atc ctt gag agt ttt cgc ccc gaa gaa cgt ttt cca atg atg agc       2978
Lys Ile Leu Glu Ser Phe Arg Pro Glu Glu Arg Phe Pro Met Met Ser
235             240             245             250 act ttt aaa gtt ctg cta tgt ggc gcg gta tta tcc cgt gtt gac gcc       3026
Thr Phe Lys Val Leu Leu Cys Gly Ala Val Leu Ser Arg Val Asp Ala
                255             260             265 ggg caa gag caa ctc ggt cgc cgc ata cac tat tct cag aat gac ttg       3074
Gly Gln Glu Gln Leu Gly Arg Arg Ile His Tyr Ser Gln Asn Asp Leu
            270             275             280 gtt gag tac tca cca gtc aca gaa aag cat ctt acg gat ggc atg aca       3122
Val Glu Tyr Ser Pro Val Thr Glu Lys His Leu Thr Asp Gly Met Thr
        285             290             295
```

| | | |
|---|---|---|
| gta aga gaa tta tgc agt gct gcc ata acc atg agt gat aac act gcg<br>Val Arg Glu Leu Cys Ser Ala Ala Ile Thr Met Ser Asp Asn Thr Ala<br>300 305 310 | | 3170 |
| gcc aac tta ctt ctg aca acg atc gga gga ccg aag gag cta acc gct<br>Ala Asn Leu Leu Leu Thr Thr Ile Gly Gly Pro Lys Glu Leu Thr Ala<br>315 320 325 330 | | 3218 |
| ttt ttg cac aac atg ggg gat cat gta act cgc ctt gat cgt tgg gaa<br>Phe Leu His Asn Met Gly Asp His Val Thr Arg Leu Asp Arg Trp Glu<br>335 340 345 | | 3266 |
| ccg gag ctg aat gaa gcc ata cca aac gac gag cgt gac acc acg atg<br>Pro Glu Leu Asn Glu Ala Ile Pro Asn Asp Glu Arg Asp Thr Thr Met<br>350 355 360 | | 3314 |
| cct gca gca atg gca aca acg ttg cgc aaa cta tta act ggc gaa cta<br>Pro Ala Ala Met Ala Thr Thr Leu Arg Lys Leu Leu Thr Gly Glu Leu<br>365 370 375 | | 3362 |
| ctt act cta gct tcc cgg caa caa tta ata gac tgg atg gag gcg gat<br>Leu Thr Leu Ala Ser Arg Gln Gln Leu Ile Asp Trp Met Glu Ala Asp<br>380 385 390 | | 3410 |
| aaa gtt gca gga cca ctt ctg cgc tcg gcc ctt ccg gct ggc tgg ttt<br>Lys Val Ala Gly Pro Leu Leu Arg Ser Ala Leu Pro Ala Gly Trp Phe<br>395 400 405 410 | | 3458 |
| att gct gat aaa tct gga gcc ggt gag cgt ggg tct cgc ggt atc att<br>Ile Ala Asp Lys Ser Gly Ala Gly Glu Arg Gly Ser Arg Gly Ile Ile<br>415 420 425 | | 3506 |
| gca gca ctg ggg cca gat ggt aag ccc tcc cgt atc gta gtt atc tac<br>Ala Ala Leu Gly Pro Asp Gly Lys Pro Ser Arg Ile Val Val Ile Tyr<br>430 435 440 | | 3554 |
| acg acg ggg agt cag gca act atg gat gaa cga aat aga cag atc gct<br>Thr Thr Gly Ser Gln Ala Thr Met Asp Glu Arg Asn Arg Gln Ile Ala<br>445 450 455 | | 3602 |
| gag ata ggt gcc tca ctg att aag cat tgg taa ctgtcagacc aagtttactc<br>Glu Ile Gly Ala Ser Leu Ile Lys His Trp<br>460 465 | | 3655 |
| atatatactt tagattgatt tacgcgccct gtagcggcgc attaagcgcg gcgggtgtgg | | 3715 |
| tggttacgcg cagcgtgacc gctacacttg ccagcgccct agcgcccgct cctttcgctt | | 3775 |
| tcttcccttc ctttctcgcc acgttcgccg gctttccccg tcaagctcta atcgggggc | | 3835 |
| tcccttagg gttccgattt agtgctttac ggcacctcga ccccaaaaaa cttgatttgg | | 3895 |
| gtgatggttc acgtagtggg ccatcgccct gatagacggt ttttcgccct ttgacgttgg | | 3955 |
| agtccacgtt ctttaatagt ggactcttgt tccaaacttg aacaacactc aaccctatct | | 4015 |
| cgggctattc ttttgattta taagggattt tgccgatttc ggcctattgg ttaaaaaatg | | 4075 |
| agctgattta acaaaaattt aacgcgaatt ttaacaaaat attaacgttt acaatttaaa | | 4135 |
| aggatctagg tgaagatcct ttttgataat ctcatgacca aaatccctta acgtgagttt | | 4195 |
| tcgttccact gagcgtcaga ccccgtagaa aagatcaaag gatcttcttg agatcctttt | | 4255 |
| tttctgcgcg taatctgctg cttgcaaaca aaaaaaccac cgctaccagc ggtggtttgt | | 4315 |
| ttgccggatc aagagctacc aactcttttt ccgaaggtaa ctggcttcag cagagcgcag | | 4375 |
| ataccaaata ctgtccttct agtgtagccg tagttaggcc accacttcaa gaactctgta | | 4435 |
| gcaccgccta catacctcgc tctgctaatc ctgttaccag tggctgctgc cagtggcgat | | 4495 |
| aagtcgtgtc ttaccgggtt ggactcaaga cgatagttac cggataaggc gcagcggtcg | | 4555 |
| ggctgaacgg ggggttcgtg cacacagccc agcttggagc gaacgaccta caccgaactg | | 4615 |
| agatacctac agcgtgagct atgagaaagc gccacgcttc ccgaagggag aaaggcggac | | 4675 |
| aggtatccgg taagcggcag ggtcggaaca ggagagcgca cgagggagct tccaggggga | | 4735 |

```
aacgcctggt atctttatag tcctgtcggg tttcgccacc tctgacttga gcgtcgattt    4795
ttgtgatgct cgtcaggggg gcggagccta tggaaaaacg ccagcaacgc ggcctttta      4855
cggttcctgg cctttgctg gcctttgct cacatgttct ttcctgcgtt atccctgat        4915
tctgtggata accgtattac cgcctttgag tgagctgata ccgctcgccg cagccgaacg     4975
accgagcgca gcgagtcagt gagcgaggaa gcggaagagc gcctgatgcg gtattttctc    5035
cttacgcatc tgtgcggtat ttcacaccgc atatggtgca ctctcagtac aatctgctct     5095
gatgccgcat agttaagcca gtatacactc cgctatcgct acgtgactgg gtcatggctg    5155
cgccccgaca cccgccaaca cccgctgacg cgccctgacg ggcttgtctg ctcccggcat     5215
ccgcttacag acaagctgtg accgtctccg ggagctgcat gtgtcagagg ttttcaccgt     5275
catcaccgaa acgcgcgagg cagcaaggag atggcgccca acagtccccc ggccacgggg    5335
cctgccacca tacccacgcc gaaacaagcg ctcatgagcc cgaagtggcg agcccgatct     5395
tccccatcgg tgatgtcggc gatataggcg ccagcaaccg cacctgtggc gccggtgatg    5455
ccggccacga tgcgtccggc gtagaggatc tgctcatgtt tgacagctta tc            5507
```

<210> SEQ ID NO 32
<211> LENGTH: 98
<212> TYPE: PRT
<213> ORGANISM: Escherichia coli

<400> SEQUENCE: 32

```
Met Gln Val Asp Leu Leu Asp Pro Lys Ser Asn Asn Ala Leu Ile Met
1               5                   10                  15

Arg Thr Ile Ser Tyr Ser Glu Ala Arg Gln Asn Leu Ser Ala Thr Met
            20                  25                  30

Met Lys Ala Val Glu Asp His Ala Pro Ile Leu Ile Thr Arg Gln Asn
        35                  40                  45

Gly Glu Ala Cys Val Leu Met Ser Leu Glu Glu Tyr Asn Ser Leu Glu
    50                  55                  60

Glu Thr Ala Tyr Leu Leu Arg Ser Pro Ala Asn Ala Arg Arg Leu Met
65                  70                  75                  80

Asp Ser Ile Asp Ser Leu Lys Ser Gly Lys Gly Thr Glu Lys Asp Ile
                85                  90                  95

Ile Glu
```

<210> SEQ ID NO 33
<211> LENGTH: 84
<212> TYPE: PRT
<213> ORGANISM: Escherichia coli

<400> SEQUENCE: 33

```
Met Lys Leu Ile Trp Ser Glu Glu Ser Trp Asp Asp Tyr Leu Tyr Trp
1               5                   10                  15

Gln Glu Thr Asp Lys Arg Ile Val Lys Lys Ile Asn Glu Leu Ile Lys
            20                  25                  30

Asp Thr Arg Arg Thr Pro Phe Glu Gly Lys Gly Lys Pro Glu Pro Leu
        35                  40                  45

Lys His Asn Leu Ser Gly Phe Trp Ser Arg Arg Ile Thr Glu Glu His
    50                  55                  60

Arg Leu Val Tyr Ala Val Thr Asp Asp Ser Leu Leu Ile Ala Ala Cys
65                  70                  75                  80

Arg Tyr His Tyr
```

<210> SEQ ID NO 34
<211> LENGTH: 286
<212> TYPE: PRT
<213> ORGANISM: Escherichia coli

<400> SEQUENCE: 34

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 35
<211> LENGTH: 336
<212> TYPE: DNA
<213> ORGANISM: Escherichia coli
<220> FEATURE:
<221> NAME/KEY: CDS
<222> LOCATION: (1)..(336)
<223> OTHER INFORMATION: mazF gene encoding a toxin protein

<400> SEQUENCE: 35

```
atg gta agc cga tac gta ccc gat atg ggc gat ctg att tgg gtt gat    48
Met Val Ser Arg Tyr Val Pro Asp Met Gly Asp Leu Ile Trp Val Asp
1               5                   10                  15
```

```
ttt gac ccg aca aaa ggt agc gag caa gct gga cat cgt cca gct gtt    96
Phe Asp Pro Thr Lys Gly Ser Glu Gln Ala Gly His Arg Pro Ala Val
            20                  25                  30 gtc ctg agt cct ttc atg tac aac aac aaa aca ggt atg tgt ctg tgt   144
Val Leu Ser Pro Phe Met Tyr Asn Asn Lys Thr Gly Met Cys Leu Cys
        35                  40                  45 gtt cct tgt aca acg caa tca aaa gga tat ccg ttc gaa gtt gtt tta   192
Val Pro Cys Thr Thr Gln Ser Lys Gly Tyr Pro Phe Glu Val Val Leu
    50                  55                  60 tcc ggt cag gaa cgt gat ggc gta gcg tta gct gat cag gta aaa agt   240
Ser Gly Gln Glu Arg Asp Gly Val Ala Leu Ala Asp Gln Val Lys Ser
65                  70                  75                  80 atc gcc tgg cgg gca aga gga gca acg aag aaa gga aca gtt gcc cca   288
Ile Ala Trp Arg Ala Arg Gly Ala Thr Lys Lys Gly Thr Val Ala Pro
                85                  90                  95 gag gaa tta caa ctc att aaa gcc aaa att aac gta ctg att ggg tag   336
Glu Glu Leu Gln Leu Ile Lys Ala Lys Ile Asn Val Leu Ile Gly
            100                 105                 110

<210> SEQ ID NO 36
<211> LENGTH: 111
<212> TYPE: PRT
<213> ORGANISM: Escherichia coli

<400> SEQUENCE: 36

Met Val Ser Arg Tyr Val Pro Asp Met Gly Asp Leu Ile Trp Val Asp
1               5                   10                  15

Phe Asp Pro Thr Lys Gly Ser Glu Gln Ala Gly His Arg Pro Ala Val
            20                  25                  30

Val Leu Ser Pro Phe Met Tyr Asn Asn Lys Thr Gly Met Cys Leu Cys
        35                  40                  45

Val Pro Cys Thr Thr Gln Ser Lys Gly Tyr Pro Phe Glu Val Val Leu
    50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
            100                 105                 110

<210> SEQ ID NO 37
<211> LENGTH: 249
<212> TYPE: DNA
<213> ORGANISM: Escherichia coli
<220> FEATURE:
<221> NAME/KEY: CDS
<222> LOCATION: (1)..(249)
<223> OTHER INFORMATION: mazE gene encoding an antitoxin protein

<400> SEQUENCE: 37 atg atc cac agt agc gta aag cgt tgg gga aat tca ccg gcg gtg cgg    48
Met Ile His Ser Ser Val Lys Arg Trp Gly Asn Ser Pro Ala Val Arg
1               5                   10                  15 atc ccg gct acg tta atg cag gcg ctc aat ctg aat att gat gat gaa    96
Ile Pro Ala Thr Leu Met Gln Ala Leu Asn Leu Asn Ile Asp Asp Glu
            20                  25                  30 gtg aag att gac ctg gtg gat ggc aaa tta att att gag cca gtg cgt   144
Val Lys Ile Asp Leu Val Asp Gly Lys Leu Ile Ile Glu Pro Val Arg
        35                  40                  45 aaa gag ccc gta ttt acg ctt gct gaa ctg gtc aac gac atc acg ccg   192
Lys Glu Pro Val Phe Thr Leu Ala Glu Leu Val Asn Asp Ile Thr Pro
```

```
              50                  55                  60
gaa aac ctc cac gag aat atc gac tgg gga gag ccg aaa gat aag gaa    240
Glu Asn Leu His Glu Asn Ile Asp Trp Gly Glu Pro Lys Asp Lys Glu
 65                  70                  75                  80 gtc tgg taa                                                        249
Val Trp

<210> SEQ ID NO 38
<211> LENGTH: 82
<212> TYPE: PRT
<213> ORGANISM: Escherichia coli

<400> SEQUENCE: 38

Met Ile His Ser Ser Val Lys Arg Trp Gly Asn Ser Pro Ala Val Arg
 1               5                  10                  15

Ile Pro Ala Thr Leu Met Gln Ala Leu Asn Leu Asn Ile Asp Asp Glu
             20                  25                  30

Val Lys Ile Asp Leu Val Asp Gly Lys Leu Ile Ile Glu Pro Val Arg
         35                  40                  45

Lys Glu Pro Val Phe Thr Leu Ala Glu Leu Val Asn Asp Ile Thr Pro
     50                  55                  60

Glu Asn Leu His Glu Asn Ile Asp Trp Gly Glu Pro Lys Asp Lys Glu
 65                  70                  75                  80

Val Trp

<210> SEQ ID NO 39
<211> LENGTH: 399
<212> TYPE: DNA
<213> ORGANISM: Shigella spp
<220> FEATURE:
<221> NAME/KEY: CDS
<222> LOCATION: (1)..(399)
<223> OTHER INFORMATION: yafO gene encoding a toxin

<400> SEQUENCE: 39 atg cgg gta ttc aaa aca aaa ctt att cgc ctg caa ctt aca gca gag     48
Met Arg Val Phe Lys Thr Lys Leu Ile Arg Leu Gln Leu Thr Ala Glu
 1               5                  10                  15 gaa ctt gat gcg tta acg gcg gat ttt att tcc tat aag cgt gac ggt     96
Glu Leu Asp Ala Leu Thr Ala Asp Phe Ile Ser Tyr Lys Arg Asp Gly
             20                  25                  30 gtt ttg cca gat ata ttt ggt cgc gat gca ctc tac gac gac tcc ttt    144
Val Leu Pro Asp Ile Phe Gly Arg Asp Ala Leu Tyr Asp Asp Ser Phe
         35                  40                  45 acc tgg cca tta atc aaa ttt gag cga gtt gct cat att cat ctg gca    192
Thr Trp Pro Leu Ile Lys Phe Glu Arg Val Ala His Ile His Leu Ala
     50                  55                  60 aat gag aat aat cca ttt ccg cca cag ttg cgc caa ttc agc aga acg    240
Asn Glu Asn Asn Pro Phe Pro Pro Gln Leu Arg Gln Phe Ser Arg Thr
 65                  70                  75                  80 aat gac gaa gcg cat ttg gta tat tgt cag ggg gcg ttt gat gag caa    288
Asn Asp Glu Ala His Leu Val Tyr Cys Gln Gly Ala Phe Asp Glu Gln
             85                  90                  95 gca tgg ttg ctc att gcc att ctg aaa cct gaa cct cat aaa ctg gct    336
Ala Trp Leu Leu Ile Ala Ile Leu Lys Pro Glu Pro His Lys Leu Ala
        100                 105                 110 cga gat aac aac caa atg cat aaa att ggg aaa atg gca gaa gcg ttt    384
Arg Asp Asn Asn Gln Met His Lys Ile Gly Lys Met Ala Glu Ala Phe
    115                 120                 125 cgc atg cgt ttt tga                                                399
```

Arg Met Arg Phe
    130

<210> SEQ ID NO 40
<211> LENGTH: 132
<212> TYPE: PRT
<213> ORGANISM: Shigella spp

<400> SEQUENCE: 40

Met Arg Val Phe Lys Thr Lys Leu Ile Arg Leu Gln Leu Thr Ala Glu
1               5                   10                  15

Glu Leu Asp Ala Leu Thr Ala Asp Phe Ile Ser Tyr Lys Arg Asp Gly
            20                  25                  30

Val Leu Pro Asp Ile Phe Gly Arg Asp Ala Leu Tyr Asp Asp Ser Phe
        35                  40                  45

Thr Trp Pro Leu Ile Lys Phe Glu Arg Val Ala His Ile His Leu Ala
    50                  55                  60

Asn Glu Asn Asn Pro Phe Pro Pro Gln Leu Arg Gln Phe Ser Arg Thr
65                  70                  75                  80

Asn Asp Glu Ala His Leu Val Tyr Cys Gln Gly Ala Phe Asp Glu Gln
                85                  90                  95

Ala Trp Leu Leu Ile Ala Ile Leu Lys Pro Glu Pro His Lys Leu Ala
            100                 105                 110

Arg Asp Asn Asn Gln Met His Lys Ile Gly Lys Met Ala Glu Ala Phe
        115                 120                 125

Arg Met Arg Phe
    130

<210> SEQ ID NO 41
<211> LENGTH: 294
<212> TYPE: DNA
<213> ORGANISM: shigella spp
<220> FEATURE:
<221> NAME/KEY: CDS
<222> LOCATION: (1)..(294)
<223> OTHER INFORMATION: yafN gene encoding an antitoxin

<400> SEQUENCE: 41 atg cat cga att ctc gct gaa aaa tcg gtc aat atc act gag tta cgt      48
Met His Arg Ile Leu Ala Glu Lys Ser Val Asn Ile Thr Glu Leu Arg
1               5                   10                  15 aaa aac cca gct aaa tac ttt att gat caa ccg gtt gcg gtt ctt tct      96
Lys Asn Pro Ala Lys Tyr Phe Ile Asp Gln Pro Val Ala Val Leu Ser
            20                  25                  30 aat aat cgc ccc gca gga tat ctc tta agt gcc agc gca ttc gaa gcg     144
Asn Asn Arg Pro Ala Gly Tyr Leu Leu Ser Ala Ser Ala Phe Glu Ala
        35                  40                  45 tta atg gac atg ctt gct gaa caa gag gag aaa aag ccc ata aag gcg     192
Leu Met Asp Met Leu Ala Glu Gln Glu Glu Lys Lys Pro Ile Lys Ala
    50                  55                  60 cgc ttc cgt cca agt gct gca aga tta gag gaa att aca cgc cgc gct     240
Arg Phe Arg Pro Ser Ala Ala Arg Leu Glu Glu Ile Thr Arg Arg Ala
65                  70                  75                  80 gaa caa tat ctt aat gat atg acg gat gat gat ttc aat gac ttt aag     288
Glu Gln Tyr Leu Asn Asp Met Thr Asp Asp Asp Phe Asn Asp Phe Lys
                85                  90                  95 gaa taa                                                              294
Glu

<210> SEQ ID NO 42

-continued

```
<211> LENGTH: 97
<212> TYPE: PRT
<213> ORGANISM: shigella spp

<400> SEQUENCE: 42

Met His Arg Ile Leu Ala Glu Lys Ser Val Asn Ile Thr Glu Leu Arg
1               5                   10                  15

Lys Asn Pro Ala Lys Tyr Phe Ile Asp Gln Pro Val Ala Val Leu Ser
            20                  25                  30

Asn Asn Arg Pro Ala Gly Tyr Leu Leu Ser Ala Ser Ala Phe Glu Ala
        35                  40                  45

Leu Met Asp Met Leu Ala Glu Gln Glu Lys Lys Pro Ile Lys Ala
    50                  55                  60

Arg Phe Arg Pro Ser Ala Ala Arg Leu Glu Glu Ile Thr Arg Arg Ala
65                  70                  75                  80

Glu Gln Tyr Leu Asn Asp Met Thr Asp Asp Phe Asn Asp Phe Lys
                85                  90                  95

Glu

<210> SEQ ID NO 43
<211> LENGTH: 288
<212> TYPE: DNA
<213> ORGANISM: Escherichia coli
<220> FEATURE:
<221> NAME/KEY: CDS
<222> LOCATION: (1)..(288)
<223> OTHER INFORMATION: Rel E gene encoding a toxin

<400> SEQUENCE: 43 atg gcg tat ttt ctg gat ttt gac gag cgg gca cta aag gaa tgg cga      48
Met Ala Tyr Phe Leu Asp Phe Asp Glu Arg Ala Leu Lys Glu Trp Arg
1               5                   10                  15 aag ctg ggc tcg acg gta cgt gaa cag ttg aaa aag aag ctg gtt gaa      96
Lys Leu Gly Ser Thr Val Arg Glu Gln Leu Lys Lys Lys Leu Val Glu
            20                  25                  30 gta ctt gag tca ccc cgg att gaa gca aac aag ctc cgt ggt atg cct     144
Val Leu Glu Ser Pro Arg Ile Glu Ala Asn Lys Leu Arg Gly Met Pro
        35                  40                  45 gat tgt tac aag att aag ctc cgg tct tca ggc tat cgc ctt gta tac     192
Asp Cys Tyr Lys Ile Lys Leu Arg Ser Ser Gly Tyr Arg Leu Val Tyr
    50                  55                  60 cag gtt ata gac gag aaa gtt gtc gtt ttc gtg att tct gtt ggg aaa     240
Gln Val Ile Asp Glu Lys Val Val Val Phe Val Ile Ser Val Gly Lys
65                  70                  75                  80 aga gaa cgc tcg gaa gta tat agc gag gcg gtc aaa cgc att ctc tga     288
Arg Glu Arg Ser Glu Val Tyr Ser Glu Ala Val Lys Arg Ile Leu
                85                  90                  95

<210> SEQ ID NO 44
<211> LENGTH: 95
<212> TYPE: PRT
<213> ORGANISM: Escherichia coli

<400> SEQUENCE: 44

Met Ala Tyr Phe Leu Asp Phe Asp Glu Arg Ala Leu Lys Glu Trp Arg
1               5                   10                  15

Lys Leu Gly Ser Thr Val Arg Glu Gln Leu Lys Lys Lys Leu Val Glu
            20                  25                  30

Val Leu Glu Ser Pro Arg Ile Glu Ala Asn Lys Leu Arg Gly Met Pro
        35                  40                  45
```

```
Asp Cys Tyr Lys Ile Lys Leu Arg Ser Ser Gly Tyr Arg Leu Val Tyr
 50                  55                  60

Gln Val Ile Asp Glu Lys Val Val Phe Val Ile Ser Val Gly Lys
 65                  70                  75                  80

Arg Glu Arg Ser Glu Val Tyr Ser Glu Ala Val Lys Arg Ile Leu
                 85                  90                  95

<210> SEQ ID NO 45
<211> LENGTH: 240
<212> TYPE: DNA
<213> ORGANISM: Escherichia coli
<220> FEATURE:
<221> NAME/KEY: CDS
<222> LOCATION: (1)..(240)
<223> OTHER INFORMATION: RelB gene encoding an antitoxin

<400> SEQUENCE: 45 atg ggt agc att aac ctg cgt att gac gat gaa ctt aaa gcg cgt tct        48
Met Gly Ser Ile Asn Leu Arg Ile Asp Asp Glu Leu Lys Ala Arg Ser
 1               5                  10                  15 tac gcc gcg ctt gaa aaa atg ggt gta act cct tct gaa gcg ctt cgt        96
Tyr Ala Ala Leu Glu Lys Met Gly Val Thr Pro Ser Glu Ala Leu Arg
                 20                  25                  30 ctc atg ctc gag tat atc gct gac aat gaa cgc ttg ccg ttc aaa cag       144
Leu Met Leu Glu Tyr Ile Ala Asp Asn Glu Arg Leu Pro Phe Lys Gln
             35                  40                  45 aca ctc ctg agt gat gaa gat gct gaa ctt gtg gag ata gtg aaa gaa       192
Thr Leu Leu Ser Asp Glu Asp Ala Glu Leu Val Glu Ile Val Lys Glu
         50                  55                  60 cgg ctt cgt aat cct aag cca gta cgt gtg acg ctg gat gaa ctc tga       240
Arg Leu Arg Asn Pro Lys Pro Val Arg Val Thr Leu Asp Glu Leu
 65                  70                  75

<210> SEQ ID NO 46
<211> LENGTH: 79
<212> TYPE: PRT
<213> ORGANISM: Escherichia coli

<400> SEQUENCE: 46

Met Gly Ser Ile Asn Leu Arg Ile Asp Asp Glu Leu Lys Ala Arg Ser
 1               5                  10                  15

Tyr Ala Ala Leu Glu Lys Met Gly Val Thr Pro Ser Glu Ala Leu Arg
                 20                  25                  30

Leu Met Leu Glu Tyr Ile Ala Asp Asn Glu Arg Leu Pro Phe Lys Gln
             35                  40                  45

Thr Leu Leu Ser Asp Glu Asp Ala Glu Leu Val Glu Ile Val Lys Glu
         50                  55                  60

Arg Leu Arg Asn Pro Lys Pro Val Arg Val Thr Leu Asp Glu Leu
 65                  70                  75

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23119 synthetic promoter

<400> SEQUENCE: 47
```
ttgacagcta gctcagtcct aggtataatg ctagc    35

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23100 synthetic promoter

<400> SEQUENCE: 48
ttgacggcta gctcagtcct aggtacagtg ctagc    35

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23101 synthetic promoter

<400> SEQUENCE: 49
tttacagcta gctcagtcct aggtattatg ctagc    35

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: Synthetic promoter

<400> SEQUENCE: 50
ttgacagcta gctcagtcct aggtactgtg ctagc    35

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23103 synthetic promoter

<400> SEQUENCE: 51
ctgatagcta gctcagtcct agggattatg ctagc    35

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: promoter
<222> LOCATION: (1)..(35)
<223> OTHER INFORMATION: J23104 synthetic promoter

<400> SEQUENCE: 52
ttgacagcta gctcagtcct aggtattgtg ctagc       35

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23105 synthetic promoter

<400> SEQUENCE: 53
tttacggcta gctcagtcct aggtactatg ctagc       35

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23106 synthetic promoter

<400> SEQUENCE: 54
tttacggcta gctcagtcct aggtatagtg ctagc       35

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23107 synthetic promoter

<400> SEQUENCE: 55
tttacggcta gctcagccct aggtattatg ctagc       35

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23108 synthetic promoter

<400> SEQUENCE: 56
ctgacagcta gctcagtcct aggtataatg ctagc       35

<210> SEQ ID NO 57
<211> LENGTH: 35

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23109 synthetic promoter

<400> SEQUENCE: 57
tttacagcta gctcagtcct agggactgtg ctagc                               35

<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23110 synthetic promoter

<400> SEQUENCE: 58
tttacggcta gctcagtcct aggtacaatg ctagc                               35

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23111 synthetic promoter

<400> SEQUENCE: 59
ttgacggcta gctcagtcct aggtatagtg ctagc                               35

<210> SEQ ID NO 60
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23112 synthetic promoter

<400> SEQUENCE: 60
ctgatagcta gctcagtcct agggattatg ctagc                               35

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23113 synthetic promoter

<400> SEQUENCE: 61
```

```
ctgatggcta gctcagtcct agggattatg ctagc                                  35
```

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23114 synthetic promoter

<400> SEQUENCE: 62

```
tttatggcta gctcagtcct aggtacaatg ctagc                                  35
```

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23115 synthetic promoter

<400> SEQUENCE: 63

```
tttatagcta gctcagccct tggtacaatg ctagc                                  35
```

<210> SEQ ID NO 64
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23116 synthetic promoter

<400> SEQUENCE: 64

```
ttgacagcta gctcagtcct agggactatg ctagc                                  35
```

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: promoter
<222> LOCATION: (1)..(35)
<223> OTHER INFORMATION: J23117 synthetic promoter

<400> SEQUENCE: 65

```
ttgacagcta gctcagtcct agggattgtg ctagc                                  35
```

<210> SEQ ID NO 66
<211> LENGTH: 355
<212> TYPE: DNA
<213> ORGANISM: Escherichia coli
<220> FEATURE:
<221> NAME/KEY: promoter
<222> LOCATION: (1)..(355)

<223> OTHER INFORMATION: pBAD promoter

<400> SEQUENCE: 66

```
acttttcata ctcccgccat tcagagaaga aaccaattgt ccatattgca tcagacattg      60
ccgtcactgc gtcttttact ggctcttctc gctaaccaaa ccggtaaccc cgcttattaa     120
aagcattctg taacaaagcg ggaccaaagc catgacaaaa acgcgtaaca aaagtgtcta     180
taatcacggc agaaaagtcc acattgatta tttgcacggc gtcacacttt gctatgccat     240
agcattttta tccataagat tagcggatcc tacctgacgc tttttatcgc aactctctac     300
tgtttctcca tacccgtttt tttgggctag cgaattcgag ctcgaggagg aaggt         355
```

<210> SEQ ID NO 67
<211> LENGTH: 720
<212> TYPE: DNA
<213> ORGANISM: Escherichia coli
<220> FEATURE:
<221> NAME/KEY: CDS
<222> LOCATION: (1)..(720)
<223> OTHER INFORMATION: FadR gene encoding a fatty acid sensor

<400> SEQUENCE: 67

```
atg gtc att aag gcg caa agc ccg gcg ggt ttc gcg gaa gag tac att       48
Met Val Ile Lys Ala Gln Ser Pro Ala Gly Phe Ala Glu Glu Tyr Ile
1               5                  10                  15 att gaa agt atc tgg aat aac cgc ttc cct ccc ggg act att ttg ccc       96
Ile Glu Ser Ile Trp Asn Asn Arg Phe Pro Pro Gly Thr Ile Leu Pro
            20                  25                  30 gca gaa cgt gaa ctt tca gaa tta att ggc gta acg cgt act acg tta      144
Ala Glu Arg Glu Leu Ser Glu Leu Ile Gly Val Thr Arg Thr Thr Leu
        35                  40                  45 cgt gaa gtg tta cag cgt ctg gca cga gat ggc tgg ttg acc att caa      192
Arg Glu Val Leu Gln Arg Leu Ala Arg Asp Gly Trp Leu Thr Ile Gln
    50                  55                  60 cat ggc aag ccg acg aag gtg aat aat ttc tgg gaa act tcc ggt tta      240
His Gly Lys Pro Thr Lys Val Asn Asn Phe Trp Glu Thr Ser Gly Leu
65                  70                  75                  80 aat atc ctt gaa aca ctg gcg cga ctg gat cac gaa agt gtg ccg cag      288
Asn Ile Leu Glu Thr Leu Ala Arg Leu Asp His Glu Ser Val Pro Gln
                85                  90                  95 ctt att gat aat ttg ctg tcg gtg cgt acc aat att tcc act att ttt      336
Leu Ile Asp Asn Leu Leu Ser Val Arg Thr Asn Ile Ser Thr Ile Phe
            100                 105                 110 att cgc acc gcg ttt cgt cag cat ccc gat aaa gcg cag gaa gtg ctg      384
Ile Arg Thr Ala Phe Arg Gln His Pro Asp Lys Ala Gln Glu Val Leu
        115                 120                 125 gct acc gct aat gaa gtg gcc gat cac gcc gat gcc ttt gcc gag ctg      432
Ala Thr Ala Asn Glu Val Ala Asp His Ala Asp Ala Phe Ala Glu Leu
    130                 135                 140 gat tac aac ata ttc cgc ggc ctg gcg ttt gct tcc ggc aac ccg att      480
Asp Tyr Asn Ile Phe Arg Gly Leu Ala Phe Ala Ser Gly Asn Pro Ile
145                 150                 155                 160 tac ggt ctg att ctt aac ggg atg aaa ggg ctg tat acg cgt att ggt      528
Tyr Gly Leu Ile Leu Asn Gly Met Lys Gly Leu Tyr Thr Arg Ile Gly
                165                 170                 175 cgt cac tat ttc gcc aat ccg gaa gcg cgc agt ctg gcg ctg ggc ttc      576
Arg His Tyr Phe Ala Asn Pro Glu Ala Arg Ser Leu Ala Leu Gly Phe
            180                 185                 190 tac cac aaa ctg tcg gcg ttg tgc agt gaa ggc gcg cac gat cag gtg      624
Tyr His Lys Leu Ser Ala Leu Cys Ser Glu Gly Ala His Asp Gln Val
        195                 200                 205
```

| | | | | | | | | | | | | |
|---|---|---|---|---|---|---|---|---|---|---|---|---|
| tac | gaa | aca | gtg | cgt | cgc | tat | ggg | cat | gag | agt | ggc | gag att tgg cac |
| Tyr | Glu | Thr | Val | Arg | Arg | Tyr | Gly | His | Glu | Ser | Gly | Glu Ile Trp His |
| | 210 | | | | | 215 | | | | | 220 | |

672

| | | | | | | | | | | | | |
|---|---|---|---|---|---|---|---|---|---|---|---|---|
| cgg | atg | cag | aaa | aat | ctg | ccg | ggt | gat | tta | gcc | att | cag ggg cga taa |
| Arg | Met | Gln | Lys | Asn | Leu | Pro | Gly | Asp | Leu | Ala | Ile | Gln Gly Arg |
| 225 | | | | | 230 | | | | | 235 | | |

720

<210> SEQ ID NO 68
<211> LENGTH: 239
<212> TYPE: PRT
<213> ORGANISM: Escherichia coli

<400> SEQUENCE: 68

Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
                20                  25                  30

Ala Glu Arg Glu Leu Ser Glu Leu Ile Gly Val Thr Arg Thr Thr Leu
            35                  40                  45

Arg Glu Val Leu Gln Arg Leu Ala Arg Asp Gly Trp Leu Thr Ile Gln
        50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95

Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
            180                 185                 190

Tyr His Lys Leu Ser Ala Leu Cys Ser Glu Gly Ala His Asp Gln Val
        195                 200                 205

Tyr Glu Thr Val Arg Arg Tyr Gly His Glu Ser Gly Glu Ile Trp His
    210                 215                 220

Arg Met Gln Lys Asn Leu Pro Gly Asp Leu Ala Ile Gln Gly Arg
225                 230                 235

<210> SEQ ID NO 69
<211> LENGTH: 240
<212> TYPE: DNA
<213> ORGANISM: Escherichia coli
<220> FEATURE:
<221> NAME/KEY: misc_feature
<222> LOCATION: (1)..(240)
<223> OTHER INFORMATION: btuB leader (adenosylcobalamin) riboswtich

<400> SEQUENCE: 69
gccggtcctg tgagttaata gggaatccag tgcgaatctg gagctgacgc gcagcggtaa    60
ggaaaggtgc gatgattgcg ttatgcggac actgccattc ggtgggaagt catcatctct   120
tagtatctta gataccccctc caagcccgaa gacctgccgg ccaacgtcgc atctggttct   180

```
catcatcgcg taatattgat gaaacctgcg gcatccttct tctattgtgg atgctttaca    240
```

<210> SEQ ID NO 70
<211> LENGTH: 279
<212> TYPE: DNA
<213> ORGANISM: Escherichia coli
<220> FEATURE:
<221> NAME/KEY: misc_feature
<222> LOCATION: (1)..(279)
<223> OTHER INFORMATION: tc3 (tetracycline) riboswitch

<400> SEQUENCE: 70

```
ccgcggccaa ttatctactt aaggcctaaa acataccaga tcgccacccg cgctttaatc    60
tggagaggtg aagaatacga ccacctaggc cttaagaacc ggtaaaacat accagatcgc    120
cacccgcgct ttaatctgga gaggtgaaga atacgaccac ctaccggtca acaacaacaa    180
caacaacaac aacaactcga ggcctaaaac ataccagatc gccacccgcg ctttaatctg    240
gagaggtgaa gaatacgacc acctaggcct cgagaacat                          279
```

<210> SEQ ID NO 71
<211> LENGTH: 1260
<212> TYPE: DNA
<213> ORGANISM: Escherichia coli
<220> FEATURE:
<221> NAME/KEY: CDS
<222> LOCATION: (1)..(1260)
<223> OTHER INFORMATION: xylR gene encoding a xyl repressor sensor
      protein

<400> SEQUENCE: 71

```
atg caa aac aac ttg ttg ttc ttg tgc aag aag tac tac aac atc atc        48
Met Gln Asn Asn Leu Leu Phe Leu Cys Lys Lys Tyr Tyr Asn Ile Ile
1               5                   10                  15 ttg aga aga aac atc aag ttg gtc acc gat aag tac acc atc aga gaa        96
Leu Arg Arg Asn Ile Lys Leu Val Thr Asp Lys Tyr Thr Ile Arg Glu
            20                  25                  30 atg aac gaa aga ttg gtc ttg gaa caa atc atc aag aac ggt cca att       144
Met Asn Glu Arg Leu Val Leu Glu Gln Ile Ile Lys Asn Gly Pro Ile
        35                  40                  45 tcc aga gct tct att gct tct act atc ggt ttg aac aag gct acc att       192
Ser Arg Ala Ser Ile Ala Ser Thr Ile Gly Leu Asn Lys Ala Thr Ile
    50                  55                  60 tct gcc att acc aag aag ttg att gac gaa tct ttg gtc cac gaa att       240
Ser Ala Ile Thr Lys Lys Leu Ile Asp Glu Ser Leu Val His Glu Ile
65                  70                  75                  80 ggt att ggt aac tct act cat tct ggt ggt aga aag cca atc ttg ttg       288
Gly Ile Gly Asn Ser Thr His Ser Gly Gly Arg Lys Pro Ile Leu Leu
                85                  90                  95 gtt ttt aac aag tgc gcc ggt atc tct ttg tct atg gat att ggt tac       336
Val Phe Asn Lys Cys Ala Gly Ile Ser Leu Ser Met Asp Ile Gly Tyr
            100                 105                 110 gac tac atc ttc tcc tca ttg tct tat ttg gac ggt act atc atc aac       384
Asp Tyr Ile Phe Ser Ser Leu Ser Tyr Leu Asp Gly Thr Ile Ile Asn
        115                 120                 125 tcc aaa aag ttg acc gat atc caa gtc tcc aag gat aac gtc att caa       432
Ser Lys Lys Leu Thr Asp Ile Gln Val Ser Lys Asp Asn Val Ile Gln
    130                 135                 140 ttg atc gac gaa att atc aac tcc tac aac att tcc aag atc gac act       480
Leu Ile Asp Glu Ile Ile Asn Ser Tyr Asn Ile Ser Lys Ile Asp Thr
145                 150                 155                 160 cca tac aag gtt att ggt ttg acc ttg gcc att cat ggt att acc tgt       528
Pro Tyr Lys Val Ile Gly Leu Thr Leu Ala Ile His Gly Ile Thr Cys
```

```
                Pro Tyr Lys Val Ile Gly Leu Thr Leu Ala Ile His Gly Ile Thr Cys
                            165                 170                 175 gaa aac aag gtt ttg ttc acc cct tac tac aac ttg aac gaa atc gac        576
Glu Asn Lys Val Leu Phe Thr Pro Tyr Tyr Asn Leu Asn Glu Ile Asp
            180                 185                 190 ttg tac tcc atc ttg tcc aag aaa tac gat ttc cca atc cac att gaa        624
Leu Tyr Ser Ile Leu Ser Lys Lys Tyr Asp Phe Pro Ile His Ile Glu
            195                 200                 205 aac gaa gct aac ttg act gct ttg gct gaa aac act ttc tct acc gtt        672
Asn Glu Ala Asn Leu Thr Ala Leu Ala Glu Asn Thr Phe Ser Thr Val
        210                 215                 220 cat aac tcc ttg ttg tct ttg tcc atc cat tct ggt ttt ggt tcc ggt        720
His Asn Ser Leu Leu Ser Leu Ser Ile His Ser Gly Phe Gly Ser Gly
225                 230                 235                 240 atc att atc aac aac aaa tta tac tcc ggt aga aac ggt atg tcc ggt        768
Ile Ile Ile Asn Asn Lys Leu Tyr Ser Gly Arg Asn Gly Met Ser Gly
                245                 250                 255 gaa att ggt cat acc att att atg cca aac ggt aaa ttg tgt cca tgc        816
Glu Ile Gly His Thr Ile Ile Met Pro Asn Gly Lys Leu Cys Pro Cys
            260                 265                 270 ggt aat aga ggt tgt ttg gaa caa tac tgc tcc gaa aag aag gtc ttt        864
Gly Asn Arg Gly Cys Leu Glu Gln Tyr Cys Ser Glu Lys Lys Val Phe
            275                 280                 285 gaa caa ttg tcc tcc ttg gaa aac atc cca aag atc gat tct gat atc        912
Glu Gln Leu Ser Ser Leu Glu Asn Ile Pro Lys Ile Asp Ser Asp Ile
        290                 295                 300 gtc aag caa ttg tac tac gaa gat aat caa aac gcc aag aag gtc atc        960
Val Lys Gln Leu Tyr Tyr Glu Asp Asn Gln Asn Ala Lys Lys Val Ile
305                 310                 315                 320 cac gaa ttt tgt tct tac ttg acc att gcc att aac aac gct att act       1008
His Glu Phe Cys Ser Tyr Leu Thr Ile Ala Ile Asn Asn Ala Ile Thr
                325                 330                 335 act tac gcc cca gaa atc atc tac ttg aac tcc caa att atc tct gac       1056
Thr Tyr Ala Pro Glu Ile Ile Tyr Leu Asn Ser Gln Ile Ile Ser Asp
            340                 345                 350 att cca gaa atc ttg caa atc acc aag gac atg ttg gtc agt tct ttc       1104
Ile Pro Glu Ile Leu Gln Ile Thr Lys Asp Met Leu Val Ser Ser Phe
        355                 360                 365 aac aag ggt atc aac atc gaa atc tcc agt ttg ggt tcc gaa gct tca       1152
Asn Lys Gly Ile Asn Ile Glu Ile Ser Ser Leu Gly Ser Glu Ala Ser
370                 375                 380 tta tat ggt ggt tct gct gtc aac atc aag agt ttc ttg aac atc caa       1200
Leu Tyr Gly Gly Ser Ala Val Asn Ile Lys Ser Phe Leu Asn Ile Gln
385                 390                 395                 400 aac ttg acc ttg att aac gaa ata ggt tcc cca aag aag aag aga aag       1248
Asn Leu Thr Leu Ile Asn Glu Ile Gly Ser Pro Lys Lys Lys Arg Lys
                405                 410                 415 gtt acc aga tga                                                       1260
Val Thr Arg <210> SEQ ID NO 72
<211> LENGTH: 419
<212> TYPE: PRT
<213> ORGANISM: Escherichia coli

<400> SEQUENCE: 72

Met Gln Asn Asn Leu Leu Phe Leu Cys Lys Lys Tyr Tyr Asn Ile Ile
1               5                   10                  15

Leu Arg Arg Asn Ile Lys Leu Val Thr Asp Lys Tyr Thr Ile Arg Glu
            20                  25                  30
```

Met Asn Glu Arg Leu Val Leu Glu Gln Ile Ile Lys Asn Gly Pro Ile
        35                  40                  45

Ser Arg Ala Ser Ile Ala Ser Thr Ile Gly Leu Asn Lys Ala Thr Ile
 50                  55                  60

Ser Ala Ile Thr Lys Lys Leu Ile Asp Glu Ser Leu Val His Glu Ile
 65                  70                  75                  80

Gly Ile Gly Asn Ser Thr His Ser Gly Gly Arg Lys Pro Ile Leu Leu
                 85                  90                  95

Val Phe Asn Lys Cys Ala Gly Ile Ser Leu Ser Met Asp Ile Gly Tyr
            100                 105                 110

Asp Tyr Ile Phe Ser Ser Leu Ser Tyr Leu Asp Gly Thr Ile Ile Asn
            115                 120                 125

Ser Lys Lys Leu Thr Asp Ile Gln Val Ser Lys Asp Asn Val Ile Gln
130                 135                 140

Leu Ile Asp Glu Ile Ile Asn Ser Tyr Asn Ile Ser Lys Ile Asp Thr
145                 150                 155                 160

Pro Tyr Lys Val Ile Gly Leu Thr Leu Ala Ile His Gly Ile Thr Cys
                165                 170                 175

Glu Asn Lys Val Leu Phe Thr Pro Tyr Tyr Asn Leu Asn Glu Ile Asp
            180                 185                 190

Leu Tyr Ser Ile Leu Ser Lys Lys Tyr Asp Phe Pro Ile His Ile Glu
            195                 200                 205

Asn Glu Ala Asn Leu Thr Ala Leu Ala Glu Asn Thr Phe Ser Thr Val
            210                 215                 220

His Asn Ser Leu Leu Ser Leu Ser Ile His Ser Gly Phe Gly Ser Gly
225                 230                 235                 240

Ile Ile Ile Asn Asn Lys Leu Tyr Ser Gly Arg Asn Gly Met Ser Gly
                245                 250                 255

Glu Ile Gly His Thr Ile Ile Met Pro Asn Gly Lys Leu Cys Pro Cys
            260                 265                 270

Gly Asn Arg Gly Cys Leu Glu Gln Tyr Cys Ser Glu Lys Lys Val Phe
            275                 280                 285

Glu Gln Leu Ser Ser Leu Glu Asn Ile Pro Lys Ile Asp Ser Asp Ile
            290                 295                 300

Val Lys Gln Leu Tyr Tyr Glu Asp Asn Gln Asn Ala Lys Lys Val Ile
305                 310                 315                 320

His Glu Phe Cys Ser Tyr Leu Thr Ile Ala Ile Asn Asn Ala Ile Thr
                325                 330                 335

Thr Tyr Ala Pro Glu Ile Ile Tyr Leu Asn Ser Gln Ile Ile Ser Asp
            340                 345                 350

Ile Pro Glu Ile Leu Gln Ile Thr Lys Asp Met Leu Val Ser Ser Phe
            355                 360                 365

Asn Lys Gly Ile Asn Ile Glu Ile Ser Ser Leu Gly Ser Glu Ala Ser
370                 375                 380

Leu Tyr Gly Gly Ser Ala Val Asn Ile Lys Ser Phe Leu Asn Ile Gln
385                 390                 395                 400

Asn Leu Thr Leu Ile Asn Glu Ile Gly Ser Pro Lys Lys Lys Arg Lys
                405                 410                 415

Val Thr Arg

<210> SEQ ID NO 73
<211> LENGTH: 351
<212> TYPE: DNA

<213> ORGANISM: Saccharomyces cerevisiae
<220> FEATURE:
<221> NAME/KEY: promoter
<222> LOCATION: (1)..(351)
<223> OTHER INFORMATION: xylR-xylose responsive promoter

<400> SEQUENCE: 73

```
atgtttctac tccttttta ctcttccaga ttttctcgga ctccgcgcat cgccgtacca      60
cttcaaaaca cccaagcaca gcatactaaa tttcccctct ttcttcctct agggtgtcgt     120
taattacccg tactaaaggt ttggaaaaga aaaagagac cgcctcgttt cttttcttc      180
gtcgaaaaag gcaataaaaa tttttatata aataagttag tttaatatac taacaaacta     240
atactttcaa cattttcagt ttgtattact tcttattcaa atgtcataaa agtatcaaca     300
aaaaattgtt aatatacctc tatactttaa cgtcaaggag aaaaaactat a              351
```

<210> SEQ ID NO 74
<211> LENGTH: 133
<212> TYPE: DNA
<213> ORGANISM: Escherichia coli
<220> FEATURE:
<221> NAME/KEY: misc_feature
<222> LOCATION: (1)..(133)
<223> OTHER INFORMATION: ThiMribo-wt (TPP) riboswitch

<400> SEQUENCE: 74

```
aaccaaacga ctcggggtgc ccttctgcgt gaaggctgag aaatacccgt atcacctgat      60
ctggataatg ccagcgtagg gaagtcacgg accaccaggt cattgcttct tcacgttatg     120
gcaggagcaa act                                                        133
```

<210> SEQ ID NO 75
<211> LENGTH: 1260
<212> TYPE: DNA
<213> ORGANISM: Escherichia coli
<220> FEATURE:
<221> NAME/KEY: CDS
<222> LOCATION: (1)..(1260)
<223> OTHER INFORMATION: MurA gene encodes UDP-N-acetylglucosamine
      enolpyruvyl transferase

<400> SEQUENCE: 75

```
atg gat aaa ttt cgt gtt cag ggg cca acg aag ctc cag ggc gaa gtc       48
Met Asp Lys Phe Arg Val Gln Gly Pro Thr Lys Leu Gln Gly Glu Val
1               5                   10                  15 aca att tcc ggc gct aaa aat gct gct ctg cct atc ctt ttt gcc gca       96
Thr Ile Ser Gly Ala Lys Asn Ala Ala Leu Pro Ile Leu Phe Ala Ala
            20                  25                  30 cta ctg gcg gaa gaa ccg gta gag atc cag aac gtc ccg aaa ctg aaa      144
Leu Leu Ala Glu Glu Pro Val Glu Ile Gln Asn Val Pro Lys Leu Lys
        35                  40                  45 gac gtc gat aca tca atg aag ctg cta agc cag ctg ggt gcg aaa gta      192
Asp Val Asp Thr Ser Met Lys Leu Leu Ser Gln Leu Gly Ala Lys Val
    50                  55                  60 gaa cgt aat ggt tct gtg cat att gat gcc cgc gac gtt aat gta ttc      240
Glu Arg Asn Gly Ser Val His Ile Asp Ala Arg Asp Val Asn Val Phe
65                  70                  75                  80 tgc gca cct tac gat ctg gtt aaa acc atg cgt gct tct atc tgg gcg      288
Cys Ala Pro Tyr Asp Leu Val Lys Thr Met Arg Ala Ser Ile Trp Ala
                85                  90                  95 ctg ggg ccg ctg gta gcg cgc ttt ggt cag ggg caa gtt tca cta cct      336
Leu Gly Pro Leu Val Ala Arg Phe Gly Gln Gly Gln Val Ser Leu Pro
            100                 105                 110
```

```
ggc ggt tgt acg atc ggt gcg cgt ccg gtt gat cta cac att tct ggc     384
Gly Gly Cys Thr Ile Gly Ala Arg Pro Val Asp Leu His Ile Ser Gly
        115                 120                 125 ctc gaa caa tta ggc gcg acc atc aaa ctg gaa gaa ggt tac gtt aaa     432
Leu Glu Gln Leu Gly Ala Thr Ile Lys Leu Glu Glu Gly Tyr Val Lys
130                 135                 140 gct tcc gtc gat ggt cgt ttg aaa ggt gca cat atc gtg atg gat aaa     480
Ala Ser Val Asp Gly Arg Leu Lys Gly Ala His Ile Val Met Asp Lys
145                 150                 155                 160 gtc agc gtt ggc gca acg gtg acc atc atg tgt gct gca acc ctg gcg     528
Val Ser Val Gly Ala Thr Val Thr Ile Met Cys Ala Ala Thr Leu Ala
                165                 170                 175 gaa ggc acc acg att att gaa aac gca gcg cgt gaa ccg gaa atc gtc     576
Glu Gly Thr Thr Ile Ile Glu Asn Ala Ala Arg Glu Pro Glu Ile Val
            180                 185                 190 gat acc gcg aac ttc ctg att acg ctg ggt gcg aaa att agc ggt cag     624
Asp Thr Ala Asn Phe Leu Ile Thr Leu Gly Ala Lys Ile Ser Gly Gln
        195                 200                 205 ggc acc gat cgt atc gtc atc gaa ggt gtg gaa cgt tta ggc ggc ggt     672
Gly Thr Asp Arg Ile Val Ile Glu Gly Val Glu Arg Leu Gly Gly Gly
210                 215                 220 gtc tat cgc gtt ctg ccg gat cgt atc gaa acc ggt act ttc ctg gtg     720
Val Tyr Arg Val Leu Pro Asp Arg Ile Glu Thr Gly Thr Phe Leu Val
225                 230                 235                 240 gcg gcg gcg att tct cgc ggc aaa att atc tgc cgt aac gcg cag cca     768
Ala Ala Ala Ile Ser Arg Gly Lys Ile Ile Cys Arg Asn Ala Gln Pro
                245                 250                 255 gat act ctc gac gcc gtg ctg gcg aaa ctg cgt gac gct gga gcg gac     816
Asp Thr Leu Asp Ala Val Leu Ala Lys Leu Arg Asp Ala Gly Ala Asp
            260                 265                 270 atc gaa gtc ggc gaa gac tgg att agc ctg gat atg cat ggc aaa cgt     864
Ile Glu Val Gly Glu Asp Trp Ile Ser Leu Asp Met His Gly Lys Arg
        275                 280                 285 ccg aag gct gtt aac gta cgt acc gcg ccg cat ccg gca ttc ccg acc     912
Pro Lys Ala Val Asn Val Arg Thr Ala Pro His Pro Ala Phe Pro Thr
290                 295                 300 gat atg cag gcc cag ttc acg ctg ttg aac ctg gtg gca gaa ggg acc     960
Asp Met Gln Ala Gln Phe Thr Leu Leu Asn Leu Val Ala Glu Gly Thr
305                 310                 315                 320 ggg ttt atc acc gaa acg gtc ttt gaa aac cgc ttt atg cat gtg cca    1008
Gly Phe Ile Thr Glu Thr Val Phe Glu Asn Arg Phe Met His Val Pro
                325                 330                 335 gag ctg agc cgt atg ggc gcg cac gcc gaa atc gaa agc aat acc gtt    1056
Glu Leu Ser Arg Met Gly Ala His Ala Glu Ile Glu Ser Asn Thr Val
            340                 345                 350 att tgt cac ggt gtt gaa aaa ctt tct ggc gca cag gtt atg gca acc    1104
Ile Cys His Gly Val Glu Lys Leu Ser Gly Ala Gln Val Met Ala Thr
        355                 360                 365 gat ctg cgt gca tca gca agc ctg gtg ctg gct ggc tgt att gcg gaa    1152
Asp Leu Arg Ala Ser Ala Ser Leu Val Leu Ala Gly Cys Ile Ala Glu
370                 375                 380 ggg acg acg gtg gtt gat cgt att tat cac atc gat cgt ggc tac gaa    1200
Gly Thr Thr Val Val Asp Arg Ile Tyr His Ile Asp Arg Gly Tyr Glu
385                 390                 395                 400 cgc att gaa gac aaa ctg cgc gct tta ggt gca aat att gag cgt gtg    1248
Arg Ile Glu Asp Lys Leu Arg Ala Leu Gly Ala Asn Ile Glu Arg Val
                405                 410                 415 aaa ggc gaa taa                                                    1260
Lys Gly Glu
```

```
<210> SEQ ID NO 76
<211> LENGTH: 419
<212> TYPE: PRT
<213> ORGANISM: Escherichia coli

<400> SEQUENCE: 76

Met Asp Lys Phe Arg Val Gln Gly Pro Thr Lys Leu Gln Gly Glu Val
1               5                   10                  15

Thr Ile Ser Gly Ala Lys Asn Ala Ala Leu Pro Ile Leu Phe Ala Ala
            20                  25                  30

Leu Leu Ala Glu Glu Pro Val Glu Ile Gln Asn Val Pro Lys Leu Lys
        35                  40                  45

Asp Val Asp Thr Ser Met Lys Leu Leu Ser Gln Leu Gly Ala Lys Val
    50                  55                  60

Glu Arg Asn Gly Ser Val His Ile Asp Ala Arg Asp Val Asn Val Phe
65                  70                  75                  80

Cys Ala Pro Tyr Asp Leu Val Lys Thr Met Arg Ala Ser Ile Trp Ala
                85                  90                  95

Leu Gly Pro Leu Val Ala Arg Phe Gly Gln Gly Gln Val Ser Leu Pro
            100                 105                 110

Gly Gly Cys Thr Ile Gly Ala Arg Pro Val Asp Leu His Ile Ser Gly
        115                 120                 125

Leu Glu Gln Leu Gly Ala Thr Ile Lys Leu Glu Glu Gly Tyr Val Lys
    130                 135                 140

Ala Ser Val Asp Gly Arg Leu Lys Gly Ala His Ile Val Met Asp Lys
145                 150                 155                 160

Val Ser Val Gly Ala Thr Val Thr Ile Met Cys Ala Ala Thr Leu Ala
                165                 170                 175

Glu Gly Thr Thr Ile Ile Glu Asn Ala Ala Arg Glu Pro Glu Ile Val
            180                 185                 190

Asp Thr Ala Asn Phe Leu Ile Thr Leu Gly Ala Lys Ile Ser Gly Gln
        195                 200                 205

Gly Thr Asp Arg Ile Val Ile Glu Gly Val Glu Arg Leu Gly Gly Gly
    210                 215                 220

Val Tyr Arg Val Leu Pro Asp Arg Ile Glu Thr Gly Thr Phe Leu Val
225                 230                 235                 240

Ala Ala Ala Ile Ser Arg Gly Lys Ile Ile Cys Arg Asn Ala Gln Pro
                245                 250                 255

Asp Thr Leu Asp Ala Val Leu Ala Lys Leu Arg Asp Ala Gly Ala Asp
            260                 265                 270

Ile Glu Val Gly Glu Asp Trp Ile Ser Leu Asp Met His Gly Lys Arg
        275                 280                 285

Pro Lys Ala Val Asn Val Arg Thr Ala Pro His Pro Ala Phe Pro Thr
    290                 295                 300

Asp Met Gln Ala Gln Phe Thr Leu Leu Asn Leu Val Ala Glu Gly Thr
305                 310                 315                 320

Gly Phe Ile Thr Glu Thr Val Phe Glu Asn Arg Phe Met His Val Pro
                325                 330                 335

Glu Leu Ser Arg Met Gly Ala His Ala Glu Ile Glu Ser Asn Thr Val
            340                 345                 350

Ile Cys His Gly Val Glu Lys Leu Ser Gly Ala Gln Val Met Ala Thr
        355                 360                 365

Asp Leu Arg Ala Ser Ala Ser Leu Val Leu Ala Gly Cys Ile Ala Glu
    370                 375                 380
```

```
Gly Thr Thr Val Val Asp Arg Ile Tyr His Ile Asp Arg Gly Tyr Glu
385                 390                 395                 400

Arg Ile Glu Asp Lys Leu Arg Ala Leu Gly Ala Asn Ile Glu Arg Val
            405                 410                 415

Lys Gly Glu

<210> SEQ ID NO 77
<211> LENGTH: 1083
<212> TYPE: DNA
<213> ORGANISM: Escherichia coli
<220> FEATURE:
<221> NAME/KEY: CDS
<222> LOCATION: (1)..(1083)
<223> OTHER INFORMATION: mraY gene encodes UDP-MurNAc-pentapeptide
      phosphotransferase

<400> SEQUENCE: 77 atg tta gtt tgg ctg gcc gaa cat ttg gtc aaa tat tat tcc ggc ttt      48
Met Leu Val Trp Leu Ala Glu His Leu Val Lys Tyr Tyr Ser Gly Phe
1               5                   10                  15 aac gtc ttt tcc tat ctg acg ttt cgc gcc atc gtc agc ctg ctg acc      96
Asn Val Phe Ser Tyr Leu Thr Phe Arg Ala Ile Val Ser Leu Leu Thr
                20                  25                  30 gcg ctg ttc atc tca ttg tgg atg ggc ccg cgt atg att gct cat ttg     144
Ala Leu Phe Ile Ser Leu Trp Met Gly Pro Arg Met Ile Ala His Leu
            35                  40                  45 caa aaa ctt tcc ttt ggt cag gtg gtg cgt aac gac ggt cct gaa tca     192
Gln Lys Leu Ser Phe Gly Gln Val Val Arg Asn Asp Gly Pro Glu Ser
        50                  55                  60 cac ttc agc aag cgc ggt acg ccg acc atg ggc ggg att atg atc ctg     240
His Phe Ser Lys Arg Gly Thr Pro Thr Met Gly Gly Ile Met Ile Leu
65                  70                  75                  80 acg gcg att gtg atc tcc gta ctg ctg tgg gct tac ccg tcc aat ccg     288
Thr Ala Ile Val Ile Ser Val Leu Leu Trp Ala Tyr Pro Ser Asn Pro
                85                  90                  95 tac gtc tgg tgc gtg ttg gtg gtg ctg gta ggt tac ggt gtt att ggc     336
Tyr Val Trp Cys Val Leu Val Val Leu Val Gly Tyr Gly Val Ile Gly
                100                 105                 110 ttt gtt gat gat tat cgc aaa gtg gtg cgt aaa gac acc aaa ggg ttg     384
Phe Val Asp Asp Tyr Arg Lys Val Val Arg Lys Asp Thr Lys Gly Leu
            115                 120                 125 atc gct cgt tgg aag tat ttc tgg atg tcg gtc att gcg ctg ggt gtc     432
Ile Ala Arg Trp Lys Tyr Phe Trp Met Ser Val Ile Ala Leu Gly Val
        130                 135                 140 gcc ttc gcc ctg tac ctt gcc ggc aaa gac acg ccc gca acg cag ctg     480
Ala Phe Ala Leu Tyr Leu Ala Gly Lys Asp Thr Pro Ala Thr Gln Leu
145                 150                 155                 160 gtg gtc cca ttc ttt aaa gat gtg atg ccg cag ctg ggg ctg ttc tac     528
Val Val Pro Phe Phe Lys Asp Val Met Pro Gln Leu Gly Leu Phe Tyr
                165                 170                 175 att ctg ctg gct tac ttc gtc att gtg ggt act ggc aac gcg gta aac     576
Ile Leu Leu Ala Tyr Phe Val Ile Val Gly Thr Gly Asn Ala Val Asn
                180                 185                 190 ctg acc gat ggt ctc gac ggc ctg gca att atg ccg acc gta ttt gtc     624
Leu Thr Asp Gly Leu Asp Gly Leu Ala Ile Met Pro Thr Val Phe Val
            195                 200                 205 gcc ggt ggt ttt gcg ctg gtg gcg tgg gcg acc ggc aat atg aac ttt     672
Ala Gly Gly Phe Ala Leu Val Ala Trp Ala Thr Gly Asn Met Asn Phe
        210                 215                 220 gcc agc tac ttg cat ata ccg tat ctg cga cac gcc ggg gaa ctg gtt     720
```

```
Ala Ser Tyr Leu His Ile Pro Tyr Leu Arg His Ala Gly Glu Leu Val
225                 230                 235                 240 att gtc tgt acc gcg ata gtc ggg gca gga ctg ggc ttc ctg tgg ttt      768
Ile Val Cys Thr Ala Ile Val Gly Ala Gly Leu Gly Phe Leu Trp Phe
                    245                 250                 255 aac acc tat ccg gcg cag gtc ttt atg ggc gat gta ggt tcg ctg gcg      816
Asn Thr Tyr Pro Ala Gln Val Phe Met Gly Asp Val Gly Ser Leu Ala
                260                 265                 270 tta ggt ggt gcg tta ggc att atc gcc gta ctg cta cgt cag gaa ttc      864
Leu Gly Gly Ala Leu Gly Ile Ile Ala Val Leu Leu Arg Gln Glu Phe
            275                 280                 285 ctg ctg gtg att atg ggg ggc gtg ttc gtg gta gaa acg ctt tct gtc      912
Leu Leu Val Ile Met Gly Gly Val Phe Val Val Glu Thr Leu Ser Val
        290                 295                 300 atc ctg cag gtc ggc tcc ttt aaa ctg cgc gga caa cgt att ttc cgc      960
Ile Leu Gln Val Gly Ser Phe Lys Leu Arg Gly Gln Arg Ile Phe Arg
305                 310                 315                 320 atg gca ccg att cat cac cac tat gaa ctg aaa ggc tgg ccg gaa ccg     1008
Met Ala Pro Ile His His His Tyr Glu Leu Lys Gly Trp Pro Glu Pro
                    325                 330                 335 cgc gtc att gtg cgt ttc tgg att att tcg ctg atg ctg gtt ctg att     1056
Arg Val Ile Val Arg Phe Trp Ile Ile Ser Leu Met Leu Val Leu Ile
                340                 345                 350 ggt ctg gca acg ctg aag gta cgt taa                                 1083
Gly Leu Ala Thr Leu Lys Val Arg
            355                 360

<210> SEQ ID NO 78
<211> LENGTH: 360
<212> TYPE: PRT
<213> ORGANISM: Escherichia coli

<400> SEQUENCE: 78

Met Leu Val Trp Leu Ala Glu His Leu Val Lys Tyr Tyr Ser Gly Phe
1               5                   10                  15

Asn Val Phe Ser Tyr Leu Thr Phe Arg Ala Ile Val Ser Leu Leu Thr
            20                  25                  30

Ala Leu Phe Ile Ser Leu Trp Met Gly Pro Arg Met Ile Ala His Leu
        35                  40                  45

Gln Lys Leu Ser Phe Gly Gln Val Val Arg Asn Asp Gly Pro Glu Ser
    50                  55                  60

His Phe Ser Lys Arg Gly Thr Pro Thr Met Gly Gly Ile Met Ile Leu
65                  70                  75                  80

Thr Ala Ile Val Ile Ser Val Leu Leu Trp Ala Tyr Pro Ser Asn Pro
                85                  90                  95

Tyr Val Trp Cys Val Leu Val Val Leu Val Gly Tyr Gly Val Ile Gly
            100                 105                 110

Phe Val Asp Asp Tyr Arg Lys Val Val Arg Lys Asp Thr Lys Gly Leu
        115                 120                 125

Ile Ala Arg Trp Lys Tyr Phe Trp Met Ser Val Ile Ala Leu Gly Val
    130                 135                 140

Ala Phe Ala Leu Tyr Leu Ala Gly Lys Asp Thr Pro Ala Thr Gln Leu
145                 150                 155                 160

Val Val Pro Phe Phe Lys Asp Val Met Pro Gln Leu Gly Leu Phe Tyr
                165                 170                 175

Ile Leu Leu Ala Tyr Phe Val Ile Val Gly Thr Gly Asn Ala Val Asn
            180                 185                 190
```

```
Leu Thr Asp Gly Leu Asp Gly Leu Ala Ile Met Pro Thr Val Phe Val
        195                 200                 205

Ala Gly Gly Phe Ala Leu Val Ala Trp Ala Thr Gly Asn Met Asn Phe
    210                 215                 220

Ala Ser Tyr Leu His Ile Pro Tyr Leu Arg His Ala Gly Glu Leu Val
225                 230                 235                 240

Ile Val Cys Thr Ala Ile Val Gly Ala Gly Leu Gly Phe Leu Trp Phe
                245                 250                 255

Asn Thr Tyr Pro Ala Gln Val Phe Met Gly Asp Val Gly Ser Leu Ala
            260                 265                 270

Leu Gly Gly Ala Leu Gly Ile Ile Ala Val Leu Leu Arg Gln Glu Phe
        275                 280                 285

Leu Leu Val Ile Met Gly Gly Val Phe Val Val Glu Thr Leu Ser Val
    290                 295                 300

Ile Leu Gln Val Gly Ser Phe Lys Leu Arg Gly Gln Arg Ile Phe Arg
305                 310                 315                 320

Met Ala Pro Ile His His His Tyr Glu Leu Lys Gly Trp Pro Glu Pro
                325                 330                 335

Arg Val Ile Val Arg Phe Trp Ile Ile Ser Leu Met Leu Val Leu Ile
            340                 345                 350

Gly Leu Ala Thr Leu Lys Val Arg
        355                 360

<210> SEQ ID NO 79
<211> LENGTH: 1338
<212> TYPE: DNA
<213> ORGANISM: Escherichia coli
<220> FEATURE:
<221> NAME/KEY: CDS
<222> LOCATION: (1)..(1338)
<223> OTHER INFORMATION: glmM encodes a phosphoglucosamine mutase

<400> SEQUENCE: 79 atg agt aat cgt aaa tat ttc ggt acc gat ggg att cgt ggt cgt gta      48
Met Ser Asn Arg Lys Tyr Phe Gly Thr Asp Gly Ile Arg Gly Arg Val
1               5                   10                  15 ggg gat gcg ccg atc aca cct gat ttt gtg ctt aag ctg ggt tgg gcc      96
Gly Asp Ala Pro Ile Thr Pro Asp Phe Val Leu Lys Leu Gly Trp Ala
                20                  25                  30 gcg ggt aaa gtg ctg gcg cgc cac ggc tcc cgt aag att att att ggt     144
Ala Gly Lys Val Leu Ala Arg His Gly Ser Arg Lys Ile Ile Ile Gly
            35                  40                  45 aaa gac acg cgt att tct ggc tat atg ctg gag tca gca ctg gaa gcg     192
Lys Asp Thr Arg Ile Ser Gly Tyr Met Leu Glu Ser Ala Leu Glu Ala
        50                  55                  60 ggt ctg gcg gca gcg ggc ctt tcc gca ctc ttc act ggc ccg atg cca     240
Gly Leu Ala Ala Ala Gly Leu Ser Ala Leu Phe Thr Gly Pro Met Pro
65                  70                  75                  80 aca ccg gcc gtg gct tat ctg acg cgt acc ttc cgc gca gag gcc gga     288
Thr Pro Ala Val Ala Tyr Leu Thr Arg Thr Phe Arg Ala Glu Ala Gly
                85                  90                  95 att gtg ata tct gca tcg cat aac ccg ttc tac gat aat ggc att aaa     336
Ile Val Ile Ser Ala Ser His Asn Pro Phe Tyr Asp Asn Gly Ile Lys
            100                 105                 110 ttc ttc tct atc gac ggc acc aaa ctg ccg gat gcg gta gaa gag gcc     384
Phe Phe Ser Ile Asp Gly Thr Lys Leu Pro Asp Ala Val Glu Glu Ala
        115                 120                 125 atc gaa gcg gaa atg gaa aag gag atc agc tgc gtt gat tcg gca gaa     432
Ile Glu Ala Glu Met Glu Lys Glu Ile Ser Cys Val Asp Ser Ala Glu
```

```
            130                 135                 140
ctg ggt aaa gcc agc cgt atc gtt gat gcc gcg ggt cgc tat atc gag    480
Leu Gly Lys Ala Ser Arg Ile Val Asp Ala Ala Gly Arg Tyr Ile Glu
145                 150                 155                 160 ttt tgc aaa gcc acg ttc ccg aac gaa ctt agc ctc agt gaa ctg aag    528
Phe Cys Lys Ala Thr Phe Pro Asn Glu Leu Ser Leu Ser Glu Leu Lys
                165                 170                 175 att gtg gtg gat tgt gca aac ggt gcg act tat cac atc gcg ccg aac    576
Ile Val Val Asp Cys Ala Asn Gly Ala Thr Tyr His Ile Ala Pro Asn
            180                 185                 190 gtg ctg cgc gaa ctg ggg gcg aac gtt atc gct atc ggt tgt gag cca    624
Val Leu Arg Glu Leu Gly Ala Asn Val Ile Ala Ile Gly Cys Glu Pro
        195                 200                 205 aac ggt gta aac atc aat gcc gaa gtg ggg gct acc gac gtt cgc gcg    672
Asn Gly Val Asn Ile Asn Ala Glu Val Gly Ala Thr Asp Val Arg Ala
    210                 215                 220 ctc cag gct cgt gtg ctg gct gaa aaa gcg gat ctc ggt att gcc ttc    720
Leu Gln Ala Arg Val Leu Ala Glu Lys Ala Asp Leu Gly Ile Ala Phe
225                 230                 235                 240 gac ggc gat ggc gat cgc gtg att atg gtt gac cat gaa ggc aat aaa    768
Asp Gly Asp Gly Asp Arg Val Ile Met Val Asp His Glu Gly Asn Lys
                245                 250                 255 gtc gat ggc gat cag atc atg tat atc atc gcg cgt gaa ggt ctt cgt    816
Val Asp Gly Asp Gln Ile Met Tyr Ile Ile Ala Arg Glu Gly Leu Arg
            260                 265                 270 cag ggc cag ctg cgt ggt ggc gct gtg ggt aca ttg atg agc aac atg    864
Gln Gly Gln Leu Arg Gly Gly Ala Val Gly Thr Leu Met Ser Asn Met
        275                 280                 285 ggg ctt gaa ctg gcg ctg aaa cag tta gga att cca ttt gcg cgc gcg    912
Gly Leu Glu Leu Ala Leu Lys Gln Leu Gly Ile Pro Phe Ala Arg Ala
    290                 295                 300 aaa gtg ggt gac cgc tac gta ctg gaa aaa atg cag gag aaa ggc tgg    960
Lys Val Gly Asp Arg Tyr Val Leu Glu Lys Met Gln Glu Lys Gly Trp
305                 310                 315                 320 cgt atc ggt gca gag aat tcc ggt cat gtg atc ctg ctg gat aaa act   1008
Arg Ile Gly Ala Glu Asn Ser Gly His Val Ile Leu Leu Asp Lys Thr
                325                 330                 335 act acc ggt gac ggc atc gtt gct ggc ttg cag gtg ctg gcg gcg atg   1056
Thr Thr Gly Asp Gly Ile Val Ala Gly Leu Gln Val Leu Ala Ala Met
            340                 345                 350 gca cgt aac cat atg agc ctg cac gac ctt tgc agc ggc atg aaa atg   1104
Ala Arg Asn His Met Ser Leu His Asp Leu Cys Ser Gly Met Lys Met
        355                 360                 365 ttc ccg cag att ctg gtt aac gta cgt tac acc gca ggt agc ggc gat   1152
Phe Pro Gln Ile Leu Val Asn Val Arg Tyr Thr Ala Gly Ser Gly Asp
    370                 375                 380 cca ctt gag cat gag tca gtt aaa gcc gtg acc gca gag gtt gaa gct   1200
Pro Leu Glu His Glu Ser Val Lys Ala Val Thr Ala Glu Val Glu Ala
385                 390                 395                 400 gcg ctg ggc aac cgt gga cgc gtg ttg ctg cgt aaa tcc ggc acc gaa   1248
Ala Leu Gly Asn Arg Gly Arg Val Leu Leu Arg Lys Ser Gly Thr Glu
                405                 410                 415 ccg tta att cgc gtg atg gtg gaa ggc gaa gac gaa gcg cag gtg act   1296
Pro Leu Ile Arg Val Met Val Glu Gly Glu Asp Glu Ala Gln Val Thr
            420                 425                 430 gaa ttt gca cac cgc atc gcc gat gca gta aaa gcc gtt taa            1338
Glu Phe Ala His Arg Ile Ala Asp Ala Val Lys Ala Val
        435                 440                 445
```

```
<210> SEQ ID NO 80
<211> LENGTH: 445
<212> TYPE: PRT
<213> ORGANISM: Escherichia coli

<400> SEQUENCE: 80

Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
            20                  25                  30

Ala Gly Lys Val Leu Ala Arg His Gly Ser Arg Lys Ile Ile Ile Gly
        35                  40                  45

Lys Asp Thr Arg Ile Ser Gly Tyr Met Leu Glu Ser Ala Leu Glu Ala
    50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95

Ile Val Ile Ser Ala Ser His Asn Pro Phe Tyr Asp Asn Gly Ile Lys
            100                 105                 110

Phe Phe Ser Ile Asp Gly Thr Lys Leu Pro Asp Ala Val Glu Glu Ala
        115                 120                 125

Ile Glu Ala Glu Met Glu Lys Glu Ile Ser Cys Val Asp Ser Ala Glu
    130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
                165                 170                 175

Ile Val Val Asp Cys Ala Asn Gly Ala Thr Tyr His Ile Ala Pro Asn
            180                 185                 190

Val Leu Arg Glu Leu Gly Ala Asn Val Ile Ala Ile Gly Cys Glu Pro
        195                 200                 205

Asn Gly Val Asn Ile Asn Ala Glu Val Gly Ala Thr Asp Val Arg Ala
    210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
                245                 250                 255

Val Asp Gly Asp Gln Ile Met Tyr Ile Ile Ala Arg Glu Gly Leu Arg
            260                 265                 270

Gln Gly Gln Leu Arg Gly Gly Ala Val Gly Thr Leu Met Ser Asn Met
        275                 280                 285

Gly Leu Glu Leu Ala Leu Lys Gln Leu Gly Ile Pro Phe Ala Arg Ala
    290                 295                 300

Lys Val Gly Asp Arg Tyr Val Leu Glu Lys Met Gln Glu Lys Gly Trp
305                 310                 315                 320

Arg Ile Gly Ala Glu Asn Ser Gly His Val Ile Leu Leu Asp Lys Thr
                325                 330                 335

Thr Thr Gly Asp Gly Ile Val Ala Gly Leu Gln Val Leu Ala Ala Met
            340                 345                 350

Ala Arg Asn His Met Ser Leu His Asp Leu Cys Ser Gly Met Lys Met
        355                 360                 365

Phe Pro Gln Ile Leu Val Asn Val Arg Tyr Thr Ala Gly Ser Gly Asp
    370                 375                 380
```

```
Pro Leu Glu His Glu Ser Val Lys Ala Val Thr Ala Glu Val Glu Ala
385                 390                 395                 400

Ala Leu Gly Asn Arg Gly Arg Val Leu Arg Lys Ser Gly Thr Glu
                405                 410                 415

Pro Leu Ile Arg Val Met Val Glu Gly Glu Asp Glu Ala Gln Val Thr
                420                 425                 430

Glu Phe Ala His Arg Ile Ala Asp Ala Val Lys Ala Val
                435                 440                 445

<210> SEQ ID NO 81
<211> LENGTH: 858
<212> TYPE: DNA
<213> ORGANISM: Escherichia coli
<220> FEATURE:
<221> NAME/KEY: CDS
<222> LOCATION: (1)..(858)
<223> OTHER INFORMATION: murI gene encoding a glutamase racemase

<400> SEQUENCE: 81 atg gct acc aaa ctg cag gac ggg aat aca cct tgt ctg gca gct aca      48
Met Ala Thr Lys Leu Gln Asp Gly Asn Thr Pro Cys Leu Ala Ala Thr
1               5                   10                  15 cct tct gaa cca cgt ccc acc gtg ctg gtg ttt gac tcc ggc gtc ggt      96
Pro Ser Glu Pro Arg Pro Thr Val Leu Val Phe Asp Ser Gly Val Gly
            20                  25                  30 ggg ttg tcg gtc tat gac gag atc cgg cat ctc tta ccg gat ctc cat    144
Gly Leu Ser Val Tyr Asp Glu Ile Arg His Leu Leu Pro Asp Leu His
        35                  40                  45 tac att tat gct ttc gat aac gtc gct ttc ccg tat ggc gaa aaa agc    192
Tyr Ile Tyr Ala Phe Asp Asn Val Ala Phe Pro Tyr Gly Glu Lys Ser
    50                  55                  60 gaa gcg ttt att gtt gag cga gtg gtg gca att gtc acc gcg gtg caa    240
Glu Ala Phe Ile Val Glu Arg Val Val Ala Ile Val Thr Ala Val Gln
65                  70                  75                  80 gaa cgt tat ccc ctt gcg ctg gct gtg gtc gct tgc aac act gcc agt    288
Glu Arg Tyr Pro Leu Ala Leu Ala Val Val Ala Cys Asn Thr Ala Ser
                85                  90                  95 acc gtt tca ctt cct gca tta cgc gaa aag ttc gac ttc ccg gtt gtt    336
Thr Val Ser Leu Pro Ala Leu Arg Glu Lys Phe Asp Phe Pro Val Val
            100                 105                 110 ggt gtc gtg ccg gcg att aaa cct gct gca cgt ctg acg gca aat ggc    384
Gly Val Val Pro Ala Ile Lys Pro Ala Ala Arg Leu Thr Ala Asn Gly
        115                 120                 125 att gtc gga tta ctg gca acc cgc gga aca gtt aaa cgt tct tat act    432
Ile Val Gly Leu Leu Ala Thr Arg Gly Thr Val Lys Arg Ser Tyr Thr
    130                 135                 140 cat gag ctg atc gcg cgt ttc gct aat gaa tgc cag ata gaa atg ctg    480
His Glu Leu Ile Ala Arg Phe Ala Asn Glu Cys Gln Ile Glu Met Leu
145                 150                 155                 160 ggc tcg gca gag atg gtt gag ttg gct gaa gcg aag cta cat ggc gaa    528
Gly Ser Ala Glu Met Val Glu Leu Ala Glu Ala Lys Leu His Gly Glu
                165                 170                 175 gat gtt tct ctg gat gca cta aaa cgt atc cta cgc ccg tgg tta aga    576
Asp Val Ser Leu Asp Ala Leu Lys Arg Ile Leu Arg Pro Trp Leu Arg
            180                 185                 190 atg aaa gag ccg cca gat acc gtt gta ttg ggt tgc acc cat ttc cct    624
Met Lys Glu Pro Pro Asp Thr Val Val Leu Gly Cys Thr His Phe Pro
        195                 200                 205 cta cta caa gaa gaa ctg tta caa gtg ctg cca gag gga acc cgg ctg    672
Leu Leu Gln Glu Glu Leu Leu Gln Val Leu Pro Glu Gly Thr Arg Leu
    210                 215                 220
```

-continued

```
gtg gat tct ggc gca gcg att gct cgc cga acg gcc tgg ttg tta gaa      720
Val Asp Ser Gly Ala Ala Ile Ala Arg Arg Thr Ala Trp Leu Leu Glu
225                 230                 235                 240 cat gaa gcc ccg gat gca aaa tct gcc gat gcg aat att gcc ttt tgt      768
His Glu Ala Pro Asp Ala Lys Ser Ala Asp Ala Asn Ile Ala Phe Cys
            245                 250                 255 atg gca atg acg cca gga gct gaa caa tta ttg ccc gtt tta cag cgt      816
Met Ala Met Thr Pro Gly Ala Glu Gln Leu Leu Pro Val Leu Gln Arg
        260                 265                 270 tac ggc ttc gaa acg ctc gaa aaa ctg gca gtt tta ggc tga              858
Tyr Gly Phe Glu Thr Leu Glu Lys Leu Ala Val Leu Gly
    275                 280                 285
```

<210> SEQ ID NO 82
<211> LENGTH: 285
<212> TYPE: PRT
<213> ORGANISM: Escherichia coli

<400> SEQUENCE: 82

```
Met Ala Thr Lys Leu Gln Asp Gly Asn Thr Pro Cys Leu Ala Ala Thr
1               5                   10                  15

Pro Ser Glu Pro Arg Pro Thr Val Leu Val Phe Asp Ser Gly Val Gly
            20                  25                  30

Gly Leu Ser Val Tyr Asp Glu Ile Arg His Leu Leu Pro Asp Leu His
        35                  40                  45

Tyr Ile Tyr Ala Phe Asp Asn Val Ala Phe Pro Tyr Gly Glu Lys Ser
    50                  55                  60

Glu Ala Phe Ile Val Glu Arg Val Val Ala Ile Val Thr Ala Val Gln
65                  70                  75                  80

Glu Arg Tyr Pro Leu Ala Leu Ala Val Val Ala Cys Asn Thr Ala Ser
                85                  90                  95

Thr Val Ser Leu Pro Ala Leu Arg Glu Lys Phe Asp Phe Pro Val Val
            100                 105                 110

Gly Val Val Pro Ala Ile Lys Pro Ala Ala Arg Leu Thr Ala Asn Gly
        115                 120                 125

Ile Val Gly Leu Leu Ala Thr Arg Gly Thr Val Lys Arg Ser Tyr Thr
    130                 135                 140

His Glu Leu Ile Ala Arg Phe Ala Asn Glu Cys Gln Ile Glu Met Leu
145                 150                 155                 160

Gly Ser Ala Glu Met Val Glu Leu Ala Glu Ala Lys Leu His Gly Glu
                165                 170                 175

Asp Val Ser Leu Asp Ala Leu Lys Arg Ile Leu Arg Pro Trp Leu Arg
            180                 185                 190

Met Lys Glu Pro Pro Asp Thr Val Val Leu Gly Cys Thr His Phe Pro
        195                 200                 205

Leu Leu Gln Glu Glu Leu Leu Gln Val Leu Pro Glu Gly Thr Arg Leu
    210                 215                 220

Val Asp Ser Gly Ala Ala Ile Ala Arg Arg Thr Ala Trp Leu Leu Glu
225                 230                 235                 240

His Glu Ala Pro Asp Ala Lys Ser Ala Asp Ala Asn Ile Ala Phe Cys
                245                 250                 255

Met Ala Met Thr Pro Gly Ala Glu Gln Leu Leu Pro Val Leu Gln Arg
            260                 265                 270

Tyr Gly Phe Glu Thr Leu Glu Lys Leu Ala Val Leu Gly
        275                 280                 285
```

-continued

```
<210> SEQ ID NO 83
<211> LENGTH: 591
<212> TYPE: DNA
<213> ORGANISM: Escherichia coli
<220> FEATURE:
<221> NAME/KEY: CDS
<222> LOCATION: (1)..(591)
<223> OTHER INFORMATION: ribA gene encoding a GTP cyclohydrolase II

<400> SEQUENCE: 83 atg cag ctt aaa cgt gtg gca gaa gcc aaa ctg cca acc cca tgg ggc      48
Met Gln Leu Lys Arg Val Ala Glu Ala Lys Leu Pro Thr Pro Trp Gly
1               5                   10                  15 gat ttc ctg atg gtg gga ttt gaa gaa ctg gca acc gga cac gat cat      96
Asp Phe Leu Met Val Gly Phe Glu Glu Leu Ala Thr Gly His Asp His
                20                  25                  30 gtc gcg cta gtc tat ggc gat att tcc ggg cat acc ccg gta ctt gcg     144
Val Ala Leu Val Tyr Gly Asp Ile Ser Gly His Thr Pro Val Leu Ala
            35                  40                  45 cgc gtc cat tcc gaa tgt ctg acc ggt gac gcc ctg ttc agc ttg cgc     192
Arg Val His Ser Glu Cys Leu Thr Gly Asp Ala Leu Phe Ser Leu Arg
        50                  55                  60 tgc gat tgt ggc ttc cag ctc gaa gcg gca ttg acg caa att gcc gag     240
Cys Asp Cys Gly Phe Gln Leu Glu Ala Ala Leu Thr Gln Ile Ala Glu
65                  70                  75                  80 gaa ggc cgt ggt att ttg cta tac cgt cag gaa ggt cgt aac att         288
Glu Gly Arg Gly Ile Leu Leu Tyr His Arg Gln Glu Gly Arg Asn Ile
                85                  90                  95 ggt ctg ctg aat aaa atc cgc gct tac gca ctg cag gat caa ggt tac     336
Gly Leu Leu Asn Lys Ile Arg Ala Tyr Ala Leu Gln Asp Gln Gly Tyr
                100                 105                 110 gat acc gta gag gct aac cac cag tta ggc ttc gcc gct gat gag cgc     384
Asp Thr Val Glu Ala Asn His Gln Leu Gly Phe Ala Ala Asp Glu Arg
            115                 120                 125 gac ttc act ctt tgc gct gat atg ttc aaa ctc ctt ggc gtc aat gaa     432
Asp Phe Thr Leu Cys Ala Asp Met Phe Lys Leu Leu Gly Val Asn Glu
        130                 135                 140 gtc cgc ttg tta acc aat aac ccg aaa aaa gtc gaa att ctg acc gaa     480
Val Arg Leu Leu Thr Asn Asn Pro Lys Lys Val Glu Ile Leu Thr Glu
145                 150                 155                 160 gca ggg att aat att gtt gaa cgc gta cca ttg att gta ggt cgt aac     528
Ala Gly Ile Asn Ile Val Glu Arg Val Pro Leu Ile Val Gly Arg Asn
                165                 170                 175 ccc aat aac gaa cat tat ctc gat acc aaa gcc gag aaa atg ggc cat     576
Pro Asn Asn Glu His Tyr Leu Asp Thr Lys Ala Glu Lys Met Gly His
                180                 185                 190 ttg ctg aac aaa taa                                                 591
Leu Leu Asn Lys
        195

<210> SEQ ID NO 84
<211> LENGTH: 196
<212> TYPE: PRT
<213> ORGANISM: Escherichia coli

<400> SEQUENCE: 84

Met Gln Leu Lys Arg Val Ala Glu Ala Lys Leu Pro Thr Pro Trp Gly
1               5                   10                  15

Asp Phe Leu Met Val Gly Phe Glu Glu Leu Ala Thr Gly His Asp His
                20                  25                  30

Val Ala Leu Val Tyr Gly Asp Ile Ser Gly His Thr Pro Val Leu Ala
```

```
                     35                  40                  45
Arg Val His Ser Glu Cys Leu Thr Gly Asp Ala Leu Phe Ser Leu Arg
 50                  55                  60

Cys Asp Cys Gly Phe Gln Leu Glu Ala Ala Leu Thr Gln Ile Ala Glu
 65                  70                  75                  80

Glu Gly Arg Gly Ile Leu Leu Tyr His Arg Gln Glu Gly Arg Asn Ile
                     85                  90                  95

Gly Leu Leu Asn Lys Ile Arg Ala Tyr Ala Leu Gln Asp Gln Gly Tyr
                100                 105                 110

Asp Thr Val Glu Ala Asn His Gln Leu Gly Phe Ala Ala Asp Glu Arg
                115                 120                 125

Asp Phe Thr Leu Cys Ala Asp Met Phe Lys Leu Leu Gly Val Asn Glu
                130                 135                 140

Val Arg Leu Leu Thr Asn Asn Pro Lys Lys Val Glu Ile Leu Thr Glu
145                 150                 155                 160

Ala Gly Ile Asn Ile Val Glu Arg Val Pro Leu Ile Val Gly Arg Asn
                    165                 170                 175

Pro Asn Asn Glu His Tyr Leu Asp Thr Lys Ala Glu Lys Met Gly His
                180                 185                 190

Leu Leu Asn Lys
            195

<210> SEQ ID NO 85
<211> LENGTH: 645
<212> TYPE: DNA
<213> ORGANISM: Escherichia coli
<220> FEATURE:
<221> NAME/KEY: CDS
<222> LOCATION: (1)..(645)
<223> OTHER INFORMATION: adk gene encoding an adenylate kinase

<400> SEQUENCE: 85 atg cgt atc att ctg ctt ggc gct ccg ggc gcg ggg aaa ggg act cag      48
Met Arg Ile Ile Leu Leu Gly Ala Pro Gly Ala Gly Lys Gly Thr Gln
  1               5                  10                  15 gct cag ttc atc atg gag aaa tat ggt att ccg caa atc tcc act ggc      96
Ala Gln Phe Ile Met Glu Lys Tyr Gly Ile Pro Gln Ile Ser Thr Gly
                 20                  25                  30 gat atg ctg cgt gct gcg gtc aaa tct ggc tcc gag ctg ggt aaa caa     144
Asp Met Leu Arg Ala Ala Val Lys Ser Gly Ser Glu Leu Gly Lys Gln
             35                  40                  45 gca aaa gac att atg gat gct ggc aaa ctg gtc acc gac gaa ctg gtg     192
Ala Lys Asp Ile Met Asp Ala Gly Lys Leu Val Thr Asp Glu Leu Val
 50                  55                  60 atc gcg ctg gtt aaa gag cgc att gct cag gaa gac tgc cgt aat ggt     240
Ile Ala Leu Val Lys Glu Arg Ile Ala Gln Glu Asp Cys Arg Asn Gly
 65                  70                  75                  80 ttc ctg ttg gac ggc ttc ccg cgt acc att ccg cag gca gac gcg atg     288
Phe Leu Leu Asp Gly Phe Pro Arg Thr Ile Pro Gln Ala Asp Ala Met
                 85                  90                  95 aaa gaa gcg ggc atc aat gtt gat tac gtt ctg gaa ttc gac gta ccg     336
Lys Glu Ala Gly Ile Asn Val Asp Tyr Val Leu Glu Phe Asp Val Pro
                100                 105                 110 gac gaa ctg atc gtt gac cgt atc gtc ggt cgc cgc gtt cat gcg ccg     384
Asp Glu Leu Ile Val Asp Arg Ile Val Gly Arg Arg Val His Ala Pro
             115                 120                 125 tct ggt cgt gtt tat cac gtt aaa ttc aat ccg ccg aaa gta gaa ggc     432
Ser Gly Arg Val Tyr His Val Lys Phe Asn Pro Pro Lys Val Glu Gly
         130                 135                 140
```

```
aaa gac gac gtt acc ggt gaa gaa ctg act acc cgt aaa gat gat cag    480
Lys Asp Asp Val Thr Gly Glu Glu Leu Thr Thr Arg Lys Asp Asp Gln
145                 150                 155                 160 gaa gag acc gta cgt aaa cgt ctg gtt gaa tac cat cag atg aca gca    528
Glu Glu Thr Val Arg Lys Arg Leu Val Glu Tyr His Gln Met Thr Ala
                165                 170                 175 ccg ctg atc ggc tac tac tcc aaa gaa gca gaa gcg ggt aat acc aaa    576
Pro Leu Ile Gly Tyr Tyr Ser Lys Glu Ala Glu Ala Gly Asn Thr Lys
            180                 185                 190 tac gcg aaa gtt gac ggc acc aag ccg gtt gct gaa gtt cgc gct gat    624
Tyr Ala Lys Val Asp Gly Thr Lys Pro Val Ala Glu Val Arg Ala Asp
        195                 200                 205 ctg gaa aaa atc ctc ggc taa                                        645
Leu Glu Lys Ile Leu Gly
    210

<210> SEQ ID NO 86
<211> LENGTH: 214
<212> TYPE: PRT
<213> ORGANISM: Escherichia coli

<400> SEQUENCE: 86

Met Arg Ile Ile Leu Leu Gly Ala Pro Gly Ala Gly Lys Gly Thr Gln
1               5                   10                  15

Ala Gln Phe Ile Met Glu Lys Tyr Gly Ile Pro Gln Ile Ser Thr Gly
            20                  25                  30

Asp Met Leu Arg Ala Ala Val Lys Ser Gly Ser Glu Leu Gly Lys Gln
        35                  40                  45

Ala Lys Asp Ile Met Asp Ala Gly Lys Leu Val Thr Asp Glu Leu Val
    50                  55                  60

Ile Ala Leu Val Lys Glu Arg Ile Ala Gln Glu Asp Cys Arg Asn Gly
65                  70                  75                  80

Phe Leu Leu Asp Gly Phe Pro Arg Thr Ile Pro Gln Ala Asp Ala Met
                85                  90                  95

Lys Glu Ala Gly Ile Asn Val Asp Tyr Val Leu Glu Phe Asp Val Pro
            100                 105                 110

Asp Glu Leu Ile Val Asp Arg Ile Val Gly Arg Arg Val His Ala Pro
        115                 120                 125

Ser Gly Arg Val Tyr His Val Lys Phe Asn Pro Pro Lys Val Glu Gly
    130                 135                 140

Lys Asp Asp Val Thr Gly Glu Glu Leu Thr Thr Arg Lys Asp Asp Gln
145                 150                 155                 160

Glu Glu Thr Val Arg Lys Arg Leu Val Glu Tyr His Gln Met Thr Ala
                165                 170                 175

Pro Leu Ile Gly Tyr Tyr Ser Lys Glu Ala Glu Ala Gly Asn Thr Lys
            180                 185                 190

Tyr Ala Lys Val Asp Gly Thr Lys Pro Val Ala Glu Val Arg Ala Asp
        195                 200                 205

Leu Glu Lys Ile Leu Gly
    210

<210> SEQ ID NO 87
<211> LENGTH: 1338
<212> TYPE: DNA
<213> ORGANISM: Escherichia coli
<220> FEATURE:
<221> NAME/KEY: CDS
<222> LOCATION: (1)..(1338)
```

<223> OTHER INFORMATION: folp encodes dihydropteroate synthase

<400> SEQUENCE: 87

```
atg agt aat cgt aaa tat ttc ggt acc gat ggg att cgt ggt cgt gta         48
Met Ser Asn Arg Lys Tyr Phe Gly Thr Asp Gly Ile Arg Gly Arg Val
1               5                   10                  15 ggg gat gcg ccg atc aca cct gat ttt gtg ctt aag ctg ggt tgg gcc         96
Gly Asp Ala Pro Ile Thr Pro Asp Phe Val Leu Lys Leu Gly Trp Ala
            20                  25                  30 gcg ggt aaa gtg ctg gcg cgc cac ggc tcc cgt aag att att att ggt        144
Ala Gly Lys Val Leu Ala Arg His Gly Ser Arg Lys Ile Ile Ile Gly
        35                  40                  45 aaa gac acg cgt att tct ggc tat atg ctg gag tca gca ctg gaa gcg        192
Lys Asp Thr Arg Ile Ser Gly Tyr Met Leu Glu Ser Ala Leu Glu Ala
    50                  55                  60 ggt ctg gcg gca gcg ggc ctt tcc gca ctc ttc act ggc ccg atg cca        240
Gly Leu Ala Ala Ala Gly Leu Ser Ala Leu Phe Thr Gly Pro Met Pro
65                  70                  75                  80 aca ccg gcc gtg gct tat ctg acg cgt acc ttc cgc gca gag gcc gga        288
Thr Pro Ala Val Ala Tyr Leu Thr Arg Thr Phe Arg Ala Glu Ala Gly
                85                  90                  95 att gtg ata tct gca tcg cat aac ccg ttc tac gat aat ggc att aaa        336
Ile Val Ile Ser Ala Ser His Asn Pro Phe Tyr Asp Asn Gly Ile Lys
            100                 105                 110 ttc ttc tct atc gac ggc acc aaa ctg ccg gat gcg gta gaa gag gcc        384
Phe Phe Ser Ile Asp Gly Thr Lys Leu Pro Asp Ala Val Glu Glu Ala
        115                 120                 125 atc gaa gcg gaa atg gaa aag gag atc agc tgc gtt gat tcg gca gaa        432
Ile Glu Ala Glu Met Glu Lys Glu Ile Ser Cys Val Asp Ser Ala Glu
    130                 135                 140 ctg ggt aaa gcc agc cgt atc gtt gat gcc gcg ggt cgc tat atc gag        480
Leu Gly Lys Ala Ser Arg Ile Val Asp Ala Ala Gly Arg Tyr Ile Glu
145                 150                 155                 160 ttt tgc aaa gcc acg ttc ccg aac gaa ctt agc ctc agt gaa ctg aag        528
Phe Cys Lys Ala Thr Phe Pro Asn Glu Leu Ser Leu Ser Glu Leu Lys
                165                 170                 175 att gtg gtg gat tgt gca aac ggt gcg act tat cac atc gcg ccg aac        576
Ile Val Val Asp Cys Ala Asn Gly Ala Thr Tyr His Ile Ala Pro Asn
            180                 185                 190 gtg ctg cgc gaa ctg ggg gcg aac gtt atc gct atc ggt tgt gag cca        624
Val Leu Arg Glu Leu Gly Ala Asn Val Ile Ala Ile Gly Cys Glu Pro
        195                 200                 205 aac ggt gta aac atc aat gcc gaa gtg ggg gct acc gac gtt cgc gcg        672
Asn Gly Val Asn Ile Asn Ala Glu Val Gly Ala Thr Asp Val Arg Ala
    210                 215                 220 ctc cag gct cgt gtg ctg gct gaa aaa gcg gat ctc ggt att gcc ttc        720
Leu Gln Ala Arg Val Leu Ala Glu Lys Ala Asp Leu Gly Ile Ala Phe
225                 230                 235                 240 gac ggc gat ggc gat cgc gtg att atg gtt gac cat gaa ggc aat aaa        768
Asp Gly Asp Gly Asp Arg Val Ile Met Val Asp His Glu Gly Asn Lys
                245                 250                 255 gtc gat ggc gat cag atc atg tat atc atc gcg cgt gaa ggt ctt cgt        816
Val Asp Gly Asp Gln Ile Met Tyr Ile Ile Ala Arg Glu Gly Leu Arg
            260                 265                 270 cag ggc cag ctg cgt ggt ggc gct gtg ggt aca ttg atg agc aac atg        864
Gln Gly Gln Leu Arg Gly Gly Ala Val Gly Thr Leu Met Ser Asn Met
        275                 280                 285 ggg ctt gaa ctg gcg ctg aaa cag tta gga att cca ttt gcg cgc gcg        912
Gly Leu Glu Leu Ala Leu Lys Gln Leu Gly Ile Pro Phe Ala Arg Ala
    290                 295                 300
```

```
aaa gtg ggt gac cgc tac gta ctg gaa aaa atg cag gag aaa ggc tgg       960
Lys Val Gly Asp Arg Tyr Val Leu Glu Lys Met Gln Glu Lys Gly Trp
305                 310                 315                 320 cgt atc ggt gca gag aat tcc ggt cat gtg atc ctg ctg gat aaa act      1008
Arg Ile Gly Ala Glu Asn Ser Gly His Val Ile Leu Leu Asp Lys Thr
                325                 330                 335 act acc ggt gac ggc atc gtt gct ggc ttg cag gtg ctg gcg gcg atg      1056
Thr Thr Gly Asp Gly Ile Val Ala Gly Leu Gln Val Leu Ala Ala Met
            340                 345                 350 gca cgt aac cat atg agc ctg cac gac ctt tgc agc ggc atg aaa atg      1104
Ala Arg Asn His Met Ser Leu His Asp Leu Cys Ser Gly Met Lys Met
        355                 360                 365 ttc ccg cag att ctg gtt aac gta cgt tac acc gca ggt agc ggc gat      1152
Phe Pro Gln Ile Leu Val Asn Val Arg Tyr Thr Ala Gly Ser Gly Asp
    370                 375                 380 cca ctt gag cat gag tca gtt aaa gcc gtg acc gca gag gtt gaa gct      1200
Pro Leu Glu His Glu Ser Val Lys Ala Val Thr Ala Glu Val Glu Ala
385                 390                 395                 400 gcg ctg ggc aac cgt gga cgc gtg ttg ctg cgt aaa tcc ggc acc gaa      1248
Ala Leu Gly Asn Arg Gly Arg Val Leu Leu Arg Lys Ser Gly Thr Glu
                405                 410                 415 ccg tta att cgc gtg atg gtg gaa ggc gaa gac gaa gcg cag gtg act      1296
Pro Leu Ile Arg Val Met Val Glu Gly Glu Asp Glu Ala Gln Val Thr
            420                 425                 430 gaa ttt gca cac cgc atc gcc gat gca gta aaa gcc gtt taa              1338
Glu Phe Ala His Arg Ile Ala Asp Ala Val Lys Ala Val
        435                 440                 445

<210> SEQ ID NO 88
<211> LENGTH: 445
<212> TYPE: PRT
<213> ORGANISM: Escherichia coli

<400> SEQUENCE: 88

Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
            20                  25                  30

Ala Gly Lys Val Leu Ala Arg His Gly Ser Arg Lys Ile Ile Gly
        35                  40                  45

Lys Asp Thr Arg Ile Ser Gly Tyr Met Leu Glu Ser Ala Leu Glu Ala
    50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95

Ile Val Ile Ser Ala Ser His Asn Pro Phe Tyr Asp Asn Gly Ile Lys
            100                 105                 110

Phe Phe Ser Ile Asp Gly Thr Lys Leu Pro Asp Ala Val Glu Glu Ala
        115                 120                 125

Ile Glu Ala Glu Met Glu Lys Glu Ile Ser Cys Val Asp Ser Ala Glu
    130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
                165                 170                 175

Ile Val Val Asp Cys Ala Asn Gly Ala Thr Tyr His Ile Ala Pro Asn
```

180                 185                 190
Val Leu Arg Glu Leu Gly Ala Asn Val Ile Ala Ile Gly Cys Glu Pro
            195                 200                 205

Asn Gly Val Asn Ile Asn Ala Glu Val Gly Ala Thr Asp Val Arg Ala
        210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
                245                 250                 255

Val Asp Gly Asp Gln Ile Met Tyr Ile Ile Ala Arg Glu Gly Leu Arg
            260                 265                 270

Gln Gly Gln Leu Arg Gly Gly Ala Val Gly Thr Leu Met Ser Asn Met
        275                 280                 285

Gly Leu Glu Leu Ala Leu Lys Gln Leu Gly Ile Pro Phe Ala Arg Ala
    290                 295                 300

Lys Val Gly Asp Arg Tyr Val Leu Glu Lys Met Gln Glu Lys Gly Trp
305                 310                 315                 320

Arg Ile Gly Ala Glu Asn Ser Gly His Val Ile Leu Leu Asp Lys Thr
                325                 330                 335

Thr Thr Gly Asp Gly Ile Val Ala Gly Leu Gln Val Leu Ala Ala Met
            340                 345                 350

Ala Arg Asn His Met Ser Leu His Asp Leu Cys Ser Gly Met Lys Met
        355                 360                 365

Phe Pro Gln Ile Leu Val Asn Val Arg Tyr Thr Ala Gly Ser Gly Asp
    370                 375                 380

Pro Leu Glu His Glu Ser Val Lys Ala Val Thr Ala Glu Val Glu Ala
385                 390                 395                 400

Ala Leu Gly Asn Arg Gly Arg Val Leu Leu Arg Lys Ser Gly Thr Glu
                405                 410                 415

Pro Leu Ile Arg Val Met Val Glu Gly Glu Asp Glu Ala Gln Val Thr
            420                 425                 430

Glu Phe Ala His Arg Ile Ala Asp Ala Val Lys Ala Val
        435                 440                 445

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: primer_bind
<222> LOCATION: (1)..(35)
<223> OTHER INFORMATION: J23118 primer

<400> SEQUENCE: 89
ttgacggcta gctcagtcct aggtattgtg ctagc                              35

<210> SEQ ID NO 90
<211> LENGTH: 142
<212> TYPE: DNA
<213> ORGANISM: Escherichia coli
<220> FEATURE:
<221> NAME/KEY: misc_feature
<222> LOCATION: (1)..(142)
<223> OTHER INFORMATION: thiC gene region corresponding to 5'UTR
<220> FEATURE:
<221> NAME/KEY: mutation
<222> LOCATION: (8)..(8)

<223> OTHER INFORMATION: Mutation; wherein B=T or C or G

<400> SEQUENCE: 90

```
attcgggbtc cgcggaacct gatcaggcta atacctgcga agggaacaag agttaatctg    60
ctatcgcatc gccctgcgg cgatcgtctc ttgcttcatc cgtcgtctga caagccacgt    120
ccttaacttt ttggaatgag ct                                             142
```

<210> SEQ ID NO 91
<211> LENGTH: 2283
<212> TYPE: DNA
<213> ORGANISM: Escherichia coli
<220> FEATURE:
<221> NAME/KEY: promoter
<222> LOCATION: (1665)..(1990)
<223> OTHER INFORMATION: pBAD promoter
<220> FEATURE:
<221> NAME/KEY: RBS
<222> LOCATION: (1980)..(1985)
<220> FEATURE:
<221> NAME/KEY: CDS
<222> LOCATION: (1991)..(2281)
<223> OTHER INFORMATION: Portion of folP gene sequence

<400> SEQUENCE: 91

```
aagatgctct catgaaatat gagactatcg acgcaccgca gattgatgac ctgatggcac    60
gtcgcgatgt acgtccgcca gcgggctggg aagaaccagg cgcttctaac aattctggcg   120
acaatggtag tccaaaggct cctcgtccgg ttgatgaacc gcgtacgccg aacccgggta   180
acaccatgtc agagcagtta ggcgacaagt aagttcccgc atcagatgac tgtatttgta   240
ccgaaaaccc cggggcgtgc tccggggttt tttcttatca attcatacca gggataacat   300
cagcgattgt gtaggctgga gctgcttcga agttcctata ctttctagag aataggaact   360
tcggaatagg aacttcaaga tccccttatt agaagaactc gtcaagaagg cgatagaagg   420
cgatgcgctg cgaatcggga gcggcgatac cgtaaagcac gaggaagcgg tcagcccatt   480
cgccgccaag ctcttcagca atatcacggg tagccaacgc tatgtcctga tagcggtccg   540
ccacacccag ccggccacag tcgatgaatc cagaaaagcg gccatttttcc accatgatat   600
tcggcaagca ggcatcgcca tgggtcacga cgagatcctc gccgtcgggc atgcgcgcct   660
tgagcctggc gaacagttcg gctggcgcga gccctgatg ctcttcgtcc agatcatcct   720
gatcgacaag accggcttcc atccgagtac gtgctcgctc gatgcgatgt ttcgcttggt   780
ggtcgaatgg gcaggtagcc ggatcaagcg tatgcagccg ccgcattgca tcagccatga   840
tggatacttt ctcggcagga gcaaggtgag atgacaggag atcctgcccc ggcacttcgc   900
ccaatagcag ccagtcccctt cccgcttcag tgacaacgtc gagcacagct gcgcaaggaa   960
cgcccgtcgt ggccagccac gatagccgcg ctgcctcgtc ctgcagttca ttcagggcac  1020
cggacaggtc ggtcttgaca aaagaaccg ggcgcccctg cgctgacagc cggaacacgg  1080
cggcatcaga gcagccgatt gtctgttgtg cccagtcata gccgaatagc ctctccaccc  1140
aagcggccgg agaacctgcg tgcaatccat cttgttcaat catgcgaaac gatcctcatc  1200
ctgtctcttg atcagatctt gatcccctgc gccatcagat ccttggcggc aagaaagcca  1260
tccagtttac tttgcagggc ttcccaacct taccagaggg cgcccagct ggcaattccg  1320
gttcgcttgc tgtccataaa accgcccagt ctagctatcg ccatgtaagc ccactgcaag  1380
ctacctgctt tctctttgcg cttgcgtttt ccttgtcca gatagcccag tagctgacat  1440
tcatccgggg tcagcaccgt ttctgcggac tggctttcta cgtgttccgc ttcctttagc  1500
```

```
agcccttgcg ccctgagtgc ttgcggcagc gtgagcttca aaagcgctct gaagttccta    1560
tactttctag agaataggaa cttcgaactg caggtcgacg gatccccgga atattcatat    1620
gtgcgcttca gccatacttt tcatactccc gccattcaga gaagaaacca attgtccata    1680
ttgcatcaga cattgccgtc actgcgtctt ttactggctc ttctcgctaa ccaaaccggt    1740
aaccccgctt attaaaagca ttctgtaaca aagcgggacc aaagccatga caaaaacgcg    1800
taacaaaagt gtctataatc acggcagaaa agtccacatt gattatttgc acggcgtcac    1860
actttgctat gccatagcat ttttatccat aagattagcg gatcctacct gacgcttttt    1920
atcgcaactc tctactgttt ctccataccc gtttttttgg gctagcgaat tcgagctcga    1980
cttgcaaggt atg aaa ctc ttt gcc cag ggt act tca ctg gac ctt agc      2029
          Met Lys Leu Phe Ala Gln Gly Thr Ser Leu Asp Leu Ser
          1               5                   10 cat cct cac gta atg ggg atc ctc aac gtc acg cct gat tcc ttt tcg     2077
His Pro His Val Met Gly Ile Leu Asn Val Thr Pro Asp Ser Phe Ser
15                  20                  25 gat ggt ggc acg cat aac tcg ctg ata gat gcg gtg aaa cat gcg aat     2125
Asp Gly Gly Thr His Asn Ser Leu Ile Asp Ala Val Lys His Ala Asn
30                  35                  40                  45 ctg atg atc aac gct ggc gcg acg atc att gac gtt ggt ggc gag tcc     2173
Leu Met Ile Asn Ala Gly Ala Thr Ile Ile Asp Val Gly Gly Glu Ser
                50                  55                  60 acg cgc cca ggg gcg gcg gaa gtt agc gtt gaa gaa gag ttg caa cgt     2221
Thr Arg Pro Gly Ala Ala Glu Val Ser Val Glu Glu Glu Leu Gln Arg
65                  70                  75 gtt att cct gtg gtt gag gca att gct caa cgc ttc gaa gtc tgg atc     2269
Val Ile Pro Val Val Glu Ala Ile Ala Gln Arg Phe Glu Val Trp Ile
        80                  85                  90 tca gtc gat aca tc                                                  2283
Ser Val Asp Thr
        95

<210> SEQ ID NO 92
<211> LENGTH: 97
<212> TYPE: PRT
<213> ORGANISM: Escherichia coli

<400> SEQUENCE: 92

Met Lys Leu Phe Ala Gln Gly Thr Ser Leu Asp Leu Ser His Pro His
1               5                   10                  15

Val Met Gly Ile Leu Asn Val Thr Pro Asp Ser Phe Ser Asp Gly Gly
                20                  25                  30

Thr His Asn Ser Leu Ile Asp Ala Val Lys His Ala Asn Leu Met Ile
            35                  40                  45

Asn Ala Gly Ala Thr Ile Ile Asp Val Gly Gly Glu Ser Thr Arg Pro
        50                  55                  60

Gly Ala Ala Glu Val Ser Val Glu Glu Glu Leu Gln Arg Val Ile Pro
65                  70                  75                  80

Val Val Glu Ala Ile Ala Gln Arg Phe Glu Val Trp Ile Ser Val Asp
                85                  90                  95

Thr

<210> SEQ ID NO 93
<211> LENGTH: 4790
<212> TYPE: DNA
<213> ORGANISM: Escherichia coli
<220> FEATURE:
<221> NAME/KEY: CDS
```

<222> LOCATION: (1945)..(2916)
<223> OTHER INFORMATION: SpecR gene in pBALspec.

<400> SEQUENCE: 93

```
atcgatgcat aatgtgcctg tcaaatggac gaagcaggga ttctgcaaac cctatgctac        60
tccgtcaagc cgtcaattgt ctgattcgtt accaattatg acaacttgac ggctacatca       120 ttcactttt cttcacaacc ggcacggaac tcgctcgggc tggccccggt gcattttta        180 aatacccgcg agaaatagag ttgatcgtca aaaccaacat tgcgaccgac ggtggcgata       240
ggcatccggg tggtgctcaa aagcagcttc gcctggctga tacgttggtc ctcgcgccag       300
cttaagacgc taatccctaa ctgctggcgg aaaagatgtg acagacgcga cggcgacaag       360
caaacatgct gtgcgacgct ggcgatatca aaattgctgt ctgccaggtg atcgctgatg       420
tactgacaag cctcgcgtac ccgattatcc atcggtggat ggagcgactc gttaatcgct       480
tccatgcgcc gcagtaacaa ttgctcaagc agatttatcg ccagcagctc cgaatagcgc       540 ccttccctt gcccggcgtt aatgatttgc ccaaacaggt cgctgaaatg cggctggtgc       600
gcttcatccg ggcgaaagaa ccccgtattg gcaaatattg acggccagtt aagccattca       660
tgccagtagg cgcgcggacg aaagtaaacc cactggcgat accattcgcg agcctccgga       720
tgacgaccta agtgaccaat ctctcctggc gggaacagca aaatatcacc cggtcggcaa       780
acaaattctc gtccctgatt tttcaccacc ccctgaccgc gaatggtgag attgagaata       840 taaccttca ttcccagcgg tcggtcgata aaaaaatcga gataaccgtt ggcctcaatc       900
gggattaaac ccgccaccag atgggcatta acgagtatc ccggcagcag gacatcattt       960
tgcgcttcag ccatactttt catactcccg ccattcagag aagaaaccaa ttgtccatat      1020
tgcatacttt tcatactccc gccattcaga gaagaaacca attgtccata ttgcatcaga      1080
cattgccgtc actgcgtctt ttactggctc ttctcgctaa ccaaaccggt aaccccgctt      1140
attaaaagca ttctgtaaca aagcgggacc aaagccatga caaaaacgcg taacaaaagt      1200
gtctataatc acggcagaaa agtccacatt gattatttgc acggcgtcac actttgctat      1260
gccatagcat ttttatccat aagattagcg gatcctacct gacgctttt atcgcaactc      1320 tctactgttt ctccatacccc gttttttgg gctagcgaat cgagctcga ggaggaaacc      1380 atggtacccg gggatcctct agagtcgacc tgcaggcatg caagcttggc tgttttggcg      1440
gatgagagaa gattttcagc ctgatacaga ttaaatcaga acgcagaagc ggtctgataa      1500
aacagaattt gcctggcggc agtagcgcgg tggtcccacc tgaccccatg ccgaactcag      1560
aagtgaaacg ccgtagcgcc gatggtagtg tggggtctcc ccatgcgaga gtagggaact      1620
gccaggcatc aaataaaacg aaaggctcag tcgaaagact gggcctttcg ttttatctgt      1680
tgtttgtcgg tgaacgctct cctgagtagg acaaatccgc cgggagcgga tttgaacgtt      1740
gcgaagcaac ggcccggagg gtggcgggca ggacgcccgc cataaactgc caggcatcaa      1800
attaagcaga aggccatcct gacggtgata tccggatgaa ggcacgaacc cagtggacat      1860
aagcctcgtt cggttcgtaa gctgtaatgc aagtagcgta actgccgtca cgcaactggt      1920 ccacaaccttt gaccgaacgc agcg gtg gta acg gcg cag tgg cgg ttt tca      1971
                                Val Val Thr Ala Gln Trp Arg Phe Ser
                                 1               5 tgg ctt ctt gtt atg aca tgt ttt ttt ggg gta cag tct atg cct cgg        2019
Trp Leu Leu Val Met Thr Cys Phe Phe Gly Val Gln Ser Met Pro Arg
 10              15                  20                  25 gca tcc aag cag caa gcg cgt tac gcc gtg ggt cga tgt ttg atg tta        2067
Ala Ser Lys Gln Gln Ala Arg Tyr Ala Val Gly Arg Cys Leu Met Leu
```

|  |  |  |  |  |  |  |  |  |  |  |  |  |  |  |  |
|---|---|---|---|---|---|---|---|---|---|---|---|---|---|---|---|
|  |  |  | 30 |  |  |  | 35 |  |  |  | 40 |  |  |  |  |
| tgg | agc | agc | aac | gat | gtt | acg | cag | cag | ggc | agt | cgc | cct | aaa | aca | aag | 2115 |
| Trp | Ser | Ser | Asn | Asp | Val | Thr | Gln | Gln | Gly | Ser | Arg | Pro | Lys | Thr | Lys |  |
|  |  |  | 45 |  |  |  | 50 |  |  |  | 55 |  |  |  |  |
| tta | aac | atc | atg | agg | gaa | gcg | gtg | atc | gcc | gaa | gta | tcg | act | caa | cta | 2163 |
| Leu | Asn | Ile | Met | Arg | Glu | Ala | Val | Ile | Ala | Glu | Val | Ser | Thr | Gln | Leu |  |
|  |  |  | 60 |  |  |  | 65 |  |  |  | 70 |  |  |  |  |
| tca | gag | gta | gtt | ggc | gtc | atc | gag | cgc | cat | ctc | gaa | ccg | acg | ttg | ctg | 2211 |
| Ser | Glu | Val | Val | Gly | Val | Ile | Glu | Arg | His | Leu | Glu | Pro | Thr | Leu | Leu |  |
| 75 |  |  |  |  | 80 |  |  |  |  | 85 |  |  |  |  |  |  |
| gcc | gta | cat | ttg | tac | ggc | tcc | gca | gtg | gat | ggc | ggc | ctg | aag | cca | cac | 2259 |
| Ala | Val | His | Leu | Tyr | Gly | Ser | Ala | Val | Asp | Gly | Gly | Leu | Lys | Pro | His |  |
| 90 |  |  |  |  | 95 |  |  |  |  | 100 |  |  |  |  | 105 |  |
| agt | gat | att | gat | ttg | ctg | gtt | acg | gtg | acc | gta | agg | ctt | gat | gaa | aca | 2307 |
| Ser | Asp | Ile | Asp | Leu | Leu | Val | Thr | Val | Thr | Val | Arg | Leu | Asp | Glu | Thr |  |
|  |  |  | 110 |  |  |  | 115 |  |  |  | 120 |  |  |  |  |
| acg | cgg | cga | gct | ttg | atc | aac | gac | ctt | ttg | gaa | act | tcg | gct | tcc | cct | 2355 |
| Thr | Arg | Arg | Ala | Leu | Ile | Asn | Asp | Leu | Leu | Glu | Thr | Ser | Ala | Ser | Pro |  |
|  |  | 125 |  |  |  | 130 |  |  |  | 135 |  |  |  |  |  |  |
| gga | gag | agc | gag | att | ctc | cgc | gct | gta | gaa | gtc | acc | att | gtt | gtg | cac | 2403 |
| Gly | Glu | Ser | Glu | Ile | Leu | Arg | Ala | Val | Glu | Val | Thr | Ile | Val | Val | His |  |
|  | 140 |  |  |  | 145 |  |  |  | 150 |  |  |  |  |  |  |  |
| gac | gac | atc | att | ccg | tgg | cgt | tat | cca | gct | aag | cgc | gaa | ctg | caa | ttt | 2451 |
| Asp | Asp | Ile | Ile | Pro | Trp | Arg | Tyr | Pro | Ala | Lys | Arg | Glu | Leu | Gln | Phe |  |
| 155 |  |  |  |  | 160 |  |  |  |  | 165 |  |  |  |  |  |  |
| gga | gaa | tgg | cag | cgc | aat | gac | att | ctt | gca | ggt | atc | ttc | gag | cca | gcc | 2499 |
| Gly | Glu | Trp | Gln | Arg | Asn | Asp | Ile | Leu | Ala | Gly | Ile | Phe | Glu | Pro | Ala |  |
| 170 |  |  |  |  | 175 |  |  |  |  | 180 |  |  |  |  | 185 |  |
| acg | tac | gac | att | gat | ctg | gct | atc | ttg | ctg | aca | aaa | gca | aga | gaa | cat | 2547 |
| Thr | Tyr | Asp | Ile | Asp | Leu | Ala | Ile | Leu | Leu | Thr | Lys | Ala | Arg | Glu | His |  |
|  |  |  | 190 |  |  |  | 195 |  |  |  | 200 |  |  |  |  |
| agc | gtt | gcc | ttg | gta | ggt | cca | gcg | gcg | gag | gaa | ctc | ttt | gat | ccg | gtt | 2595 |
| Ser | Val | Ala | Leu | Val | Gly | Pro | Ala | Ala | Glu | Glu | Leu | Phe | Asp | Pro | Val |  |
|  |  |  | 205 |  |  |  | 210 |  |  |  | 215 |  |  |  |  |
| cct | gaa | cag | gat | cta | ttt | gag | gcg | cta | aat | gaa | acc | tta | acg | cta | tgg | 2643 |
| Pro | Glu | Gln | Asp | Leu | Phe | Glu | Ala | Leu | Asn | Glu | Thr | Leu | Thr | Leu | Trp |  |
|  |  | 220 |  |  |  | 225 |  |  |  | 230 |  |  |  |  |  |  |
| aac | tcg | ccg | ccc | gac | tgg | gct | ggc | gat | gag | cga | aat | gta | gtg | ctt | acg | 2691 |
| Asn | Ser | Pro | Pro | Asp | Trp | Ala | Gly | Asp | Glu | Arg | Asn | Val | Val | Leu | Thr |  |
|  | 235 |  |  |  | 240 |  |  |  | 245 |  |  |  |  |  |  |  |
| ttg | tcc | cgc | att | tgg | tac | agc | gca | gta | acc | ggc | aaa | atc | gcg | ccg | aag | 2739 |
| Leu | Ser | Arg | Ile | Trp | Tyr | Ser | Ala | Val | Thr | Gly | Lys | Ile | Ala | Pro | Lys |  |
| 250 |  |  |  |  | 255 |  |  |  |  | 260 |  |  |  |  | 265 |  |
| gat | gtc | gct | gcc | gac | tgg | gca | atg | gag | cgc | ctg | ccg | gcc | cag | tat | cag | 2787 |
| Asp | Val | Ala | Ala | Asp | Trp | Ala | Met | Glu | Arg | Leu | Pro | Ala | Gln | Tyr | Gln |  |
|  |  |  | 270 |  |  |  | 275 |  |  |  | 280 |  |  |  |  |
| ccc | gtc | ata | ctt | gaa | gct | aga | cag | gct | tat | ctt | gga | caa | gaa | gaa | gat | 2835 |
| Pro | Val | Ile | Leu | Glu | Ala | Arg | Gln | Ala | Tyr | Leu | Gly | Gln | Glu | Glu | Asp |  |
|  |  | 285 |  |  |  | 290 |  |  |  | 295 |  |  |  |  |  |  |
| cgc | ttg | gcc | tcg | cgc | gca | gat | cag | ttg | gaa | gaa | ttt | gtc | cac | tac | gtg | 2883 |
| Arg | Leu | Ala | Ser | Arg | Ala | Asp | Gln | Leu | Glu | Glu | Phe | Val | His | Tyr | Val |  |
|  |  | 300 |  |  |  | 305 |  |  |  | 310 |  |  |  |  |  |  |
| aaa | ggc | gag | atc | acc | aag | gta | gtc | ggc | aaa | taa | tgtctaacaa | ttcgttcaag |  |  |  | 2936 |
| Lys | Gly | Glu | Ile | Thr | Lys | Val | Val | Gly | Lys |  |  |  |  |  |  |  |
|  | 315 |  |  |  | 320 |  |  |  |  |  |  |  |  |  |  |  |

```
ccgacggata tctagattga tttacgcgcc ctgtagcggc gcattaagcg cggcgggtgt    2996
ggtggttacg cgcagcgtga ccgctacact tgccagcgcc ctagcgcccg ctcctttcgc    3056
tttcttccct tcctttctcg ccacgttcgc cggctttccc cgtcaagctc taaatcgggg    3116
```

-continued

```
gctcccttta gggttccgat ttagtgcttt acggcacctc gacccccaaaa aacttgattt    3176
gggtgatggt tcacgtagtg ggccatcgcc ctgatagacg ttttttcgcc ctttgacgtt    3236
ggagtccacg ttctttaata gtggactctt gttccaaact tgaacaacac tcaaccctat    3296
ctcgggctat tcttttgatt tataagggat tttgccgatt tcggcctatt ggttaaaaaa    3356
tgagctgatt taacaaaaat ttaacgcgaa ttttaacaaa atattaacgt ttacaattta    3416
aaaggatcta ggtgaagatc cttttttgata atctcatgac caaaatccct taacgtgagt    3476
tttcgttcca ctgagcgtca gaccccgtag aaaagatcaa aggatcttct tgagatcctt    3536
tttttctgcg cgtaatctgc tgcttgcaaa caaaaaaacc accgctacca gcggtggttt    3596
gtttgccgga tcaagagcta ccaactcttt ttccgaaggt aactggcttc agcagagcgc    3656
agataccaaa tactgtcctt ctagtgtagc cgtagttagg ccaccacttc aagaactctg    3716
tagcaccgcc tacataccct gctctgctaa tcctgttacc agtggctgct gccagtggcg    3776
ataagtcgtg tcttaccggg ttggactcaa gacgatagtt accggataag gcgcagcggt    3836
cgggctgaac ggggggttcg tgcacacagc ccagcttgga gcgaacgacc tacaccgaac    3896
tgagatacct acagcgtgag ctatgagaaa gcgccacgct tcccgaaggg agaaaggcgg    3956
acaggtatcc ggtaagcggc agggtcggaa caggagagcg cacgagggag cttccagggg    4016
gaaacgcctg gtatctttat agtcctgtcg ggtttcgcca cctctgactt gagcgtcgat    4076
ttttgtgatg ctcgtcaggg gggcggagcc tatggaaaaa cgccagcaac gcggcctttt    4136
tacggttcct ggccttttgc tggccttttg ctcacatgtt ctttcctgcg ttatcccctg    4196
attctgtgga taaccgtatt accgcctttg agtgagctga taccgctcgc cgcagccgaa    4256
cgaccgagcg cagcgagtca gtgagcgagg aagcggaaga gcgcctgatg cggtattttc    4316
tccttacgca tctgtgcggt atttcacacc gcatatggtg cactctcagt acaatctgct    4376
ctgatgccgc atagttaagc cagtatacac tccgctatcg ctacgtgact gggtcatggc    4436
tgcgccccga cacccgccaa cacccgctga cgcgccctga cgggcttgtc tgctcccggc    4496
atccgcttac agacaagctg tgaccgtctc cgggagctgc atgtgtcaga ggttttcacc    4556
gtcatcaccg aaacgcgcga ggcagcaagg agatggcgcc caacagtccc ccggccacgg    4616
ggcctgccac catacccacg ccgaaacaag cgctcatgag cccgaagtgg cgagcccgat    4676
cttccccatc ggtgatgtcg gcgatatagg cgccagcaac cgcacctgtg cgccggtga    4736
tgccggccac gatgcgtccg gcgtagagga tctgctcatg tttgacagct tatc         4790
```

<210> SEQ ID NO 94
<211> LENGTH: 323
<212> TYPE: PRT
<213> ORGANISM: Escherichia coli

<400> SEQUENCE: 94

Val Val Thr Ala Gln Trp Arg Phe Ser Trp Leu Leu Val Met Thr Cys
1               5                   10                  15

Phe Phe Gly Val Gln Ser Met Pro Arg Ala Ser Lys Gln Gln Ala Arg
            20                  25                  30

Tyr Ala Val Gly Arg Cys Leu Met Leu Trp Ser Ser Asn Asp Val Thr
        35                  40                  45

Gln Gln Gly Ser Arg Pro Lys Thr Lys Leu Asn Ile Met Arg Glu Ala
    50                  55                  60

Val Ile Ala Glu Val Ser Thr Gln Leu Ser Glu Val Val Gly Val Ile
65                  70                  75                  80

```
Glu Arg His Leu Glu Pro Thr Leu Leu Ala Val His Leu Tyr Gly Ser
                85                  90                  95

Ala Val Asp Gly Gly Leu Lys Pro His Ser Asp Ile Asp Leu Leu Val
            100                 105                 110

Thr Val Thr Val Arg Leu Asp Glu Thr Thr Arg Arg Ala Leu Ile Asn
        115                 120                 125

Asp Leu Leu Glu Thr Ser Ala Ser Pro Gly Glu Ser Glu Ile Leu Arg
    130                 135                 140

Ala Val Glu Val Thr Ile Val Val His Asp Asp Ile Ile Pro Trp Arg
145                 150                 155                 160

Tyr Pro Ala Lys Arg Glu Leu Gln Phe Gly Trp Gln Arg Asn Asp
                165                 170                 175

Ile Leu Ala Gly Ile Phe Glu Pro Ala Thr Tyr Asp Ile Asp Leu Ala
            180                 185                 190

Ile Leu Leu Thr Lys Ala Arg Glu His Ser Val Ala Leu Val Gly Pro
        195                 200                 205

Ala Ala Glu Glu Leu Phe Asp Pro Val Pro Glu Gln Asp Leu Phe Glu
    210                 215                 220

Ala Leu Asn Glu Thr Leu Thr Leu Trp Asn Ser Pro Pro Asp Trp Ala
225                 230                 235                 240

Gly Asp Glu Arg Asn Val Val Leu Thr Leu Ser Arg Ile Trp Tyr Ser
                245                 250                 255

Ala Val Thr Gly Lys Ile Ala Pro Lys Asp Val Ala Ala Asp Trp Ala
            260                 265                 270

Met Glu Arg Leu Pro Ala Gln Tyr Gln Pro Val Ile Leu Glu Ala Arg
        275                 280                 285

Gln Ala Tyr Leu Gly Gln Glu Glu Asp Arg Leu Ala Ser Arg Ala Asp
    290                 295                 300

Gln Leu Glu Glu Phe Val His Tyr Val Lys Gly Glu Ile Thr Lys Val
305                 310                 315                 320

Val Gly Lys

<210> SEQ ID NO 95
<211> LENGTH: 930
<212> TYPE: DNA
<213> ORGANISM: Escherichia coli
<220> FEATURE:
<221> NAME/KEY: CDS
<222> LOCATION: (1)..(930)
<223> OTHER INFORMATION: AraCtal gene encoding AraCtal biosensor

<400> SEQUENCE: 95 atg caa tat gga caa ttg gtt tct tct ctg aat ggc ggg agt atg aaa    48
Met Gln Tyr Gly Gln Leu Val Ser Ser Leu Asn Gly Gly Ser Met Lys
1               5                   10                  15 agt atg gct gaa gcg caa aat gat gtc ctg ctg ccg gga tac tcg ttt    96
Ser Met Ala Glu Ala Gln Asn Asp Val Leu Leu Pro Gly Tyr Ser Phe
            20                  25                  30 aat gcc cat ctg gtg gcg ggt tta atc ccg att gag gcc aac ggt tat   144
Asn Ala His Leu Val Ala Gly Leu Ile Pro Ile Glu Ala Asn Gly Tyr
        35                  40                  45 ctc gat ttt ttt atc gac cga ccg ctg gga atg aaa ggt tat att ctc   192
Leu Asp Phe Phe Ile Asp Arg Pro Leu Gly Met Lys Gly Tyr Ile Leu
    50                  55                  60 aat ctc acc att cgc ggt cag ggg gtg gtg aaa aat cag gga cga gaa   240
Asn Leu Thr Ile Arg Gly Gln Gly Val Val Lys Asn Gln Gly Arg Glu
65                  70                  75                  80
```

```
ttt gtt tgc cga ccg ggt gat att ttg ctg ttc ccg cca gga gag att    288
Phe Val Cys Arg Pro Gly Asp Ile Leu Leu Phe Pro Pro Gly Glu Ile
                85                  90                  95 ggt cac tta ggt cgt cat ccg gag gct cgc gaa tgg tat cgc cag tgg    336
Gly His Leu Gly Arg His Pro Glu Ala Arg Glu Trp Tyr Arg Gln Trp
            100                 105                 110 gtt tac ttt cgt ccg cgc gcc tac tgg cat gaa tgg ctt aac tgg ccg    384
Val Tyr Phe Arg Pro Arg Ala Tyr Trp His Glu Trp Leu Asn Trp Pro
        115                 120                 125 tca ata ttt gcc aat acg ggg ttc ttt cgc ccg gat gaa gcg cac cag    432
Ser Ile Phe Ala Asn Thr Gly Phe Phe Arg Pro Asp Glu Ala His Gln
    130                 135                 140 ccg cat ttc agc gac ctg ttt ggg caa atc att aac gcc ggg caa ggg    480
Pro His Phe Ser Asp Leu Phe Gly Gln Ile Ile Asn Ala Gly Gln Gly
145                 150                 155                 160 gaa ggg cgc tat tcg gag ctg ctg gcg ata aat ctg ctt gag caa ttg    528
Glu Gly Arg Tyr Ser Glu Leu Leu Ala Ile Asn Leu Leu Glu Gln Leu
                165                 170                 175 tta ctg cgg cgc atg gaa gcg att aac gag tcg ctc cat cca ccg atg    576
Leu Leu Arg Arg Met Glu Ala Ile Asn Glu Ser Leu His Pro Pro Met
            180                 185                 190 gat aat cgg gta cgc gag gct tgt cag tac atc agc gat cac ctg gca    624
Asp Asn Arg Val Arg Glu Ala Cys Gln Tyr Ile Ser Asp His Leu Ala
        195                 200                 205 gac agc aat ttt gat atc gcc agc gtc gca cag cat gtt tgc ttg tcg    672
Asp Ser Asn Phe Asp Ile Ala Ser Val Ala Gln His Val Cys Leu Ser
    210                 215                 220 ccg tcg cgt ctg tca cat ctt ttc cgc cag cag tta ggg att agc gtc    720
Pro Ser Arg Leu Ser His Leu Phe Arg Gln Gln Leu Gly Ile Ser Val
225                 230                 235                 240 tta agc tgg cgc gag gac caa cgt atc agc cag gcg aag ctg ctt ttg    768
Leu Ser Trp Arg Glu Asp Gln Arg Ile Ser Gln Ala Lys Leu Leu Leu
                245                 250                 255 agc acc acc cgg atg cct atc gcc acc gtc ggt cgc aat gtt ggt ttt    816
Ser Thr Thr Arg Met Pro Ile Ala Thr Val Gly Arg Asn Val Gly Phe
            260                 265                 270 gac gat caa ctc tat ttc tcg cgg gta ttt aaa aaa tgc acc ggg gcc    864
Asp Asp Gln Leu Tyr Phe Ser Arg Val Phe Lys Lys Cys Thr Gly Ala
        275                 280                 285 agc ccg agc gag ttc cgt gcc ggt tgt gaa gaa aaa gtg aat gat gta    912
Ser Pro Ser Glu Phe Arg Ala Gly Cys Glu Glu Lys Val Asn Asp Val
    290                 295                 300 gcc gtc aag ttg tca taa                                            930
Ala Val Lys Leu Ser
305

<210> SEQ ID NO 96
<211> LENGTH: 309
<212> TYPE: PRT
<213> ORGANISM: Escherichia coli

<400> SEQUENCE: 96

Met Gln Tyr Gly Gln Leu Val Ser Ser Leu Asn Gly Gly Ser Met Lys
1               5                   10                  15

Ser Met Ala Glu Ala Gln Asn Asp Val Leu Leu Pro Gly Tyr Ser Phe
            20                  25                  30

Asn Ala His Leu Val Ala Gly Leu Ile Pro Ile Glu Ala Asn Gly Tyr
        35                  40                  45

Leu Asp Phe Phe Ile Asp Arg Pro Leu Gly Met Lys Gly Tyr Ile Leu
```

```
            50                  55                  60
Asn Leu Thr Ile Arg Gly Gln Gly Val Val Lys Asn Gln Gly Arg Glu
 65                  70                  75                  80

Phe Val Cys Arg Pro Gly Asp Ile Leu Leu Phe Pro Pro Gly Glu Ile
                 85                  90                  95

Gly His Leu Gly Arg His Pro Glu Ala Arg Glu Trp Tyr Arg Gln Trp
            100                 105                 110

Val Tyr Phe Arg Pro Arg Ala Tyr Trp His Glu Trp Leu Asn Trp Pro
        115                 120                 125

Ser Ile Phe Ala Asn Thr Gly Phe Phe Arg Pro Asp Glu Ala His Gln
    130                 135                 140

Pro His Phe Ser Asp Leu Phe Gly Gln Ile Ile Asn Ala Gly Gln Gly
145                 150                 155                 160

Glu Gly Arg Tyr Ser Glu Leu Leu Ala Ile Asn Leu Leu Glu Gln Leu
                165                 170                 175

Leu Leu Arg Arg Met Glu Ala Ile Asn Glu Ser Leu His Pro Pro Met
            180                 185                 190

Asp Asn Arg Val Arg Glu Ala Cys Gln Tyr Ile Ser Asp His Leu Ala
        195                 200                 205

Asp Ser Asn Phe Asp Ile Ala Ser Val Ala Gln His Val Cys Leu Ser
    210                 215                 220

Pro Ser Arg Leu Ser His Leu Phe Arg Gln Gln Leu Gly Ile Ser Val
225                 230                 235                 240

Leu Ser Trp Arg Glu Asp Gln Arg Ile Ser Gln Ala Lys Leu Leu Leu
                245                 250                 255

Ser Thr Thr Arg Met Pro Ile Ala Thr Val Gly Arg Asn Val Gly Phe
            260                 265                 270

Asp Asp Gln Leu Tyr Phe Ser Arg Val Phe Lys Lys Cys Thr Gly Ala
        275                 280                 285

Ser Pro Ser Glu Phe Arg Ala Gly Cys Glu Glu Lys Val Asn Asp Val
    290                 295                 300

Ala Val Lys Leu Ser
305

<210> SEQ ID NO 97
<211> LENGTH: 4452
<212> TYPE: DNA
<213> ORGANISM: Escherichia coli
<220> FEATURE:
<221> NAME/KEY: CDS
<222> LOCATION: (1607)..(2578)
<223> OTHER INFORMATION: SpecR gene in pBANspec

<400> SEQUENCE: 97
atcgatgcat aatgtgcctg tcaaatggac gaagcaggga ttctgcaaac cctatgctac     60
tccgtcaagc cgtcaattgt ctgattcgtt accactcaat ttcaatccgt aaacaggtca    120
aacatcagtt gccgcaacca atattggct aggtccttgt ggtacttcgc atgccagaac    180
atgttgatgg ctatttcagg caagacgact gggtgcggca aggcgcttag ccgaagggc    240 tccacgcagc agtcggctaa cgtatcggc acagtggcga gcagtcggt gcgctggagg    300 atgtggccaa cggcggcgaa gtgcggcact tccagacgga tgtcgcgccg gatgccgacc    360
cgtgtcatgt acgtgtccac ctcgccgtgg ccgtgccag cggcgatgac acgcacgtgg    420
ccgtaggaac agaagcgctc cagagtcagg ggttcgcggg tgactggatg gtccttgcga    480
cataggcaca cgtagtgatt ctggagcagc cggcgctgaa agaagccagt ttgcagattg    540
```

```
ggaagcaggc ccacggccaa gtccacggtt ccgttctgca aggcctgcat caggctcatc    600
gaactgtcgc gcaccgtact gatcacgcaa ttgggggcct ggtgagccag cacatccatc    660
agccgcggca tgaagtagat ctcgccaatg tcggtcatgg ccagggtgaa ggtacgctcg    720
ctggtcagcg gatcgaagct ttcatggtgc tgtaggggcgt tgcgcagtgc gtgcatggcc    780
gaagtgacgg gctcggccag atgcgcggca tagggtgtgg gttccattcc ctgatgtgtg    840
cgcacgaaga gtgggtcctg tagcgaggtg cgcaggcgtt tcagcgcatt gctcacggca    900
ggctgggtca ggcccaggtt ctccgcagtg atagagacgc gtctgtcgac cagcaactgg    960
ttgaacacca ccagcaggtt taaatccagg tcacgcagtt ccatggggcc tcgcttgggt   1020
tgctagcatt gtacctagga ctgagctagc cgtaaatcct ctagagtcga cctgcaggca   1080
tgcaagcttg gctgttttgg cggatgagag aagattttca gcctgataca gattaaatca   1140
gaacgcagaa gcggtctgat aaaacagaat ttgcctggcg gcagtagcgc ggtggtccca   1200
cctgacccca tgccgaactc agaagtgaaa cgccgtagcg ccgatggtag tgtgggggtct   1260 ccccatgcga gagtagggaa ctgccaggca tcaaataaaa cgaaaggctc agtcgaaaga   1320
ctgggccttt cgttttatct gttgtttgtc ggtgaacgct ctcctgagta ggacaaatcc   1380
gccgggagcg gatttgaacg ttgcgaagca acggcccgga gggtggcggg caggacgccc   1440
gccataaact gccaggcatc aaattaagca gaaggccatc ctgacggtga tatccggatg   1500
aaggcacgaa cccagtggac ataagcctcg ttcggttcgt aagctgtaat gcaagtagcg   1560
taactgccgt cacgcaactg gtccacaacc ttgaccgaac gcagcg gtg gta acg       1615
                                                    Val Val Thr
                                                     1 gcg cag tgg cgg ttt tca tgg ctt ctt gtt atg aca tgt ttt ttt ggg      1663
Ala Gln Trp Arg Phe Ser Trp Leu Leu Val Met Thr Cys Phe Phe Gly
 5              10                  15 gta cag tct atg cct cgg gca tcc aag cag caa gcg cgt tac gcc gtg      1711
Val Gln Ser Met Pro Arg Ala Ser Lys Gln Gln Ala Arg Tyr Ala Val
 20             25                  30                  35 ggt cga tgt ttg atg tta tgg agc agc aac gat gtt acg cag cag ggc      1759
Gly Arg Cys Leu Met Leu Trp Ser Ser Asn Asp Val Thr Gln Gln Gly
            40                  45                  50 agt cgc cct aaa aca aag tta aac atc atg agg gaa gcg gtg atc gcc      1807
Ser Arg Pro Lys Thr Lys Leu Asn Ile Met Arg Glu Ala Val Ile Ala
        55                  60                  65 gaa gta tcg act caa cta tca gag gta gtt ggc gtc atc gag cgc cat      1855
Glu Val Ser Thr Gln Leu Ser Glu Val Val Gly Val Ile Glu Arg His
        70                  75                  80 ctc gaa ccg acg ttg ctg gcc gta cat ttg tac ggc tcc gca gtg gat      1903
Leu Glu Pro Thr Leu Leu Ala Val His Leu Tyr Gly Ser Ala Val Asp
 85                 90                  95 ggc ggc ctg aag cca cac agt gat att gat ttg ctg gtt acg gtg acc      1951
Gly Gly Leu Lys Pro His Ser Asp Ile Asp Leu Leu Val Thr Val Thr
 100                105                 110                 115 gta agg ctt gat gaa aca acg cgg cga gct ttg atc aac gac ctt ttg      1999
Val Arg Leu Asp Glu Thr Thr Arg Arg Ala Leu Ile Asn Asp Leu Leu
            120                 125                 130 gaa act tcg gct tcc cct gga gag agc gag att ctc cgc gct gta gaa      2047
Glu Thr Ser Ala Ser Pro Gly Glu Ser Glu Ile Leu Arg Ala Val Glu
            135                 140                 145 gtc acc att gtt gtg cac gac gac atc att ccg tgg cgt tat cca gct      2095
Val Thr Ile Val Val His Asp Asp Ile Ile Pro Trp Arg Tyr Pro Ala
            150                 155                 160
```

| | | |
|---|---|---|
| aag cgc gaa ctg caa ttt gga gaa tgg cag cgc aat gac att ctt gca<br>Lys Arg Glu Leu Gln Phe Gly Glu Trp Gln Arg Asn Asp Ile Leu Ala<br>165                    170                    175 | | 2143 |
| ggt atc ttc gag cca gcc acg tac gac att gat ctg gct atc ttg ctg<br>Gly Ile Phe Glu Pro Ala Thr Tyr Asp Ile Asp Leu Ala Ile Leu Leu<br>180                    185                    190                    195 | | 2191 |
| aca aaa gca aga gaa cat agc gtt gcc ttg gta ggt cca gcg gcg gag<br>Thr Lys Ala Arg Glu His Ser Val Ala Leu Val Gly Pro Ala Ala Glu<br>                    200                    205                    210 | | 2239 |
| gaa ctc ttt gat ccg gtt cct gaa cag gat cta ttt gag gcg cta aat<br>Glu Leu Phe Asp Pro Val Pro Glu Gln Asp Leu Phe Glu Ala Leu Asn<br>                215                    220                    225 | | 2287 |
| gaa acc tta acg cta tgg aac tcg ccg ccc gac tgg gct ggc gat gag<br>Glu Thr Leu Thr Leu Trp Asn Ser Pro Pro Asp Trp Ala Gly Asp Glu<br>230                    235                    240 | | 2335 |
| cga aat gta gtg ctt acg ttg tcc cgc att tgg tac agc gca gta acc<br>Arg Asn Val Val Leu Thr Leu Ser Arg Ile Trp Tyr Ser Ala Val Thr<br>245                    250                    255 | | 2383 |
| ggc aaa atc gcg ccg aag gat gtc gct gcc gac tgg gca atg gag cgc<br>Gly Lys Ile Ala Pro Lys Asp Val Ala Ala Asp Trp Ala Met Glu Arg<br>260                    265                    270                    275 | | 2431 |
| ctg ccg gcc cag tat cag ccc gtc ata ctt gaa gct aga cag gct tat<br>Leu Pro Ala Gln Tyr Gln Pro Val Ile Leu Glu Ala Arg Gln Ala Tyr<br>                    280                    285                    290 | | 2479 |
| ctt gga caa gaa gaa gat cgc ttg gcc tcg cgc gca gat cag ttg gaa<br>Leu Gly Gln Glu Glu Asp Arg Leu Ala Ser Arg Ala Asp Gln Leu Glu<br>                295                    300                    305 | | 2527 |
| gaa ttt gtc cac tac gtg aaa ggc gag atc acc aag gta gtc ggc aaa<br>Glu Phe Val His Tyr Val Lys Gly Glu Ile Thr Lys Val Val Gly Lys<br>310                    315                    320 | | 2575 |
| taa tgtctaacaa ttcgttcaag ccgacggata tctagattga tttacgcgcc | | 2628 |
| ctgtagcggc gcattaagcg cggcgggtgt ggtggttacg cgcagcgtga ccgctacact | | 2688 |
| tgccagcgcc ctagcgcccg ctcctttcgc tttcttccct tcctttctcg ccacgttcgc | | 2748 |
| cggctttccc cgtcaagctc taaatcgggg gctcccttta gggttccgat ttagtgcttt | | 2808 |
| acggcacctc gaccccaaaa aacttgattt gggtgatggt tcacgtagtg gccatcgcc | | 2868 |
| ctgatagacg gttttttcgcc ctttgacgtt ggagtccacg ttctttaata gtggactctt | | 2928 |
| gttccaaact tgaacaacac tcaaccctat ctcgggctat tcttttgatt tataagggat | | 2988 |
| tttgccgatt tcggcctatt ggttaaaaaa tgagctgatt taacaaaaat ttaacgcgaa | | 3048 |
| ttttaacaaa atattaacgt ttacaattta aaaggatcta ggtgaagatc cttttttgata | | 3108 |
| atctcatgac caaaatccct taacgtgagt tttcgttcca ctgagcgtca gacccccgtag | | 3168 |
| aaaagatcaa aggatcttct tgagatcctt ttttctgcg cgtaatctgc tgcttgcaaa | | 3228 |
| caaaaaaacc accgctacca gcggtggttt gtttgccgga tcaagagcta ccaactcttt | | 3288 |
| ttccgaaggt aactggcttc agcagagcgc agataccaaa tactgtcctt ctagtgtagc | | 3348 |
| cgtagttagg ccaccacttc aagaactctg tagcaccgcc tacatacctc gctctgctaa | | 3408 |
| tcctgttacc agtggctgct gccagtggcg ataagtcgtg tcttaccggg ttggactcaa | | 3468 |
| gacgatagtt accggataag gcgcagcggt cgggctgaac gggggggttcg tgcacacagc | | 3528 |
| ccagcttgga gcgaacgacc tacaccgaac tgagatacct acagcgtgag ctatgagaaa | | 3588 |
| gcgccacgct tcccgaaggg agaaaggcgg acaggtatcc ggtaagcggc agggtcggaa | | 3648 |
| caggagagcg cacgagggag cttccagggg gaaacgcctg gtatctttat agtcctgtcg | | 3708 |
| ggtttcgcca cctctgactt gagcgtcgat ttttgtgatg ctcgtcaggg gggcggagcc | | 3768 |

```
tatggaaaaa cgccagcaac gcggccttt tacggttcct ggccttttgc tggccttttg     3828
ctcacatgtt ctttcctgcg ttatcccctg attctgtgga taaccgtatt accgcctttg     3888
agtgagctga taccgctcgc cgcagccgaa cgaccgagcg cagcgagtca gtgagcgagg     3948
aagcggaaga gcgcctgatg cggtatttc tccttacgca tctgtgcggt atttcacacc     4008
gcatatggtg cactctcagt acaatctgct ctgatgccgc atagttaagc cagtatacac     4068
tccgctatcg ctacgtgact gggtcatggc tgcgccccga cacccgccaa cacccgctga     4128
cgcgccctga cgggcttgtc tgctcccggc atccgcttac agacaagctg tgaccgtctc     4188
cgggagctgc atgtgtcaga ggttttcacc gtcatcaccg aaacgcgcga ggcagcaagg     4248
agatggcgcc caacagtccc ccggccacgg ggcctgccac catacccacg ccgaaacaag     4308
cgctcatgag cccgaagtgg cgagcccgat cttccccatc ggtgatgtcg cgatataggg     4368
cgccagcaac cgcacctgtg gcgccggtga tgccggccac gatgcgtccg gcgtagagga     4428
tctgctcatg tttgacagct tatc                                            4452
```

<210> SEQ ID NO 98
<211> LENGTH: 323
<212> TYPE: PRT
<213> ORGANISM: Escherichia coli

<400> SEQUENCE: 98

```
Val Val Thr Ala Gln Trp Arg Phe Ser Trp Leu Leu Val Met Thr Cys
1               5                   10                  15

Phe Phe Gly Val Gln Ser Met Pro Arg Ala Ser Lys Gln Gln Ala Arg
            20                  25                  30

Tyr Ala Val Gly Arg Cys Leu Met Leu Trp Ser Ser Asn Asp Val Thr
        35                  40                  45

Gln Gln Gly Ser Arg Pro Lys Thr Lys Leu Asn Ile Met Arg Glu Ala
    50                  55                  60

Val Ile Ala Glu Val Ser Thr Gln Leu Ser Glu Val Val Gly Val Ile
65                  70                  75                  80

Glu Arg His Leu Glu Pro Thr Leu Leu Ala Val His Leu Tyr Gly Ser
                85                  90                  95

Ala Val Asp Gly Gly Leu Lys Pro His Ser Asp Ile Asp Leu Leu Val
            100                 105                 110

Thr Val Thr Val Arg Leu Asp Glu Thr Thr Arg Arg Ala Leu Ile Asn
        115                 120                 125

Asp Leu Leu Glu Thr Ser Ala Ser Pro Gly Glu Ser Glu Ile Leu Arg
    130                 135                 140

Ala Val Glu Val Thr Ile Val Val His Asp Asp Ile Ile Pro Trp Arg
145                 150                 155                 160

Tyr Pro Ala Lys Arg Glu Leu Gln Phe Gly Glu Trp Gln Arg Asn Asp
                165                 170                 175

Ile Leu Ala Gly Ile Phe Glu Pro Ala Thr Tyr Asp Ile Asp Leu Ala
            180                 185                 190

Ile Leu Leu Thr Lys Ala Arg Glu His Ser Val Ala Leu Val Gly Pro
        195                 200                 205

Ala Ala Glu Glu Leu Phe Asp Pro Val Pro Glu Gln Asp Leu Phe Glu
    210                 215                 220

Ala Leu Asn Glu Thr Leu Thr Leu Trp Asn Ser Pro Pro Asp Trp Ala
225                 230                 235                 240

Gly Asp Glu Arg Asn Val Val Leu Thr Leu Ser Arg Ile Trp Tyr Ser
```

```
                    245                 250                 255
Ala Val Thr Gly Lys Ile Ala Pro Lys Asp Val Ala Ala Asp Trp Ala
                260                 265                 270

Met Glu Arg Leu Pro Ala Gln Tyr Gln Pro Val Ile Leu Glu Ala Arg
            275                 280                 285

Gln Ala Tyr Leu Gly Gln Glu Asp Arg Leu Ala Ser Arg Ala Asp
        290                 295                 300

Gln Leu Glu Glu Phe Val His Tyr Val Lys Gly Glu Ile Thr Lys Val
305                 310                 315                 320

Val Gly Lys

<210> SEQ ID NO 99
<211> LENGTH: 903
<212> TYPE: DNA
<213> ORGANISM: Escherichia coli
<220> FEATURE:
<221> NAME/KEY: CDS
<222> LOCATION: (1)..(903)
<223> OTHER INFORMATION: NahR_Asn169 gene encoding Salicylic acid
      biosensor protein

<400> SEQUENCE: 99 atg gaa ctg cgt gac ctg gat tta aac ctg ctg gtg gtg ttc aac cag      48
Met Glu Leu Arg Asp Leu Asp Leu Asn Leu Leu Val Val Phe Asn Gln
1               5                  10                  15 ttg ctg gtc gac aga cgc gtc tct atc act gcg gag aac ctg ggc ctg      96
Leu Leu Val Asp Arg Arg Val Ser Ile Thr Ala Glu Asn Leu Gly Leu
                20                  25                  30 acc cag cct gcc gtg agc aat gcg ctg aaa cgc ctg cgc acc tcg cta     144
Thr Gln Pro Ala Val Ser Asn Ala Leu Lys Arg Leu Arg Thr Ser Leu
            35                  40                  45 cag gac cca ctc ttc gtg cgc aca cat cag gga atg gaa ccc aca ccc     192
Gln Asp Pro Leu Phe Val Arg Thr His Gln Gly Met Glu Pro Thr Pro
        50                  55                  60 tat gcc gcg cat ctg gcc gag ccc gtc act tcg gcc atg cac gca ctg     240
Tyr Ala Ala His Leu Ala Glu Pro Val Thr Ser Ala Met His Ala Leu
65                  70                  75                  80 cgc aac gcc cta cag cac cat gaa agc ttc gat ccg ctg acc agc gag     288
Arg Asn Ala Leu Gln His His Glu Ser Phe Asp Pro Leu Thr Ser Glu
                85                  90                  95 cgt acc ttc acc ctg gcc atg acc gac att ggc gag atc tac ttc atg     336
Arg Thr Phe Thr Leu Ala Met Thr Asp Ile Gly Glu Ile Tyr Phe Met
                100                 105                 110 ccg cgg ctg atg gat gtg ctg gct cac cag gcc ccc aat tgc gtg atc     384
Pro Arg Leu Met Asp Val Leu Ala His Gln Ala Pro Asn Cys Val Ile
            115                 120                 125 agt acg gtg cgc gac agt tcg atg agc ctg atg cag gcc ttg cag aac     432
Ser Thr Val Arg Asp Ser Ser Met Ser Leu Met Gln Ala Leu Gln Asn
        130                 135                 140 gga acc gtg gac ttg gcc gtg ggc ctg ctt ccc aat ctg caa act ggc     480
Gly Thr Val Asp Leu Ala Val Gly Leu Leu Pro Asn Leu Gln Thr Gly
145                 150                 155                 160 ttc ttt cag cgc cgg ctg ctc cag aat cac tac gtg tgc cta tgt cgc     528
Phe Phe Gln Arg Arg Leu Leu Gln Asn His Tyr Val Cys Leu Cys Arg
                165                 170                 175 aag gac cat cca gtc acc cgc gaa ccc ctg act ctg gag cgc ttc tgt     576
Lys Asp His Pro Val Thr Arg Glu Pro Leu Thr Leu Glu Arg Phe Cys
                180                 185                 190 tcc tac ggc cac gtg cgt gtc atc gcc gct ggc acc ggc cac ggc gag     624
Ser Tyr Gly His Val Arg Val Ile Ala Ala Gly Thr Gly His Gly Glu
```

```
                195                 200                 205
gtg gac acg tac atg aca cgg gtc ggc atc cgg cgc gac atc cgt ctg    672
Val Asp Thr Tyr Met Thr Arg Val Gly Ile Arg Arg Asp Ile Arg Leu
210                 215                 220 gaa gtg ccg cac ttc gcc gcc gtt ggc cac atc ctc cag cgc acc gat    720
Glu Val Pro His Phe Ala Ala Val Gly His Ile Leu Gln Arg Thr Asp
225                 230                 235                 240 ctg ctc gcc act gtg ccg ata cgt tta gcc gac tgc tgc gtg gag ccc    768
Leu Leu Ala Thr Val Pro Ile Arg Leu Ala Asp Cys Cys Val Glu Pro
                245                 250                 255 ttc ggc cta agc gcc ttg ccg cac cca gtc gtc ttg cct gaa ata gcc    816
Phe Gly Leu Ser Ala Leu Pro His Pro Val Val Leu Pro Glu Ile Ala
260                 265                 270 atc aac atg ttc tgg cat gcg aag tac cac aag gac cta gcc aat att    864
Ile Asn Met Phe Trp His Ala Lys Tyr His Lys Asp Leu Ala Asn Ile
        275                 280                 285 tgg ttg cgg caa ctg atg ttt gac ctg ttt acg gat tga                903
Trp Leu Arg Gln Leu Met Phe Asp Leu Phe Thr Asp
290                 295                 300

<210> SEQ ID NO 100
<211> LENGTH: 300
<212> TYPE: PRT
<213> ORGANISM: Escherichia coli

<400> SEQUENCE: 100

Met Glu Leu Arg Asp Leu Asp Leu Asn Leu Val Val Phe Asn Gln
1               5                   10                  15

Leu Leu Val Asp Arg Arg Val Ser Ile Thr Ala Glu Asn Leu Gly Leu
                20                  25                  30

Thr Gln Pro Ala Val Ser Asn Ala Leu Lys Arg Leu Arg Thr Ser Leu
            35                  40                  45

Gln Asp Pro Leu Phe Val Arg Thr His Gln Gly Met Glu Pro Thr Pro
        50                  55                  60

Tyr Ala Ala His Leu Ala Glu Pro Val Thr Ser Ala Met His Ala Leu
65                  70                  75                  80

Arg Asn Ala Leu Gln His His Glu Ser Phe Asp Pro Leu Thr Ser Glu
                85                  90                  95

Arg Thr Phe Thr Leu Ala Met Thr Asp Ile Gly Glu Ile Tyr Phe Met
            100                 105                 110

Pro Arg Leu Met Asp Val Leu Ala His Gln Ala Pro Asn Cys Val Ile
        115                 120                 125

Ser Thr Val Arg Asp Ser Ser Met Ser Leu Met Gln Ala Leu Gln Asn
130                 135                 140

Gly Thr Val Asp Leu Ala Val Gly Leu Leu Pro Asn Leu Gln Thr Gly
145                 150                 155                 160

Phe Phe Gln Arg Arg Leu Leu Gln Asn His Tyr Val Cys Leu Cys Arg
                165                 170                 175

Lys Asp His Pro Val Thr Arg Glu Pro Leu Thr Leu Glu Arg Phe Cys
            180                 185                 190

Ser Tyr Gly His Val Arg Val Ile Ala Ala Gly Thr Gly His Gly Glu
        195                 200                 205

Val Asp Thr Tyr Met Thr Arg Val Gly Ile Arg Arg Asp Ile Arg Leu
210                 215                 220

Glu Val Pro His Phe Ala Ala Val Gly His Ile Leu Gln Arg Thr Asp
225                 230                 235                 240
```

```
Leu Leu Ala Thr Val Pro Ile Arg Leu Ala Asp Cys Cys Val Glu Pro
            245                 250                 255

Phe Gly Leu Ser Ala Leu Pro His Pro Val Val Leu Pro Glu Ile Ala
            260                 265                 270

Ile Asn Met Phe Trp His Ala Lys Tyr His Lys Asp Leu Ala Asn Ile
        275                 280                 285

Trp Leu Arg Gln Leu Met Phe Asp Leu Phe Thr Asp
290                 295                 300

<210> SEQ ID NO 101
<211> LENGTH: 2233
<212> TYPE: DNA
<213> ORGANISM: Escherichia coli
<220> FEATURE:
<221> NAME/KEY: promoter
<222> LOCATION: (1794)..(1929)
<223> OTHER INFORMATION: pSAL promoter
<220> FEATURE:
<221> NAME/KEY: RBS
<222> LOCATION: (1930)..(1935)
<220> FEATURE:
<221> NAME/KEY: CDS
<222> LOCATION: (1941)..(2231)
<223> OTHER INFORMATION: Portion of folp gene

<400> SEQUENCE: 101
aagatgctct catgaaatat gagactatcg acgcaccgca gattgatgac ctgatggcac      60
gtcgcgatgt acgtccgcca gcgggctggg aagaaccagg cgcttctaac aattctggcg     120
acaatggtag tccaaaggct cctcgtccgg ttgatgaacc cgtacgccg aacccgggta      180 acaccatgtc agagcagtta ggcgacaagt aagttcccgc atcagatgac tgtatttgta     240
ccgaaaaccc cggggcgtgc tccggggttt tttcttatca attcatacca gggataacat     300
cagcgattgt gtaggctgga gctgcttcga agttcctata ctttctagag aataggaact     360
tcggaatagg aacttcaaga tccccttatt agaagaactc gtcaagaagg cgatagaagg     420
cgatgcgctg cgaatcggga gcggcgatac cgtaaagcac gaggaagcgg tcagcccatt     480
cgccgccaag ctcttcagca atatcacggg tagccaacgc tatgtcctga tagcggtccg     540
ccacacccag ccggccacag tcgatgaatc cagaaaagcg gccattttcc accatgatat     600
tcggcaagca ggcatcgcca tgggtcacga cgagatcctc gccgtcgggc atgcgcgcct     660
tgagcctggc gaacagttcg gctggcgcga gcccctgatg ctcttcgtcc agatcatcct     720
gatcgacaag accggcttcc atccgagtac gtgctcgctc gatgcgatgt ttcgcttggt     780
ggtcgaatgg gcaggtagcc ggatcaagcg tatgcagccg ccgcattgca tcagccatga     840
tggatacttt ctcggcagga gcaaggtgag atgacaggag atcctgcccc ggcacttcgc     900
ccaatagcag ccagtccctt cccgcttcag tgacaacgtc gagcacagct gcgcaaggaa     960
cgcccgtcgt ggccagccac gatagccgcg ctgcctcgtc ctgcagttca ttcagggcac    1020
cggacaggtc ggtcttgaca aaaagaaccg ggcgccctg cgctgacagc ggaacacgg     1080 cggcatcaga gcagccgatt gtctgttgtg cccagtcata gccgaatagc ctctccaccc    1140
aagcggccgg agaacctgcg tgcaatccat cttgttcaat catgcgaaac gatcctcatc    1200
ctgtctcttg atcagatctt gatccctgc gccatcagat ccttggcggc aagaagcca     1260 tccagtttac tttgcagggc ttcccaacct taccagaggg cgccccagct ggcaattccg    1320
gttcgcttgc tgtccataaa accgccagt ctagctatcg ccatgtaagc ccactgcaag    1380
ctacctgctt tctctttgcg cttgcgtttt cccttgtcca gatagcccag tagctgacat    1440
```

-continued

```
tcatccgggg tcagcaccgt ttctgcggac tggctttcta cgtgttccgc ttcctttagc      1500
agcccttgcg ccctgagtgc ttgcggcagc gtgagcttca aaagcgctct gaagttccta      1560
tactttctag agaataggaa cttcgaactg caggtcgacg gatccccgga atattcatat      1620
gtctatgtgc gcacgaagag tgggtcctgt agcgaggtgc gcaggcgttt cagcgcattg      1680
ctcacggcag gctgggtcag gcccaggttc tccgcagtga tagagacgcg tctgtcgacc      1740
agcaactggt tgaacaccac cagcaggttt aaatccaggt cacgcagttc catgggcct      1800 cgcttgggtt attgctggtg cccggccggg cgcaatattc atgttgatga tttattatat      1860
atcgagtggg tatttatca atattgtttg ctccgttatc gttattaaca agtcatcaat      1920
aaagccatca ggagtaaggt atg aaa ctc ttt gcc cag ggt act tca ctg gac      1973
                      Met Lys Leu Phe Ala Gln Gly Thr Ser Leu Asp
                       1               5                  10 ctt agc cat cct cac gta atg ggg atc ctc aac gtc acg cct gat tcc      2021
Leu Ser His Pro His Val Met Gly Ile Leu Asn Val Thr Pro Asp Ser
            15                  20                  25 ttt tcg gat ggt ggc acg cat aac tcg ctg ata gat gcg gtg aaa cat      2069
Phe Ser Asp Gly Gly Thr His Asn Ser Leu Ile Asp Ala Val Lys His
        30                  35                  40 gcg aat ctg atg atc aac gct ggc gcg acg atc att gac gtt ggt ggc      2117
Ala Asn Leu Met Ile Asn Ala Gly Ala Thr Ile Ile Asp Val Gly Gly
    45                  50                  55 gag tcc acg cgc cca ggg gcg gcg gaa gtt agc gtt gaa gaa gag ttg      2165
Glu Ser Thr Arg Pro Gly Ala Ala Glu Val Ser Val Glu Glu Glu Leu
60                  65                  70                  75 caa cgt gtt att cct gtg gtt gag gca att gct caa cgc ttc gaa gtc      2213
Gln Arg Val Ile Pro Val Val Glu Ala Ile Ala Gln Arg Phe Glu Val
                80                  85                  90 tgg atc tca gtc gat aca tc                                            2233
Trp Ile Ser Val Asp Thr
                95
```

<210> SEQ ID NO 102
<211> LENGTH: 97
<212> TYPE: PRT
<213> ORGANISM: Escherichia coli

<400> SEQUENCE: 102

```
Met Lys Leu Phe Ala Gln Gly Thr Ser Leu Asp Leu Ser His Pro His
1               5                   10                  15

Val Met Gly Ile Leu Asn Val Thr Pro Asp Ser Phe Ser Asp Gly Gly
            20                  25                  30

Thr His Asn Ser Leu Ile Asp Ala Val Lys His Ala Asn Leu Met Ile
        35                  40                  45

Asn Ala Gly Ala Thr Ile Ile Asp Val Gly Gly Glu Ser Thr Arg Pro
    50                  55                  60

Gly Ala Ala Glu Val Ser Val Glu Glu Glu Leu Gln Arg Val Ile Pro
65                  70                  75                  80

Val Val Glu Ala Ile Ala Gln Arg Phe Glu Val Trp Ile Ser Val Asp
                85                  90                  95

Thr
```

<210> SEQ ID NO 103
<211> LENGTH: 4452
<212> TYPE: DNA
<213> ORGANISM: Escherichia coli
<220> FEATURE:
<221> NAME/KEY: CDS
<222> LOCATION: (1607)..(2578)
<223> OTHER INFORMATION: SpecR gene in pBABspec

<400> SEQUENCE: 103

```
atcgatgcat aatgtgcctg tcaaatggac gaagcaggga ttctgcaaac cctatgctac      60
tccgtcaagc cgtcaattgt ctgattcgtt accactcaat ttcaatccgt aaacaggtca     120
aacatcagtt gccgcaacca aatattggct aggtccttgt ggtacttcgc atgccagaac     180
atgttgatgg ctatttcagg caagacgact gggtgcggca aggcgcttag ccgaagggc      240 tccacgcagc agtcggctaa acgtatcggc acagtggcga gcagatcggt gcgctggagg     300
atgtggccaa cggcggcgaa gtgcggcact tccagacgga tgtcgcgccg gatgccgacc     360
cgtgtcatgt acgtgtccac ctcgccgtgg ccggtgccag cggcgatgac acgcacgtgg     420
ccgtaggaac agaagcgctc cagagtcagg ggttcgcggg tgactggatg gtccttgcga     480
cataggcaca cgtagtgatc ctggagcagc cggcgctgaa agaagccagt ttgcagattg     540
ggaagcaggc ccacgccaa  gtccacggtt ccgttctgca aggcctgcat caggctcatc     600
gaactgtcgc gcaccgtact gatcacgcaa ttggggggcct ggtgagccag cacatccatc    660
agccgcggca tgaagtagat ctcgccaatg tcggtcatgg ccagggtgaa ggtacgctcg     720
ctggtcagcg gatcgaagct ttcatggtgc tgtagggcgt gcgcagtgc gtgcatggcc      780 gaagtgacgg gctcggccag atgcgcggca taggtgtgg gttccattcc ctgatgtgtg      840
cgcacgaaga gtgggtcctg tagcgaggtg cgcaggcgtt tcagcgcatt gctcacggca     900
ggctgggtca ggcccaggtt ctccgcagtg atagagacgc gtctgtcgac cagcaactgg     960
ttgaacacca ccagcaggtt taaatccagg tcacgcagtt ccatggggcc tcgcttgggt    1020
tgctagcatt gtacctagga ctgagctagc cgtaaatcct ctagagtcga cctgcaggca    1080
tgcaagcttg gctgttttgg cggatgagag aagattttca gcctgataca gattaaatca    1140
gaacgcagaa gcggtctgat aaaacagaat ttgcctggcg gcagtagcgc ggtggtccca    1200
cctgacccca tgccgaactc agaagtgaaa cgccgtagcg ccgatggtag tgtggggtct    1260
ccccatgcga gagtagggaa ctgccaggca tcaaataaaa cgaaaggctc agtcgaaaga    1320
ctgggccttt cgttttatct gttgtttgtc ggtgaacgct ctcctgagta ggacaaatcc    1380
gccgggagcg gatttgaacg ttgcgaagca acggcccgga gggtggcggg caggacgccc    1440
gccataaact gccaggcatc aaattaagca gaaggccatc ctgacggtga tatccggatg    1500
aaggcacgaa cccagtggac ataagcctcg ttcggttcgt aagctgtaat gcaagtagcg    1560
taactgccgt cacgcaactg gtccacaacc ttgaccgaac gcagcg gtg gta acg       1615
                                                      Val Val Thr
                                                       1
```

```
gcg cag tgg cgg ttt tca tgg ctt ctt gtt atg aca tgt ttt ttt ggg      1663
Ala Gln Trp Arg Phe Ser Trp Leu Leu Val Met Thr Cys Phe Phe Gly
      5                  10                  15 gta cag tct atg cct cgg gca tcc aag cag caa gcg cgt tac gcc gtg      1711
Val Gln Ser Met Pro Arg Ala Ser Lys Gln Gln Ala Arg Tyr Ala Val
 20                  25                  30                  35 ggt cga tgt ttg atg tta tgg agc agc aac gat gtt acg cag cag ggc      1759
Gly Arg Cys Leu Met Leu Trp Ser Ser Asn Asp Val Thr Gln Gln Gly
                 40                  45                  50 agt cgc cct aaa aca aag tta aac atc atg agg gaa gcg gtg atc gcc      1807
Ser Arg Pro Lys Thr Lys Leu Asn Ile Met Arg Glu Ala Val Ile Ala
             55                  60                  65 gaa gta tcg act caa cta tca gag gta gtt ggc gtc atc gag cgc cat      1855
Glu Val Ser Thr Gln Leu Ser Glu Val Val Gly Val Ile Glu Arg His
```

-continued

|  |  |  |  |  |  |  |  |  |  |  |  |  |  |  |  |
|---|---|---|---|---|---|---|---|---|---|---|---|---|---|---|---|
|  |  | 70 |  |  |  | 75 |  |  |  | 80 |  |  |  |  |  | ctc gaa ccg acg ttg ctg gcc gta cat ttg tac ggc tcc gca gtg gat    1903
Leu Glu Pro Thr Leu Leu Ala Val His Leu Tyr Gly Ser Ala Val Asp
         85                  90                  95 ggc ggc ctg aag cca cac agt gat att gat ttg ctg gtt acg gtg acc    1951
Gly Gly Leu Lys Pro His Ser Asp Ile Asp Leu Leu Val Thr Val Thr
100              105                 110                 115 gta agg ctt gat gaa aca acg cgg cga gct ttg atc aac gac ctt ttg    1999
Val Arg Leu Asp Glu Thr Thr Arg Arg Ala Leu Ile Asn Asp Leu Leu
             120                 125                 130 gaa act tcg gct tcc cct gga gag agc gag att ctc cgc gct gta gaa    2047
Glu Thr Ser Ala Ser Pro Gly Glu Ser Glu Ile Leu Arg Ala Val Glu
             135                 140                 145 gtc acc att gtt gtg cac gac gac atc att ccg tgg cgt tat cca gct    2095
Val Thr Ile Val Val His Asp Asp Ile Ile Pro Trp Arg Tyr Pro Ala
         150                 155                 160 aag cgc gaa ctg caa ttt gga gaa tgg cag cgc aat gac att ctt gca    2143
Lys Arg Glu Leu Gln Phe Gly Glu Trp Gln Arg Asn Asp Ile Leu Ala
     165                 170                 175 ggt atc ttc gag cca gcc acg tac gac att gat ctg gct atc ttg ctg    2191
Gly Ile Phe Glu Pro Ala Thr Tyr Asp Ile Asp Leu Ala Ile Leu Leu
180              185                 190                 195 aca aaa gca aga gaa cat agc gtt gcc ttg gta ggt cca gcg gcg gag    2239
Thr Lys Ala Arg Glu His Ser Val Ala Leu Val Gly Pro Ala Ala Glu
             200                 205                 210 gaa ctc ttt gat ccg gtt cct gaa cag gat cta ttt gag gcg cta aat    2287
Glu Leu Phe Asp Pro Val Pro Glu Gln Asp Leu Phe Glu Ala Leu Asn
             215                 220                 225 gaa acc tta acg cta tgg aac tcg ccg ccc gac tgg gct ggc gat gag    2335
Glu Thr Leu Thr Leu Trp Asn Ser Pro Pro Asp Trp Ala Gly Asp Glu
             230                 235                 240 cga aat gta gtg ctt acg ttg tcc cgc att tgg tac agc gca gta acc    2383
Arg Asn Val Val Leu Thr Leu Ser Arg Ile Trp Tyr Ser Ala Val Thr
         245                 250                 255 ggc aaa atc gcg ccg aag gat gtc gct gcc gac tgg gca atg gag cgc    2431
Gly Lys Ile Ala Pro Lys Asp Val Ala Ala Asp Trp Ala Met Glu Arg
260              265                 270                 275 ctg ccg gcc cag tat cag ccc gtc ata ctt gaa gct aga cag gct tat    2479
Leu Pro Ala Gln Tyr Gln Pro Val Ile Leu Glu Ala Arg Gln Ala Tyr
             280                 285                 290 ctt gga caa gaa gaa gat cgc ttg gcc tcg cgc gca gat cag ttg gaa    2527
Leu Gly Gln Glu Glu Asp Arg Leu Ala Ser Arg Ala Asp Gln Leu Glu
             295                 300                 305 gaa ttt gtc cac tac gtg aaa ggc gag atc acc aag gta gtc ggc aaa    2575
Glu Phe Val His Tyr Val Lys Gly Glu Ile Thr Lys Val Val Gly Lys
             310                 315                 320 taa tgtctaacaa ttcgttcaag ccgacggata tctagattga tttacgcgcc        2628
ctgtagcggc gcattaagcg cggcgggtgt ggtggttacg cgcagcgtga ccgctacact  2688
tgccagcgcc ctagcgcccg ctcctttcgc tttcttccct tcctttctcg ccacgttcgc  2748
cggctttccc cgtcaagctc taaatcgggg ctcccttta gggttccgat ttagtgcttt   2808
acggcacctc gaccccaaaa aacttgattt gggtgatggt tcacgtagtg gccatcgcc   2868 ctgatagacg gttttcgcc ctttgacgtt ggagtccacg ttctttaata gtggactctt   2928
gttccaaact tgaacaacac tcaacccat ctcgggctat tcttttgatt tataagggat   2988
tttgccgatt tcggctatt ggttaaaaaa tgagctgatt taacaaaaat ttaacgcgaa   3048
ttttaacaaa atattaacgt ttacaattta aaaggatcta ggtgaagatc cttttgata   3108

```
atctcatgac caaaatccct taacgtgagt tttcgttcca ctgagcgtca gaccccgtag    3168
aaaagatcaa aggatcttct tgagatcctt tttttctgcg cgtaatctgc tgcttgcaaa    3228
caaaaaaacc accgctacca gcggtggttt gtttgccgga tcaagagcta ccaactcttt    3288
ttccgaaggt aactggcttc agcagagcgc agataccaaa tactgtcctt ctagtgtagc    3348
cgtagttagg ccaccacttc aagaactctg tagcaccgcc tacatacctc gctctgctaa    3408
tcctgttacc agtggctgct gccagtggcg ataagtcgtg tcttaccggg ttggactcaa    3468
gacgatagtt accggataag gcgcagcggt cgggctgaac ggggggttcg tgcacacagc    3528
ccagcttgga gcgaacgacc tacaccgaac tgagatacct acagcgtgag ctatgagaaa    3588
gcgccacgct tcccgaaggg agaaaggcgg acaggtatcc ggtaagcggc agggtcggaa    3648
caggagagcg cacgagggag cttccagggg gaaacgcctg gtatctttat agtcctgtcg    3708
ggtttcgcca cctctgactt gagcgtcgat ttttgtgatg ctcgtcaggg gggcggagcc    3768
tatggaaaaa cgccagcaac gcggccttttt acggttcct ggcttttgc tggccttttg    3828 ctcacatgtt ctttcctgcg ttatcccctg attctgtgga taaccgtatt accgcctttg    3888
agtgagctga taccgctcgc cgcagccgaa cgaccgagcg cagcgagtca gtgagcgagg    3948
aagcggaaga gcgcctgatg cggtattttc tccttacgca tctgtgcggt atttcacacc    4008
gcatatggtg cactctcagt acaatctgct ctgatgccgc atagttaagc cagtatacac    4068
tccgctatcg ctacgtgact gggtcatggc tgcgccccga cacccgccaa cacccgctga    4128
cgcgccctga cgggcttgtc tgctcccggc atccgcttac agacaagctg tgaccgtctc    4188
cgggagctgc atgtgtcaga ggttttcacc gtcatcaccg aaacgcgcga ggcagcaagg    4248
agatggcgcc caacagtccc ccggccacgg ggcctgccac catacccacg ccgaaacaag    4308
cgctcatgag cccgaagtgg cgagcccgat cttccccatc ggtgatgtcg gcgatatagg    4368
cgccagcaac cgcacctgtg gcgccggtga tgccggccac gatgcgtccg gcgtagagga    4428
tctgctcatg tttgacagct tatc                                          4452
```

<210> SEQ ID NO 104
<211> LENGTH: 323
<212> TYPE: PRT
<213> ORGANISM: Escherichia coli

<400> SEQUENCE: 104

```
Val Val Thr Ala Gln Trp Arg Phe Ser Trp Leu Leu Val Met Thr Cys
1               5                   10                  15

Phe Phe Gly Val Gln Ser Met Pro Arg Ala Ser Lys Gln Gln Ala Arg
            20                  25                  30

Tyr Ala Val Gly Arg Cys Leu Met Leu Trp Ser Ser Asn Asp Val Thr
        35                  40                  45

Gln Gln Gly Ser Arg Pro Lys Thr Lys Leu Asn Ile Met Arg Glu Ala
    50                  55                  60

Val Ile Ala Glu Val Ser Thr Gln Leu Ser Glu Val Val Gly Val Ile
65                  70                  75                  80

Glu Arg His Leu Glu Pro Thr Leu Leu Ala Val His Leu Tyr Gly Ser
                85                  90                  95

Ala Val Asp Gly Gly Leu Lys Pro His Ser Asp Ile Asp Leu Leu Val
            100                 105                 110

Thr Val Thr Val Arg Leu Asp Glu Thr Thr Arg Arg Ala Leu Ile Asn
        115                 120                 125
```

```
Asp Leu Leu Glu Thr Ser Ala Ser Pro Gly Glu Ser Glu Ile Leu Arg
    130                 135                 140

Ala Val Glu Val Thr Ile Val Val His Asp Asp Ile Ile Pro Trp Arg
145                 150                 155                 160

Tyr Pro Ala Lys Arg Glu Leu Gln Phe Gly Glu Trp Gln Arg Asn Asp
                165                 170                 175

Ile Leu Ala Gly Ile Phe Glu Pro Ala Thr Tyr Asp Ile Asp Leu Ala
            180                 185                 190

Ile Leu Leu Thr Lys Ala Arg Glu His Ser Val Ala Leu Val Gly Pro
        195                 200                 205

Ala Ala Glu Glu Leu Phe Asp Pro Val Pro Glu Gln Asp Leu Phe Glu
210                 215                 220

Ala Leu Asn Glu Thr Leu Thr Leu Trp Asn Ser Pro Pro Asp Trp Ala
225                 230                 235                 240

Gly Asp Glu Arg Asn Val Val Leu Thr Leu Ser Arg Ile Trp Tyr Ser
                245                 250                 255

Ala Val Thr Gly Lys Ile Ala Pro Lys Asp Val Ala Ala Asp Trp Ala
            260                 265                 270

Met Glu Arg Leu Pro Ala Gln Tyr Gln Pro Val Ile Leu Glu Ala Arg
        275                 280                 285

Gln Ala Tyr Leu Gly Gln Glu Asp Arg Leu Ala Ser Arg Ala Asp
290                 295                 300

Gln Leu Glu Glu Phe Val His Tyr Val Lys Gly Glu Ile Thr Lys Val
305                 310                 315                 320

Val Gly Lys

<210> SEQ ID NO 105
<211> LENGTH: 903
<212> TYPE: DNA
<213> ORGANISM: Escherichia coli
<220> FEATURE:
<221> NAME/KEY: CDS
<222> LOCATION: (1)..(903)
<223> OTHER INFORMATION: NahR gene encoding NahR benzoic acid biosensor

<400> SEQUENCE: 105 atg gaa ctg cgt gac ctg gat tta aac ctg ctg gtg gtg ttc aac cag      48
Met Glu Leu Arg Asp Leu Asp Leu Asn Leu Leu Val Val Phe Asn Gln
1               5                   10                  15 ttg ctg gtc gac aga cgc gtc tct atc act gcg gag aac ctg ggc ctg      96
Leu Leu Val Asp Arg Arg Val Ser Ile Thr Ala Glu Asn Leu Gly Leu
            20                  25                  30 acc cag cct gcc gtg agc aat gcg ctg aaa cgc ctg cgc acc tcg cta     144
Thr Gln Pro Ala Val Ser Asn Ala Leu Lys Arg Leu Arg Thr Ser Leu
        35                  40                  45 cag gac cca ctc ttc gtg cgc aca cat cag gga atg gaa ccc aca ccc     192
Gln Asp Pro Leu Phe Val Arg Thr His Gln Gly Met Glu Pro Thr Pro
    50                  55                  60 tat gcc gcg cat ctg gcc gag ccc gtc act tcg gcc atg cac gca ctg     240
Tyr Ala Ala His Leu Ala Glu Pro Val Thr Ser Ala Met His Ala Leu
65                  70                  75                  80 cgc aac gcc cta cag cac cat gaa agc ttc gat ccg ctg acc agc gag     288
Arg Asn Ala Leu Gln His His Glu Ser Phe Asp Pro Leu Thr Ser Glu
                85                  90                  95 cgt acc ttc acc ctg gcc atg acc gac att ggc gag atc tac ttc atg     336
Arg Thr Phe Thr Leu Ala Met Thr Asp Ile Gly Glu Ile Tyr Phe Met
            100                 105                 110 ccg cgg ctg atg gat gtg ctg gct cac cag gcc ccc aat tgc gtg atc     384
```

| | | |
|---|---|---|
| Pro Arg Leu Met Asp Val Leu Ala His Gln Ala Pro Asn Cys Val Ile<br>     115                    120                    125 | | |
| agt acg gtg cgc gac agt tcg atg agc ctg atg cag gcc ttg cag aac<br>Ser Thr Val Arg Asp Ser Ser Met Ser Leu Met Gln Ala Leu Gln Asn<br>    130                    135                    140 | | 432 |
| gga acc gtg gac ttg gcc gtg ggc ctg ctt ccc aat ctg caa act ggc<br>Gly Thr Val Asp Leu Ala Val Gly Leu Leu Pro Asn Leu Gln Thr Gly<br>145                   150                    155                  160 | | 480 |
| ttc ttt cag cgc cgg ctg ctc cag gat cac tac gtg tgc cta tgt cgc<br>Phe Phe Gln Arg Arg Leu Leu Gln Asp His Tyr Val Cys Leu Cys Arg<br>                165                    170                    175 | | 528 |
| aag gac cat cca gtc acc cgc gaa ccc ctg act ctg gag cgc ttc tgt<br>Lys Asp His Pro Val Thr Arg Glu Pro Leu Thr Leu Glu Arg Phe Cys<br>            180                    185                    190 | | 576 |
| tcc tac ggc cac gtg cgt gtc atc gcc gct ggc acc ggc cac ggc gag<br>Ser Tyr Gly His Val Arg Val Ile Ala Ala Gly Thr Gly His Gly Glu<br>                195                    200                    205 | | 624 |
| gtg gac acg tac atg aca cgg gtc ggc atc cgg cgc gac atc cgt ctg<br>Val Asp Thr Tyr Met Thr Arg Val Gly Ile Arg Arg Asp Ile Arg Leu<br>    210                    215                    220 | | 672 |
| gaa gtg ccg cac ttc gcc gcc gtt ggc cac atc ctc cag cgc acc gat<br>Glu Val Pro His Phe Ala Ala Val Gly His Ile Leu Gln Arg Thr Asp<br>225                   230                    235                  240 | | 720 |
| ctg ctc gcc act gtg ccg ata cgt tta gcc gac tgc tgc gtg gag ccc<br>Leu Leu Ala Thr Val Pro Ile Arg Leu Ala Asp Cys Cys Val Glu Pro<br>                245                    250                    255 | | 768 |
| ttc ggc cta agc gcc ttg ccg cac cca gtc gtc ttg cct gaa ata gcc<br>Phe Gly Leu Ser Ala Leu Pro His Pro Val Val Leu Pro Glu Ile Ala<br>            260                    265                    270 | | 816 |
| atc aac atg ttc tgg cat gcg aag tac cac aag gac cta gcc aat att<br>Ile Asn Met Phe Trp His Ala Lys Tyr His Lys Asp Leu Ala Asn Ile<br>    275                    280                    285 | | 864 |
| tgg ttg cgg caa ctg atg ttt gac ctg ttt acg gat tga<br>Trp Leu Arg Gln Leu Met Phe Asp Leu Phe Thr Asp<br>    290                    295                    300 | | 903 |

<210> SEQ ID NO 106
<211> LENGTH: 300
<212> TYPE: PRT
<213> ORGANISM: Escherichia coli

<400> SEQUENCE: 106

Met Glu Leu Arg Asp Leu Asp Leu Asn Leu Val Val Phe Asn Gln
1               5                   10                  15

Leu Leu Val Asp Arg Arg Val Ser Ile Thr Ala Glu Asn Leu Gly Leu
            20                  25                  30

Thr Gln Pro Ala Val Ser Asn Ala Leu Lys Arg Leu Arg Thr Ser Leu
        35                  40                  45

Gln Asp Pro Leu Phe Val Arg Thr His Gln Gly Met Glu Pro Thr Pro
    50                  55                  60

Tyr Ala Ala His Leu Ala Glu Pro Val Thr Ser Ala Met His Ala Leu
65                  70                  75                  80

Arg Asn Ala Leu Gln His His Glu Ser Phe Asp Pro Leu Thr Ser Glu
                85                  90                  95

Arg Thr Phe Thr Leu Ala Met Thr Asp Ile Gly Glu Ile Tyr Phe Met
            100                 105                 110

Pro Arg Leu Met Asp Val Leu Ala His Gln Ala Pro Asn Cys Val Ile
        115                 120                 125

```
Ser Thr Val Arg Asp Ser Ser Met Ser Leu Met Gln Ala Leu Gln Asn
    130                 135                 140

Gly Thr Val Asp Leu Ala Val Gly Leu Leu Pro Asn Leu Gln Thr Gly
145                 150                 155                 160

Phe Phe Gln Arg Arg Leu Leu Gln Asp His Tyr Val Cys Leu Cys Arg
                165                 170                 175

Lys Asp His Pro Val Thr Arg Glu Pro Leu Thr Leu Glu Arg Phe Cys
                180                 185                 190

Ser Tyr Gly His Val Arg Val Ile Ala Ala Gly Thr Gly His Gly Glu
                195                 200                 205

Val Asp Thr Tyr Met Thr Arg Val Gly Ile Arg Arg Asp Ile Arg Leu
210                 215                 220

Glu Val Pro His Phe Ala Ala Val Gly His Ile Leu Gln Arg Thr Asp
225                 230                 235                 240

Leu Leu Ala Thr Val Pro Ile Arg Leu Ala Asp Cys Cys Val Glu Pro
                245                 250                 255

Phe Gly Leu Ser Ala Leu Pro His Pro Val Val Leu Pro Glu Ile Ala
                260                 265                 270

Ile Asn Met Phe Trp His Ala Lys Tyr His Lys Asp Leu Ala Asn Ile
                275                 280                 285

Trp Leu Arg Gln Leu Met Phe Asp Leu Phe Thr Asp
290                 295                 300

<210> SEQ ID NO 107
<211> LENGTH: 175
<212> TYPE: DNA
<213> ORGANISM: Escherichia coli
<220> FEATURE:
<221> NAME/KEY: promoter
<222> LOCATION: (1)..(175)
<223> OTHER INFORMATION: dmpRKLM promoter

<400> SEQUENCE: 107
gcatttgctc aagcggcctt gggcaattga tcaaatgctt aaaaagtctg cgcaagcgcg     60
gcttaatttc gctcgctccg atcattctaa aaattagaaa cacattgaaa aacattacct   120
tgaagtctgt tttcagacct tggcacagcc gttgcttgat gtcctgcgta ctaga        175

<210> SEQ ID NO 108
<211> LENGTH: 1692
<212> TYPE: DNA
<213> ORGANISM: Escherichia coli
<220> FEATURE:
<221> NAME/KEY: CDS
<222> LOCATION: (1)..(1692)
<223> OTHER INFORMATION: DmpR gene encoding DmpR biosensor

<400> SEQUENCE: 108 atg ccg atc aag tac aag cct gaa atc cag cac tcc gat ttc aag gac     48
Met Pro Ile Lys Tyr Lys Pro Glu Ile Gln His Ser Asp Phe Lys Asp
1               5                   10                  15 ctg acc aac ctg atc cac ttc cag agc atg gaa ggc aag atc tgg ctt     96
Leu Thr Asn Leu Ile His Phe Gln Ser Met Glu Gly Lys Ile Trp Leu
                20                  25                  30 ggc gaa cag cgc atg ctg ttg ctt cag ttt tca gcg atg gcc agc ttt    144
Gly Glu Gln Arg Met Leu Leu Leu Gln Phe Ser Ala Met Ala Ser Phe
            35                  40                  45 cgc cgg gaa atg gtc aat acc ctg ggc atc gaa cgc gcc aag ggc ttg    192
Arg Arg Glu Met Val Asn Thr Leu Gly Ile Glu Arg Ala Lys Gly Leu
    50                  55                  60
```

| | | |
|---|---|---|
| ttc ctg cgc cat ggt tac cag tcc ggc ctg aag gat gcc gaa ctg gcc<br>Phe Leu Arg His Gly Tyr Gln Ser Gly Leu Lys Asp Ala Glu Leu Ala<br>65                                  70                     75                       80 | | 240 |
| agg aag ctg aga ccg aat gcc agc gaa gtc ggc atg ttc ctc gct ggg<br>Arg Lys Leu Arg Pro Asn Ala Ser Glu Val Gly Met Phe Leu Ala Gly<br>                     85                           90                     95 | | 288 |
| ccg cag atg cat tca ctc aag ggt ctg gtc aag gtc cgc ccc acc gag<br>Pro Gln Met His Ser Leu Lys Gly Leu Val Lys Val Arg Pro Thr Glu<br>                  100                       105                 110 | | 336 |
| ctc gat atc gac aag gaa tac ggg cgc ttc tat gcc gag atg gag tgg<br>Leu Asp Ile Asp Lys Glu Tyr Gly Arg Phe Tyr Ala Glu Met Glu Trp<br>               115                       120                 125 | | 384 |
| atc gac tcc ttc gag gtg gaa atc tgc cag acc gac ctg ggg cag atg<br>Ile Asp Ser Phe Glu Val Glu Ile Cys Gln Thr Asp Leu Gly Gln Met<br>130                              135                   140 | | 432 |
| caa gac ccg gtg tgc tgg act ctc ctc ggc tac gcc tgc gcc tat tcc<br>Gln Asp Pro Val Cys Trp Thr Leu Leu Gly Tyr Ala Cys Ala Tyr Ser<br>145                              150                   155                 160 | | 480 |
| tcg gcg ttc atg ggc cgg gaa atc atc ttc aag gaa gtc agc tgc ggc<br>Ser Ala Phe Met Gly Arg Glu Ile Ile Phe Lys Glu Val Ser Cys Gly<br>                  165                       170                 175 | | 528 |
| ggc tgc ggc ggc gac aag tgc cgg gtc att ggc aag ccg gcc gaa gag<br>Gly Cys Gly Gly Asp Lys Cys Arg Val Ile Gly Lys Pro Ala Glu Glu<br>            180                       185                     190 | | 576 |
| tgg gac gac gtt gcc agc ttc aaa cag tat ttc aag aac gac ccc atc<br>Trp Asp Asp Val Ala Ser Phe Lys Gln Tyr Phe Lys Asn Asp Pro Ile<br>               195                       200                 205 | | 624 |
| atc gag gaa ctc tac gag ttg caa tcg caa ctg ttg tcg ctg cgt acc<br>Ile Glu Glu Leu Tyr Glu Leu Gln Ser Gln Leu Leu Ser Leu Arg Thr<br>210                              215                   220 | | 672 |
| aac ctc gac aaa cag gaa ggc cag tac tac ggc atc ggt cag acc ccg<br>Asn Leu Asp Lys Gln Glu Gly Gln Tyr Tyr Gly Ile Gly Gln Thr Pro<br>225                              230                   235                 240 | | 720 |
| gcc tac cag acc gtg cgc aat atg atg gac aag gcc gca cag ggc aaa<br>Ala Tyr Gln Thr Val Arg Asn Met Met Asp Lys Ala Ala Gln Gly Lys<br>                     245                       250                 255 | | 768 |
| gtc tcg gtg ctg ctg ctt ggc gag acc ggg gtc ggc aag gag gtc atc<br>Val Ser Val Leu Leu Leu Gly Glu Thr Gly Val Gly Lys Glu Val Ile<br>            260                       265                     270 | | 816 |
| gcg cgt agc gtg cac ctg cgc agc aaa cgc gcc gcc gag ccc ttt gtc<br>Ala Arg Ser Val His Leu Arg Ser Lys Arg Ala Ala Glu Pro Phe Val<br>               275                       280                 285 | | 864 |
| gcg gtg aac tgt gcg gcg atc ccg ccg gac ctg atc gag tcc gaa ttg<br>Ala Val Asn Cys Ala Ala Ile Pro Pro Asp Leu Ile Glu Ser Glu Leu<br>290                              295                   300 | | 912 |
| ttc ggc gtg gaa aaa ggc gcc ttc acc ggc gcc tcc cag tca cgc atg<br>Phe Gly Val Glu Lys Gly Ala Phe Thr Gly Ala Ser Gln Ser Arg Met<br>305                              310                   315                 320 | | 960 |
| ggc cgc ttc gag cgg gcc gac aag ggc acc atc ttc ctt gac gag gtg<br>Gly Arg Phe Glu Arg Ala Asp Lys Gly Thr Ile Phe Leu Asp Glu Val<br>                     325                       330                 335 | | 1008 |
| atc gaa ctc agc ccg cgc gct cag gcc agt ctg ctg cgc gtg ctg caa<br>Ile Glu Leu Ser Pro Arg Ala Gln Ala Ser Leu Leu Arg Val Leu Gln<br>               340                       345                 350 | | 1056 |
| gaa ggc gag ctg gag cga gtt ggc gac aac cgc acg cgc aag atc gac<br>Glu Gly Glu Leu Glu Arg Val Gly Asp Asn Arg Thr Arg Lys Ile Asp<br>               355                       360                 365 | | 1104 |
| gta agg gtt atc gcc gcc acc cac gag gac ctg gcc gaa gcg gtc aag<br>Val Arg Val Ile Ala Ala Thr His Glu Asp Leu Ala Glu Ala Val Lys<br>370                              375                   380 | | 1152 |

```
gcc ggg cgt ttt cgc gcc gac ctg tac tac cga ctg aac gtt ttc ccg    1200
Ala Gly Arg Phe Arg Ala Asp Leu Tyr Tyr Arg Leu Asn Val Phe Pro
385                 390                 395                 400 gtg gcg atc ccg gcg ttg cgc gaa cgc cgc gag gac att cca ctg ctg    1248
Val Ala Ile Pro Ala Leu Arg Glu Arg Arg Glu Asp Ile Pro Leu Leu
            405                 410                 415 gtt gag cac ttc ctt cag cgc ttc cac cag gag tac ggc aag aga acc    1296
Val Glu His Phe Leu Gln Arg Phe His Gln Glu Tyr Gly Lys Arg Thr
        420                 425                 430 ctc ggc ctt tca gac aaa gcc ctg gag gcc tgc ctg cat tac agt tgg    1344
Leu Gly Leu Ser Asp Lys Ala Leu Glu Ala Cys Leu His Tyr Ser Trp
    435                 440                 445 ccg ggc aat atc cgt gag ctg gag aac gtc atc gag cgc ggc atc atc    1392
Pro Gly Asn Ile Arg Glu Leu Glu Asn Val Ile Glu Arg Gly Ile Ile
450                 455                 460 ctc acc gat ccg aac gaa agc atc agc gtg cag gcg ctg ttc cta cgg    1440
Leu Thr Asp Pro Asn Glu Ser Ile Ser Val Gln Ala Leu Phe Leu Arg
465                 470                 475                 480 gcg ccg gaa gag ccg cag acc gcc agc gag cgg gtg tcg ttg gac ggc    1488
Ala Pro Glu Glu Pro Gln Thr Ala Ser Glu Arg Val Ser Leu Asp Gly
            485                 490                 495 gtg ctg att cag cca ggc aat ggc cag ggc agt tgg atc agc cag ttg    1536
Val Leu Ile Gln Pro Gly Asn Gly Gln Gly Ser Trp Ile Ser Gln Leu
        500                 505                 510 ttg agc agc ggc ctg agc ctc gac gag atc gag gaa agc ctg atg cgc    1584
Leu Ser Ser Gly Leu Ser Leu Asp Glu Ile Glu Glu Ser Leu Met Arg
    515                 520                 525 gaa gcc atg caa cag gcc aac caa aac gtc tcc ggt gcc gcg cgc ttg    1632
Glu Ala Met Gln Gln Ala Asn Gln Asn Val Ser Gly Ala Ala Arg Leu
530                 535                 540 ctc ggc cta agc cga ccg gca ctg gcc tat cgg ctg aag aaa atc ggc    1680
Leu Gly Leu Ser Arg Pro Ala Leu Ala Tyr Arg Leu Lys Lys Ile Gly
545                 550                 555                 560 atc gaa ggc tag                                                    1692
Ile Glu Gly <210> SEQ ID NO 109
<211> LENGTH: 563
<212> TYPE: PRT
<213> ORGANISM: Escherichia coli

<400> SEQUENCE: 109

Met Pro Ile Lys Tyr Lys Pro Glu Ile Gln His Ser Asp Phe Lys Asp
1               5                   10                  15

Leu Thr Asn Leu Ile His Phe Gln Ser Met Glu Gly Lys Ile Trp Leu
            20                  25                  30

Gly Glu Gln Arg Met Leu Leu Gln Phe Ser Ala Met Ala Ser Phe
        35                  40                  45

Arg Arg Glu Met Val Asn Thr Leu Gly Ile Glu Arg Ala Lys Gly Leu
    50                  55                  60

Phe Leu Arg His Gly Tyr Gln Ser Gly Leu Lys Asp Ala Glu Leu Ala
65                  70                  75                  80

Arg Lys Leu Arg Pro Asn Ala Ser Glu Val Gly Met Phe Leu Ala Gly
                85                  90                  95

Pro Gln Met His Ser Leu Lys Gly Leu Val Lys Val Arg Pro Thr Glu
            100                 105                 110

Leu Asp Ile Asp Lys Glu Tyr Gly Arg Phe Tyr Ala Glu Met Glu Trp
        115                 120                 125
```

```
Ile Asp Ser Phe Glu Val Glu Ile Cys Gln Thr Asp Leu Gly Gln Met
    130                 135                 140

Gln Asp Pro Val Cys Trp Thr Leu Leu Gly Tyr Ala Cys Ala Tyr Ser
145                 150                 155                 160

Ser Ala Phe Met Gly Arg Glu Ile Ile Phe Lys Glu Val Ser Cys Gly
                165                 170                 175

Gly Cys Gly Gly Asp Lys Cys Arg Val Ile Gly Lys Pro Ala Glu Glu
            180                 185                 190

Trp Asp Val Ala Ser Phe Lys Gln Tyr Phe Lys Asn Asp Pro Ile
        195                 200                 205

Ile Glu Glu Leu Tyr Glu Leu Gln Ser Gln Leu Leu Ser Leu Arg Thr
    210                 215                 220

Asn Leu Asp Lys Gln Glu Gly Gln Tyr Tyr Gly Ile Gly Gln Thr Pro
225                 230                 235                 240

Ala Tyr Gln Thr Val Arg Asn Met Met Asp Lys Ala Ala Gln Gly Lys
                245                 250                 255

Val Ser Val Leu Leu Gly Glu Thr Gly Val Gly Lys Glu Val Ile
                260                 265                 270

Ala Arg Ser Val His Leu Arg Ser Lys Arg Ala Ala Glu Pro Phe Val
            275                 280                 285

Ala Val Asn Cys Ala Ala Ile Pro Pro Asp Leu Ile Glu Ser Glu Leu
            290                 295                 300

Phe Gly Val Glu Lys Gly Ala Phe Thr Gly Ala Ser Gln Ser Arg Met
305                 310                 315                 320

Gly Arg Phe Glu Arg Ala Asp Lys Gly Thr Ile Phe Leu Asp Glu Val
                325                 330                 335

Ile Glu Leu Ser Pro Arg Ala Gln Ala Ser Leu Leu Arg Val Leu Gln
            340                 345                 350

Glu Gly Glu Leu Glu Arg Val Gly Asp Asn Arg Thr Arg Lys Ile Asp
        355                 360                 365

Val Arg Val Ile Ala Ala Thr His Glu Asp Leu Ala Glu Ala Val Lys
    370                 375                 380

Ala Gly Arg Phe Arg Ala Asp Leu Tyr Tyr Arg Leu Asn Val Phe Pro
385                 390                 395                 400

Val Ala Ile Pro Ala Leu Arg Glu Arg Arg Glu Asp Ile Pro Leu Leu
                405                 410                 415

Val Glu His Phe Leu Gln Arg Phe His Gln Glu Tyr Gly Lys Arg Thr
            420                 425                 430

Leu Gly Leu Ser Asp Lys Ala Leu Glu Ala Cys Leu His Tyr Ser Trp
        435                 440                 445

Pro Gly Asn Ile Arg Glu Leu Glu Asn Val Ile Glu Arg Gly Ile Ile
    450                 455                 460

Leu Thr Asp Pro Asn Glu Ser Ile Ser Val Gln Ala Leu Phe Leu Arg
465                 470                 475                 480

Ala Pro Glu Glu Pro Gln Thr Ala Ser Glu Arg Val Ser Leu Asp Gly
                485                 490                 495

Val Leu Ile Gln Pro Gly Asn Gly Gln Gly Ser Trp Ile Ser Gln Leu
            500                 505                 510

Leu Ser Ser Gly Leu Ser Leu Asp Glu Ile Glu Glu Ser Leu Met Arg
        515                 520                 525

Glu Ala Met Gln Gln Ala Asn Gln Asn Val Ser Gly Ala Ala Arg Leu
    530                 535                 540
```

```
Leu Gly Leu Ser Arg Pro Ala Leu Ala Tyr Arg Leu Lys Lys Ile Gly
545                 550                 555                 560

Ile Glu Gly

<210> SEQ ID NO 110
<211> LENGTH: 589
<212> TYPE: DNA
<213> ORGANISM: Escherichia coli
<220> FEATURE:
<221> NAME/KEY: promoter
<222> LOCATION: (1)..(589)
<223> OTHER INFORMATION: hbpC promoter

<400> SEQUENCE: 110
gtggtggtgg gattcagaat atggtgaaac cagctcgtcc gagcaggcgc attctggcat      60
ctgccgacgg atccatattc ccttcagtct tactgtgtgt aggtgcatgg atcgggctgt     120
cgcctagcca gatgcgtcct tcgttgtggg gagggaatgc agaccgaacg ccgaaacatg     180
gatttcaggg cgcgatagat cggcaacgat ggtgcggttt tcatggttct tattttttgtt    240 agatttcatg gtgatagctc atgccaggta ggagtagata gggttctcgt agatttaata     300
aatttatgaa atcgtggttg tgagttttca taatatggtg aagcttgccc gccatggcaa     360
gtgcatttcg gcagctgttg gcgaccgcgg aaggggttta cagccgtctg gagctaggct     420
ttctggcgct cattaaaata aaaatcctta taaaacagta tcctagcttt tatgtctgag     480
gctgcttagt caacctggca cggtactggc tacgagtccc gcaaggcagc cgtgagttcg     540
actgtactgc tgcctattaa aacaatatga acgcggagac gtgataaca               589

<210> SEQ ID NO 111
<211> LENGTH: 1713
<212> TYPE: DNA
<213> ORGANISM: Escherichia coli
<220> FEATURE:
<221> NAME/KEY: CDS
<222> LOCATION: (1)..(1713)
<223> OTHER INFORMATION: HbpR gene encoding HbpR biosensor

<400> SEQUENCE: 111 atg aaa tca aat aaa aat aat agc gac gat cgc tcc atc gtt gcc gac       48
Met Lys Ser Asn Lys Asn Asn Ser Asp Asp Arg Ser Ile Val Ala Asp
1               5                   10                  15 ctt gcg ctc ccc gaa gtc cat gct tta gtt tcc aag ctg cac ttt tct       96
Leu Ala Leu Pro Glu Val His Ala Leu Val Ser Lys Leu His Phe Ser
                20                  25                  30 ccc aac gaa gga cgt atc tgg cta gac gaa agc cga tgc ctg ctc cta      144
Pro Asn Glu Gly Arg Ile Trp Leu Asp Glu Ser Arg Cys Leu Leu Leu
            35                  40                  45 caa gtg gag aca ctg aag gat ata tac aag gaa ttg cag gcc tat tct      192
Gln Val Glu Thr Leu Lys Asp Ile Tyr Lys Glu Leu Gln Ala Tyr Ser
        50                  55                  60 ggc cca gac tac acg cgg gag ttt ttg act cgt atc ggc ttc acc acc      240
Gly Pro Asp Tyr Thr Arg Glu Phe Leu Thr Arg Ile Gly Phe Thr Thr
65                  70                  75                  80 ggc caa cgc gat gca gaa atg att ata aaa aaa caa ggt ata tcc tct      288
Gly Gln Arg Asp Ala Glu Met Ile Ile Lys Lys Gln Gly Ile Ser Ser
                85                  90                  95 atc aaa gaa cag att tat gca ggt ggt gtc ttg cac gcc ttg caa ggg      336
Ile Lys Glu Gln Ile Tyr Ala Gly Gly Val Leu His Ala Leu Gln Gly
            100                 105                 110 ttt cta aca tct ata caa gct gga tca tcg gcg cta aat gcg gtc gat      384
Phe Leu Thr Ser Ile Gln Ala Gly Ser Ser Ala Leu Asn Ala Val Asp
        115                 120                 125
```

-continued

```
             115                 120                 125
atg aag agc atg gat tat cat gct gag gcc tac tgg cag aac tct atc      432
Met Lys Ser Met Asp Tyr His Ala Glu Ala Tyr Trp Gln Asn Ser Ile
    130                 135                 140 gaa gct gaa att cac tta gcg atg cat ggt gtc agt tca cat gcg gta      480
Glu Ala Glu Ile His Leu Ala Met His Gly Val Ser Ser His Ala Val
145                 150                 155                 160 tgt tgg ttt tcc gtt gcg tat tgc tca ggg tac cta agc gca tgc gct      528
Cys Trp Phe Ser Val Ala Tyr Cys Ser Gly Tyr Leu Ser Ala Cys Ala
                165                 170                 175 gga aaa ccc att gtc gtg gaa gag atc gaa tgc caa gcg atg gga cac      576
Gly Lys Pro Ile Val Val Glu Glu Ile Glu Cys Gln Ala Met Gly His
            180                 185                 190 act cat tgc cgt att caa gcg aag ccc gcc gaa atg tgg gcg ctc agt      624
Thr His Cys Arg Ile Gln Ala Lys Pro Ala Glu Met Trp Ala Leu Ser
        195                 200                 205 cag tcg gag caa tcc cag atc acc acg cac cct att ccc gat gat gat      672
Gln Ser Glu Gln Ser Gln Ile Thr Thr His Pro Ile Pro Asp Asp Asp
    210                 215                 220 cag ggc ggc gag ctc gtc att ggt tcg tcg gca gtg ttc aag gtg ctc      720
Gln Gly Gly Glu Leu Val Ile Gly Ser Ser Ala Val Phe Lys Val Leu
225                 230                 235                 240 cgt cac aaa aca gcc tgt gtg gca gag act gat gcg act gtt ctt tta      768
Arg His Lys Thr Ala Cys Val Ala Glu Thr Asp Ala Thr Val Leu Leu
                245                 250                 255 ctt gga gaa agt ggg agc ggc aag agc ctt att gca cgc gag atc cac      816
Leu Gly Glu Ser Gly Ser Gly Lys Ser Leu Ile Ala Arg Glu Ile His
            260                 265                 270 cgt ttg agc aac aga gcc gac caa gct ttc gtc gaa gtg aac tgt gcc      864
Arg Leu Ser Asn Arg Ala Asp Gln Ala Phe Val Glu Val Asn Cys Ala
        275                 280                 285 gct ata ccc gat caa tta atc gag tcg gag ctg ttc ggc gta gag cgc      912
Ala Ile Pro Asp Gln Leu Ile Glu Ser Glu Leu Phe Gly Val Glu Arg
    290                 295                 300 gga gcc ttt aca ggt gcg acc gct acg cga gag ggg cgt ttc gag gcg      960
Gly Ala Phe Thr Gly Ala Thr Ala Thr Arg Glu Gly Arg Phe Glu Ala
305                 310                 315                 320 gct cat caa ggc act ctc ttc ctt gac gaa att gcc acc ctc agt atg     1008
Ala His Gln Gly Thr Leu Phe Leu Asp Glu Ile Ala Thr Leu Ser Met
                325                 330                 335 acc gct caa agt aaa ctt ctc cgt gta ttg cag aat ggc gaa cta gaa     1056
Thr Ala Gln Ser Lys Leu Leu Arg Val Leu Gln Asn Gly Glu Leu Glu
            340                 345                 350 cgt ctc ggt agc aac cgg aca atc cac acc agt gtc cga ctg att gcc     1104
Arg Leu Gly Ser Asn Arg Thr Ile His Thr Ser Val Arg Leu Ile Ala
        355                 360                 365 gcc acg aac gct gat ctg aaa aaa gct gtc caa gat ggt cac ttc cga     1152
Ala Thr Asn Ala Asp Leu Lys Lys Ala Val Gln Asp Gly His Phe Arg
    370                 375                 380 gag gat ctt tac tat cga ctg aac gtc ttt ccc atc cag att ccc cct     1200
Glu Asp Leu Tyr Tyr Arg Leu Asn Val Phe Pro Ile Gln Ile Pro Pro
385                 390                 395                 400 ctg cga gaa cgc cgc gat gat att tca ctc att acc agc gta ctc atc     1248
Leu Arg Glu Arg Arg Asp Asp Ile Ser Leu Ile Thr Ser Val Leu Ile
                405                 410                 415 gct cga ttt tct aaa cgc cac gga cgt aag tta aaa ggc ata tcg tct     1296
Ala Arg Phe Ser Lys Arg His Gly Arg Lys Leu Lys Gly Ile Ser Ser
            420                 425                 430 gcc gcc atg cag gta ctt atc tac cat gac tgg cca ggc aat att cga     1344
```

```
                Ala Ala Met Gln Val Leu Ile Tyr His Asp Trp Pro Gly Asn Ile Arg
                        435                 440                 445 gaa ttg gag aac gtg att gag aga gcc ata atc atg gct caa gac gtc        1392
Glu Leu Glu Asn Val Ile Glu Arg Ala Ile Ile Met Ala Gln Asp Val
            450                 455                 460 gat ttt ttg gac acc cac cat tta acg aca att gaa ggc acc ctc act        1440
Asp Phe Leu Asp Thr His His Leu Thr Thr Ile Glu Gly Thr Leu Thr
465                 470                 475                 480 aca caa gac ttc cta agt ctt aac cag aaa ggt gat cta acc ttg agc        1488
Thr Gln Asp Phe Leu Ser Leu Asn Gln Lys Gly Asp Leu Thr Leu Ser
                485                 490                 495 agc gag cta ata cgg aac gcg gct gag aac gcc aac cct aaa gtt ctc        1536
Ser Glu Leu Ile Arg Asn Ala Ala Glu Asn Ala Asn Pro Lys Val Leu
            500                 505                 510 tca tta gat gag ttt gcc gag cag atg gtg cat caa ggg tct att aac        1584
Ser Leu Asp Glu Phe Ala Glu Gln Met Val His Gln Gly Ser Ile Asn
        515                 520                 525 ctg gac cag gtt caa gac gcc atc acc cga gca gct gtc aaa cat agc        1632
Leu Asp Gln Val Gln Asp Ala Ile Thr Arg Ala Ala Val Lys His Ser
530                 535                 540 ggt ggc aat att tcc cgg gcg gcc tcc ctt ctt ggg ata act cga gcc        1680
Gly Gly Asn Ile Ser Arg Ala Ala Ser Leu Leu Gly Ile Thr Arg Ala
545                 550                 555                 560 cgg ctt gat tac cgc gtc aaa aag atc aca tag                            1713
Arg Leu Asp Tyr Arg Val Lys Lys Ile Thr
                565                 570

<210> SEQ ID NO 112
<211> LENGTH: 570
<212> TYPE: PRT
<213> ORGANISM: Escherichia coli

<400> SEQUENCE: 112

Met Lys Ser Asn Lys Asn Asn Ser Asp Asp Arg Ser Ile Val Ala Asp
1               5                   10                  15

Leu Ala Leu Pro Glu Val His Ala Leu Val Ser Lys Leu His Phe Ser
            20                  25                  30

Pro Asn Glu Gly Arg Ile Trp Leu Asp Glu Ser Arg Cys Leu Leu Leu
        35                  40                  45

Gln Val Glu Thr Leu Lys Asp Ile Tyr Lys Glu Leu Gln Ala Tyr Ser
    50                  55                  60

Gly Pro Asp Tyr Thr Arg Glu Phe Leu Thr Arg Ile Gly Phe Thr Thr
65                  70                  75                  80

Gly Gln Arg Asp Ala Glu Met Ile Ile Lys Lys Gln Gly Ile Ser Ser
                85                  90                  95

Ile Lys Glu Gln Ile Tyr Ala Gly Gly Val Leu His Ala Leu Gln Gly
            100                 105                 110

Phe Leu Thr Ser Ile Gln Ala Gly Ser Ser Ala Leu Asn Ala Val Asp
        115                 120                 125

Met Lys Ser Met Asp Tyr His Ala Glu Ala Tyr Trp Gln Asn Ser Ile
    130                 135                 140

Glu Ala Glu Ile His Leu Ala Met His Gly Val Ser Ser His Ala Val
145                 150                 155                 160

Cys Trp Phe Ser Val Ala Tyr Cys Ser Gly Tyr Leu Ser Ala Cys Ala
                165                 170                 175

Gly Lys Pro Ile Val Val Glu Gly Ile Glu Cys Gln Ala Met Gly His
            180                 185                 190
```

```
Thr His Cys Arg Ile Gln Ala Lys Pro Ala Glu Met Trp Ala Leu Ser
            195                 200                 205

Gln Ser Glu Gln Ser Gln Ile Thr Thr His Pro Ile Pro Asp Asp Asp
        210                 215                 220

Gln Gly Gly Glu Leu Val Ile Gly Ser Ser Ala Val Phe Lys Val Leu
225                 230                 235                 240

Arg His Lys Thr Ala Cys Val Ala Glu Thr Asp Ala Thr Val Leu Leu
                245                 250                 255

Leu Gly Glu Ser Gly Ser Gly Lys Ser Leu Ile Ala Arg Glu Ile His
            260                 265                 270

Arg Leu Ser Asn Arg Ala Asp Gln Ala Phe Val Glu Val Asn Cys Ala
        275                 280                 285

Ala Ile Pro Asp Gln Leu Ile Glu Ser Glu Leu Phe Gly Val Glu Arg
    290                 295                 300

Gly Ala Phe Thr Gly Ala Thr Ala Thr Arg Glu Gly Arg Phe Glu Ala
305                 310                 315                 320

Ala His Gln Gly Thr Leu Phe Leu Asp Glu Ile Ala Thr Leu Ser Met
                325                 330                 335

Thr Ala Gln Ser Lys Leu Leu Arg Val Leu Gln Asn Gly Glu Leu Glu
            340                 345                 350

Arg Leu Gly Ser Asn Arg Thr Ile His Thr Ser Val Arg Leu Ile Ala
        355                 360                 365

Ala Thr Asn Ala Asp Leu Lys Lys Ala Val Gln Asp Gly His Phe Arg
    370                 375                 380

Glu Asp Leu Tyr Tyr Arg Leu Asn Val Phe Pro Ile Gln Ile Pro Pro
385                 390                 395                 400

Leu Arg Glu Arg Arg Asp Asp Ile Ser Leu Ile Thr Ser Val Leu Ile
                405                 410                 415

Ala Arg Phe Ser Lys Arg His Gly Arg Lys Leu Lys Gly Ile Ser Ser
            420                 425                 430

Ala Ala Met Gln Val Leu Ile Tyr His Asp Trp Pro Gly Asn Ile Arg
        435                 440                 445

Glu Leu Glu Asn Val Ile Glu Arg Ala Ile Ile Met Ala Gln Asp Val
    450                 455                 460

Asp Phe Leu Asp Thr His His Leu Thr Thr Ile Glu Gly Thr Leu Thr
465                 470                 475                 480

Thr Gln Asp Phe Leu Ser Leu Asn Gln Lys Gly Asp Leu Thr Leu Ser
                485                 490                 495

Ser Glu Leu Ile Arg Asn Ala Ala Glu Asn Ala Asn Pro Lys Val Leu
            500                 505                 510

Ser Leu Asp Glu Phe Ala Glu Gln Met Val His Gln Gly Ser Ile Asn
        515                 520                 525

Leu Asp Gln Val Gln Asp Ala Ile Thr Arg Ala Ala Val Lys His Ser
    530                 535                 540

Gly Gly Asn Ile Ser Arg Ala Ala Ser Leu Leu Gly Ile Thr Arg Ala
545                 550                 555                 560

Arg Leu Asp Tyr Arg Val Lys Lys Ile Thr
                565                 570

<210> SEQ ID NO 113
<211> LENGTH: 1584
<212> TYPE: DNA
<213> ORGANISM: Escherichia coli
<220> FEATURE:
<221> NAME/KEY: CDS
```

```
<222> LOCATION: (1)..(1584)
<223> OTHER INFORMATION: CapR gene encoding CapR biosensor

<400> SEQUENCE: 113 atg ctg ttg ctg caa gtt tca gca atg gcc agc ttt cgc cgg gaa atg      48
Met Leu Leu Leu Gln Val Ser Ala Met Ala Ser Phe Arg Arg Glu Met
1               5                   10                  15 gtc aat acc ctg ggc atc gaa cgc gcc aag ggc ttc ttc ctg cgc cag      96
Val Asn Thr Leu Gly Ile Glu Arg Ala Lys Gly Phe Phe Leu Arg Gln
            20                  25                  30 ggt tac cag tcc ggc ctg aag gat gcc gaa ctg gcc agg aag ctt aga     144
Gly Tyr Gln Ser Gly Leu Lys Asp Ala Glu Leu Ala Arg Lys Leu Arg
        35                  40                  45 ccg aat gcc agc gag tac gac atg ttc ctc gcc ggc ccg cag ctg cat     192
Pro Asn Ala Ser Glu Tyr Asp Met Phe Leu Ala Gly Pro Gln Leu His
    50                  55                  60 tcg ctc aag ggt ctg gtc aag gtc cgc ccc acc gag gtc gat atc gac     240
Ser Leu Lys Gly Leu Val Lys Val Arg Pro Thr Glu Val Asp Ile Asp
65                  70                  75                  80 aag gaa tgc ggg cgc ttc tat gcc gag atg gag tgg atc gac tcc ttc     288
Lys Glu Cys Gly Arg Phe Tyr Ala Glu Met Glu Trp Ile Asp Ser Phe
                85                  90                  95 gag gtg gaa atc tgc cag acc gac ctg ggg cag atg caa gac ccg gtg     336
Glu Val Glu Ile Cys Gln Thr Asp Leu Gly Gln Met Gln Asp Pro Val
            100                 105                 110 tgc tgg act ctg ctc ggc tac gcc tgc gcc tat tcc tcg gcg ttc atg     384
Cys Trp Thr Leu Leu Gly Tyr Ala Cys Ala Tyr Ser Ser Ala Phe Met
        115                 120                 125 ggc cgg gaa atc atc ttc aag gaa gta agc tgc cgc ggc tgc ggc ggc     432
Gly Arg Glu Ile Ile Phe Lys Glu Val Ser Cys Arg Gly Cys Gly Gly
    130                 135                 140 gac aag tgc cgg gtc att ggc aag ccg gcc gaa gag tgg gac gac gtt     480
Asp Lys Cys Arg Val Ile Gly Lys Pro Ala Glu Glu Trp Asp Asp Val
145                 150                 155                 160 gcc agc ttc aaa cag tat ttc aag aac gac ccc atc atc gag gaa ctc     528
Ala Ser Phe Lys Gln Tyr Phe Lys Asn Asp Pro Ile Ile Glu Glu Leu
                165                 170                 175 tac gag ttg caa tcg caa ctg gtg tcg ctg cgt acc aac ctc gac aaa     576
Tyr Glu Leu Gln Ser Gln Leu Val Ser Leu Arg Thr Asn Leu Asp Lys
            180                 185                 190 cag gaa ggc cag tac tac ggc atc ggt cag acc ccg gcc tac cag acc     624
Gln Glu Gly Gln Tyr Tyr Gly Ile Gly Gln Thr Pro Ala Tyr Gln Thr
        195                 200                 205 gtg cgc aat atg atg gac aag gcc gca cag ggc aaa gtc tcg gtg ctg     672
Val Arg Asn Met Met Asp Lys Ala Ala Gln Gly Lys Val Ser Val Leu
    210                 215                 220 ctg ctt ggc gag acc ggg gtc ggc aag gag gtc atc gcg cgt agc gtg     720
Leu Leu Gly Glu Thr Gly Val Gly Lys Glu Val Ile Ala Arg Ser Val
225                 230                 235                 240 cac ctg cgc agc aaa cgc gcc gcc gag ccc ttt gtc gcg gtg aac tgt     768
His Leu Arg Ser Lys Arg Ala Ala Glu Pro Phe Val Ala Val Asn Cys
                245                 250                 255 gcg gcg atc ccg ccg gac ctg atc gag tcc gaa ttg ttc ggc gtg gaa     816
Ala Ala Ile Pro Pro Asp Leu Ile Glu Ser Glu Leu Phe Gly Val Glu
            260                 265                 270 aaa ggc gcc ttc acc ggc gcc acc cag tca cgc atg ggc cgc ttc gag     864
Lys Gly Ala Phe Thr Gly Ala Thr Gln Ser Arg Met Gly Arg Phe Glu
        275                 280                 285 cgg gcc gac aag ggc acc atc ttc ctt gac gag gtg atc gaa ctc agc     912
Arg Ala Asp Lys Gly Thr Ile Phe Leu Asp Glu Val Ile Glu Leu Ser
```

```
                 290                 295                 300
ccg cgc gct cag gcc agt ctg ctg cgc gtg ctg caa gaa ggc gag ctg      960
Pro Arg Ala Gln Ala Ser Leu Leu Arg Val Leu Gln Glu Gly Glu Leu
305                 310                 315                 320 gag cga gtt ggc gac aac cgc acg cgc aag atc gac gta agg gtt atc     1008
Glu Arg Val Gly Asp Asn Arg Thr Arg Lys Ile Asp Val Arg Val Ile
                325                 330                 335 gca gcc acc cac gag gac ctg gcc gaa gcg gtc aag gcc ggg cgt ttt     1056
Ala Ala Thr His Glu Asp Leu Ala Glu Ala Val Lys Ala Gly Arg Phe
                340                 345                 350 cgc gcc gac ctg tac tac cgg ctg aac gtt ttc ccg gtg gcg atc ccg     1104
Arg Ala Asp Leu Tyr Tyr Arg Leu Asn Val Phe Pro Val Ala Ile Pro
            355                 360                 365 gcg ttg cgc gaa cgc cgc gag gac att cca ctg ctg gtt gag cac ttc     1152
Ala Leu Arg Glu Arg Arg Glu Asp Ile Pro Leu Leu Val Glu His Phe
370                 375                 380 ctt cag cgc ttc cac cag gag tac ggc aag aga acc ctc ggc ctt tca     1200
Leu Gln Arg Phe His Gln Glu Tyr Gly Lys Arg Thr Leu Gly Leu Ser
385                 390                 395                 400 gac aaa gcc ctg gag gcc tgc ctg cat tac agt tgg ccg ggc aat atc     1248
Asp Lys Ala Leu Glu Ala Cys Leu His Tyr Ser Trp Pro Gly Asn Ile
                405                 410                 415 cgt gag ctg gag aac gtc atc gag cgc ggc atc atc ctc acc gat ccg     1296
Arg Glu Leu Glu Asn Val Ile Glu Arg Gly Ile Ile Leu Thr Asp Pro
                420                 425                 430 aac gaa agc atc agc gtg cag gcg ctg ttc cca cgg gcg ccg gaa gag     1344
Asn Glu Ser Ile Ser Val Gln Ala Leu Phe Pro Arg Ala Pro Glu Glu
                435                 440                 445 ccg cag acc gcc agc gag cgg gtg tcg tcg gac ggc gtg ctg att cag     1392
Pro Gln Thr Ala Ser Glu Arg Val Ser Ser Asp Gly Val Leu Ile Gln
450                 455                 460 cca ggc aat ggc cag ggc agt tgg atc agc cag ttg ttg agc agc ggc     1440
Pro Gly Asn Gly Gln Gly Ser Trp Ile Ser Gln Leu Leu Ser Ser Gly
465                 470                 475                 480 ctg agc ctc gac gag atc gag gaa agc ctg atg cgc gaa gcc atg caa     1488
Leu Ser Leu Asp Glu Ile Glu Glu Ser Leu Met Arg Glu Ala Met Gln
                485                 490                 495 cag gcc aac caa aac gtc tcc ggt gcc gcg cgc ttg ctc ggc cta agc     1536
Gln Ala Asn Gln Asn Val Ser Gly Ala Ala Arg Leu Leu Gly Leu Ser
                500                 505                 510 cga ccg gca ctg gcc tat cgg ctg aag aaa atc ggc atc gaa ggc tag     1584
Arg Pro Ala Leu Ala Tyr Arg Leu Lys Lys Ile Gly Ile Glu Gly
            515                 520                 525

<210> SEQ ID NO 114
<211> LENGTH: 527
<212> TYPE: PRT
<213> ORGANISM: Escherichia coli

<400> SEQUENCE: 114

Met Leu Leu Leu Gln Val Ser Ala Met Ala Ser Phe Arg Arg Glu Met
1               5                   10                  15

Val Asn Thr Leu Gly Ile Glu Arg Ala Lys Gly Phe Phe Leu Arg Gln
                20                  25                  30

Gly Tyr Gln Ser Gly Leu Lys Asp Ala Glu Leu Ala Lys Leu Arg
            35                  40                  45

Pro Asn Ala Ser Glu Tyr Asp Met Phe Leu Ala Gly Pro Gln Leu His
        50                  55                  60

Ser Leu Lys Gly Leu Val Lys Val Arg Pro Thr Glu Val Asp Ile Asp
```

-continued

```
            65                  70                  75                  80
Lys Glu Cys Gly Arg Phe Tyr Ala Glu Met Glu Trp Ile Asp Ser Phe
                    85                  90                  95
Glu Val Glu Ile Cys Gln Thr Asp Leu Gly Gln Met Gln Asp Pro Val
                100                 105                 110
Cys Trp Thr Leu Leu Gly Tyr Ala Cys Ala Tyr Ser Ser Ala Phe Met
                115                 120                 125
Gly Arg Glu Ile Ile Phe Lys Glu Val Ser Cys Arg Gly Cys Gly Gly
            130                 135                 140
Asp Lys Cys Arg Val Ile Gly Lys Pro Ala Glu Glu Trp Asp Asp Val
145                 150                 155                 160
Ala Ser Phe Lys Gln Tyr Phe Lys Asn Asp Pro Ile Ile Glu Glu Leu
                165                 170                 175
Tyr Glu Leu Gln Ser Gln Leu Val Ser Leu Arg Thr Asn Leu Asp Lys
                180                 185                 190
Gln Glu Gly Gln Tyr Tyr Gly Ile Gly Gln Thr Pro Ala Tyr Gln Thr
                195                 200                 205
Val Arg Asn Met Met Asp Lys Ala Ala Gln Gly Lys Val Ser Val Leu
            210                 215                 220
Leu Leu Gly Glu Thr Gly Val Gly Lys Glu Val Ile Ala Arg Ser Val
225                 230                 235                 240
His Leu Arg Ser Lys Arg Ala Ala Glu Pro Phe Val Ala Val Asn Cys
                245                 250                 255
Ala Ala Ile Pro Pro Asp Leu Ile Glu Ser Glu Leu Phe Gly Val Glu
                260                 265                 270
Lys Gly Ala Phe Thr Gly Ala Thr Gln Ser Arg Met Gly Arg Phe Glu
                275                 280                 285
Arg Ala Asp Lys Gly Thr Ile Phe Leu Asp Glu Val Ile Glu Leu Ser
            290                 295                 300
Pro Arg Ala Gln Ala Ser Leu Leu Arg Val Leu Gln Glu Gly Glu Leu
305                 310                 315                 320
Glu Arg Val Gly Asp Asn Arg Thr Arg Lys Ile Asp Val Arg Val Ile
                325                 330                 335
Ala Ala Thr His Glu Asp Leu Ala Glu Ala Val Lys Ala Gly Arg Phe
                340                 345                 350
Arg Ala Asp Leu Tyr Tyr Arg Leu Asn Val Phe Pro Val Ala Ile Pro
            355                 360                 365
Ala Leu Arg Glu Arg Arg Glu Asp Ile Pro Leu Leu Val Glu His Phe
370                 375                 380
Leu Gln Arg Phe His Gln Glu Tyr Gly Lys Arg Thr Leu Gly Leu Ser
385                 390                 395                 400
Asp Lys Ala Leu Glu Ala Cys Leu His Tyr Ser Trp Pro Gly Asn Ile
                405                 410                 415
Arg Glu Leu Glu Asn Val Ile Glu Arg Gly Ile Ile Leu Thr Asp Pro
                420                 425                 430
Asn Glu Ser Ile Ser Val Gln Ala Leu Phe Pro Arg Ala Pro Glu Glu
            435                 440                 445
Pro Gln Thr Ala Ser Glu Arg Val Ser Ser Asp Gly Val Leu Ile Gln
        450                 455                 460
Pro Gly Asn Gly Gln Gly Ser Trp Ile Ser Gln Leu Leu Ser Ser Gly
465                 470                 475                 480
Leu Ser Leu Asp Glu Ile Glu Glu Ser Leu Met Arg Glu Ala Met Gln
                485                 490                 495
```

```
Gln Ala Asn Gln Asn Val Ser Gly Ala Ala Arg Leu Leu Gly Leu Ser
            500                 505                 510
Arg Pro Ala Leu Ala Tyr Arg Leu Lys Lys Ile Gly Ile Glu Gly
        515                 520                 525

<210> SEQ ID NO 115
<211> LENGTH: 434
<212> TYPE: DNA
<213> ORGANISM: Escherichia coli
<220> FEATURE:
<221> NAME/KEY: promoter
<222> LOCATION: (1)..(434)
<223> OTHER INFORMATION: gudP promoter

<400> SEQUENCE: 115
tatgttcagc gagcggtaaa tgtcgtttta gcggtgctga atcgaatctt ttcaggcaaa      60
tgccagtaaa aactgcttca tagcgcggat ttttactggc gtttgcctgg agtcaagcga     120
tccatttcat actcttcttt atttcttcgt tttaacccct cctttcttgt tcttgttttc     180
atttccgtga agtggattcc accgtccagg gctaatgcca aaatcgggcc tcattgaacg     240
cattaatgtt gtgttgttgc acggtgagcc gctatggcgc gctttttata ctgctattgc     300
cagatataaa cacgcgccgt attcggcgaa cgacctataa aaacggcaaa aaacacccta     360
cgtcacctct gatttcctgg cgatgtcgca gtccagagtg agcgtggcta acgcgaattt     420
tcaggagtgc aaca                                                      434

<210> SEQ ID NO 116
<211> LENGTH: 1158
<212> TYPE: DNA
<213> ORGANISM: Escherichia coli
<220> FEATURE:
<221> NAME/KEY: CDS
<222> LOCATION: (1)..(1158)
<223> OTHER INFORMATION: CdaR gene encoding CdaR biosensor

<400> SEQUENCE: 116 atg gct ggc tgg cat ctt gat acc aaa atg gcg cag gat atc gtg gca      48
Met Ala Gly Trp His Leu Asp Thr Lys Met Ala Gln Asp Ile Val Ala
1               5                  10                  15 cgt acc atg cgc atc atc gat acc aat atc aac gta atg gat gcc cgt      96
Arg Thr Met Arg Ile Ile Asp Thr Asn Ile Asn Val Met Asp Ala Arg
            20                  25                  30 ggg cga att atc ggc agc ggc gat cgt gag cgt att ggt gaa ttg cac     144
Gly Arg Ile Ile Gly Ser Gly Asp Arg Glu Arg Ile Gly Glu Leu His
        35                  40                  45 gaa ggt gca ttg ctg gta ctt tca cag gga cga gtc gtc gat atc gat     192
Glu Gly Ala Leu Leu Val Leu Ser Gln Gly Arg Val Val Asp Ile Asp
    50                  55                  60 gac gcg gta gca cgt cat ctg cac ggt gtg cgg cag ggg att aat cta     240
Asp Ala Val Ala Arg His Leu His Gly Val Arg Gln Gly Ile Asn Leu
65                  70                  75                  80 ccg tta cgg ctg gaa ggt gaa att gtc ggc gta att ggc ctg aca ggt     288
Pro Leu Arg Leu Glu Gly Glu Ile Val Gly Val Ile Gly Leu Thr Gly
                85                  90                  95 gaa cca gag aat ctg cgt aaa tat ggc gaa ctg gtc tgc atg acg gct     336
Glu Pro Glu Asn Leu Arg Lys Tyr Gly Glu Leu Val Cys Met Thr Ala
            100                 105                 110 gaa atg atg ctg gaa cag tcg cgg ttg atg cac ttg ttg gcg cag gat     384
Glu Met Met Leu Glu Gln Ser Arg Leu Met His Leu Leu Ala Gln Asp
        115                 120                 125
```

```
agc cgt ttg cgg gaa gaa ctg gtg atg aac ctg att cag gca gag gag    432
Ser Arg Leu Arg Glu Glu Leu Val Met Asn Leu Ile Gln Ala Glu Glu
    130                 135                 140 aat act ccc gca ctt act gaa tgg gcg caa cgg ctg ggg atc gat ctc    480
Asn Thr Pro Ala Leu Thr Glu Trp Ala Gln Arg Leu Gly Ile Asp Leu
145                 150                 155                 160 aat caa ccg cga gtg gtg gct att gtt gag gtc gac agc ggt cag ctt    528
Asn Gln Pro Arg Val Val Ala Ile Val Glu Val Asp Ser Gly Gln Leu
                165                 170                 175 ggc gtg gac agc gca atg gcg gag tta caa caa ctg caa aac gcg ctg    576
Gly Val Asp Ser Ala Met Ala Glu Leu Gln Gln Leu Gln Asn Ala Leu
            180                 185                 190 act acg ccc gag cgt aat aat ctg gtg gcg att gtc tcg cta acc gaa    624
Thr Thr Pro Glu Arg Asn Asn Leu Val Ala Ile Val Ser Leu Thr Glu
        195                 200                 205 atg gtg gtg ttg aaa ccg gcg ttg aac tct ttt ggg cgc tgg gat gca    672
Met Val Val Leu Lys Pro Ala Leu Asn Ser Phe Gly Arg Trp Asp Ala
    210                 215                 220 gaa gat cat cgt aag cga gtt gaa caa ctg att acc cgc atg aaa gag    720
Glu Asp His Arg Lys Arg Val Glu Gln Leu Ile Thr Arg Met Lys Glu
225                 230                 235                 240 tac ggc cag ctg cgt ttt cgc gtt tca ctg ggc aac tat ttt acc ggt    768
Tyr Gly Gln Leu Arg Phe Arg Val Ser Leu Gly Asn Tyr Phe Thr Gly
                245                 250                 255 cct ggc agt att gcc cga tcc tat cgt acg gcg aaa acg acg atg gtg    816
Pro Gly Ser Ile Ala Arg Ser Tyr Arg Thr Ala Lys Thr Thr Met Val
            260                 265                 270 gtg ggt aaa cag cgg atg cca gaa agt cgc tgc tat ttt tat cag gat    864
Val Gly Lys Gln Arg Met Pro Glu Ser Arg Cys Tyr Phe Tyr Gln Asp
        275                 280                 285 ctg atg tta cct gtg tta ctc gac agt ttg cgt ggc gac tgg cag gcc    912
Leu Met Leu Pro Val Leu Leu Asp Ser Leu Arg Gly Asp Trp Gln Ala
    290                 295                 300 aac gaa ctg gcg cga ccg ctg gcg cgg ctg aaa acg atg gac aat aac    960
Asn Glu Leu Ala Arg Pro Leu Ala Arg Leu Lys Thr Met Asp Asn Asn
305                 310                 315                 320 ggc ttg ctg cga cga acg ctg gcg gcg tgg ttt cgc cac aat gtg caa   1008
Gly Leu Leu Arg Arg Thr Leu Ala Ala Trp Phe Arg His Asn Val Gln
                325                 330                 335 ccg ctg gca acg tca aag gcg ttg ttt att cat cgt aat acc ctg gag   1056
Pro Leu Ala Thr Ser Lys Ala Leu Phe Ile His Arg Asn Thr Leu Glu
            340                 345                 350 tat cgg ctt aat cgt ata tcg gaa ctg acc ggg ctt gat ttg ggc aat   1104
Tyr Arg Leu Asn Arg Ile Ser Glu Leu Thr Gly Leu Asp Leu Gly Asn
        355                 360                 365 ttt gat gac agg ttg ctg ctg tat gtg gcg tta caa ctg gat gaa gag   1152
Phe Asp Asp Arg Leu Leu Leu Tyr Val Ala Leu Gln Leu Asp Glu Glu
    370                 375                 380 cgg tag                                                            1158
Arg
385

<210> SEQ ID NO 117
<211> LENGTH: 385
<212> TYPE: PRT
<213> ORGANISM: Escherichia coli

<400> SEQUENCE: 117

Met Ala Gly Trp His Leu Asp Thr Lys Met Ala Gln Asp Ile Val Ala
1               5                   10                  15
```

```
Arg Thr Met Arg Ile Ile Asp Thr Asn Ile Asn Val Met Asp Ala Arg
            20                  25                  30

Gly Arg Ile Ile Gly Ser Gly Asp Arg Glu Arg Ile Gly Glu Leu His
        35                  40                  45

Glu Gly Ala Leu Leu Val Leu Ser Gln Gly Arg Val Val Asp Ile Asp
50                  55                  60

Asp Ala Val Ala Arg His Leu His Gly Val Arg Gln Gly Ile Asn Leu
65                  70                  75                  80

Pro Leu Arg Leu Glu Gly Glu Ile Val Gly Val Ile Gly Leu Thr Gly
                85                  90                  95

Glu Pro Glu Asn Leu Arg Lys Tyr Gly Glu Leu Val Cys Met Thr Ala
            100                 105                 110

Glu Met Met Leu Glu Gln Ser Arg Leu Met His Leu Leu Ala Gln Asp
            115                 120                 125

Ser Arg Leu Arg Glu Glu Leu Val Met Asn Leu Ile Gln Ala Glu Glu
130                 135                 140

Asn Thr Pro Ala Leu Thr Glu Trp Ala Gln Arg Leu Gly Ile Asp Leu
145                 150                 155                 160

Asn Gln Pro Arg Val Val Ala Ile Val Glu Val Asp Ser Gly Gln Leu
                165                 170                 175

Gly Val Asp Ser Ala Met Ala Glu Leu Gln Gln Leu Gln Asn Ala Leu
            180                 185                 190

Thr Thr Pro Glu Arg Asn Asn Leu Val Ala Ile Val Ser Leu Thr Glu
            195                 200                 205

Met Val Val Leu Lys Pro Ala Leu Asn Ser Phe Gly Arg Trp Asp Ala
210                 215                 220

Glu Asp His Arg Lys Arg Val Glu Gln Leu Ile Thr Arg Met Lys Glu
225                 230                 235                 240

Tyr Gly Gln Leu Arg Phe Arg Val Ser Leu Gly Asn Tyr Phe Thr Gly
                245                 250                 255

Pro Gly Ser Ile Ala Arg Ser Tyr Arg Thr Ala Lys Thr Thr Met Val
            260                 265                 270

Val Gly Lys Gln Arg Met Pro Glu Ser Arg Cys Tyr Phe Tyr Gln Asp
            275                 280                 285

Leu Met Leu Pro Val Leu Leu Asp Ser Leu Arg Gly Asp Trp Gln Ala
290                 295                 300

Asn Glu Leu Ala Arg Pro Leu Ala Arg Leu Lys Thr Met Asp Asn Asn
305                 310                 315                 320

Gly Leu Leu Arg Arg Thr Leu Ala Ala Trp Phe Arg His Asn Val Gln
                325                 330                 335

Pro Leu Ala Thr Ser Lys Ala Leu Phe Ile His Arg Asn Thr Leu Glu
            340                 345                 350

Tyr Arg Leu Asn Arg Ile Ser Glu Leu Thr Gly Leu Asp Leu Gly Asn
            355                 360                 365

Phe Asp Asp Arg Leu Leu Leu Tyr Val Ala Leu Gln Leu Asp Glu Glu
370                 375                 380

Arg
385

<210> SEQ ID NO 118
<211> LENGTH: 136
<212> TYPE: DNA
<213> ORGANISM: Escherichia coli
<220> FEATURE:
<221> NAME/KEY: promoter
```

```
<222> LOCATION: (1)..(136)
<223> OTHER INFORMATION: pSAL promoter

<400> SEQUENCE: 118
ggggcctcgc ttgggttatt gctggtgccc ggccgggcgc aatattcatg ttgatgattt      60
attatatatc gagtggtgta tttatcaata ttgtttgctc cgttatcgtt attaacaagt     120
catcaataaa gccatc                                                    136
```

SYSTEM FOR IMPROVED PRODUCTION TITERS IN FERMENTATIONS

CROSS REFERENCE TO RELATED APPLICATIONS

This application is a 371 National Phase Entry of International Patent Application No. PCT/EP2016/073132 filed Sep. 28, 2016 which claims benefit under 35 U.S.C. § 119(b) of EP Application No. 15187150.6 filed Sep. 28, 2015, the contents of which are incorporated herein by reference in their entirety.

The sequence listing of the present application has been submitted electronically via EFS-Web as an ASCII formatted sequence listing with a file name "059244-000087USPX SL.txt", creation date of Apr. 26, 2018 and a size of 390,721 bytes. The sequence listing submitted via EFS-Web is part of the specification and is herein incorporated by reference in its entirety.

TECHNICAL FIELD OF THE INVENTION

The invention provides a genetically modified microorganism for intracellular biosynthesis of a cellular metabolite, comprising a synthetic error correction system having a penalty gene, whose expression can either lead to arrested growth or cell death (e.g. a toxin gene) in combination with a survival gene, whose expression provides an antidote that can restore cell viability and normal growth (e.g. a cognate antitoxin gene). Alternatively, the system has a survival gene, alone, whose expression is essential for growth (i.e. essential gene). Additionally, the synthetic error correction system has a biosensor, whose function is to induce expression of the survival gene leading to cell growth, only, when the cell produces a pre-defined level of a given metabolite. The invention further encompasses: a method for producing the genetically modified micro-organism; a method for producing a cellular metabolite with the genetically modified micro-organism; and use of the genetically modified micro-organism for producing a cellular metabolite.

BACKGROUND OF THE INVENTION

An increasing share of the world's chemical production relies on microorganisms or mammalian cells that are genetically engineered to function as cell factories, and tailor-made for the biosynthesis of a given molecule. Production processes, employing these cell-factories, are typically initiated from a starter culture of a small number of cells of a production organism, which go through a phase of growth and expansion of cell numbers in large fermentation tanks (up to 30,000 L volume). In some setups, production of a given molecule proceeds both during the growth phase and during a subsequent period (batch and fed-batch cultures). Alternatively, in order not to waste resources associated with cleaning and growing up a new batch, production is continuous. A chemostat fermentor allows a production organism to be grown in a fermentation broth that is constantly diluted, thus tapping product and cells from the culture, while replenishing with fresh nutrient medium. On an industrial scale, such production processes may continue operation for 1-2 months before starting a new culture in a clean tank. The fermentation processes and equipment used in this industry are very similar, both for the production of a wide range of commodity small molecules and for therapeutic proteins, and consequently these processes are subject to similar problems.

In particular, the appearance of non-producing cells (unable to produce the product molecule) is commonly observed, especially when the production run is for extended periods of time (chemostat). Such non-producing cells within an industrial fermentation are highly undesirable, as they consume nutrients, oxygen and space. Furthermore, non-producing cells can have a selective advantage over producing cells, and may as such grow faster. In a growing cell culture, such improvements in fitness can lead to significant out-competition of the producing cells over time. This drift from the optimal production state is an eventual reason for discarding the fermentation broth and spending resources on cleaning, sterilization, not to mention nutrients, to replenish the fermentation tank with new, producing organisms. Such non-producing cells originate from genetic mutations that arise in the cells of an original producing organism undergoing many growth divisions.

Since the occurrence of genetic mutations in cells of a production organism that lead to a loss of product formation by the cells during a production run, cannot be avoided, there is a need for methods for eliminating or slowing the growth of non-producing cells in the production. Preferably, such methods of elimination are sufficiently effective that they prevent the observed drift from the production state, and thereby prolong the life-time of an industrial fermentation.

If the system employs a penalty gene alone (and no antidote), then an "OFF" type sensor is required. If the system employs a survival gene alone (e.g. essential genes) a metabolite-linked "ON" type sensor is needed as in the first scenario.

SUMMARY OF THE INVENTION

The invention provides a genetically modified microbial cell for intracellular biosynthesis of a cellular metabolite comprising:
a) a first nucleic acid molecule wherein the transcription and/or translation of said molecule yields a biosensor capable of binding said cellular metabolite to form a complex; and any one selected from the group consisting of ((b), (c) and (d)):
b) a second nucleic acid molecule comprising a coding sequence encoding a first protein required for cell growth and/or survival, wherein the second nucleic acid molecule is operably linked to a first promoter; wherein expression of said first protein encoded by said second nucleic acid molecule is induced when said biosensor and said cellular metabolite form a complex;
c) a second nucleic acid molecule comprising a coding sequence encoding a first protein required for cell growth and/or survival, wherein the second nucleic acid molecule is operably linked to a first promoter; and a third nucleic acid molecule encoding a second protein that is toxic for cell growth and/or survival, wherein said third nucleic acid molecule comprises a coding sequence operably linked to a second constitutive promoter; wherein expression of said first protein encoded by said second nucleic acid molecule is induced when said biosensor and said cellular metabolite form a complex; and
d) a second nucleic acid molecule encoding a protein that is toxic for cell growth and/or survival, wherein said second nucleic acid molecule comprises a coding sequence operably linked to a promoter; wherein expression of said protein is prevented when said biosensor and said cellular metabolite form a complex;

whereby arrest of growth and/or death of said cell due to an absence of complex formation does not depend on externally supplied growth inhibitor or growth retardant.

According to one embodiment of the genetically modified microbial cell of invention comprising the features of (a) and (b), the first promoter is an inducible promoter, and the first protein (encoded by the second nucleic acid molecule) is essential for growth of the cell.

According to a further embodiment, the genetically modified microbial cell of the invention comprises the features of (a) and (c), wherein:
said first promoter linked to said second nucleic acid molecule is inducible, and said second protein (encoded by the third nucleic acid molecule) is a toxin; and said first protein (encoded by the second nucleic acid molecule) is an anti-toxin protein cognate to said toxin protein;
and said biosensor is a transcription factor capable of binding to said metabolite to form a complex, and wherein said complex is capable of binding to said inducible promoter so as to induce expression of the first protein.

According to a further embodiment, the genetically modified microbial cell of the invention comprises the features of (a) and (c), wherein:
said second protein (encoded by the third nucleic acid molecule) is a toxin; and wherein:
said first protein (encoded by the second nucleic acid molecule) is an anti-toxin cognate to said toxin;
said first nucleic acid molecule is operably linked to said second nucleic acid molecule upstream to its coding sequence and is operably linked downstream of the first promoter, and wherein the first promoter is a constitutive promoter, and
said biosensor obtained on transcription of said first nucleic acid molecule is a riboswitch capable of binding to said metabolite to form a complex.

According to a further embodiment, the genetically modified microbial cell of the invention comprises the features of (a) and (d), wherein:
said protein (encoded by the second nucleic acid molecule) is a toxin; and said promoter is inducible; and
and said biosensor is a transcription factor capable of binding to said metabolite to form a complex, and wherein said complex is capable of binding to said inducible promoter so as to induce expression of the protein.

According to a further embodiment, the genetically modified microbial cell of the invention comprises the features of (a) and (d), wherein:
said protein (encoded by the nucleic acid molecule) is a toxin;
said first nucleic acid molecule is operably linked to said second nucleic acid molecule upstream of its coding sequence and is operably linked downstream of the first promoter, and wherein the first promoter is a constitutive promoter, and wherein
said biosensor obtained on transcription of said first nucleic acid molecule is a riboswitch capable of binding to said metabolite to form a complex.

According to a further embodiment of the genetically modified microbial cell of the invention, the cellular metabolite is selected from the groups consisting of: isoprenoid(s), vitamin(s), carboxylic acid(s), amino acid(s), fatty acid(s), alcohol(s), and polyketide(s).

The invention further provides a method of genetically modifying a microbial cell for the biosynthesis of a metabolite comprising the steps of introducing into the cell:
a nucleic acid molecule encoding a toxin operably linked to a constitutive promoter;
a nucleic acid molecule encoding an anti-toxin cognate to the toxin, wherein the molecule is linked to an inducible promoter; and
a nucleic acid molecule wherein the transcription and/or translation of said molecule yields a biosensor capable of binding to the metabolite; wherein expression of said anti-toxin is induced when said biosensor and said cellular metabolite form a complex and bind to said inducible promoter; and wherein arrest of growth and/or death of said cell due to an absence of complex formation does not depend on externally supplied growth inhibitor or growth retardant.

The invention further provides a method for producing a biosynthetic metabolite comprising the steps of:
providing a genetically modified microbial cell according to any one embodiment of the invention,
introducing the genetically modified microbial cell into a cultivation medium comprising a substrate for production of said metabolite, and
optionally cultured in a culture vessel by continuous culture for a period of at least 24 cell multiplications; and then recovering metabolite produced by said culture,
wherein a lack of metabolite production in said genetically modified microbial cell or progeny cell thereof attenuates multiplication of said cell as compared to a non-genetically modified parent cell from which said modified microbial cell was derived.

The invention further includes the use of a genetically modified microbial cell according to any one embodiment of the invention, for producing a biosynthetic metabolite, wherein a lack of metabolite production in said genetically modified microbial cell or progeny cell thereof attenuates multiplication of said cell as compared to the metabolite producing genetically modified microbial cell.

DESCRIPTION OF THE INVENTION

Figures

FIG. 1. Cartoon of the general concept of synthetic error-correction.

Figure 2:
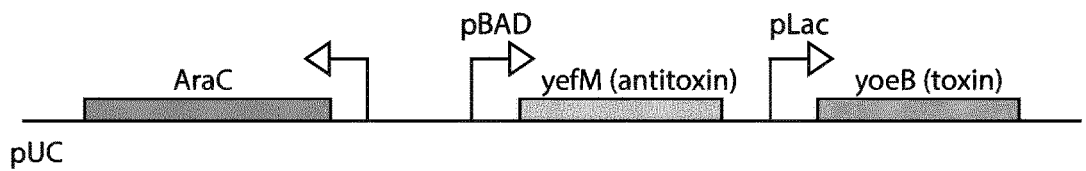

FIG. 2. Cartoon of L-arabinose-addiction regulated TA-system Dual expression TA gene construct comprising the toxin gene yoeB whose expression is regulated by the $p_{Lac}$ promoter; and the antitoxin gene yefM whose expression is regulated by the $p_{BAD}$ promoter, and the araC L-arabinose sensor gene.

FIG. 3. Growth dependency through the yoeB-yefM system on induction of respectively toxin and antitoxin, as measured by cell density ($OD_{600\ nm}$) as a function of time (hr).

A) Cell growth in the absence of an inducer (L-arabinose) of antitoxin expression, and with a supply of IPTG (I), a toxin expression inducer, at a range of concentrations rising from 0, 0.005, 0.025, 0.1, 0.5, 1.5 mM IPTG, (corresponding to 01 to 51, respectively).

B) Cell growth in the presence of an inducer (0.1% L-arabinose) of antitoxin expression, and with a supply of IPTG (I), a toxin expression inducer, at a range of concentrations rising from 0, 0.005, 0.025, 0.1, 0.5, 1.5 mM IPTG, (corresponding to 01 to 51, respectively). Growth curves are averages (n=3).

Figure 4:
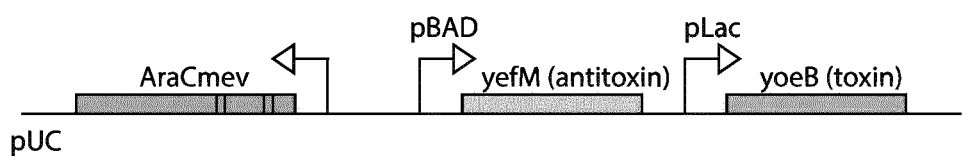

FIG. 4. Cartoon of mevalonate addiction regulated TA-system Dual expression TA gene construct comprising the toxin gene yoeB whose expression is regulated by the $p_{Lac}$ promoter; and the antitoxin gene yefM, whose expression is regulated by the $p_{BAD}$ promoter, and the mutated araCmev mevalonate sensor gene with 4 point mutations.

Figure 5:
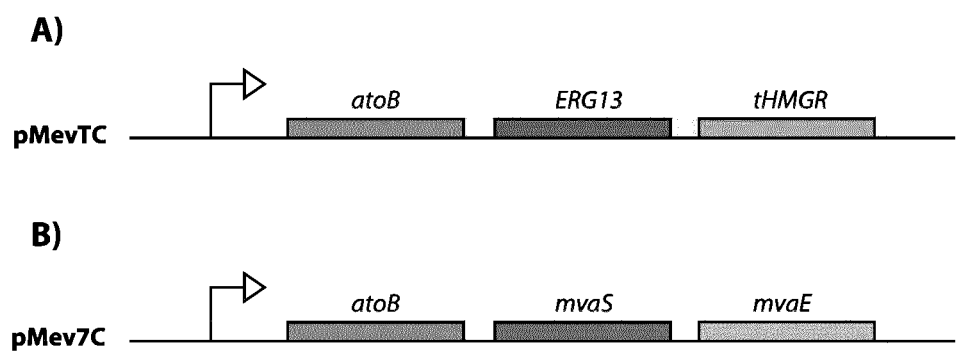
Figure 5:
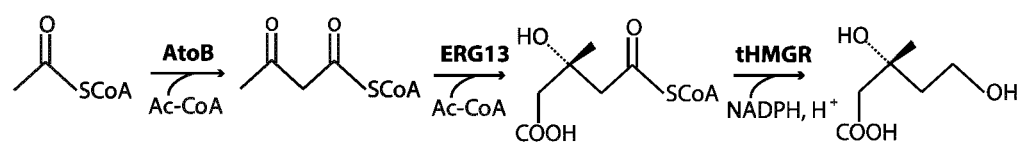

FIG. 5. Cartoon of the operon encoding two mevalonate biosynthesis pathways from acetyl-CoA:

A) pMevTC operon comprising *E. coli* atoB encoding an acetyl-CoA acetyltransferase; *Saccharomyces cerevisiae* ERG13 encoding an HMG-CoA synthase, and tHMGR, a truncated version of *Saccharomyces cerevisiae* HMGR, encoding an HMG-CoA reductase;

B) pMEV7C operon comprising *E. coli* atoB; a *Lactococcus lactis* gene mvaS encoding an HMG-CoA synthase, and a *Lactococcus lactis* mvaE gene encoding a HMG-CoA reductase; and C) mevalonate biosynthetic pathway: the atoB encoded acetoacetyl-CoA thiolase catalyzes the formation of acetoacetyl-CoA from two molecules of acetyl-CoA; the ERG13/mvaS encoded HMG-CoA synthase, which creates 3-hydroxy-methylglutayl-CoA (HMG-CoA) by a condensation reaction between acetoacetyl-CoA and another molecule of acetyl-CoA; and tHMGR/mvaE encoded HMG-CoA reductase which converts HMG-CoA to mevalonate.

FIG. 6. Cancelling the fitness advantage of non-producing cells.

A) Cell growth over time (measured by cell density at $OD_{600\,nm}$) of *E. coli* at 30° C. in 2×YT medium, comprising the plasmid (pMEV7C) for 'high' level mevalonate synthesis and the control plasmid (pMevT5c) for no mevalonate synthesis.

B) Growth curves of strains harbouring the same pathway plasmids as well as the mevalonate-TA correction system.

Figure 7:
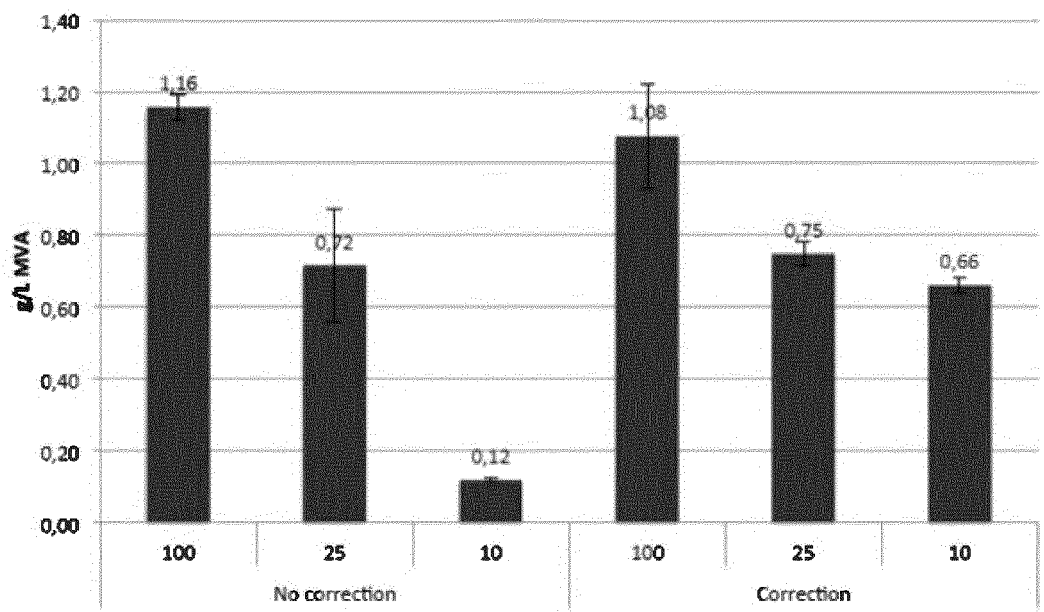

FIG. 7. Enhancing mevalonate production in fermentation populations using the TA system to eliminate non-producing cells. Histogram showing mevalonate (MVA) levels produced by mixture cultures with the indicated percentage (x-axis) of producing cells among non-producing cells. Producing cells comprised the mevalonate production plasmid (pMEV7C) while non-producing cells comprised the control plasmid (pMevT5c) with the inactivated production pathway. The cells were tested with/without the plasmid expressing the mevalonate-TA system for "correction" (pBAM-TA5).

Figure 8:
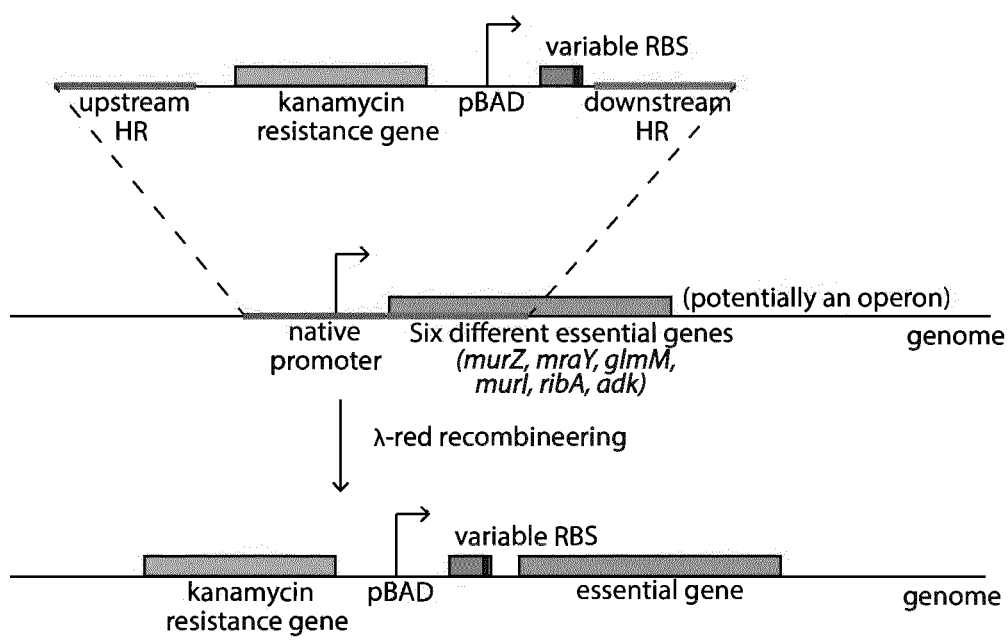

FIG. 8. Cartoon showing a cloning and strain construction strategy for addiction through essential genes. The metabolite-responsive promoter is introduced in the genome of the host strain, replacing the native promoter of an essential gene (optionally operon). Upstream and downstream homologous regions (HR) guide replacement of native DNA with the responsive promoter and a kanamycin resistance gene for selection of genomic DNA insertion. Using a variable ribosome binding site (RBS) with redundant nucleotide, a wider range of responses can be screened in order to identify a host strain, which has become addiction an internally produced metabolite.

Figure 9:
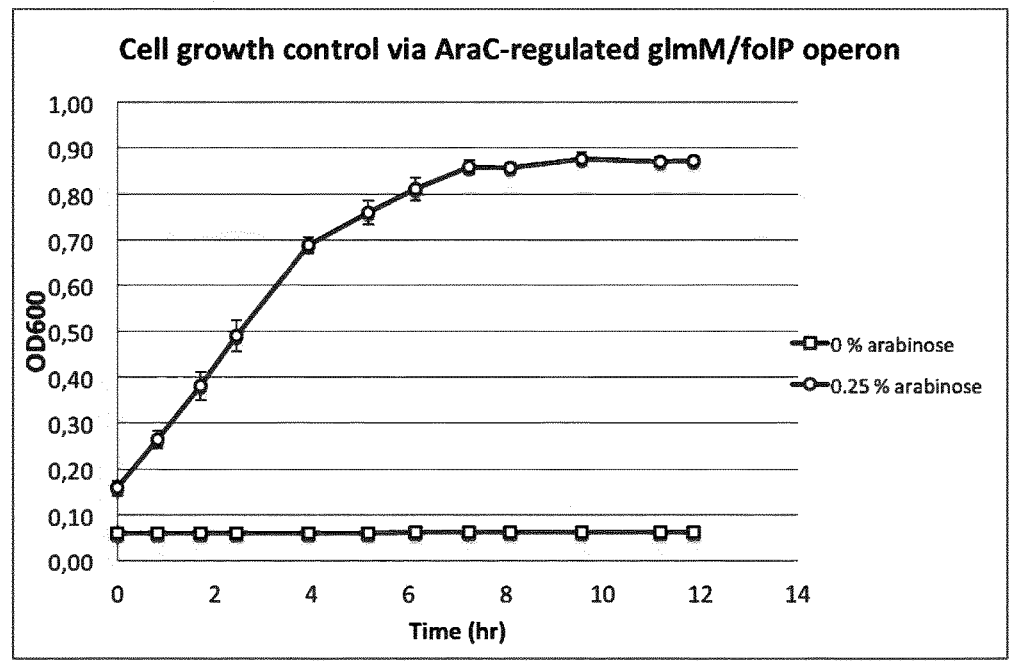

FIG. 9. Cell growth controlled by the L-arabinose-addiction regulated essential gene system. Cell growth over time (measured by cell density at $OD_{600\,nm}$) of *E. coli* comprising the essential gene operon folP/glmM driven by the $p_{BAD}$ promoter were cultivated at 37° C. in 2×YT growth medium supplemented with 0% or 0.25% L-arabinose. Growth curves are averages (n=3). Error bars denote standard error.

Figure 10:
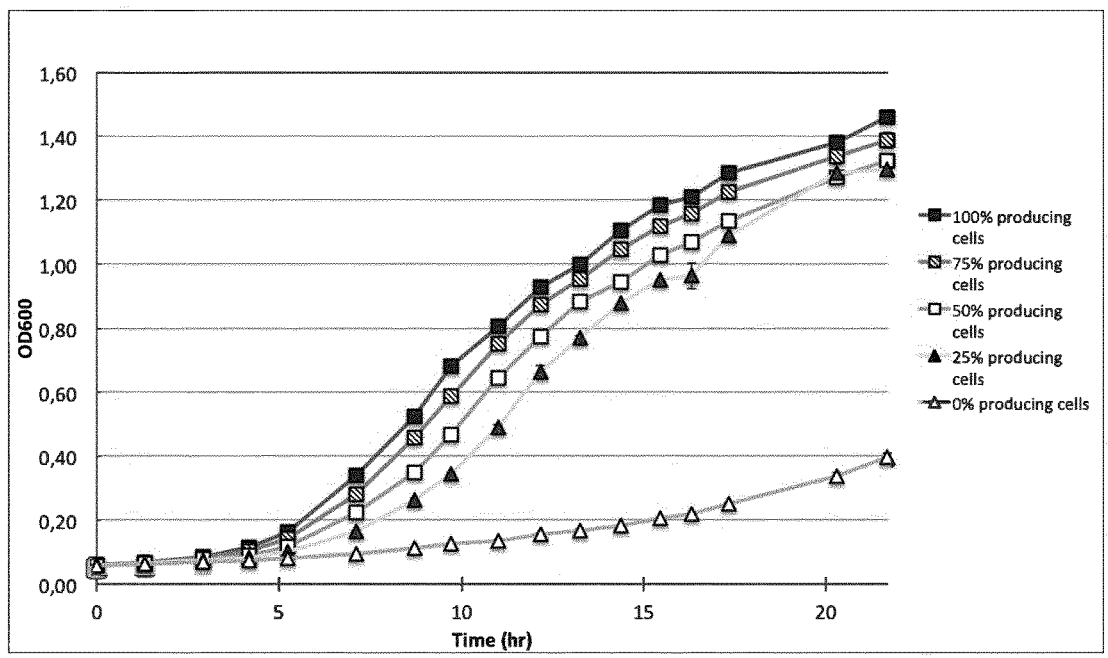

FIG. 10. Growth of *E. coli* strains addicted to internal production of mevalonate. Cell growth over time (measured by cell density at $OD_{600\,nm}$) of *E. coli* strains engineered to be mevalonate-addicted through the essential gene operon folP/glmM, comprising inoculums of the 100% mevalonate producing strain (e3.9) and inoculum mixtures with the given percentages of the mevalonate producing strain (e3.9) and a mevalonate pathway non-producing strain (e3.8). Growth curves are averages (n=3). Error bars denote standard error.

Figure 11:
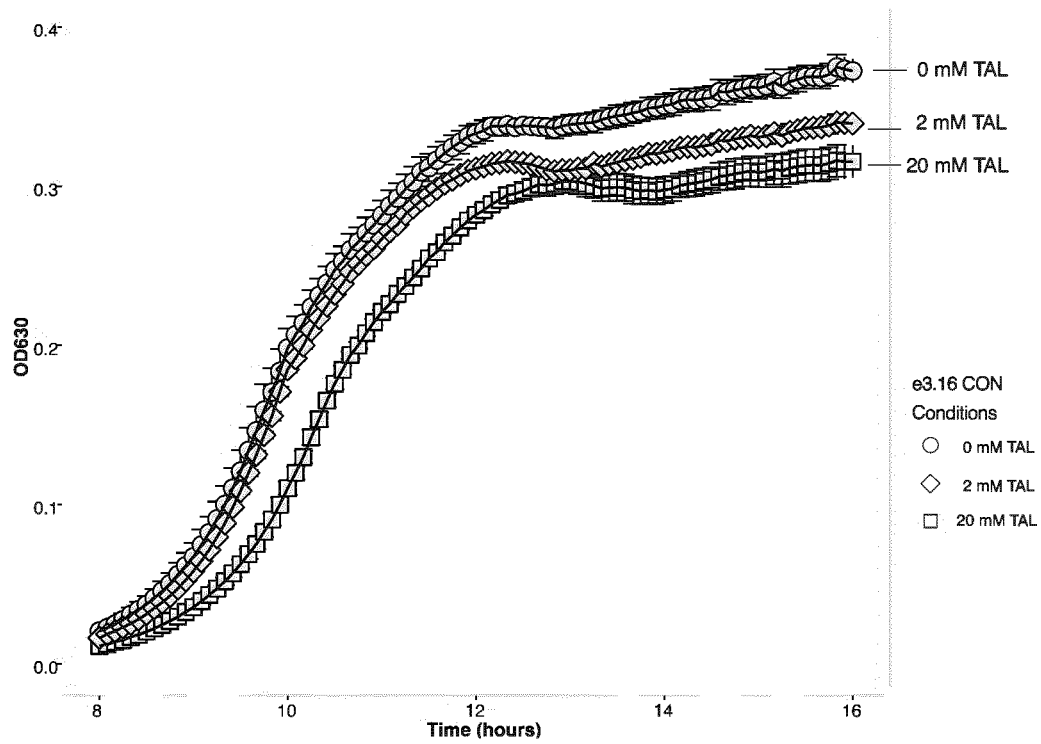

FIG. 11. Fitness cost to non-addicted control cells of supplemented triacetic acid lactone (TAL). Growth of *E. coli* control strain e3.16CON, measured as increase in cell density ($OD_{630\,nm}$) over time, in 2×YT medium (with kanamycin and spectinomycin) supplemented with respectively 0, 2 and 20 mM triacetic acid lactone at 37 deg. C. in 200 μL microtiter plates with continuous shaking. All wells were inoculated with the same number of cells. Error bars depict the standard error of the mean (n=3).

Figure 12:
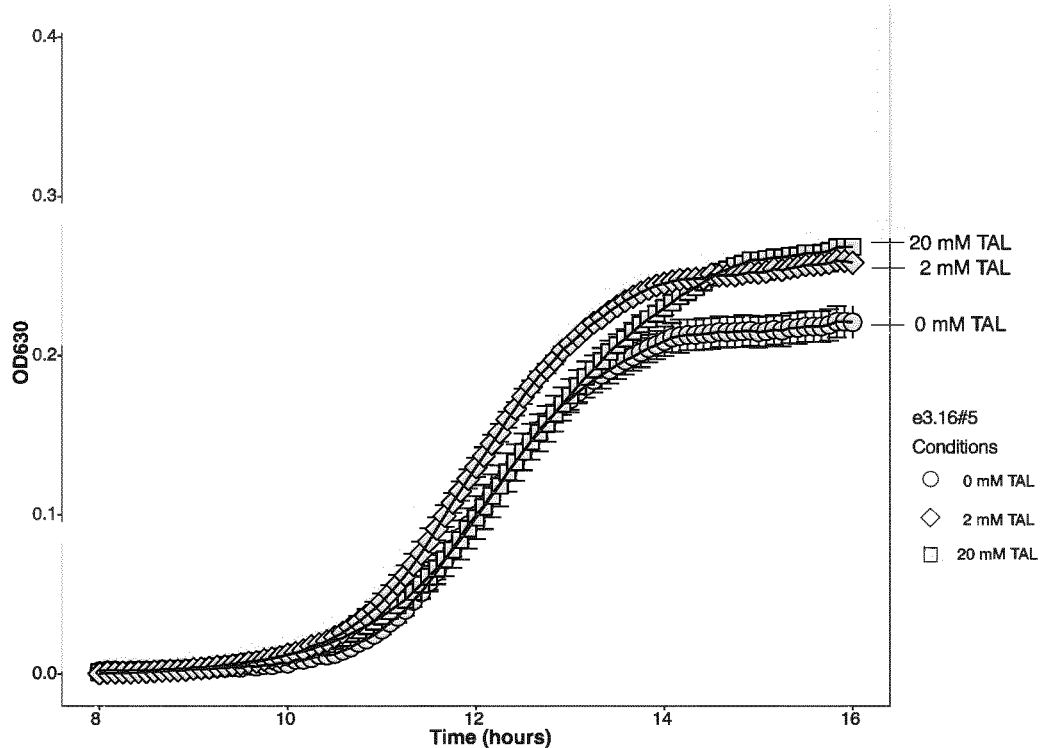

FIG. 12: Triacetic acid lactone-addicted growth of *E. coli* strain e3.16 #5 in 2×YT medium (with kanamycin and spectinomycin) supplemented with respectively 0, 2 and 20 mM triacetic acid lactone (TAL), measured as increase in cell density ($OD_{630\,nm}$) over time. Cells of the strain were grown at 37 deg. C. in 200 μL microtiter plates with continuous shaking. All wells were inoculated with the same number of cells. Error bars depict the standard error of the mean (n=3).

Figure 13:
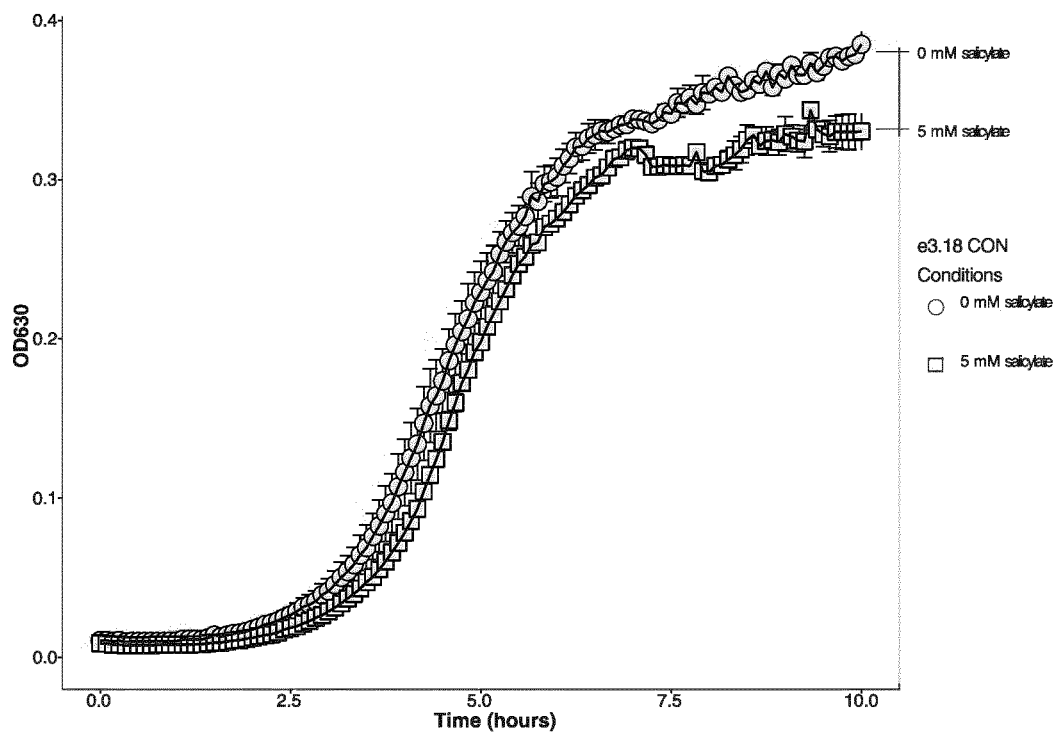

FIG. 13: Fitness cost to non-addicted control cells of supplemented salicylic acid. Growth of *E. coli* e3.18CON, measured as increase in cell density ($OD_{630\,nm}$) over time, in 2×YT medium (with kanamycin and spectinomycin) supplemented with respectively 0 or 5 mM salicylic acid and grown at 37 deg. C. in 200 μL microtiter plates with continuous shaking. All wells were inoculated with the same number of cells. Error bars depict the standard error of the mean (n=3).

Figure 14:
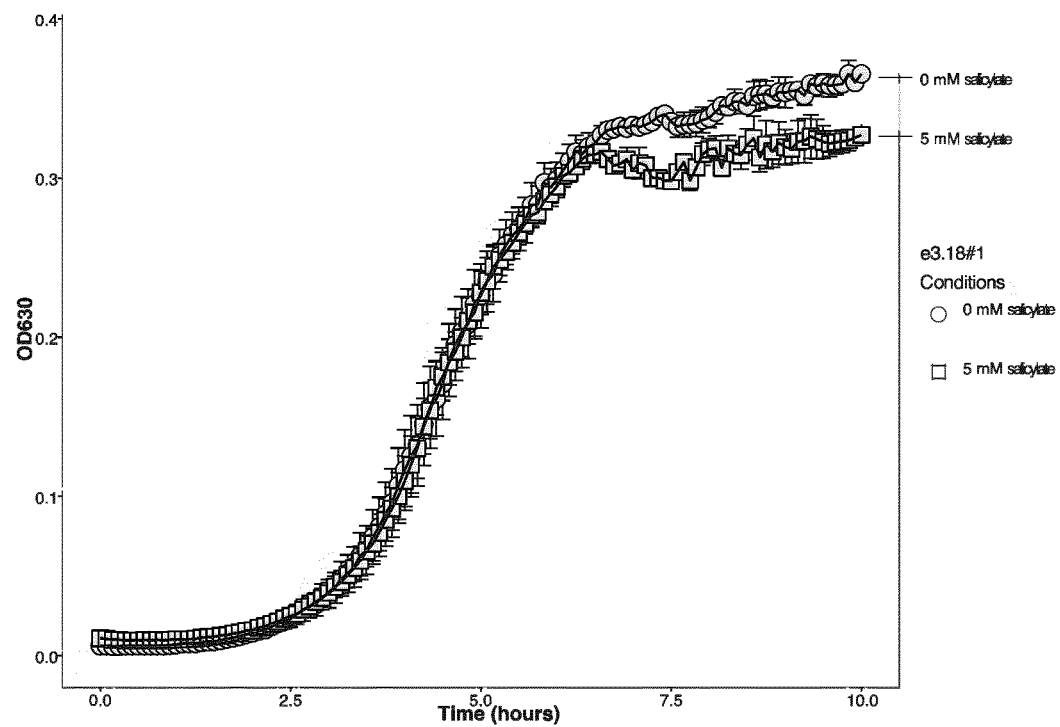

FIG. 14: The salicylic acid-addicted growth of *E. coli* e3.18 #1, measured as increase in cell density ($OD_{630\,nm}$) over time, cultured in 2×YT medium (with kanamycin and spectinomycin) supplemented with respectively 0 or 5 mM salicylic acid and grown at 37 deg. C. in 200 μL microtiter plates with continuous shaking. All wells were inoculated with the same number of cells.

Error bars depict the standard error of the mean (n=3).

Figure 15:
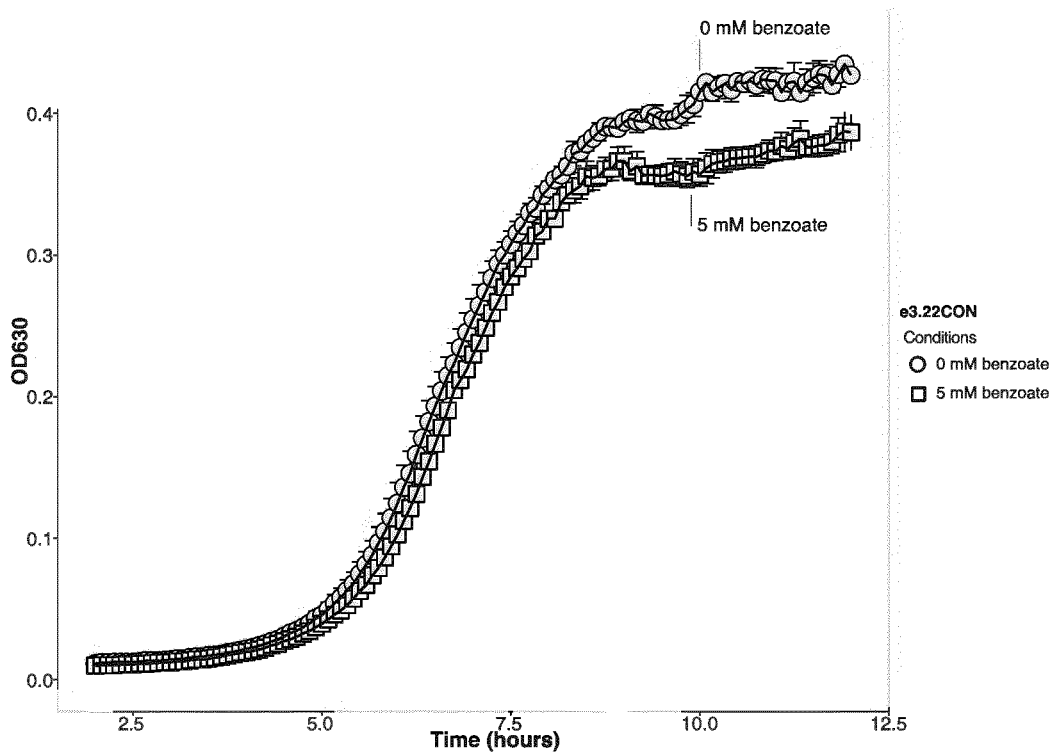

FIG. 15: Fitness cost to control cells of supplemented benzoic acid. Growth of *E. coli* e3.22CON, measured as increase in cell density ($OD_{630\,nm}$) over time, in 2×YT medium (with kanamycin and spectinomycin) supplemented with respectively 0 or 5 mM benzoic acid and grown at 37 deg. C. in 200 μL microtiter plates with continuous shaking. All wells were inoculated with the same number of cells. Error bars depict the standard error of the mean (n=3).

Figure 16:
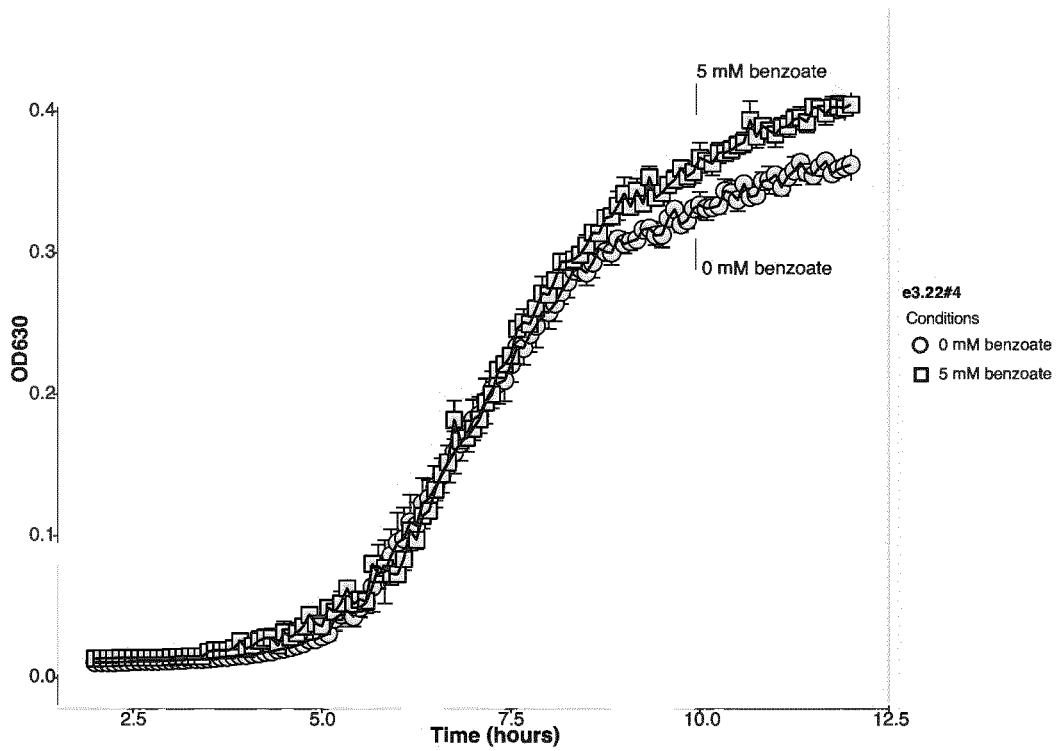

FIG. 16: Benzoic acid-addicted growth of *E. coli* e3.22 #4, measured as increase in cell density ($OD_{630\,nm}$) over time, in 2×YT medium (with kanamycin and spectinomycin) supplemented with respectively 0 or 5 mM benzoic acid and grown at 37 deg. C. in 200 μL microtiter plates with continuous shaking. All wells were inoculated with the same number of cells. Error bars depict the standard error of the mean (n=3).

Figure 17:
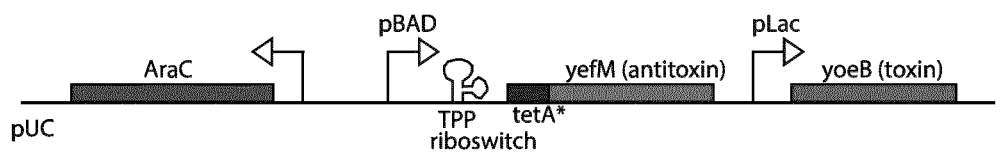

FIG. 17. Cartoon of a DNA construct comprising a TPP-addiction riboswitch-regulated TA system.

Figure 18:
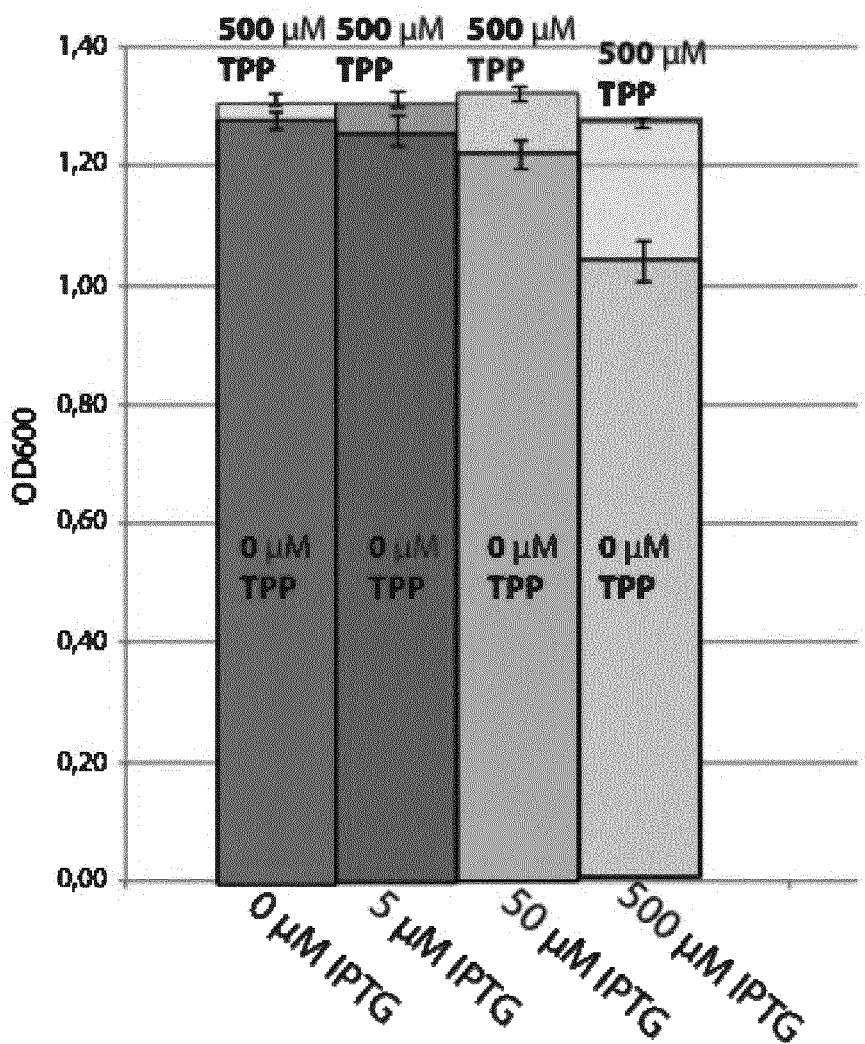

FIG. 18. Cell growth controlled by the thiamine pyrophosphate (TPP)-responsive riboswitch linked to a TA system. Cell density following 15 hours of incubation at 37° C. (measured by cell density at $OD_{600\,nm}$) of *E. coli* comprising TPP-responsive riboswitch controlling the translational rate of the antitoxin, YefM, and a constitutively expressed toxin, YoeB (0 μM IPTG) or induced toxin by LacI with IPTG inducer (5, 50 and 500 μM IPTG). Cell density measured in presence and absence of 500 μM TPP added to the growth medium.

Figure 19:
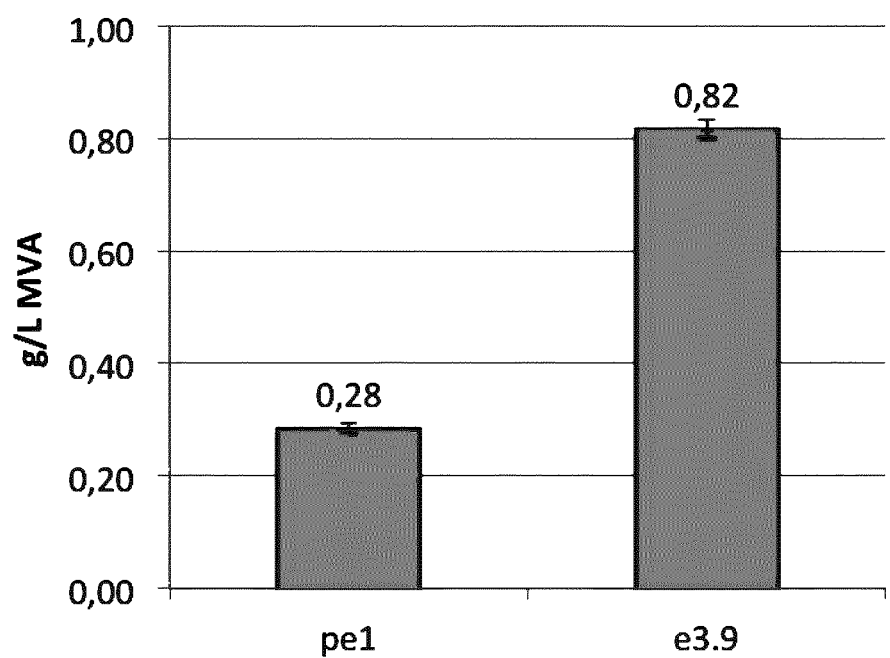

FIG. 19. Improvement with metabolite-addiction system following long-term culture. Concentration of mevalonate (MVA) accumulated in E. coli XL1 featuring the same MVA pathway plasmid following a total of 55 cell generations. Strain e3.9 unlike pe1 further features a chromosomal change in the promoter of an essential gene operon rendering its expression dependent on the product, MVA. Error bars denote standard deviation of biological replicates (n=3).

ABBREVIATIONS AND TERMS gi number: (genInfo identifier) is a unique integer which identifies a particular sequence, independent of the database source, which is assigned by NCBI to all sequences processed into Entrez, including nucleotide sequences from DDBJ/EMBL/GenBank, protein sequences from SWISS-PROT, PIR and many others.

Amino acid sequence identity: The term "sequence identity" as used herein, indicates a quantitative measure of the degree of homology between two amino acid sequences of substantially equal length. The two sequences to be compared must be aligned to give a best possible fit, by means of the insertion of gaps or alternatively, truncation at the ends of the protein sequences. The sequence identity can be calculated as ((Nref-Ndif)100)/(Nref), wherein Ndif is the total number of non-identical residues in the two sequences when aligned and wherein Nref is the number of residues in one of the sequences. Sequence identity can alternatively be calculated by the BLAST program e.g. the BLASTP program (Pearson W. R and D. J. Lipman (1988)) (www.ncbi.nlm.nih.gov/cgi-bin/BLAST). In one embodiment of the invention, alignment is performed with the sequence alignment method ClustalW with default parameters as described by Thompson J., et al 1994, available at http://www2.ebi.ac.uk/clustalw/.

Preferably, the numbers of substitutions, insertions, additions or deletions of one or more amino acid residues in the polypeptide as compared to its comparator polypeptide is limited, i.e. no more than 1, 2, 3, 4, 5, 6, 7, 8, 9, or 10 substitutions, no more than 1, 2, 3, 4, 5, 6, 7, 8, 9, or 10 insertions, no more than 1, 2, 3, 4, 5, 6, 7, 8, 9, or 10 additions, and no more than 1, 2, 3, 4, 5, 6, 7, 8, 9, or 10 deletions. Preferably the substitutions are conservative amino acid substitutions: limited to exchanges within members of group 1: Glycine, Alanine, Valine, Leucine, Isoleucine; group 2: Serine, Cysteine, Selenocysteine, Threonine, Methionine; group 3: Proline; group 4: Phenylalanine, Tyrosine, Tryptophan; Group 5: Aspartate, Glutamate, Asparagine, Glutamine.

Native gene: endogenous gene in a microbial cell genome, homologous to host micro-organism.

Biosensor: Suitable biosensor effectors (small molecules or metabolites detectable by a sensor) and their sensors can be found in the RegPrecise Collection of Manually Curated Inferences of Regulons in Prokaryotic Genomes, available at: http://regprecise.lbl.gov/RegPrecise/collections_effector.jsp Cell multiplication: process whereby cells multiply in number, as one cell divides into two cells, these two cells both divides to become four cells, four cells become eight, eight cells become sixteen etc. Each round of cell multiplication, by cell division, yields a new cell generation.

Cognate: in the context of Toxin-Antitoxin systems; an antitoxin protein interacts with its cognate toxin to neutralise the activity of the toxin.

Fitness cost: reduction in growth rate of a microbial cell e.g. due to producing a small molecule or metabolite (including a protein), measured relative to the growth rate of a reference microbial cell where production is inactivated. Fitness cost of a metabolic pathway can also be observed as an increase in growth lag phase, again relative to a reference cell where this pathway is inactivated.

Growth inhibitor/retardant of external origin: in the context of the invention, a growth inhibitor/retardant is a component of external origin that can inhibit or retard the growth of a micro-organism (such as a toxin or antibiotic), that is not produced by the micro-organism itself, but instead is supplied to the micro-organism either by addition to or its presence in the growth medium or environment in which the micro-organism is cultured.

Operably linked: a gene (nucleic acid molecule comprising a coding sequence) is operably linked to a promoter when its transcription is under the control of the promoter and where transcription results in a transcript whose subsequent translation yields the product encoded by the gene. Similarly a first nucleic acid molecule encoding a riboswitch may be operably linked to a second nucleic acid molecule upstream of its coding sequence; and also operably linked downstream of a promoter; whereby transcription of the downstream first nucleic acid molecule comprising the riboswitch linked to the second nucleic is under the control of the promoter and results in a transcript; and whereby translation of the transcript so produced (comprising the riboswitch and coding sequence) is under the control of the riboswitch.

Toxic: in the context of the invention a protein is defined as toxic if arrests or limits cell growth and/or prevents cell survival; e.g. a protein toxin.

DETAILED DESCRIPTION OF THE INVENTION

The present invention aims to prolong the productive life-time of an industrial fermentation by preventing the observed drift of a population of cells in an industrial fermentation from a productive state to a non-productive state. This drift typically arises as a result of spontaneous genetic mutations in cells of the production organism during continuous growth, and where a competitive advantage of a non-producing mutant favors its proliferation.

I: A Genetically Modified Microbial Cell Comprising a Synthetic Error Correction System Controlled by a Metabolite Biosensor The invention is based on the general concept of a synthetic error correction system which is illustrated in FIG. 1. This system uses either a penalty gene, whose expression can either lead to arrested growth or cell death (e.g. a toxin gene) in combination with a survival gene, whose expression provides an antidote that can restore cell viability and normal growth (e.g. a cognate antitoxin gene). Alternatively, the system uses a survival gene, alone, whose expression is essential for growth (i.e. essential gene).

The second key component of the system is a biosensor, whose function is to induce an appropriate gene regulation response leading to cell growth only when the cell produces a pre-defined level of a given metabolite. Cell survival and growth is said to be "addicted" to the presence of its metabolite i.e. to its addiction molecule. The functional properties of the biosensor depend on the type of gene regulation response required. If the system employs a penalty gene (such as a toxin gene) in combination with a survival gene (a cognate anti-toxin gene), then cell survival requires an "ON" type sensor linked to the expression of the survival gene. If the system employs a penalty gene alone (and no antidote), then an "OFF" type sensor is required. If the system employs a survival gene alone (e.g. essential genes) a metabolite-linked "ON" type sensor is needed as in the first scenario.

Accordingly, the fate of a cell, namely its survival and growth versus its arrested growth and eventual death, when employing this system, is determined by its continued production of a given metabolite, which is the product, or a close biosynthesis intermediate of the product of the industrial fermentation. A key feature of the synthetic error correction system in cells of the invention, is that the penalty executed by means of the error correction system in non-producing cells is realized by the expression of the penalty gene(s) and/or the failure to express the survival gene(s) (i.e. the expression of these genes and the cellular products thereof is both necessary and sufficient for achieving error correction). Accordingly, the arrest of growth or death of non-producing cells of the invention does not require the presence or addition of externally supplied compounds (e.g. toxins or antibiotics) for the execution of the penalty. This is an advantageous feature of the present invention, since the use of antibiotics or other growth retardants in the cultivation medium during industrial scale microbial fermentation would compromise the economics, biosafety and stability of production. The invention provides a genetically modified microbial cell for use in the intracellular biosynthesis of a cellular metabolite, comprising the above described synthetic error correction system. The genetically modified microbial cell comprises at least: a first nucleic acid molecule wherein the transcription and/or translation of said molecule yields a biosensor capable of binding the cellular metabolite to form a complex; and a second nucleic acid molecule comprising a coding sequence operably linked to a promoter, and encoding a protein required for cell growth and/or survival; and optionally a third nucleic acid molecule comprising a coding sequence operably linked to a promoter, and encoding a protein that inhibits the growth and/or survival of the cell. The expression of the protein encoded by the second nucleic acid molecule is induced when the biosensor and the cellular metabolite form a complex. Various embodiments of the genetically modified microbial cell of the invention are described below:

II: A Genetically Modified Microbial Cell Comprising a Toxin-Antitoxin System Controlled by a Metabolite Biosensor According to a first embodiment, the genetically modified microbial cell, which is for use in the intracellular biosynthesis of a given cellular metabolite, is a cell comprising a toxin-antitoxin system controlled by a metabolite biosensor which has at least the following features:

1. a first nucleic acid molecule encoding a transcription factor that functions as a biosensor and is capable of binding to the cellular metabolite produced by the cell to form a complex. The complex functions as an "activated transcription complex" in that it is able to interact with a gene promoter and induce expression of its cognate coding sequence; and 2. a second nucleic acid molecule which is operably linked to an inducible promoter and comprises a coding sequence encoding an anti-toxin protein that is cognate to and binds to the toxin, whereby the anti-toxin acts as an antidote to the toxin and permits the survival and growth of the cell; and 3. a third nucleic acid molecule encoding a toxin protein wherein the nucleic acid molecule comprises a coding sequence that is operably linked to a constitutive promoter; wherein expression of the antitoxin encoded by the second nucleic acid molecule is induced when the transcription factor and the cellular metabolite form a complex. As stated above, this complex, which functions as an "activated transcription complex" is capable of binding to the inducible promoter of the second nucleic acid molecule so as to induce expression of the antitoxin.

The Toxin/Antitoxin (TA) system, as used herein, is a two-component system whose features are used to slow the growth, or eliminate, non-producing micro-organisms that arise in a proliferating cell population during production of a metabolite e.g. during fermentation. The general concept of TA systems is given by the name: one component is a toxin molecule which affects a critical function in a cell, and the second component is an antitoxin that, upon expression in the cell, can cancel the effect of the toxin. The toxin usually causes growth arrest or cell death by impairing functions such as transcription, translation, cell division (replication and cytoskeleton formation), or membrane stability.

Examples of suitable TA systems include the type II TA pair, yefM-yoeB, from *E. coli*. The YoeB protein is a toxin that functions as an mRNA interferase, and binds to the 50S subunit of the ribosome to block translation initiation. The YoeB protein also has endoribonuclease activity without association to the ribosome. The antitoxin, YefM, forms a dimer which binds a single YoeB molecule to form a stable complex, which inactivates the mRNA-degrading action of YoeB. The YefM antitoxin is very sensitive to degradation by the Lon protease, whereby YoeB is then released and causes a growth arrest. Since the antitoxin has a short half-life, the absence of cellular metabolite required for continued expression of the antitoxin rapidly leads to release of the toxin and subsequent growth arrest.

The amino acid sequence of a functional YefM anti-toxin encoded by the coding sequence of the second nucleic acid molecule, has at least 74, 76, 78, 80, 82, 84, 86, 88, 90, 92, 94, 96, 98, 99, or 100% sequence identity to SEQ ID No: 2.

The amino acid sequence of a functional YoeB toxin encoded by the coding sequence of the third nucleic acid molecule, has at least 74, 76, 78, 80, 82, 84, 86, 88, 90, 92, 94, 96, 98, 99, or 100% sequence identity to SEQ ID No: 3.

Alternative suitable TA pairs include mazF-mazE (SEQ ID No. 36 and 38; encoded by SEQ ID No: 35 and 37 respectively), yafO-yafN (SEQ ID No. 40 and 42; encoded by SEQ ID No: 39 and 41 respectively) and relE-relB (SEQ ID No. 44 and 46; encoded by SEQ ID No: 43 and 45 respectively).

Use of alternative, suitable TA pairs when using the pBAD-TA5 vector requires that the DNA sequences encoding yoeB and yefM in pBAD-TA5 are replaced with the respective toxin and antitoxin encoding sequence above.

The third nucleic acid molecule comprises a constitutive promoter, operably linked to a coding sequence encoding a toxin protein that drives expression of the toxin protein. A suitable promoter is a constitutive promoter, whereby toxin protein is expressed continuously within the cell, for example J23100 having nucleotide sequence SEQ ID No: 48.

The second nucleic acid molecule comprises a coding sequence encoding an anti-toxin protein, operably linked to an inducible promoter that drives expression of the anti-toxin protein. A suitable inducible promoter is one that is activated and induces expression of the cognate coding sequence encoding the antitoxin protein, when the biosensor (a transcription factor) and the cellular metabolite form a complex. More specifically, transcription (and expression of the anti-toxin protein) may be induced on binding of this complex to this inducible promoter.

By way of example only, a suitable inducible promoter includes the $p_{BAD}$ (SEQ ID No: 66), that is inducible by the transcription factor biosensors that bind to the metabolites L-arabinose, and mevalonate, (see examples).

The first nucleic acid molecule encodes a transcription factor that is capable of binding to the cellular metabolite produced by the cell to form a complex. The complex functions as an "activated transcription complex" in that it is able to interact with a gene promoter and induce expression of its cognate coding sequence.

By way of example only, suitable transcription factors encoded by the coding sequence of the first nucleic acid molecule include AraC (SEQ ID No: 6), AraCmev (SEQ ID No: 12) and FadR (SEQ ID No: 68) that function as biosensors by binding to the metabolites L-arabinose, mevalonate and fatty acid/fatty acid acyl-CoA respectively (see examples illustrating biosensor:inducible promoter pairs for a range of metabolites).

The first nucleic acid molecule comprises a promoter operatively linked to a coding sequence encoding the transcription factor. If a eukaryotic host cell is used, the transcription factor should comprise a nuclear localization signal peptide e.g. encoding the protein sequence Pro-Lys-Lys-Lys-Arg-Lys-Val.

A suitable promoter is a constitutive promoter, whereby the biosensor (transcription factor) is expressed continuously within the cell at a level where binding of effector yields responsive gene regulation, for example selected from among the synthetic promoters listed below, for example J23100 having nucleotide sequence of SEQ ID No: 48.

| Promoter | Sequence (5'-) | SEQ ID No |
|---|---|---|
| J23119 | ttgacagctagctcagtcctaggtataatgctagc | 47 |
| J23100 | ttgacggctagctcagtcctaggtacagtgctagc | 48 |
| J23101 | tttacagctagctcagtcctaggtattatgctagc | 49 |
| J23102 | ttgacagctagctcagtcctaggtactgtgctagc | 50 |
| J23103 | ctgatagctagctcagtcctagggattatgctagc | 51 |
| J23104 | ttgacagctagctcagtcctaggtattgtgctagc | 52 |
| J23105 | tttacggctagctcagtcctaggtactatgctagc | 53 |
| J23106 | tttacggctagctcagtcctaggtatagtgctagc | 54 |
| J23107 | tttacggctagctcagcccctaggtattatgctagc | 55 |
| J23108 | ctgacagctagctcagtcctaggtataatgctagc | 56 |
| J23109 | tttacagctagctcagtcctagggactgtgctagc | 57 |
| J23110 | tttacggctagctcagtcctaggtacaatgctagc | 58 |
| J23111 | ttgacggctagctcagtcctaggtatagtgctagc | 59 |
| J23112 | ctgatagctagctcagtcctagggattatgctagc | 60 |
| J23113 | ctgatggctagctcagtcctagggattatgctagc | 61 |
| J23114 | tttatgctagctcagtcctaggtacaatgctagc | 62 |
| J23115 | tttatagctagctcagccctttggtacaatgctagc | 63 |
| J23116 | ttgacagctagctcagtcctagggactatgctagc | 64 |
| J23117 | ttgacagctagctcagtcctagggattgtgctagc | 65 |
| J23118 | ttgacggctagctcagtcctaggtattgtgctagc | 89 |

III: A Genetically Modified Microbial Cell Comprising a Toxin-Antitoxin System Controlled by a Metabolite Riboswitch Biosensor According to a second embodiment, the genetically modified microbial cell, which is for use in the intracellular biosynthesis of a given cellular metabolite, is a cell comprising a toxin-antitoxin system controlled by a metabolite biosensor which has at least the following features:

1. a first nucleic acid molecule, and
2. a second nucleic acid molecule comprising a coding sequence, wherein the first nucleic acid molecule is operably linked to the second nucleic acid molecule upstream if its coding sequence and operably linked downstream of a constitutive promoter; and wherein the second nucleic acid molecule comprises a coding sequence encoding an anti-toxin protein that is cognate to and binds to the toxin, whereby the anti-toxin acts as an antidote to the toxin and permits the survival and growth of the cell; and wherein the transcription product of the first nucleic acid molecule is a a riboswitch capable of binding to the cellular metabolite to form a complex;

3. a third nucleic acid molecule encoding a toxin protein wherein the nucleic acid molecule comprises a coding sequence that is operably linked to a constitutive promoter; wherein expression of the antitoxin encoded by the second nucleic acid molecule is induced when the riboswitch and the cellular metabolite form a complex.

The riboswitch system, as used herein, is a method of regulating expression of the component genes of the synthetic error correction system in the genetically modified micro-organisms of the invention. The regulation takes place at the translational level, and is mediated by mRNA structures which can be formed upstream or downstream of the coding region in the 3'- or 5'-untranslated region (UTR). These riboswitches are RNA structures, which are capable of binding effectors (e.g. small-molecules or metabolites) and modulate transcription or translation of a gene in cis. A riboswitch is composed of two separate domains: an aptamer domain responsible for ligand recognition and binding, and an expression system. These two typically overlap, and the overlap is known as a switching sequence, since it will base pair with either domain depending on the state of the riboswitch. Riboswitches can also modulate gene translation by forming a structure prone to degradation by RNases. Riboswitches can be both ON and OFF switches upon ligand binding, and transcriptional control can be carried out by the formation of terminators and anti-terminators (or anti-antiterminators) in response to molecule recognition. Translational regulation is also carried out by affecting the availability of the ribosome binding site. The riboswitch two-dimensional structure will either sequester or expose the ribosome binding site upon binding of the small molecule, resulting in the existence of both ON switches (Ribosome binding site exposed upon molecule binding), and in the opposite case, OFF switches, for example by forming a 'road-block' preventing progress of the already bound ribosomal machinery.

By way of example, the nucleotide sequence of a first nucleic acid molecule that is transcribed into a suitable OFF riboswitch is selected from the group consisting of: btuB leader (adenosylcobalamin-responsive) [SEQ ID No: 69]; tc3 (tetracycline-responsive) [SEQ ID No: 70]; and ThiMwt (TPP-responsive) [SEQ ID No: 71].

An ON riboswitch, ThiMN15 #19, is exemplified in Example 3.

IV: A Genetically Modified Microbial Cell Comprising a Toxin Gene Controlled by a Metabolite OFF-Type Biosensor According to a third embodiment, the genetically modified microbial cell, which is for use in the intracellular biosynthesis of a given cellular metabolite, is a cell comprising a toxin system controlled by a metabolite biosensor which has at least the following features:

1. a first nucleic acid molecule wherein the transcription and/or translation of said molecule yields a biosensor capable of binding said cellular metabolite to form a complex, and
2. a second nucleic acid molecule which is operably linked to a constitutive promoter and where the second nucleic acid molecule comprises a coding sequence encoding a toxin protein that prevents the survival and/or growth of the cell; and wherein the complex functions to block the transcription and/or translation of the second nucleic acid molecule.

When the first nucleic acid encodes a transcription factor, the complex that is formed on its binding to the cellular metabolite is an "activated transcription complex" that is capable of interacting with the promoter of the second nucleic acid molecule so as to block expression of the toxin.

Alternatively, first nucleic acid molecule is operably linked to the second nucleic acid molecule upstream of its coding sequence of and operably linked downstream of the constitutive promoter, said biosensor obtained on transcription of said first nucleic acid molecule is a riboswitch capable of binding to said metabolite to form a complex, and thereby blocking expression of the toxin.

A suitable "OFF" transcription factor for this third embodiment includes XylR (repressor) biosensor (xylose-responsive) [SEQ ID No: 72] and its cognate responsive promoter [SEQ ID No: 73]); and a suitable "OFF" riboswitch for this variant of the third embodiment includes ThiMwt (TPP-responsive, SEQ ID No: 74)

V: A Genetically Modified Microbial Cell Comprising an Essential Gene Controlled by a Metabolite Biosensor According to a fourth embodiment, the genetically modified microbial cell, which is for use in the intracellular biosynthesis of a given cellular metabolite, is a cell comprising an essential gene whose expression is controlled by a metabolite biosensor and which has at least the following features:

1. a first nucleic acid molecule encoding a transcription factor that functions as a biosensor and is capable of binding to the cellular metabolite produced by the cell to form a complex. The complex functions as an "activated transcription complex" in that it is able to interact with a gene promoter and induce expression of its cognate coding sequence; and
2. a second nucleic acid molecule (also known as an essential gene), which is operably linked to an inducible promoter, and comprises a coding sequence encoding an essential protein, and wherein expression of this essential protein permits the survival and growth of the cell; and wherein expression of the essential protein encoded by the second nucleic acid molecule is induced when the transcription factor and the cellular metabolite form a complex. As stated above, this complex, which functions as an "activated transcription complex" is capable of binding to the inducible promoter of the second nucleic acid molecule so as to induce expression of the essential protein. Examples of biosensors, encoded by the first nucleic acid molecule, and inducible promoters in the second nucleic acid molecule that control expression of the essential protein, are described in section II.

Essential genes, as used herein, provide an alternative synthetic error correction system, whereby the expression of a single gene product is used to control the fate of the genetically modified micro-organism of the invention. As the name reveals, the products of essential genes include those found necessary for cell growth under a defined set of conditions, as well as genes that become essential for growth of the genetically modified micro-organism of the invention. These conditions include the criteria that most of the necessary components for growth are present, alongside a temperature allowing for optimal growth rates. Characteristic of *E. coli* essential genes is that it is not possible to create viable cells of *E. coli* with knock-outs of these genes under the defined set of conditions.

By way of example only, the following six essential genes are suitable for use as this alternative synthetic error correction system. A characteristic of the following six essential genes is that their over-expression is not lethal for the cell:

murZ [SEQ ID No. 75], encodes an enzyme in the first committed step of peptidoglycan biosynthesis (also known as MurA) [SEQ ID No. 76];

mraY [SEQ ID No. 77], encodes a membrane-bound translocase [SEQ ID No. 78] also termed a UDP-MurNAc-pentapeptide phosphotransferase, located at the inner membrane of the ER which, alongside the gene product of murG, facilitates lipid II synthesis;

glmM [SEQ ID No. 79], encodes a phosphoglucosamine mutase [SEQ ID No. 80]; The g/mM gene in *E. coli* encodes a phosphoglucosamine mutase; which catalyzes the isomeric conversion between glucosamine-6-phosphate and glucosamine-1-phosphate. This reaction is one of the first in the biosynthetic pathway leading to the metabolite precursor UDP-Nacetylglucosamine (UDPGlcNAc). This compound forms a branch-point for pathways leading to both peptidoglycan and lipopolysaccaride synthesis, which are both essential cell wall constituents;

murI [SEQ ID No. 81], encodes a glutamase racemase [SEQ ID No. 82], required for synthesis of D-glutamic acid—another essential building block of peptidoglycan, also known as btuB;

ribA [SEQ ID No. 83], encodes a GTP cyclohydrolase II [SEQ ID No. 84], which catalyses the first committed step in riboflavin biosynthesis;

adk [SEQ ID No. 85], encodes an adenylate kinase [SEQ ID No. 86], which is an essential part of the nucleotide metabolism and catalyzes phosphorylation of AMP to ADP and dAMP to dATP (and nucleoside diphosphates to their correspond triphosphates).

In one embodiment the essential gene is g/mM, which is present in a two-gene operon with another essential gene: folP. The folP gene functions as the essential gene because it is the first gene in this operon, but as seen in the examples, the presence of more than one essential gene in the synthetic error correction system can be used to control the fate of the genetically modified micro-organism of the invention. The folP gene [SEQ ID No: 87], encodes dihydropteroate synthase [SEQ ID No. 88], which is part of the enzymatic pathway leading to production of tetrahydrofolate (vitamin B9). This compound is essential to normal cell growth, as folic acid cofactors are necessary for production of purines, methionine, thymidine, lysine and pantothenic acid.

VI a Cellular Metabolite Produced by a Genetically Modified Micro-Organism of the Invention A cellular metabolite produced by intracellular biosynthesis by the genetically modified micro-organism of the invention may range from a small molecule up to larger products, such as proteins.

A small molecule, by way of example only, is mevalonate, which is a precursor to a diverse group of compounds termed isoprenoids. Isoprenoids cover a group of chemicals with a diverse range of functions, structures, and applications. With over 50.000 known compounds, isoprenoid functions include flavors and perfumes, hormones, mediators of membrane fluidity, and pharmaceuticals. Plants have especially been found to be an incredible reservoir of these diverse secondary metabolites. The existing method of obtaining these interesting molecules (e.g. by plant extraction) is however inefficient. Microbial production of isoprenoids represents a green and feasible alternative to obtaining these compounds.

Further small molecules, may include fatty acid ethyl esters and other biodiesel molecules, which represent another branch of biochemicals that can be produced in microbial cells, ultimately converting glucose or other carbon sources into combustible fuels. Polyunsaturated fatty acids, and many other metabolic products, such as amino acids and organic acids, are already existing or potential fermentation products that can be produced by the microbial cells of the invention and for which synthetic error correction system of the invention can be used, making use of known or adapted transcription or translation regulatory elements. For example, natural riboswitches have been found responsive to various vitamin B family molecules.

The present invention provides a powerful tool for enhancing the productivity of isoprenoid production by microbial cell factories, by eliminating non-producers from continuous fermentation. This is illustrated with respect to mevalonate production in the examples herein.

By way of example, a genetically modified micro-organism for production of mevalonate comprises three genes encoding a biosynthetic pathway for the production of mevalonate from acetyl-CoA, namely: the *E. coli* gene atoB, and the two genes HMGS (ERG13), and tHMGR from *S. cerevisiae*. The atoB gene encodes an acetoacetyl-CoA thiolase, which catalyzes the formation of acetoacetyl-CoA from two molecules of acetyl-CoA. The HMGS gene encodes a HMG-CoA synthase, which forms 3-hydroxymethylglutayl-CoA (HMG-CoA) by a condensation reaction between acetoacetyl-CoA and another molecule of acetyl-CoA. Finally, HMG-CoA is converted to mevalonate by the tHMGR gene product, which is a truncated version of an HMGR gene. The product of HMG-CoA synthase activity is toxic to the cell, and it is the accumulation of HMG-CoA which promotes growth inhibition.

Figure 6A:
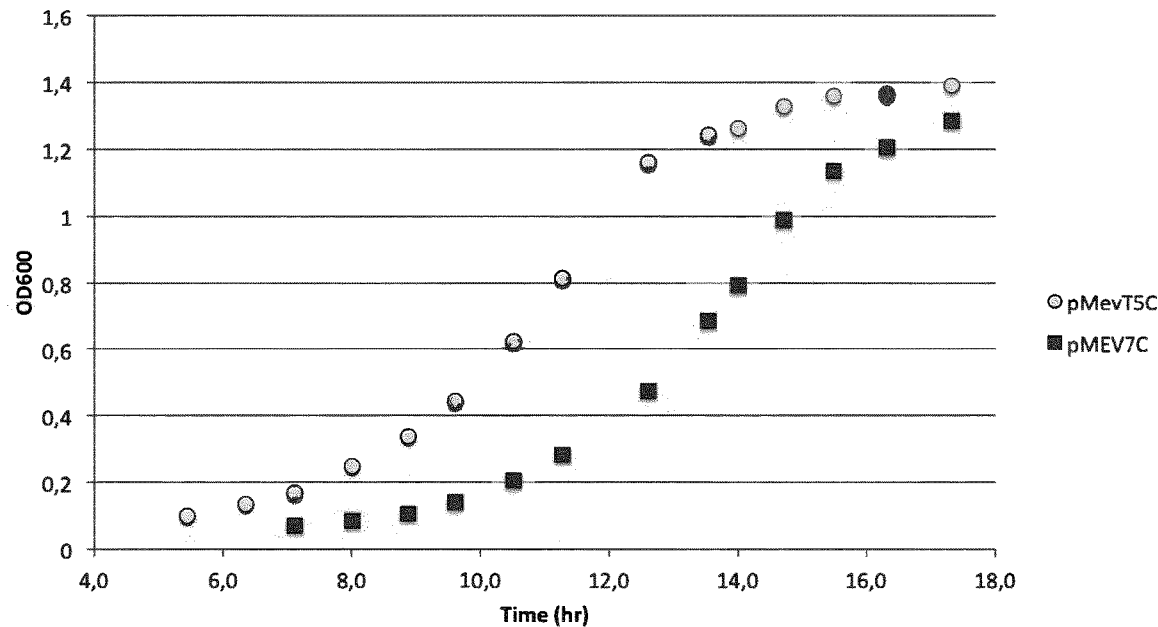

There is a fitness cost related to production of mevalonate, both in the length of the lag phase and the final OD of a producing strain (FIG. 6A). Both of these traits underline the potential effect of having non-producers appear in a fermentation. As the culture is inoculated, the producing cells will have a long lag phase, leaving room for non-producers to grow and overtake the population. As mutations would most likely appear in relation to growth, this phenomenon would likely be of greater importance when transferring a growing culture into fresh medium, at which point cheater cells had already appeared in the previous cultivation. This would also apply to batch fermentations, where one or more serial pre-cultures are used, as well as for chemostat cultures. As presented in the examples, the TA-correction system is shown to be effective in reducing the relative fitness cost between a producing and non-producing strain by lowering the fitness of the non-producers.

VII Methods for Producing a Cellular Metabolite Using the Genetically Modified Micro-Organism of the Invention According to a further embodiment, the invention provides a method for producing a biosynthetic metabolite comprising the steps of: a) providing a genetically modified microbial cell as defined above in sections I—IV, b) introducing the genetically modified microbial cell into a cultivation medium comprising a substrate for production of said metabolite, and c) recovering metabolite produced by said culture, wherein a lack of metabolite production in said genetically modified microbial cell or progeny cell thereof attenuates multiplication of said cell as compared to a non-genetically modified parent cell from which said modified microbial cell was derived.

In step b) it is contemplated that the cell in culture medium are cultivated under continuous; fed-batch or batch culture; and that the cells undergo at least 10, 15, 20, 25, 30, 35, 40, 45 or 50 generations of cell multiplication. The period of cultivation will depend on the micro-organism cultivated; but where the micro-organism is a bacterial cell, the accumulated period of cultivation is typically at least 2, 4, 6, 8, 10, 12, 14, 16, 18 or 20 days. In the context of the present invention the term "accumulated period of cultivation" is to be understood to include the cultivation of a pre-seed culture; further cultivation after subsequent inoculation of the pre-seed culture into a larger fermenter, and optionally cultivation after subsequent inoculation of the previous culture into an even larger fermenter. Production of a metabolite using the genetically modified microbial cell of the invention wherein the production of the metabolite has a high fitness cost of production, such as ≥5%, ≥10%, ≥15%, ≥20%, and ≥25%.

VIII Micro-Organisms for the Intracellular Biosynthesis of a Cellular Metabolite The micro-organism for the intracellular biosynthesis of a cellular metabolite according to the invention, may be a bacterium, a non-exhaustive list of suitable bacteria is given as follows: a species belonging to the genus *Bacillus*, a species belonging to the genus *Escherichia*, a species belonging to the genus *Lactobacillus*, a species belonging to the genus *Lactococcus*, a species belonging to the genus *Corynebacterium*, a species belonging to the genus *Acetobacter*, a species belonging to the genus *Acinetobacter*, a species belonging to the genus *Pseudomonas*; a species belonging to the genus *Proprionibacterium*, and a species belonging to the genus *Bifidobacterium*.

Alternatively, the micro-organism according to the invention may be a yeast belonging to the genus of *Saccharomyces*, e.g. *S. cerevisiae, S. kluyveri, S. bayanus, S. exiguus, S. sevazzi, S. uvarum*; a yeast belonging to the genus *Kluyveromyces*, e.g. *K. lactis K. marxianus* var. *marxianus, K. thermotolerans*; a yeast belonging to the genus *Candida*, e.g. *C. utilis C. tropicalis, C. albicans, C. lipolytica, C. versatilis*; a yeast belonging to the genus *Pichia*, e.g. *P. stipidis, P. pastoris, P. sorbitophila*, or other yeast genera, e.g. *Cryptococcus, Debaromyces, Hansenula, Yarrowia, Zygosaccharomyces* or *Schizosaccharomyces*. Alternatively, the micro-organisms may be a filamentous fungus belonging to the genus of *Penicillium, Rhizopus, Fusarium, Fusidium, Gibberella, Mucor, Mortierella, Trichoderma Thermomyces, Streptomyces* and *Aspergillus*. More specifically, the micro-organism may be *Fusarium Oxysporum, A. niger, A. awamori, A. oryzae,* and *A. nidulans*.

The preferred micro-organisms of the invention may be *S. cerevisiae, E. coli, L. lactis* or *L. plantarum. Bacillus subtilis, B. licheniformis, Trichoderma resei, Aspergillus niger, Aspergillus oryzae, Yarrowia lypolytica,* and *Pichia pastoris*.

IX Methods for Producing a Micro-Organism of the Invention

Integration and self-replicating vectors, suitable for cloning and introducing a first, second, third or additional nucleic acid molecules into a micro-organism for the intracellular biosynthesis of a cellular metabolite, are commercially available and known to those skilled in the art (see, e.g., Sambrook et al., Molecular Cloning: A Laboratory Manual, Second Edition, Cold Spring Harbor Laboratory Press, 1989). Cells of a micro-organism are genetically engineered by the introduction into the cells of heterologous DNA (RNA). Heterologous expression of genes encoding one or more polypeptide of the correction system in a micro-organism of the invention is demonstrated in the Examples.

A first, second, third or additional nucleic acid molecule(s) according to the invention, can be introduced into a cell or cells on plasmids or optionally integrated into the host cell genome using methods and techniques that are standard in the art. For example, nucleic acid molecules can be introduced by standard protocols such as transformation including chemical transformation and electroporation, transduction, particle bombardment, etc.

EXAMPLES

Example 1. TA Systems 1.1 L-Arabinose Addiction Coupled to a Type II TA System is Shown to Control Bacterial Cell Growth The yefM-yoeB TA pair comprises two genes, where the yoeB gene encodes a toxin, and the yefM gene encodes its cognate antitoxin (FIG. 2). The YoeB toxin has two properties that serve to block cell growth: 1) acting as an mRNA interferase, and binding to the 50S subunit of the ribosome to block translation initiation; 2) acting as an endoribonuclease, and degrading mRNA independent of the ribosome. When a cognate YefM dimer is expressed, this binds a single YoeB molecule to form a stable complex and thereby prevents the growth inhibitory properties of the toxin. The half-life of the YefM antitoxin is short, since it is rapidly proteolytically degraded (Lon protease). Accordingly, a failure to express the YefM antitoxin leads to release of the YoeB toxin, which in turn arrests cell growth.

The use of the yefM-yoeB TA pair system to control the growth of bacteria based on L-arabinose addiction was demonstrated in *E. coli*, as follows.

The yefM-yoeB TA pair was cloned into a plasmid (pBAD-TA5: araC, $p_{BAD}$-yefM, $p_{Lac}$-yoeB, ampR) (Table 1) employing standard PCR cloning protocols (known in the art) and the plasmid was transformed into the host stain *E. coli* XL-1 with the genotype: recA1endA1 gyrA96 thi-1 hsdR17 supE44 re/A1 lac[F'proAB lacIqZM15 Tn10 (TetR)]. Electroporation recovery of transformed cells was carried out in SOC medium (2% tryptone, 0.5% yeast extract, 10 mM NaCl, 2.5 mM KCl, 10 mM MgCl2, 10 mM MgSO4, and 20 mM glucose).

Transformed *E. coli* cultures were grown in 2×YT medium (10 g/L yeast extract, 16 g/L tryptone, 5 g/L NaCl). Antibiotics were added to select for maintenance of plasmids in strains transformed with these, according to their respective antibiotic resistance gene. Antibiotic concentrations when added were as follows: ampicillin 100 µg/mL, chloramphenicol 30 µg/mL, spectinomycin 50 µg/mL, kanamycin 50 µg/mL.

Figure 3A:
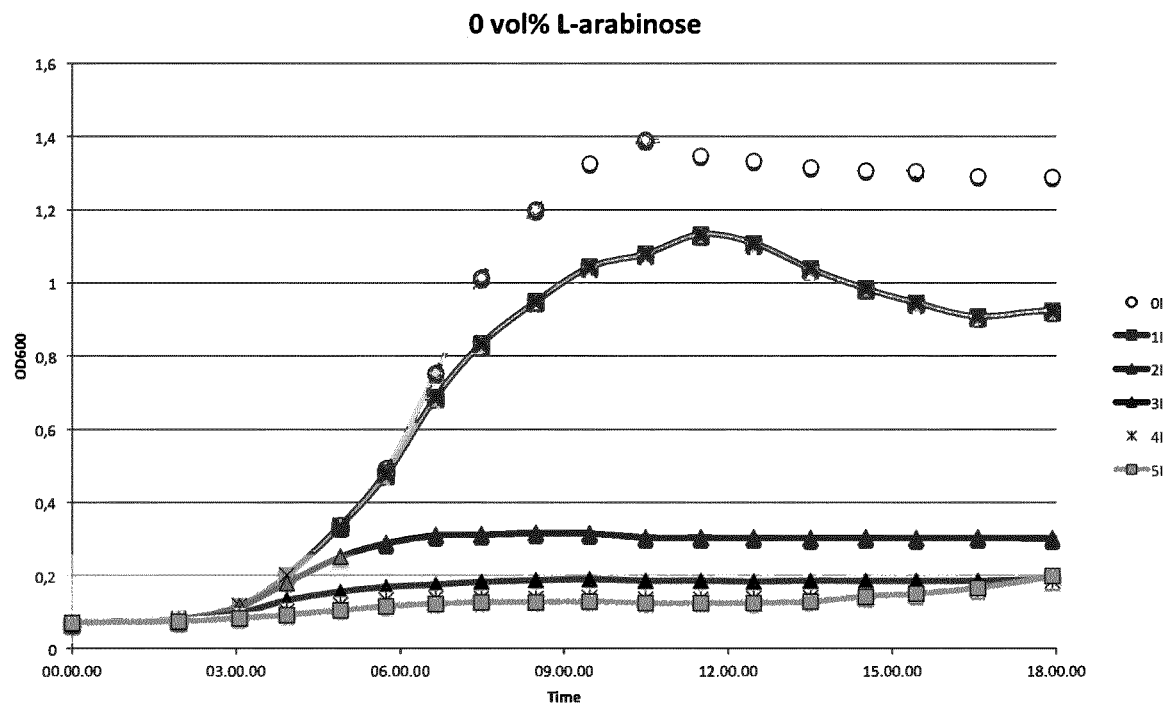

The expression of the yoeB gene in the yefM-yoeB TA pair construct (FIG. 2) was placed under the control of the Lac promoter, which is inducible by isopropyl β-D-1-thiogalactopyranoside (IPTG). Exposure of the cells to increasing concentrations of IPTG induced sufficient expression of the YoeB toxin to prevent growth, when the cells were grown in the absence of any source of L-arabinose (FIG. 3A). The expression of the yefM gene is placed under the control of the $p_{BAD}$ promoter, which is inducible by L-arabinose.

The regulation of the $p_{BAD}$ promoter by AraC is dual. In the absence of L-arabinose, the AraC protein binds to operator sites within $p_{BAD}$ effectively repressing transcription. Upon binding of L-arabinose, the complex changes to another DNA-binding conformation leading to activation of $p_{BAD}$ and induction of transcription of a cognate gene.

Figure 3B:
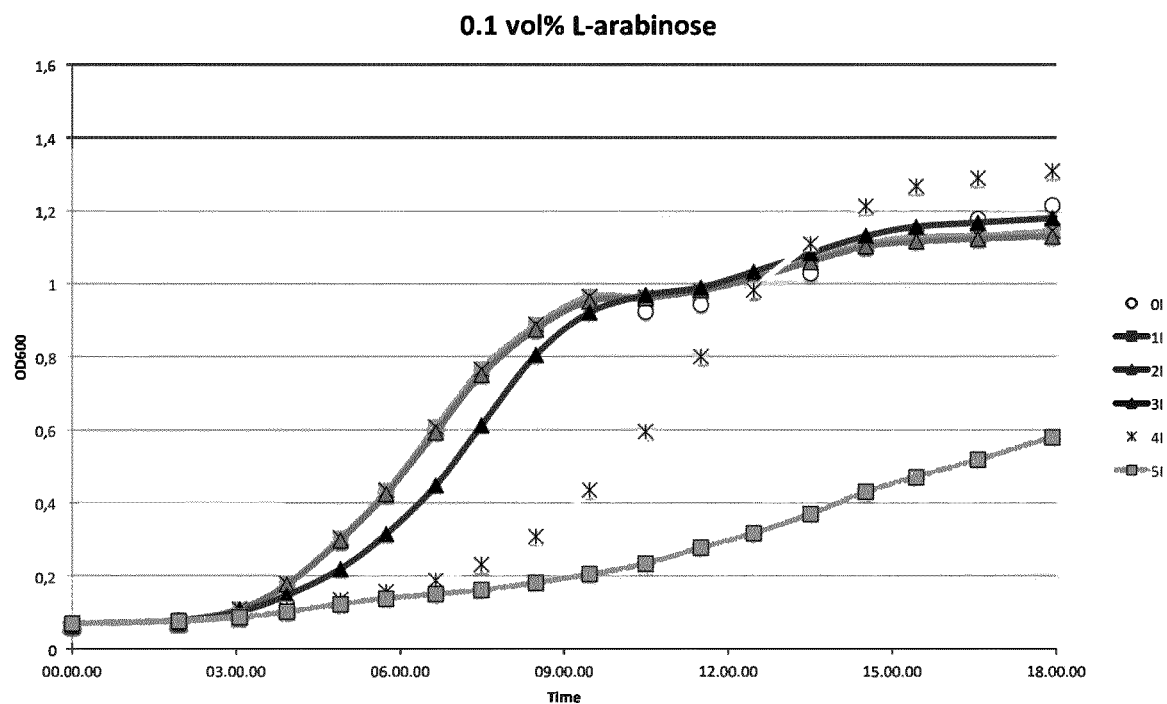

While cell growth was strongly inhibited by addition of ≥0.1 mM IPTG of the toxin inducer; the co-addition of 0.1% L-arabinose was sufficient to restore wild-type growth in the presence of IPTG at concentrations up to 0.5 mM (FIG. 3B).

These data demonstrate that the TA system has a wide dynamic range, with gradual response in respect of growth inhibition. Thus a small change in the level of toxin expression relative to antitoxin expression, does not give rise to a dramatic change in cell growth rates, but is still provides sufficiently strong growth control to prevent growth as well as allow normal growth at extremes in the concentration of the inducer L-arabinose.

Table 1 listing the genetic features of the L-arabinose TA addicted strain based on the *E. coli* XL1 parent strain.

TABLE 1

| Plasmid/chromosome | Gene | SEQ ID No: | Protein | SEQ ID No |
|---|---|---|---|---|
| pBAD-TA5 | araC* | SEQ ID No: 1 | | |
| | $p_{BAD}$-yefM | | YefM | SEQ ID No: 2 |
| | $p_{Lac}$-yoeB | | YoeB | SEQ ID No: 3 |
| | ampR | | Beta-lactamase | SEQ ID No: 4 |
| | araC | SEQ ID No: 5 | araC | SEQ ID No: 6 |

*araC gene [SEQ ID No: 5] encoding araC biosensor protein [SEQ ID No: 6] is located on the complementary strand to SEQ ID No: 1 at nucleotide positions: 96-974. The $p_{BAD}$ promoter is located a position 1246-1318 in SEQ ID No: 1.

Table 2 listing the genetic features of the mevalonate TA addicted strain m14 based on the *E. coli* XL1 parent strain. The chromosomally located sequence is an excerpt of the genome sequence that fully comprises the engineered features.

TABLE 2

| Plasmid/ chromosome | Gene | SEQ ID No: | Protein | SEQ ID No |
|---|---|---|---|---|
| pBAM-TA5 | araCmev* | SEQ ID No: 7 | | |
| | $p_{BAD}$-yefM | | YefM | SEQ ID No: 8 |
| | $p_{Lac}$-yoeB | | YoeB | SEQ ID No: 9 |
| | ampR | | Beta-lactamase | SEQ ID No: 10 |
| | araCmev | SEQ ID No: 11 | araCmev | SEQ ID No: 12 |
| chromosome | yefM-FRT-kanR-FRT-yoeB** | SEQ ID No: 13 | Neomycin phosphotransferase II | SEQ ID No: 14 |

*araCmev gene [SEQ ID No: 11] encoding araCmev biosensor protein [SEQ ID No: 12] is located on the complementary strand to SEQ ID No: 7 at nucleotide positions: 96-974;
**(1$^{st}$) "FRT site" is located on complementary stand to SEQ ID No 13 at nucleotide positions: 247-281; (2$^{nd}$) "FRT site" is located on complementary stand to SEQ ID No 13 at nucleotide positions: 1469-1503.
The $p_{BAD}$ promoter is located a position 1241-1318 in SEQ ID No: 7.

In order to enhance to the stability of this plasmid based TA correction system, the native genomic copy of the yefM-yoeB gene pair was knocked-out. This was achieved using a DNA fragment comprising a FRT-kana-FRT resistance cassette fused to flanking sequences homologous to circa 200 bp flanking sequences homologous to each side of the junction between the chromosomal yefM-yoeB gene pair. Site specific integration of the FRT-kana-FRT resistance cassette into the native yefM-yoeB gene pair and functional knock-out was achieved by means of lambda-red-mediated recombineering.

1.2 Mevalonate Addiction Coupled to a Type II TA System is Shown to Control Bacterial Cell Growth Mevalonate is one of the early precursors in the biosynthesis of a diverse group of compounds termed isoprenoids with a range of applications. The production of mevalonate in micro-organisms is seen to place a metabolic strain on the producing cells, meaning there is a fitness cost, and where the appearance of non-producing cells compromises the economics of mevalonate production. A Type II TA system coupled to mevalonate addiction according to the invention provides a method for slowing the growth or eliminating cells that are non-producers.

In order to control bacterial cell growth by mevalonate addiction, a mevalonate biosensor was introduced into the yefM-yoeB TA pair plasmid, pBAD-TA5 (Table 2), in place of the L-arabinose biosensor. The mevalonate-responsive biosensor was derived from the AraC sensor by introducing 4 point mutations (FIG. 4). In the absence of expression of the yefM antitoxin, cell growth was inhibited by the yoeB gene expressed under the control of the $p_{LAC}$ promoter. Addition of the inducer, IPTG, was not required, since the baseline activity of the Lac promoter was sufficient to drive expression of toxin at cell growth inhibitory levels; likely due to the leakiness of the Lac promoter.

Addition of mevalonate (37 mM) was sufficient to bind to the mevalonate biosensor and induce the cognate $p_{BAD}$ promoter to express the YefM antitoxin at levels sufficient to allow an increase in cell growth when compared to cell cultures devoid of mevalonate.

1.3 Engineering a Bacterial Strain Addicted to Internal Small Molecule Production Mevalonate-addicted E. coli strains (as described in 1.2) were additionally engineered to produce mevalonate. Strains were transformed with a plasmid comprising genes encoding one of three alternative biosynthetic pathways for the conversion of endogenous acetyl CoA to mevalonate (FIG. 5). The plasmid, pMevTC, comprises an operon with the E. coli gene AtoB, encoding an acetyl-CoA acetyltransferase; an S. cerevisiae ERG13 gene encoding an HMG-CoA synthase, and tHMGR, a truncated version of S. cerevisiae HMGR, encoding an HMG-CoA reductase. This plasmid directs intermediate levels of mevalonate production in a host strain (1-2 g/L).

The plasmid, pMEV7C, comprises the E. coli gene AtoB; a Lactococcus lactis gene mvaS encoding an HMG-CoA synthase, and a Lactococcus lactis mvaE gene encoding a HMG-CoA reductase. This plasmid directs high level mevalonate production in a host strain (≤14.6 g/L in batch fermentation).

A negative control pathway pMevT5c features a point mutation in the ERG13 gene, rendering the strain incapable of producing mevalonate, but otherwise it maintains the same promoter, enzymatic pathway reactions, antibiotic selection gene and plasmid origin of replication. The pathway operon promoter in both plasmids pMEV7C and pMevT5C was the synthetic promoter J23100 [SEQ ID No: 48].

Table 3 listing the genetic features of the mevalonate TA addicted strain m29 with internal mevalonate biosynthesis, based on the E. coli XL1 parent strain.

TABLE 3

| Plasmid/ chromosome | Gene | SEQ ID No: | Protein | SEQ ID No |
|---|---|---|---|---|
| pBAM-TA5 | araCmev* | SEQ ID No: 7 | | |
| | $p_{BAD}$-yefM | | YefM | SEQ ID No: 8 |
| | $p_{Lac}$-yoeB | | YoeB | SEQ ID No: 9 |
| | ampR | | Beta-lactamase | SEQ ID No: 10 |
| | araCmev | SEQ ID No: 11 | araCmev | SEQ ID No: 12 |
| chromosome | yefM-FRT-kanR-FRT-yoeB** | SEQ ID No: 13 | Neomycin phosphotransferase II | SEQ ID No: 14 |
| pMEV7C | atoB | SEQ ID No: 15 | acetyl-CoA acetyltransferase | SEQ ID No: 16 |
| | mvaS | | HMG-CoA synthase | SEQ ID No: 17 |
| | mvaE | | HMG-CoA reductase | SEQ ID No: 18 |
| | camR*** | | | |
| | camR | SEQ ID No: 19 | Chloramphenicol acetyltransferase | SEQ ID No: 20 |

*araCmev gene [SEQ ID No: 11] encoding araCmev biosensor protein [SEQ ID No: 12] is located on the complementary strand to SEQ ID No: 7 at nucleotide positions: 96-974;
**(1$^{st}$) "FRT site" is located on complementary stand to SEQ ID No 13 at nucleotide positions: 247-281; (2$^{nd}$) "FRT site" is located on complementary stand to SEQ ID No 13 at nucleotide positions: 1469-1503.
***camR gene [SEQ ID No: 19] encoding chloramphenicol acetyltransferase [SEQ ID No: 20] is located on the complementary strand to SEQ ID No: 15 at nucleotide positions 4745-5404.
The $p_{BAD}$ promoter is located a position 1241-1318 in SEQ ID No: 7.

Table 4 listing the genetic features of the mevalonate TA addicted strain m16 without internal mevalonate biosynthesis, based on the E. coli XL1 parent strain.

TABLE 4

| Plasmid/chromosome | Gene | SEQ ID No: | Protein | SEQ ID No |
|---|---|---|---|---|
| pBAM-TA5 | araCmev* | SEQ ID No: 7 | | |
| | p$_{BAD}$-yefM | | YefM | SEQ ID No: 8 |
| | p$_{Lac}$-yoeB | | YoeB | SEQ ID No: 9 |
| | ampR | | Beta-lactamase | SEQ ID No: 10 |
| | araCmev | SEQ ID No: 11 | araCmev | SEQ ID No: 12 |
| chromosome | yefM-FRT-kanR-FRT-yoeB** | SEQ ID No: 13 | Neomycin phosphotransferase II | SEQ ID No: 14 |
| pMevT5C | atoB | SEQ ID No: 21 | acetyl-CoA acetyltransferase | SEQ ID No: 22 |
| | Mutant ERG13 | | Non-functional HMG-CoA synthase | SEQ ID No: 23 |
| | tHMGR | | Truncated HMG-CoA reductase | SEQ ID No: 24 |
| | camR*** | | | |
| | camR | SEQ ID No: 19 | Chloramphenicol acetyltransferase | SEQ ID No: 20 |

*araCmev gene [SEQ ID No: 11] encoding araCmev biosensor protein [SEQ ID No: 12] is located on the complementary strand to SEQ ID No: 7 at nucleotide positions: 96-974;
**(1$^{st}$) "FRT site" located on complementary stand to SEQ ID No 13 at nucleotide positions: 247-281; (2$^{nd}$) "FRT site" located on complementary stand to SEQ ID No 13 at nucleotide positions: 1469-1503.
***camR gene [SEQ ID No: 19] encoding chloramphenicol acetyltransferase [SEQ ID No: 20] is located on the complementary strand to SEQ ID No: 21 at nucleotide positions 5293-5952.

1.4 Mevalonate-Addiction Coupled to a TA System Cancels the Fitness Advantage of Non-Mevalonate Producing Cells.

Mevalonate production has a fitness cost for a bacterial cell. This is shown by the retarded growth of an E. coli strain, comprising the plasmid (pMEV7C) and producing 'high' level mevalonate, as compared to an E. coli strain, comprising the control plasmid (pMevT5c) and producing no mevalonate, but still having the metabolic burden of expressing the enzymes of the inactivated mevalonate biosynthesis pathway (FIG. 6A). The product of HGMS activity is known to be toxic to the cell, and it is the accumulation of HMG-CoA which promotes growth inhibition.

Figure 6B:
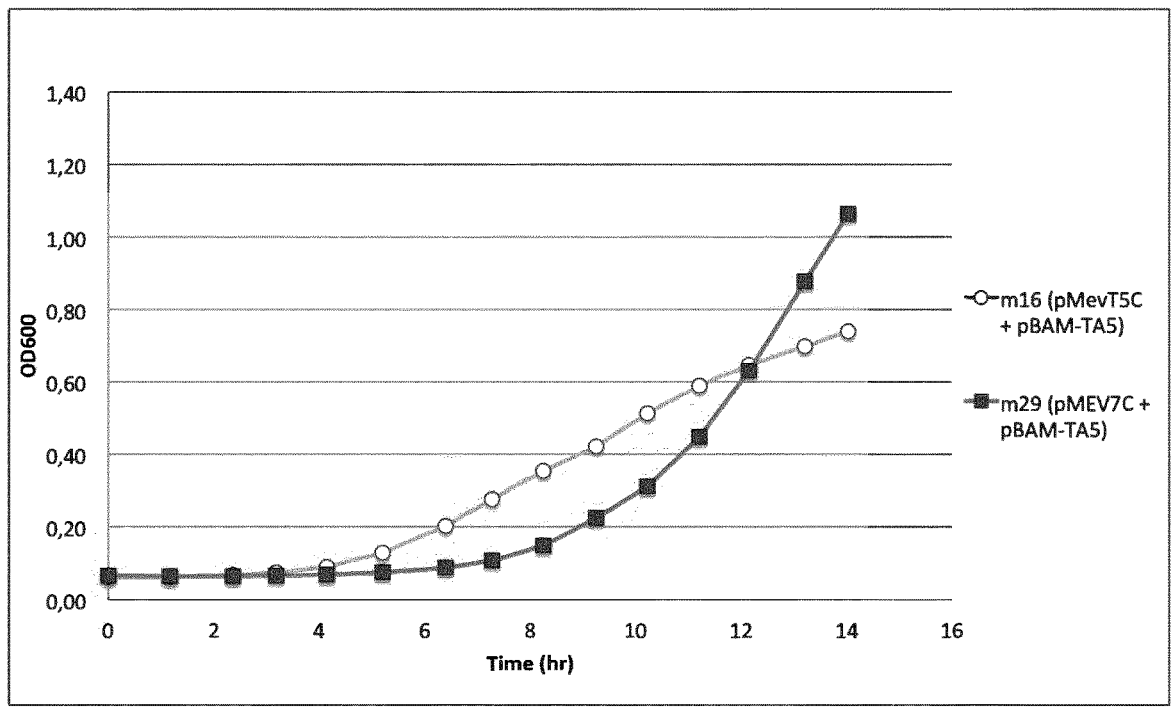

Co-expression of the mevalonate-addiction TA system (pBAM-TA5), despite a longer lag phase in these cells, was effective in countering the fitness advantage of non-producing cells (FIG. 6B). Survival and growth of cells expressing the TA system (pBAM-TA5), depends on a sufficient level of mevalonate to induce expression of antitoxin. The rate of accumulation of internally synthesized mevalonate to levels sufficient to induce antitoxin production may be a factor contributing to the observed lag phase in producing cells that express mevalonate-addiction TA system.

1.5 Use of the TA System to Increase Small-Molecule Production by Bacterial Cultures Comprising Non-Producing Cells The ability of the TA system to favor survival and growth of productive cells (i.e. cells producing the addiction molecule, mevalonate), was demonstrated by co-culturing mevalonate-producing cells, comprising the pMEV7C plasmid, and non-producing strains, comprising the pMevT5C plasmid. The ratios of non-producing:producing cells tested were: 0:100, 75:25 and 90:10. The total mevalonate production of the 3 co-cultured strains was tested with and without co-expression of the mevalonate-addiction TA system, encoded on the plasmid pBAM-TA5.

Previous experiments with strains possessing the mevalonate pathway had established a fitness cost of harboring a functional production plasmid (pMEV7c) versus a non-functional production plasmid (pMevT5c) to be a reduction in growth rate of approximately 20% (FIG. 6A). Accordingly, the growth of producing cells was by default expected to be disfavored compared to the non-producing cells (i.e. without any synthetic correction system). The same cell inoculum mixes were cultured with the producing and non-producing strains, but both also harbored the correction plasmid (pBAM-TA5). This addition of the correction system was shown to significantly enhance mevalonate production in the co-cultures comprising non-producing cells (FIG. 7).

Example 2 Essential Genes 2.1 L-Arabinose Addiction by Regulated Expression of an Essential Gene is Shown to Control Bacterial Cell Growth The essential genes, used to control bacterial growth, are the E. coli genes folP and glmM, which are comprised together within a two-gene operon. The gene glmM encodes a phosphoglucosamine mutase; and the gene folP encodes a dihydropteroate synthase, which is part of the enzymatic pathway leading tetrahydrofolate (vitamin B9) synthesis, which is essential for normal cell growth.

The native single genomic copy of the essential gene operon folP, g/mM in E. coli host strain XL1, was modified to allow its transcriptional control by the L-arabinose/mevalonate-responsive promoter p$_{BAD}$. Replacement of the native promoter by the p$_{BAD}$ promoter was engineered by introducing a knockout fragment containing a kanamycin resistance cassette and the p$_{BAD}$ promoter, as illustrated in the cartoon in FIG. 8. An L-arabinose biosensor (AraC) (Table 1) was introduced into the modified host strain on the plasmid pBAD18-cam. The modified and transformed E. coli strains were grown in 2×YT medium (10 g/L yeast extract, 16 g/L tryptone, 5 g/L NaCl). Antibiotics were added to select for maintenance of plasmids in transformed strains, according to their respective antibiotic resistance gene. Antibiotic concentrations when added were as follows: ampicillin 100 μg/mL, chloramphenicol 30 μg/mL, spectinomycin 50 μg/mL, kanamycin 50 μg/mL. Table 5 lists the genetic features of the essential gene-based mevalonate-addicted strain e3.9, based on an E. coli XL1 parent strain. The chromosomally located sequence is an excerpt of the genome sequence that fully comprises the engineered features.

TABLE 5

| Plasmid/chromosome | Gene | SEQ ID No: | Protein | SEQ ID No |
|---|---|---|---|---|
| chromosome | (FRT-kanR-FRT)-$p_{BAD}$-folP* | SEQ ID No: 25 | Dihydropteroate synthase | SEQ ID No: 26 |
| | kanR** | SEQ ID No: 27 | Neomycin phosphotransferase II | SEQ ID No: 28 |
| pBAMspec | araCmev*** specR | SEQ ID No: 29 | spectinomycin resistance protein | SEQ ID No: 30 |
| pMEV7C | atoB | SEQ ID No: 15 | acetyl-CoA acetyltransferase | SEQ ID No: 16 |
| | mvaS | | HMG-CoA synthase | SEQ ID No: 17 |
| | mvaE | | HMG-CoA reductase | SEQ ID No: 18 |
| | camR**** | | | |

*The native promoter of the chromosomal folP-glmM operon is replaced by the $p_{BAD}$ promoter via the (FRT-KanR-FRT)-$p_{BAD}$-folP cassette [SEQ ID No: 25]; which comprises the pBAD promoter at position 1907-1979 and a portion of the folP gene. The nucleotide sequence of the folP gene in the e3.9 strain is SEQ ID No: 87.
**kanR gene [SEQ ID No: 27] encoding Neomycin phosphotransferase II [SEQ ID No: 28] is located on the complementary strand to SEQ ID No: 25 at nucleotide positions 389-1183.
***araCmev gene [SEQ ID No: 11] encoding araCmev biosensor protein [SEQ ID No: 12] is located on the complementary strand to SEQ ID No: 29 at nucleotide positions: 96-974.
****camR gene [SEQ ID No: 19] encoding chloramphenicol acetyltransferase [SEQ ID No: 20] is located on the complementary strand to SEQ ID No: 21 at nucleotide positions 4745-5404.

Table 6 listing the genetic features of the essential gene-based L-arabinose-addicted strain e3.5, based on an *E. coli* XL1 parent strain. The chromosomally located sequence is an excerpt of the genome sequence that fully comprises the engineered features.

TABLE 6

| Plasmid/chromosome | Gene | SEQ ID No: | Protein | SEQ ID No |
|---|---|---|---|---|
| chromosome | (FRT-kanR**-FRT)-$p_{BAD}$-folP* | SEQ ID No: 25 | Dihydropteroate synthase | SEQ ID No: 26 |
| pBAD18-cam*** | araC cam | | AraC Chloramphenicol acetyltransferase | |

*The native promoter of the chromosomal folp-glmM operon is replaced by the $p_{BAD}$ promoter via the (FRT-KanR-FRT)-$p_{BAD}$-folP cassette [SEQ ID No: 25]; which comprises the pBAD promoter at position 1907-1979 and a portion of the folP gene. The nucleotide sequence of the folp gene in the e3.5 strain is SEQ ID No: 87.
**kanR gene [SEQ ID No: 27] encoding Neomycin phosphotransferase II [SEQ ID No: 28] is located on the complementary strand to SEQ ID No: 25 at nucleotide positions 389-1183.
***Guzman et al, 1995

Table 7 listing the genetic features of the pe1 control strain producing mevalonate without the addiction system, based on an *E. coli* XL1 parent strain.

TABLE 7

| Plasmid/chromosome | Gene | SEQ ID No: | Protein | SEQ ID No |
|---|---|---|---|---|
| pBAM18-spec | araCmev* specR | SEQ ID No: 29 | AraCmev aminoglycoside nucleotidyl-transferase | SEQ ID No: 12 SEQ ID No: 30 |
| pMEV7C | atoB | SEQ ID No: 15 | acetyl-CoA acetyltransferase | SEQ ID No: 16 |
| | mvaS | | HMG-CoA synthase | SEQ ID No: 17 |

TABLE 7-continued

| Plasmid/chromosome | Gene | SEQ ID No: | Protein | SEQ ID No |
|---|---|---|---|---|
| | mvaE | | HMG-CoA reductase | SEQ ID No: 18 |
| | camR** | | chloramphenicol acetyltransferase | SEQ ID No: 20 |

*araCmev gene [SEQ ID No: 11] encoding araCmev biosensor protein [SEQ ID No: 12] is located on the complementary strand to SEQ ID No: 29 at nucleotide positions: 96-974;
**camR gene [SEQ ID No: 19] encoding chloramphenicol acetyltransferase [SEQ ID No: 20] is located on the complementary strand to SEQ ID No: 21 at nucleotide positions 4745-5404; specR = spectomycin resistance protein (e.g. aminoglycoside nucleotidyl-transferase).

Since the expression levels of essential genes is important for optimizing their use for growth control, a micro-library of four different ribosome binding sites (created by a single random base pair in one of the primers covering the RBS in front of the $p_{BAD}$ promoter), having different (RBS) strengths, were tested and one RBS was found to give a particularly good conditional growth, strictly in response to providing L-arabinose in the growth medium (FIG. 9). When cells, comprising the essential gene operon (folP/glmM) driven by the L-arabinose responsive $p_{BAD}$ promoter, were cultured in 2×YT growth medium supplemented with 0.25% L-arabinose at 37° C., their growth was exponential, whereas cells with supplemented with only 0.0025% and 0% L-arabinose completely failed to grow over a 12-hour time course.

2.2 Use of Essential Genes to Enhance Small Molecule Production in Bacteria.

An *E. coli* strain comprising the essential gene operon folP-g/mM, whose expression was regulated by a mevalonate-addiction, was engineered in order to demonstrate its use for the regulation of mevalonate-dependent cell growth.

The native single genomic copy of the essential gene operon folP-g/mM in *E. coli* host strain XL1, was modified to allow its transcriptional control by the L-arabinose/mevalonate-responsive promoter $p_{BAD}$ (FIG. 8). A mevalonate biosensor (AraCmev) (Table 3) was introduced into the modified host strain on the plasmid pBAM 18-spec.

In order to demonstrate that growth and mevalonate production by the "essential gene" regulated *E. coli* strain was dependent on internal mevalonate production the cells were also transformed with a plasmid carrying the genes encoding the mevalonate biosynthetic pathway (pMEV7C (Table 2) or genes encoding the inactivated the mevalonate biosynthetic pathway (pMevT5C). Growth of these *E. coli* strains of producing strains (having a functional mevalonate pathway) was exponential, while growth of non-producing strains (having an inactivated mevalonate pathway) was strongly inhibited (FIG. 10).

2.3 Triacetic Acid Lactone Addiction by Regulated Expression of an Essential Gene is Shown to Control Bacterial Cell Growth The native single genomic copy of the essential gene operon folP-g/mM in the *E. coli* XL1 host strain was modified to allow its transcriptional control by the triacetic acid lactone-responsive promoter $p_{BAD}$. First, a gene encoding a triacetic acid lactone biosensor (AraCtal (Tang et al., 2013)) was introduced into the XL1 host strain on the plasmid pBALspec (Table 8). Then, replacement of the native folP-g/mM promoter in this host strain by the $p_{BAD}$ promoter was engineered by means of lambda red-mediated recombineering. Recombineering was performed using well-described methods utilizing the pKD46 plasmid (Datsenko and Wanner, 2000), but instead of gene disruption, a specific set of knock-out DNA fragments (produced by PCR) was used to only replace the native essential folP-g/mM operon promoter and folP ribosomal binding site (RBS). This set of knockout DNA fragments each contained a kanamycin resistance cassette and the $p_{BAD}$ promoter, as illustrated in the cartoon in FIG. 8. The nucleotide sequence of the set of gene knockout DNA fragments differed only with respect to the redundant nucleotide ("N", wherein "N" is any of A, T, G or C) in the RBS sequence (ACTTGC) for folP-g/mM, which generated a four-membered library of folP translational strengths. This library allowed selection of a translational strength for folP that resulted in control of normal cell growth in response to transcriptional regulation by the AraCtaI biosensor.

TABLE 8

TAL responsive e3.16#5 clone

| Plasmid/chromosome | Gene | SEQ ID No: | Protein | SEQ ID No |
|---|---|---|---|---|
| chromosome | (FRT-kanR-FRT)-$p_{BAD}$-folP* | SEQ ID No: 91* | Dihydropteroate synthase | SEQ ID No: 26 |
|  | kanR** | SEQ ID No: 27 | Neomycin phosphotransferase II | SEQ ID No: 28 |
| pBALspec | AraCtaI*** | SEQ ID No: 93 | Triacetic acid lactone sensor protein | SEQ ID No: 96 |
|  | specR | | spectinomycin resistance protein | SEQ ID No: 94 |

*The native promoter of the chromosomal folP-glmM operon is replaced by the $p_{BAD}$ promoter via the (FRT-KanR-FRT)-$p_{BAD}$-folp cassette [SEQ ID No. 91]; which comprises a $p_{BAD}$ promoter at position 1665-1990, a RBS at position 1980-1985, having the nucleotide sequence ACTTGC; and a portion of the folP gene. The nucleotide sequence of the complete folP gene in the e3.16#5 strain is SEQ ID No: 87.
**kanR gene [SEQ ID No: 27] encoding Neomycin phosphotransferase II [SEQ ID No: 28] is located on the complementary strand to SEQ ID No: 91 at nucleotide positions 389-1183.
***araCtaI gene [SEQ ID No: 95] encoding araCtaI biosensor protein [SEQ ID No: 96] is located on the complementary strand to SEQ ID No: 93 at nucleotide positions: 96-1025.
****specR gene encoding spectinomycin resistance protein [SEQ ID No: 94] is located at nucleotide positions 1945-2916 of SEQ ID No: 93.

For recombineering, as performed in standard pKD46 protocols, the target strain was first transformed with pKD46, and a single colony of this strain was then cultured in a 25 mL 2×YT culture at 30 degrees C. and 250 rpm horizontal shaking. When the culture reached $OD_{600}$=0.1, the lambda Red system of pKD46 was induced by addition of 0.2 vol % L-arabinose, and then further cultured to grow to $OD_{600}$=0.4. The cells from the culture were then transformed with 300-500 ng knock-out DNA fragments by standard high-efficiency electroporation; the electroporated cells were then cultured in SOC medium (20 g/L tryptone, 5 g/L yeast extract, 10 mM NaCl, 2.5 mM KCl, 10 mM $MgCl_2$, 10 mM $MgSO_4$, 20 mM glucose) at 37 degrees for at least 1-2 hours to recover and simultaneously cure the cells of the pKD46 plasmid. Following recovery, candidate recombineered cells were selected for by plating on LB agar plates supplemented with 10 mM triacetic acid lactone and spectinomycin for maintenance of pBALspec and kanamycin for selection of inserted knockout fragment.

A non-addicted control *E. coli* strain (e3.16CON), also equipped with spectinomycin and kanamycin resistance genes, but with wildtype control of folP-glmM expression (Table 9), was constructed in order to test the toxicity of triacetic acid lactone.

TABLE 9

Non-addicted control strain e3.16CON

| Plasmid/chromosome | Gene | SEQ ID No: | Protein | SEQ ID No |
|---|---|---|---|---|
| chromosome | kanR | SEQ ID No: 27 | Neomycin phosphotransferase II | SEQ ID No: 28 |
| pBALspec | AraCtaI*** | SEQ ID No: 93 | Triacetic acid lactone sensor protein | SEQ ID No: 96 |
|  | specR |  | Spectinomycin resistance protein | SEQ ID No: 98 |

***araCtaI gene [SEQ ID No: 95] encoding araCtaI biosensor protein [SEQ ID No: 96] is located on the complementary strand to SEQ ID No: 93 at nucleotide positions: 96-1025.

The non-addicted control *E. coli* strain (e3.16CON), and a selected addicted strain (e3.16 #5) were then tested and compared for triacetic acid lactone-dependent growth by cultivation in a microtiter plate reader in liquid 2×YT medium supplemented with spectinomycin and kanamycin and a three-step gradient of triacetic acid lactone (0, 2 and 20 mM). As seen in FIG. 11, the control strain showed a relative reduction in growth rate as a result of supplementation with triacetic acid lactone, indicating that triacetic acid lactone is toxic for growth. The observed growth depression was greatest at a concentration of 20 mM triacetic acid lactone.

The addicted strain e3.16 #5 was able to grow in the absence of triacetic acid lactone, indicating that under non-inducing conditions the basal expression of the essential folP-glmM operon in this strain was sufficient to support growth.

Cell growth was however significantly reduced to a level matching the growth of the control strain under toxic condition of 20 mM triacetic acid lactone (FIG. 11 and FIG. 12). In contrast to the control strain, the growth rate of the addicted strain e3.16 #5 was enhanced by the presence of 2 mM triacetic acid lactone, and the final cell yield was increased by the presence of both 2 mM and 20 mM triacetic acid lactone (FIG. 12). The dependence of the addicted strain on a supply of triacetic acid lactone for maximal growth (FIG. 12), confirms that the triacetic acid lactone biosensor is able to induce the $p_{BAD}$ promoter and the expression of dihydropteroate synthase, in the pathway leading tetrahydrofolate (vitamin B9) synthesis, which is essential for normal cell growth.

2.4. Salicylic Acid Addiction by Regulated Expression of an Essential Gene is Shown to Control Bacterial Cell Growth The native single genomic copy of the essential gene operon folP-glmM in the *E. coli* XL1 host strain was modified to allow its transcriptional control by the salicylic acid-responsive promoter $p_{SAL}$ [SEQ ID No: 118]. First, a gene encoding a salicylic acid biosensor (*Pseudomonas putida* nahR_Asn169 (Cebolla et al., 1997)) was introduced into the XL1 host strain on the plasmid pBANspec (Table 10). Then, replacement of the native folP-g/mM promoter by the $p_{SAL}$ promoter was engineered by means of lambda red-mediated recombineering.

TABLE 10

Salicylic acid responsive e3.18#1 clone

| Plasmid/chromosome | Gene | SEQ ID No: | Protein | SEQ ID No |
|---|---|---|---|---|
| chromosome | (FRT-kanR-FRT)-$p_{SAL}$-folP* | SEQ ID No: 101 | Dihydropteroate synthase | SEQ ID No: 102 |
| | kanR** | SEQ ID No: 27 | Neomycin phosphotransferase II | SEQ ID No: 28 |
| pBANspec | NahRAsn169*** | SEQ ID No: 97 | Salicylic acid biosensor protein | SEQ ID No: 100 |
| | specR | | Spectinomycin resistance protein | SEQ ID No: 98 |

*The native promoter of the chromosomal folP-glmM operon is replaced by the $p_{SAL}$ promoter via the (FRT-KanR-FRT)-$p_{BAD}$-folP cassette [SEQ ID No. 101]; which comprises $p_{SAL}$ promoter at position 1794-1929; a RBS at position 1930-1935, having the nucleotide sequence ACTTGT; and a portion of the folP gene (to direct homologous recombination). The nucleotide sequence of the complete folP gene in the e3.18#1 strain is SEQ ID No: 87.

**kanR gene [SEQ ID No: 27] encoding Neomycin phosphotransferase II [SEQ ID No: 28] is located on the complementary strand to SEQ ID No: 91 at nucleotide positions 389-1183.

***nahRAsn169 gene [SEQ ID No: 99] encoding salicylic acid biosensor protein [SEQ ID No: 100] is located on the complementary strand to SEQ ID No: 97 at nucleotide positions: 102-1004.

Recombineering was performed as described in section 2.3 using well-described methods utilizing the pKD46 plasmid (Datsenko and Wanner, 2000). Instead of gene disruption, a specific set of knock-out DNA fragments was used to only replace the native essential folP-glmM operon promoter and folP RBS. This set of knockout DNA fragments contained a kanamycin resistance cassette and the $p_{SAL}$ promoter, as illustrated in the cartoon in FIG. 8, as well as a redundant nucleotide ("N", wherein "N" is any of A, T, G or C) in the RBS for folP-glmM to generate a four-membered library of folP translational strengths. This library allows selection of a translational strength for folP that suits the transcriptional regulation by the biosensor. Finally, candidate recombineered cells were selected for by plating on LB agar plates supplemented with 5 mM salicylic acid and spectinomycin for maintenance of pBANspec; and kanamycin for selection of inserted knockout fragment. A control host strain e3.18CON (Table 11) also equipped with spectinomycin and kanamycin resistance genes, but with wild-type control of folP-glmM expression) was used to in order to test the toxicity of Salicylic acid.

TABLE 11

Non-addicted control strain e3.18CON

| Plasmid/chromosome | Gene | SEQ ID No: | Protein | SEQ ID No |
|---|---|---|---|---|
| chromosome | kanR | SEQ ID No: 27 | Neomycin phosphotransferase II | SEQ ID No: 28 |
| pBANspec | NahRAsn169* | SEQ ID No: 97 | Salicylic acid biosensor protein | SEQ ID No: 100 |
| | specR | | Spectinomycin resistance protein | SEQ ID No: 98 |

*nahRAsn169 gene [SEQ ID No: 99] encoding salicylic acid biosensor protein [SEQ ID No: 100] is located on the complementary strand to SEQ ID No: 97 at nucleotide positions: 102-1004.

A selected addicted strain (e3.18 #1) and the non-addicted control E. coli strain (e3.18CON) were then tested for salicylic acid dependent growth by cultivation in a microtiter plate reader in liquid 2×YT medium supplemented with spectinomycin and kanamycin and presence/absence of salicylic acid (0 or 5 mM). As seen in FIG. 13, the control strain showed a relative reduction in growth rate and final biomass yield as a result of supplementation with salicylic acid, indicating that salicylic acid is toxic for growth. In contrast to the control strain, the growth rate of the addicted strain e3.18 #1 was not reduced by the presence of salicylic acid, but rather the growth rate was higher in presence of 5 mM salicylic acid than the otherwise expected rate for non-addicted strains (FIG. 14). The dependence of the addicted strain on a supply of salicylic acid for maximal growth (FIG. 14), confirms that the salicylic acid biosensor is able to induce the $p_{SAL}$ promoter and the expression of dihydropteroate synthase, in the pathway leading tetrahydrofolate (vitamin B9) synthesis, which is essential for normal cell growth.

2.5 Benzoic Acid Addiction by Regulated Expression of an Essential Gene is Shown to Control Bacterial Cell Growth The native single genomic copy of the essential gene operon folP-glmM in the E. coli XL1 host strain was modified to allow its transcriptional control by the benzoic acid-responsive promoter $p_{SAL}$ [SEQ ID No: 118]. First, a gene encoding a benzoic acid biosensor (Pseudomonas putida nahR) (Table 12) was introduced into the XL1 host strain on the plasmid pBABspec. Then, replacement of the native folP-g/mM promoter by the $p_{SAL}$ promoter was engineered by means of lambda red-mediated recombineering.

TABLE 12

Benzoic acid addicted e3.22#4 clone

| Plasmid/chromosome | Gene | SEQ ID No: | Protein | SEQ ID No |
|---|---|---|---|---|
| chromosome | (FRT-kanR-FRT)-p$_{SAL}$-folP* | SEQ ID No: 101 | Dihydropteroate synthase | SEQ ID No: 102 |
|  | kanR** | SEQ ID No: 27 | Neomycin phosphotransferase II | SEQ ID No: 28 |
| pBABspec | NahR*** | SEQ ID No: 103 | Benzoic acid sensor protein | SEQ ID No: 106 |
|  | specR |  | Spectinomycin resistance protein | SEQ ID No: 104 |

*The native promoter of the chromosomal folP-glmM operon is replaced by the p$_{SAL}$ promoter via the (FRT-KanR-FRT)-p$_{SAL}$-folp cassette [SEQ ID No. 101]; which comprises a p$_{SAL}$ promoter at position 1794-1929; a RBS at position 1930-1935, having the nucleotide sequence ACTTGC; and a portion of the folp gene. The nucleotide sequence of the complete folp gene in the e3.22#4 strain is SEQ ID No: 87.
**kanR gene [SEQ ID No: 27] encoding Neomycin phosphotransferase II [SEQ ID No: 28] is located on the complementary strand to SEQ ID No: 91 at nucleotide positions 389-1183.
***nahR gene [SEQ ID No: 105] encoding benzoic biosensor protein [SEQ ID No: 106] is located on the complementary strand to SEQ ID No: 103 at nucleotide positions: 102-1004.

Recombineering was performed as described in section 2.3 using well-described methods utilizing the pKD46 plasmid (Datsenko and Wanner, 2000)). Instead of gene disruption, a specific set of knock-out DNA fragments was used to only replace the native essential folP-glmM operon promoter and folP RBS. This set of knockout DNA fragments contained a kanamycin resistance cassette and the p$_{SAL}$ promoter, as illustrated in the cartoon in FIG. 8, as well as a redundant nucleotide ("N", wherein "N" is any of A, T, G or C) in the RBS for folP-g/mM to generate a four-membered library of folP translational strengths. This library allows selection of a translational strength for folP that suits the transcriptional regulation by the biosensor.

A non-addicted control *E. coli* strain (e3.22CON), also equipped with spectinomycin and kanamycin resistance genes, but wild-type control of folP-glmM expression (Table 13), was constructed in order to test the toxicity of benzoic acid.

TABLE 13

Benzoic acid non-addicted control e3.22CON

| Plasmid/chromosome | Gene | SEQ ID No: | Protein | SEQ ID No |
|---|---|---|---|---|
| Chromosome | kanR | SEQ ID No: 27 | Neomycin phosphotransferase II | SEQ ID No: 28 |
| pBABspec | NahR | SEQ ID No: 103 | Benzoic acid sensor protein | SEQ ID No: 106 |
|  | specR |  | Spectinomycin resistance protein | SEQ ID No: 104 |

*kanR gene [SEQ ID No: 27] encoding Neomycin phosphotransferase II [SEQ ID No: 28].
***nahR gene [SEQ ID No: 105] encoding benzoic biosensor protein [SEQ ID No: 106] is located on the complementary strand to SEQ ID No: 103 at nucleotide positions: 102-1004.

Finally, candidate recombineered cells were selected for by plating on LB agar plates supplemented with 5 mM benzoic acid and spectinomycin for maintenance of pBABspec and kanamycin for selection of inserted knockout fragment.

A selected addicted strain (e3.22 #4) and the non-addicted control *E. coli* strain (e3.18CON) were then tested for benzoic acid dependent growth by cultivation in a microtiter plate reader in liquid 2×YT medium supplemented with spectinomycin and kanamycin and w/wo salicylic acid (0 or 5 mM). As seen in FIG. 15, the control strain showed a relative reduction in growth rate and final biomass yield as a result of supplementation with benzoic acid, indicating that benzoic acid is toxic for growth. In contrast to the control strain, the growth rate and final biomass yield of the addicted strain e3.18 #1 was enhanced by supplementation with benzoic acid with a growth rate higher than otherwise expected for non-addicted strains (FIG. 16).

The dependence of the addicted strain on a supply of benzoic acid for maximal growth (FIG. 16), confirms that the benzoic acid biosensor is able to induce the p$_{SAL}$ promoter and the expression of dihydropteroate synthase, in the pathway leading tetrahydrofolate (vitamin B9) synthesis, which is essential for normal cell growth.

2.6 General Scheme for Engineering and Optimization of Addiction to Effector Metabolite by Regulated Expression of an Essential Gene As exemplified in the previous examples, biosensors can be engineered into cells to control growth by addiction to an effector metabolite produced by the cell. The degree of addiction, which results in a relative growth advantage for cells that produce and accumulate the effector metabolite, may be increased by reducing the growth of an addicted cell in which the cellular levels of effector metabolite are below a given threshold. The degree of addiction of the addicted cell can be controlled by regulating the basal expression of the biosensor and/or the regulated essential gene.

2.6.1 The degree of growth reduction for a given host cell that fails to produce sufficient effector metabolite can be increased by providing the regulated essential gene with a weaker RBS sequence e.g. generated with the "RBS Calculator" (https://salislab.net/software), thereby reducing its rate of translation. Alternatively, the basal transcription strength of the regulated essential gene can be reduced by providing a biosensor-regulated, but weaker, promoter to drive its expression. Inversely, the degree of addiction can be reduced, to minimize the growth reduction for non-producing cells, by employing a stronger RBS sequence or stronger promoter to enhance basal expression of the regulated essential gene.

2.6.2 The biosensor gene, engineered into the cell, is expressed under the control of a constitutive promoter. A suitable promoter can be selected from the set of the exemplary constitutive promoters provided in SEQ ID: 47-65. A suitable promoter is one that drives expression of the biosensor in an amount that is responsive to the effector metabolite concentration, while avoiding constitutive saturation of the promoter of the essential gene. Preferably, the engineered addicted cell of the invention is one whose growth rate is not reduced (no fitness cost) so long as the cell produces the effector metabolite at or above a predetermined amount.

2.7 Method for Engineering Host Cell Addiction to its Metabolic Product Using Tailor-Made Biosensor:Promoter Pairs A large number of biosensors are described in the literature, in particular in the RegPrecise and Genbank databases, each being characterized for its specific detection of one of a wide range of metabolic products of interest, and which are suitable for engineering host cell addiction to a particular effector metabolite of interest.

By way of example, a list of suitable biosensor and cognate promoter pairs is given in Table 13 for respective effector metabolites, that are suitable for engineering host cell addiction, and for regulating the expression of a gene in the host cell required for its growth and/or survival. A host cell addicted to one of the effector metabolites listed in Table 13 can be constructed using the corresponding biosensor: promoter pairs to regulate the expression of the essential gene folP-glmM, as follows. The native folP-glmM promoter in the selected host strain is replaced by the respective promoter listed in Table 13, by means of lambda red-mediated recombineering as described in section 2.3 for insertion of the $p_{BAD}$ promoter. Further, the gene encoding the respective biosensor listed in Table 13, is introduced into the selected host strain on a plasmid, as described for the introduction of the plasmid pBALspec comprising the triacetic acid lactone biosensor in Example 2.3. Standard molecular expression tuning may additionally be employed to optimize the degree of addiction as described above.

where ThiMN15 #19 had been identified. An alternative TPP-responsive riboswitch was constructed, where an "OFF-type" riboswitch was inserted into the DNA region of the pBAD-TA5 gene construct that encodes the 5'-UTR of the toxin-encoding sequence to yield the same ligand-responsive growth.

Table 14 listing the genetic features of the TPP-addicted-TA-regulated E. coli strain based on the E. coli XL1 parent strain

TABLE 14

| Plasmid/chromosome | Gene | SEQ ID No: | Protein | SEQ ID No |
|---|---|---|---|---|
| pBAT-TA5 | araC* | SEQ ID No: 31 | AraC | |
| | Thi-tet-yefM** | | Tet-YefM | SEQ ID No: 32 |
| | yoeB | | YoeB | SEQ ID No: 33 |
| | ampR | | Beta-lactamase | SEQ ID No: 34 |

*araC gene [SEQ ID No: 5] encoding araC biosensor protein [SEQ ID No: 6] is located on the complementary strand to SEQ ID No: 31 at nucleotide positions: 96-974;
**thi riboswitch is located at nucleotides 1291-1452 of SEQ ID No.: 31

A modified E. coli strain comprising the TPP responsive-riboswitch-regulated TA correction system (pBAT-TA5) showed enhanced growth in the presence of the inducer TPP, thereby demonstrating functionality of the TPP-addiction mediated via a riboswitch and TA system (FIG. 18). An alternative TPP responsive-riboswitch-regulated TA correction system was engineered with a constitutive promoter driving expression of the riboswitch-yefM mRNA. From a selection of constitutive promoters (SEQ ID Nos.: 47-65,

TABLE 13

Specific implementations of biosensors for diverse effectors

| Effector metabolite | Promoter | Promoter name | Biosensor name | Biosensor nucleotide sequence | Biosensor protein sequence | Effector metabolite conc. (µM) |
|---|---|---|---|---|---|---|
| Phenol | SEQ ID No: 107 | dmpRKLM | DmpR | SEQ No: 108 | SEQ No: 109 | 1000 |
| 2-Amino-biphenol | SEQ No: 110 | hbpC | HbpR | SEQ No: 111 | SEQ No: 112 | 100 |
| Catechol | SEQ No: 107 | dmpRKLM | CapR | SEQ No: 113 | SEQ No: 114 | 100 |
| D-glycerate | SEQ No: 115 | gudP | CdaR | SEQ No: 116 | SEQ No: 117 | 750 |
| triacetic acid lactone | SEQ ID No: 66 | $p_{BAD}$ | AraCtal | SEQ ID No: 95 | SEQ ID No: 96 | |
| salicylic acid | SEQ ID No: 118 | $p_{SAL}$ | NahR_Asn169 | SEQ ID No: 99 | SEQ ID No: 100 | |
| benzoic acid | SEQ ID No: 118 | $p_{SAL}$ | NahR | SEQ ID No: 105 | SEQ ID No: 106 | |

Example 3. Riboswitch Biosensors Extend the Range of Addiction Molecules for Regulating Cell Growth 3.1 Use of Thiamine Pyrophosphate (TPP)-Sensitive Riboswitch-Controlled TA System to Regulate Bacterial Cell Growth A TPP-responsive riboswitch (ThiMN15 #19) was engineered into the previously constructed L-arabinose-responsive TA-based correction system (pBAD-TA5 to yield pBAT-TA5). This TPP riboswitch functions as an "ON-type" when in the presence of its ligand TPP, and it is functional at the level of translation. The riboswitch was inserted into the DNA region of the pBAD-TA5 gene construct that encodes the 5' untranslated region (UTR) of the antitoxin mRNA sequence (FIG. 17). For optimal functionality of the riboswitch, a protein-encoding sequence tet was also added as N-terminal fusion to YefM as it originated from the screen 89) of different strengths, the $p_{BAD}$ promoter of pBAT-TA5 was replaced and the resulting plasmids transformed into E. coli XL1. These were tested to identify plasmids where the strength of the constitutive promoter allowed the riboswitch-yefM transcript to cause good TPP-conditional growth of the transformed E. coli cell, i.e. when grown in liquid medium with and without addition of 500 µM TPP.

3.1 Use of a TPP-Sensitive Riboswitch-Regulated TA System to Enhance Small Molecule Production in Bacteria.

In order to demonstrate that modified E. coli strain comprising the TPP riboswitch (ThiMN15 #19) TA system, was dependent on internal TPP overproduction, the cells were further genetically modified to biosynthesize higher concentrations of TPP, which were compared with a reference strain cells retaining the wild-type intracellular TPP accumulation level. Biosynthesis of elevated TPP concentration was engineered by translational deregulation of the chromosomal native E. coli thiC gene. This was achieved by introducing a point mutation (by substituting wild-type nucleotide residue A at position (−135), with nucleotide B (=any one of C, G and T) in the region of the native *E. coli* thiC gene [GeneID: 948492], to give the following 142nt sequence located directly upstream of the thiC open reading frame, corresponding to the transcribed 5'-UTR: ATTCGGG BTCCGCGGAACCTGATCAGGCTAATACCTGCGAAG GGAACAAGAGTTAATCTGCTA TCG- CATCGCCCCTGCGGCGATCGTCTCTTGCTT- CATCCGTCGTCTGACAAGCCACGTCCTTAA CTTTTTGGAATGAGCT [SEQ ID No: 90] which when transcribed yields a mutant *E. coli* riboswitch transcript, that is insensitive to TPP feedback regulation. Growth and TPP production by these *E. coli* strains comprising, or lacking, the TPP-sensitive riboswitch-regulated TA gene correction system in the modified and reference stains, are then compared.

Example 4 Improved Fermentation Productivity Through Use of Product-Addicted Strain Based on Control of Essential Genes A plasmid (pMEV7C), encoding the genes for the metabolic pathway to mevalonate, was inserted in *E. coli* XL1. The strain was further engineered to encompass a biosensor-based addiction module according to the invention e.g. by following the methods for construction of strain e3.9 comprising the plasmid (FRT-kana-FRT-$p_{BAD}$-RBS1)-folP-glmM), where growth requires expression of an essential gene (see Example 2.2). As a control, the same pathway plasmid (pMEV7C) was inserted in an *E. coli* XL1 strain to generate pe1 only differing in way of genetic engineering from e3.9 (Table 3) by the fact that no genetic changes had been introduced on the chromosome (i.e. the expression of essential genes were not linked to presence of the metabolic pathway product).

The two strains e3.9 and pe1 were grown at 37 deg. C. with 250-300 rpm horizontal shaking in 2×YT medium (with 30 μg/mL chloramphenicol and 50 μg/mL spectinomycin) for 55 cell generations to simulate a fermentation of large industrial size. This generation number was obtained in 25 mL shake flask cultures by transferring ≥0.5 vol % culture to fresh 2×YT medium an appropriate number of times according to the cell densities measured when transferring the culture. Final productivity of the cell population was evaluated by taking a sample for HPLC analysis following culturing at 37 deg. C. for 72 hours after the final transferring. As seen in FIG. 19, the concentration of mevalonate (MVA) in the control strain pe1 was only 35% of the concentration in the e3.9 strain, demonstrating the advantage of linking product-presence to growth of the strain during cultivations with many cell divisions.

A high generation number could be reached using a continuous chemostat fermentor, in which the cells are constantly dividing through inlet of new medium and outlet of culture. Optionally, the strains could also be cultured at another temperature such as 30 deg. C. The productivity of the cells could further be measured at various numbers of generations such as (but not limited to) 20, 30, 40, 50, 60, 70 and 150 generations. To evaluate the stability of the pathway over time (cell generations), the cells can be re-cultured from a stored sample of the generation of cells in a 25% glycerol stock at −80 degrees Celsius. This sample could be re-cultured in 15 mL 2×YT (with 30 μg/mL chloramphenicol and 50 μg/mL spectinomycin) under otherwise same culture conditions and measuring the productivity (according to method described in previous section).

To evaluate whether genetic mutations were less predominant in the product pathway of the product-addicted strain, DNA sequencing of the strains could be performed.

The cultivations can be carried out in growth medium, which can direct higher mevalonate productivity, such as M9 minimal medium supplemented with 0.4-4 (w/v) % glucose.

Mevalonate production (in the culture medium) was detected by HPLC, following treatment of 300 μL sampled culture broth with 23 μL 20% sulfuric acid for conversion to the mevalonolactone form. The mixture was vortexed and cells separated from the medium by centrifugation at 17,000 g for 3 mins. 30 μL supernatant (medium) was injected in an Ultimate 3000 HPLC running with a 5 mM sulfuric acid mobile phase (0.6 mL/min) on an Aminex HPX-87H ion exclusion column (300 mm×7.8 mm, Bio-Rad Laboratories, Hercules, Calif., USA) at 50° C., with detection using refractive-index (RI) channel.

Example 5 Improved Fermentation Productivity Through Use of Product-Addicted Strain Based on Control of Toxin-Antitoxin Systems A plasmid (pMEV7C) encoding the genes for the metabolic pathway to mevalonate was inserted in *E. coli* XL1. The strain was further engineered to encompass a biosensor-based addiction module according to the invention e.g. by following the methods for construction of strain m29, which comprises (pBAM-TA5), where growth is controlled by expression of the anti-toxin and toxin pair (see Example 1.4). As a control, the exact same pathway plasmid was inserted in an *E. coli* XL1 strain, to create a strain only differing from m29 by the fact that a plasmid featuring the invented system had not been introduced (i.e. the expression of antitoxin was not linked to presence of the metabolic pathway product).

Pre-cultures in 2×YT were inoculated from single colonies of the two strains, and main cultures were inoculated from these when OD600 (measured on 200 μL sample in a BioTek SynergyH1 plate reader) was 0.1-0.5. From there, the two strains were grown at 30 deg. C. with 250-300 rpm horizontal shaking in 2×YT medium for 70 cell generations to simulate a fermentation of large industrial size. This generation number was obtained in 50 mL shake flask cultures by transferring ≥0.5 vol % culture to fresh medium an appropriate number of times according to the cell densities measured before transferring the culture. Optionally, the generation number could be reached using a continuous chemostat fermentor, in which the cells are constantly dividing through inlet of new medium and outlet of culture. The productivity of the cells was measured at various numbers of generations such as (but not limited to) 20, 30, 40, 50, 60 and 70 generations. This was done by recording a sample of the generation of cells in a 25% glycerol stock stored at −80 deg. C. and re-culturing them in tubes with 15 mL 2×YT under otherwise same culture conditions and measuring the productivity (according to method described in Example 4).

REFERENCES

Cebolla, A., Sousa, C., De Lorenzo, V., 1997. Effector Specificity Mutants of the Transcriptional Activator NahR of Naphthalene Degrading *Pseudomonas* Define Protein Sites Involved in Binding of Aromatic Inducers. J. Biol. Chem. 272, 3986-3992. doi:10.1074/jbc.272.7.3986

Datsenko, K. a, Wanner, B. L., 2000. One-step inactivation of chromosomal genes in *Escherichia coli* K-12 using PCR products. Proc. Natl. Acad. Sci. U.S.A 97, 6640-6645. doi:10.1073/pnas.120163297

Guzman, L. M., Belin, D., Carson, M. J., & Beckwith, J. (1995): Tight regulation, modulation, and high-level expression by vectors containing the arabinose P BAD Promoter. Journal of Bacteriology, 177(14), 4121-4130.

Tang, S. Y., Qian, S., Akinterinwa, O., Frei, C. S., Gredell, J. A., Cirino, P. C., 2013. Screening for enhanced triacetic acid lactone production by recombinant *Escherichia coli* expressing a designed triacetic acid lactone reporter. J. Am. Chem. Soc. 135, 10099-10103. doi:10.1021/ja402654z

The invention claimed is:

1. A method of producing a biosynthetic metabolite comprising the steps of:
   a) providing a pre-seed microbial cell culture of genetically modified microbial cells, wherein each cell comprises:
      i. a first nucleic acid molecule wherein said molecule is transcribed and/or translated to yield a biosensor and said biosensor binds to said biosynthetic metabolite to form a complex; and
      ii. a second nucleic acid molecule comprising a coding sequence encoding an essential protein required for cell growth and/or survival, wherein said cell is not viable when said coding sequence encoding said essential protein is knocked-out, wherein the essential protein is:
         (1) a protein having UDP-MurNAc-pentapeptide phosphotransferase activity and an amino acid sequence having at least 80% sequence identity to SEQ ID NO:78, (2) a protein having phosphoglucosamine mutase activity and an amino acid sequence having at least 80% sequence identity to: SEQ ID NO: 80, or (3) a protein having glutamate racemase activity and an amino acid sequence having at least 80% sequence identity to: SEQ ID NO: 82, wherein the second nucleic acid molecule is operably linked to a first promoter;
      wherein said essential protein encoded by said second nucleic acid molecule is expressed when said second nucleic acid molecule is induced by said complex when said biosensor and said biosynthetic metabolite form a complex;
      whereby growth of said cell is arrested by an absence of complex formation and wherein said arrest of growth does not depend on externally supplied growth inhibitor or growth retardant;
   b) introducing the pre-seed microbial cell culture into a nutrient rich cultivation medium comprising a substrate for production of said biosynthetic metabolite, wherein the cells of the cell culture produce said biosynthetic metabolite and undergo at least 40, 45, 50, 60, 70 or 150 generations of cell multiplication, and
   c) recovering the biosynthetic metabolite produced by said cell culture, wherein (i) a lack of metabolite production in genetically modified microbial cells or progeny cells of said cell culture thereof attenuates multiplication of said cells as compared to a parent cells lacking said first nucleic acid molecule and said second nucleic acid molecule from which said genetically modified microbial cells were derived, and (ii) the productive life-time of said culture is prolonged by preventing proliferation of non-producing spontaneous mutants.

2. The method of claim 1, wherein the genetically modified microbial cells in the culture medium-are cultivated under batch culture.

3. The method of claim 1, wherein the production of the metabolite has a high fitness cost of production of greater than or equal to about 15%, greater than or equal to about 20%, or greater than or equal to about 25%.

4. The method of claim 1, wherein the genetically modified microbial cells-in the culture medium are cultivated under continuous culture.

5. The method of claim 1, wherein the genetically modified microbial cells in the culture medium are cultivated under fed-batch culture.

6. The method of claim 1, wherein the genetically modified microbial cells are bacterial cells.

* * * * *